(12) United States Patent
Zhong et al.

(10) Patent No.: US 12,338,253 B2
(45) Date of Patent: Jun. 24, 2025

(54) NITROGEN-CONTAINING POLYCYCLIC FUSED RING COMPOUND, PHARMACEUTICAL COMPOSITION THEREOF, PREPARATION METHOD THEREFOR AND USE THEREOF

(71) Applicant: APPLIED PHARMACEUTICAL SCIENCE, INC., Beijing (CN)

(72) Inventors: Jun Zhong, Beijing (CN); Yongbo Liu, Beijing (CN); Libin Liu, Beijing (CN); Xiaohu Chen, Beijing (CN); Hao Wang, Beijing (CN); Ying Lu, Beijing (CN)

(73) Assignee: Applied Pharmaceutical Science, Inc., Beijing (CN)

( * ) Notice: Subject to any disclaimer, the term of this patent is extended or adjusted under 35 U.S.C. 154(b) by 813 days.

(21) Appl. No.: 17/633,137

(22) PCT Filed: Aug. 5, 2020

(86) PCT No.: PCT/CN2020/107049
§ 371 (c)(1),
(2) Date: Feb. 4, 2022

(87) PCT Pub. No.: WO2021/023209
PCT Pub. Date: Feb. 11, 2021

(65) Prior Publication Data
US 2022/0332731 A1 Oct. 20, 2022

(30) Foreign Application Priority Data

Aug. 5, 2019 (CN) .......................... 201910719005.2

(51) Int. Cl.
C07D 519/00 (2006.01)
(52) U.S. Cl.
CPC .................... C07D 519/00 (2013.01)
(58) Field of Classification Search
CPC .................................................. C07D 519/00
See application file for complete search history.

(56) References Cited

U.S. PATENT DOCUMENTS

| | | | |
|---|---|---|---|
| 8,426,437 B2 | 4/2013 | Bienayme et al. | |
| 10,112,942 B2 * | 10/2018 | Andrews | A61P 35/00 |
| 10,138,243 B2 | 11/2018 | Andrews et al. | |
| 10,174,027 B2 | 1/2019 | Andrews et al. | |
| 10,174,028 B2 | 1/2019 | Andrews et al. | |

FOREIGN PATENT DOCUMENTS

| | | |
|---|---|---|
| WO | 2017011776 A1 | 1/2017 |
| WO | 2020064009 A1 | 4/2020 |

OTHER PUBLICATIONS

Takahashl, Mashide et al.; Activation of a Novel Human Transforming Gene, ret, by DNA Rearrangement, Cell, Sep. 1985, 42(2): 581-588.
Houvras, Yariv et al.; Completing the Arc: Targeted Inhibition of RET in Medullary Thyroid Cancer, Journal of Clinical Oncology, Jan. 10, 2012, 30(2): 200-202.
Grieco, Michele et al.; PTC is a Novel Rearranged from of the ret Proto-Oncogene and is Frequently Detected In vico in Human Thyroid Papillary Carcinomas, Cell, Feb. 23, 1990, 60(4): 557-563.
Kloos, Richard T. et al.; Medullary Thyroid Cancer: management Guidelines of the American Thyroid Association, Thyroid, Nov. 6, 2009, 19(6): 565-612.
De Groot, Jan Willem B. et al.; RET as a Diagnostic and Therapeutic Target in Sporadic and Hereditary Endocrine Tumors, Endocrine Reviews, Aug. 2006, 27(5): 535-560.
Bolk, Stacey et al.; A human model for multigenic inheritance: Phenotypic expression in Hirschsprung disease requires both the RET gene and a new 9q31 locus, Proc Natl Acad Sci USA, Jan. 4, 2000, 97(1): 268-273.
Cai, Weijing et al.; KIF5B-RET Fusions in Chinese Patients With Non-Small Cell Lung Cancer, Cancer, 2013, 119(8): 1486-1494, published online Nov. 26, 2012.
Ju, Yououng Seok et al.; A transforming KIF5B and RET gene fusion in lung adenocarcinoma revealed from whole-genome and transcriptome sequencing, Genome Research, 2012, 22(3): 436-445. Originally published online Dec. 22, 2011.
Wong, Daisy Wing-Sze et al.; A Novel KIF5B-ALK Variant in Nonsmall Cell Lung Cancer, Cancer, Jun. 15, 2011, 117(12): 2709-2718.
Qian, Yingying et al.; KIF5B-RET Fusions kinase promotes cell growth by multilevel activation of STAT3 in lung cancer, Molecular Cancer, 2014, 13: 176.
Solomon, Benjamin J. et al.; RET Solvent Front Mutations Mediate Acquired Resistance to Selective RET Inhibition in RET-Driven Malignancies, Journal of Thoracic Oncology, Apr. 2020, vol. 15, No. 4, 541-549.
Kohno, Takashi et al.; KIF5B-RET fusions in lung adenocarcinoma, Nature Medicine, Feb. 12, 2012, 18(3): 375-377.

* cited by examiner

*Primary Examiner* — Timothy R Rozof
(74) *Attorney, Agent, or Firm* — NKL Law; Allen Xue

(57) ABSTRACT

A nitrogen-containing polycyclic fused ring compound of formula I, a pharmaceutical composition thereof, a preparation method therefor and use thereof are related to the field of medicinal chemistry. The compound can be used as a selective and effective RET inhibitor. It has strong inhibitory effect on the RET gatekeeper residue mutant RET V804M, RET solvent-front residue mutant RET G810R and other clinically relevant RET mutants, as well as RET wt. The compound can also inhibit the growth of TT cell line derived from thyroid cancer and Ba/F3 cells transformed with various RET mutants, and induce the death of TT cells.

92 Claims, 1 Drawing Sheet

NITROGEN-CONTAINING POLYCYCLIC FUSED RING COMPOUND, PHARMACEUTICAL COMPOSITION THEREOF, PREPARATION METHOD THEREFOR AND USE THEREOF

CROSS-REFERENCE TO RELATED APPLICATIONS

This application is a U.S. national stage entry of PCT International Application No. PCT/CN2020/107049, filed Aug. 5, 2020, which claims priority to Chinese Patent Application No. 201910719005.2 filed with China National Intellectual Property Administration on Aug. 5, 2019 and entitled "NITROGEN-CONTAINING POLYCYCLIC FUSED RING COMPOUND, PHARMACEUTICAL COMPOSITION THEREOF, PREPARATION METHOD THEREFOR AND USE THEREOF", the context of which is incorporated herein by reference in its entirety.

TECHNICAL FIELD

The present disclosure relates to the field of medicinal chemistry, in particular to a nitrogen-containing polycyclic fused ring compound, a pharmaceutical composition thereof, a preparation method therefor and use thereof.

BACKGROUND

RET (rearranged during transfection) proto-oncogene was first demonstrated in 1985 by transfection of NIH3T3 (mouse embryonic fibroblast cell line) cells with human lymphoma DNA (*Cell*, 1985, 42(2): 581-588). RET proto-oncogene, located on chromosome 10q11.2, has 60 kb of DNA, contains 21 exons, and encodes a RET protein consisting of 1100 amino acids. The RET protein is a tyrosine kinase receptor containing an extracellular domain composed of cysteine, a transmembrane domain, and an intracellular domain capable of catalyzing tyrosine kinase (*Mol Cell Endocrinol*, 2010, 322(1-2): 2-7). RET is involved in cell proliferation, nerve conduction, cell migration and cell differentiation, and activates various downstream pathways, such as RAS/RAF/MEK/ERK, PI3K/AKT and STAT through the signal from ligand/receptor complex/RET multiprotein complex pathway to induce cell proliferation (*J Clin Oncol*, 2012, 30(2): 200-202).

With the development of researches, mutations in RET genes have been found to be closely related to the occurrence of many diseases, including papillary thyroid carcinoma (PTC) (*Cell*, 1990, 60(4): 557-563), medullary thyroid carcinoma (MTC) (*hyroid*, 2009, 19(6): 565-612), multiple endocrineneoplasia type II (MEN2) (*Endocr Rev,* 2006, 27(5): 535-560), Hirschsprung's disease (*Proc Natl Acad Sci USA*, 2000, 97(1): 268-273), lung adenocarcinoma (*Nat Med*, 2012, 18(3): 375-377), and the like. At present, only four RET fusion genes of KIF5B-RET, CCDC6-RET, TRIM33-RET, NCOA4-RET have been reported in non-small cell lung cancer, with KIF5B-RET predominated (*Cancer*, 2013, 119(8): 1486-1494). KIF5B-RET, a fusion gene formed by the chromosome inversion (p11; q11) of KIF5B (kinesin family member 5B) gene and RET gene, was first demonstrated in adenocarcinoma in non-smoking Koreans through whole-genome and transcriptome sequencing. KIF5B-RET accounts for a low proportion in lung cancer patients, but is common in non-smokers and adenocarcinoma patients, and is repelled with other mutations such as EGFR, KRAS, BRAF, ErbB2 and EML4-ALK (*Genome Res*, 2012, 22(3): 436-445). The KIF5B-RET fusion protein contains a motor domain and a coiled-coil domain of KIF5B. Through the dimerization of the coiled-coil domain, the tyrosine kinase of RET in the fusion protein can be abnormally activated, thereby promoting lung tumorigenesis (*Cancer*, 2011, 117(12): 2709-2718). In the research by Qian et al (*Mol Cancer*, 2014, 13: 176), KIF5B-RET fusion kinase was confirmed to have significant oncogenic activity both in vitro and in vivo, and the signal transduction pathway of STAT3 may be the main downstream mediator of tumorigenesis. There is evidence that KIF5B-RET can regulate the continuous activation of STAT3. KIF5B-RET fusion kinase can bind to STAT3 to directly phosphorylate and activate STAT3-Tyr705. It can also mediate the activation of STAT3-Tyr705 through the JAK/STAT3-dependent pathway, and trigger the phosphorylation of Ser727 through the RAS/RAF/MEK/ERK1 pathway.

The demonstration that the RET fusions are drivers in some cancers facilitates the use of multi-kinase inhibitors, which already have RET inhibitory activity, in the treatment of tumor patients loaded with RET fusion proteins. At present, there are no approved agents that can specifically target this oncogene. The current treatments for RET-specific cancers are limited to multi-kinase inhibitors and chemotherapy, which, however, have poor clinical performance-undesirable ORR (objective response rate) and great off-target toxicity. Furthermore, one of the biggest challenges in cancer treatment is that tumor cells become resistant to treatment after a certain duration. Once they are resistant, the treatment options for patients are usually extremely limited, and in most cases, the cancer remains progressive and unchecked.

In many human cancers such as thyroid cancer, the RET kinase signal transduction plays an important role. The mutation in gatekeeper residue RET 804V of RET is an important cause of tumor resistance to currently approved non-selective RET inhibitors (such as cabozantinib and vandetanib). One of the important mutations in the extracellular or intracellular domain of RET in isolated familial medullary thyroid carcinoma, i.e., the mutation in gatekeeper residue V804M in the kinase ATP binding site, leads to a decrease in the affinity of existing drugs for the ATP binding site. It has been reported in the document (RET Solvent Front Mutations Mediate Acquired Resistance to Selective RET Inhibition in RET-Driven Malignancies, *Journal of Thoracic Oncology*, 2020, Vol. 15, No 4, 541-549) that upon the use of the selective RET inhibitor LOXO-292 (Selpercatinib), the aforementioned RET 804V mutation can be avoided, but there are still other mutations that lead to drug resistance. For example, mutations in residue G810 such as G810R, G810S and G801C, which can result in a solvent-front of the kinase ATP binding site in non-small cell lung cancer, lead to a decrease in the binding of LOXO-292 to the ATP binding site, resulting in drug resistance and cancer progression. Accordingly, there is a need to develop compounds with good RET mutation inhibitory activity.

SUMMARY

In order to get improved from the above problems, the present disclosure provides a compound of formula I or a pharmaceutically acceptable salt thereof:

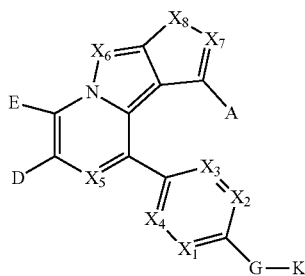

I wherein $X^1$, $X^2$, $X^3$, $X^4$, $X^5$, $X^6$ and $X^7$ are the same or different, and are independently selected from $CR^1$ and N;

$X_8$ is selected from $CR^1R^{1'}$ and $NR^1$; wherein each $R^1$ and $R^{1'}$ are the same or different, and are independently selected from H, halogen, CN, $NH_2$ and OH, or each $R^1$ and $R^{1'}$ are the same or different, and are independently selected from the following groups unsubstituted or optionally substituted with 1, 2 or 3 $R^a$: $C_{1-6}$ alkyl, $C_{3-6}$ cycloalkyl, $C_{1-6}$ alkoxy and $C_{3-6}$ cycloalkyloxy; and each $R^a$ is the same or different, and is independently selected from halogen, CN, OH, $C_{1-6}$ alkyl, $C_{3-6}$ cycloalkyl and $C_{1-6}$ alkoxy;

A is selected from H, halogen, CN, OH and $NH_2$, or

A is selected from the following groups unsubstituted or optionally substituted with 1, 2 or 3 $R^b$: $C_{1-6}$ alkyl, $C_{2-6}$ alkenyl, $C_{3-6}$ cycloalkyl, $C_{1-6}$ alkoxy and $C_{3-6}$ cycloalkyloxy; wherein each $R^b$ is the same or different, and is independently selected from halogen, CN, OH, $C_{1-6}$ alkyl, $C_{3-6}$ cycloalkyl and $C_{1-6}$ alkoxy;

D and E are the same or different, and are independently selected from H, halogen, CN, OH and $NH_2$, or D and E are the same or different, and are independently selected from the following groups unsubstituted or optionally substituted with 1, 2 or 3 $R^c$: —$C_{1-6}$ alkyl, —$C_{1-6}$ alkoxy, —$O(CH_2)_nO(CH_2)_nC_{3-6}$ carbocyclic ring, —$O(CH_2)_n$-3- to 8-membered heterocyclic ring, and —$O(CH_2)_nC_{6-10}$ aromatic ring; wherein each $R^c$ is the same or different, and is independently selected from halogen, CN, OH, oxo (=O), $C_{1-6}$ alkyl, $C_{1-6}$ alkoxy, $C_{3-6}$ cycloalkyl, 3- to 10-membered heterocyclyl, 5- to 7-membered heteroaryl, 6- to 10-membered aryl, $C_{1-6}$ alkoxy, 3- to 6-membered cycloalkyloxy and 3- to 8-membered heterocyclyloxy;

each n is the same or different, and is independently selected from 0, 1, 2 and 3; and each heterocyclic ring, heterocyclyl and heteroaryl in D, E and $R^c$ have the same or different numbers and types of heteroatoms, and independently contain 1, 2 or 3 heteroatoms selected from N, O and S;

G is selected from the following groups: (1) saturated 4- to 8-membered heterocyclic ring containing 2 heteroatoms; (2) saturated 7- to 10-membered heterocyclic ring containing 2 heteroatoms; (3) saturated 7- to 11-membered heterospiro ring containing 2 heteroatoms; and (4) saturated 7- to 10-membered bicyclic fused heterocyclic ring containing 2 heteroatoms; wherein the above heteroatoms are selected from N and O respectively, and each ring is independently unsubstituted or optionally substituted with 1, 2, 3 or 4 $R^G$;

each $R^G$ is the same or different, and is independently selected from H, halogen, OH, $NH_2$, $C_{1-6}$ alkyl, halogen-substituted $C_{1-6}$ alkyl, $C_{1-6}$ alkoxy and halogen-substituted $C_{1-6}$ alkoxy; and K is selected from the following groups unsubstituted or optionally substituted with 1, 2, 3 or 4 $R^K$: $C_{1-6}$ alkyl, $C_{3-6}$ cycloalkyl, $C_{6-10}$ aryl, —$C_{1-6}$ alkylene $C_{6-10}$ aromatic ring, —$COC_{1-6}$ alkylene $C_{6-10}$ aromatic ring, —$C_{1-6}$ alkylene 5- to 10-membered aromatic heterocyclic ring, —$COC_{1-6}$ alkylene 5- to 10-membered aromatic heterocyclic ring, —$CONR^{K1}R^{K2}$, 3- to 10-membered heterocyclyl, $C_{1-6}$ alkoxy, $C_{3-6}$ cycloalkyloxy, $C_{6-10}$ aryloxy, 5- to 10-membered heteroaryloxy, and 3- to 10-membered heterocyclyloxy; wherein each $R^K$ is the same or different, and is independently selected from the following groups: —CN, OH, —$NH_2$, $C_{1-6}$ alkyl, $C_{1-6}$ alkoxy, $C_{3-6}$ cycloalkyl, halogen-substituted $C_{1-6}$ alkyl and halogen-substituted $C_{1-6}$ alkoxy;

$R^{K1}$ and $R^{K2}$ are the same or different, and are independently selected from the following groups: —CN, $C_{1-6}$ alkyl, $C_{1-6}$ alkoxy, $C_{3-6}$ cycloalkyl, halogen-substituted $C_{1-6}$ alkyl and halogen-substituted $C_{1-6}$ alkoxy; and each aromatic heterocyclic ring, heterocyclic ring and heterocyclyl in K is the same or different, and independently contains one or two N.

As a preferred embodiment, the present disclosure also provides a compound of formula I or a pharmaceutically acceptable salt, wherein $X^1$, $X^3$ and $X^4$ are independently selected from $CR^1$.

As a preferred embodiment, the present disclosure also provides a compound of formula I or a pharmaceutically acceptable salt, wherein $X^5$ is selected from $CR^1$.

As a preferred embodiment, the present disclosure also provides a compound of formula I or a pharmaceutically acceptable salt, wherein $X^8$ is selected from $NR^1$.

As a preferred embodiment, the present disclosure also provides a compound of formula I or a pharmaceutically acceptable salt, wherein each $R^1$ and $R^{1'}$ are the same or different, and are independently selected from H, F, Cl, Br, CN, $NH_2$ and OH, or each $R^1$ and $R^{1'}$ are the same or different, and are independently selected from the following groups unsubstituted or optionally substituted with 1, 2 or 3 $R^a$: $C_{1-3}$ alkyl, $C_{4-6}$ cycloalkyl, $C_{1-3}$ alkoxy and $C_{4-6}$ cycloalkyloxy.

As a preferred embodiment, the present disclosure also provides a compound of formula I or a pharmaceutically acceptable salt, wherein each $R^1$ and $R^{1'}$ are the same or different, and are independently selected from H, F, Cl, CN and $NH_2$, or each $R^1$ and $R^{1'}$ are the same or different, and are independently selected from the following groups unsubstituted or optionally substituted with 1, 2 or 3 $R^a$: methyl, ethyl, propyl, 5-membered cycloalkyl, 6-membered cycloalkyl, methoxy, ethoxy, propoxy, 5-membered cycloalkyloxy and 6-membered cycloalkyloxy.

As a preferred embodiment, the present disclosure also provides a compound of formula I or a pharmaceutically acceptable salt, wherein each $R^a$ is the same or different, and is independently selected from F, Cl, Br, CN, OH, $C_{1-3}$ alkyl, $C_{4-6}$ cycloalkyl and $C_{1-3}$ alkoxy;

As a preferred embodiment, the present disclosure also provides a compound of formula I or a pharmaceutically acceptable salt, wherein each $R^a$ is the same or different, and is independently selected from F, Cl, CN, OH, methyl, ethyl, propyl, 5-membered cycloalkyl, 6-membered cycloalkyl, methoxy, ethoxy, propoxy, 5-membered cycloalkyloxy and 6-membered cycloalkyloxy.

As a preferred embodiment, the present disclosure also provides a compound of formula I or a pharmaceutically acceptable salt, wherein $X^1$ is selected from CH.

As a preferred embodiment, the present disclosure also provides a compound of formula I or a pharmaceutically acceptable salt, wherein $X^3$ is selected from CH.

As a preferred embodiment, the present disclosure also provides a compound of formula I or a pharmaceutically acceptable salt, wherein $X^5$ is selected from CH.

As a preferred embodiment, the present disclosure also provides a compound of formula I or a pharmaceutically acceptable salt, wherein $X^5$ is selected from CH.

As a preferred embodiment, the present disclosure also provides a compound of formula I or a pharmaceutically acceptable salt, wherein $X^8$ is selected from NH.

As a preferred embodiment, the present disclosure also provides a compound of formula I or a pharmaceutically acceptable salt, wherein $X^1$, $X^3$, $X^4$ and $X^5$ are all selected from CH, and $X^8$ is selected from NH.

As a preferred embodiment, the present disclosure also provides a compound of formula I or a pharmaceutically acceptable salt, wherein $X^2$ is selected from N.

As a preferred embodiment, the present disclosure also provides a compound of formula I or a pharmaceutically acceptable salt, wherein $X^6$ is selected from N.

As a preferred embodiment, the present disclosure also provides a compound of formula I or a pharmaceutically acceptable salt, wherein $X^7$ is selected from N.

As a preferred embodiment, the present disclosure also provides a compound of formula I or a pharmaceutically acceptable salt, wherein $X^1$, $X^3$, $X^4$ and $X^5$ are all selected from CH, $X^2$, $X^6$ and $X^7$ are all selected from N, and $X^8$ is selected from NH.

As a preferred embodiment, the present disclosure also provides a compound of formula I or a pharmaceutically acceptable salt, wherein A is selected from H, F, Cl, Br, CN, OH and $NH_2$, or A is selected from the following groups unsubstituted or optionally substituted with 1, 2 or 3 $R^b$: $C_{1-3}$ alkyl, $C_{4-6}$ cycloalkyl, $C_{1-3}$ alkoxy and $C_{4-6}$ cycloalkyloxy; wherein each $R^b$ is the same or different, and is independently selected from F, Cl, Br, CN, OH, $C_{1-3}$ alkyl and $C_{1-3}$ alkoxy.

As a preferred embodiment, the present disclosure also provides a compound of formula I or a pharmaceutically acceptable salt, wherein A is selected from H, F, Cl, CN, OH and $NH_2$, or A is selected from the following groups unsubstituted or optionally substituted with 1, 2 or 3 $R^b$: methyl, ethyl, propyl, 5-membered cycloalkyl, 6-membered cycloalkyl, methoxy, ethoxy, propoxy, 5-membered cycloalkyloxy and 6-membered cycloalkyloxy; wherein each $R^b$ is the same or different, and is independently selected from F, Cl, methyl, ethyl, methoxy and ethoxy.

As a preferred embodiment, the present disclosure also provides a compound of formula I or a pharmaceutically acceptable salt, wherein A is selected from H, —F, —Cl, —CN, —OH, —$NH_2$ and —$CH_3$.

As a preferred embodiment, the present disclosure also provides a compound of formula I or a pharmaceutically acceptable salt, wherein D and E are the same or different, and are independently selected from H, F, Cl, Br, CN, OH and $NH_2$, or D and E are the same or different, and are independently selected from the following groups unsubstituted or optionally substituted with 1, 2 or 3 $R^c$: —$C_{1-3}$ alkyl, —$C_{1-3}$ alkoxy, —$O(CH_2)_nO(CH_2)_nC_{3-6}$ carbocyclic ring, —$O(CH_2)_n$-4- to 6-membered heterocyclic ring, —$O(CH_2)_nC_6$ aromatic ring, and —$O(CH_2)_nC_{10}$ aromatic ring.

As a preferred embodiment, the present disclosure also provides a compound of formula I or a pharmaceutically acceptable salt, wherein D and E are the same or different, and are independently selected from H, F, Cl, Br, CN, OH and $NH_2$, or D and E are the same or different, and are independently selected from the following groups unsubstituted or optionally substituted with 1, 2 or 3 $R^c$: methyl, ethyl, propyl, methoxy, ethoxy, propoxy, —$O(CH_2)_nO(CH_2)_n$-3-membered carbocyclic ring, —$O(CH_2)_nO(CH_2)_n$-4-membered carbocyclic ring, —$O(CH_2)_nO(CH_2)_n$-5-membered carbocyclic ring, —$O(CH_2)_n$-5-membered heterocyclic ring, —$O(CH_2)_n$-6-membered heterocyclic ring, and —$O(CH_2)_n$-phenyl ring.

As a preferred embodiment, the present disclosure also provides a compound of formula I or a pharmaceutically acceptable salt, wherein D and E are the same or different, and are independently selected from H, F, Cl, Br, CN, OH and $NH_2$, or D and E are the same or different, and are independently selected from the following groups unsubstituted or optionally substituted with 1, 2 or 3 $R^c$: methyl, methoxy, —$O(CH_2)_nO(CH_2)_n$-3-membered carbocyclic ring, —$O(CH_2)_n$-6-membered heterocyclic ring, and —$O(CH_2)_n$-phenyl ring.

As a preferred embodiment, the present disclosure also provides a compound of formula I or a pharmaceutically acceptable salt, wherein each n is the same or different, and is independently selected from 0, 1 and 2.

As a preferred embodiment, the present disclosure also provides a compound of formula I or a pharmaceutically acceptable salt, wherein each n is the same or different, and is independently selected from 1 and 2.

As a preferred embodiment, the present disclosure also provides a compound of formula I or a pharmaceutically acceptable salt, wherein each $R^c$ is the same or different, and is independently selected from F, Cl, Br, CN, OH, $C_{1-3}$ alkyl, $C_{3-5}$ cycloalkyl, 4- to 6-membered heterocyclyl, 5- to 6-membered heteroaryl, phenyl, $C_{1-3}$ alkoxy, 3- to 5-membered cycloalkyloxy, and 4- to 6-membered saturated heterocyclyloxy.

As a preferred embodiment, the present disclosure also provides a compound of formula I or a pharmaceutically acceptable salt, wherein each $R^c$ is the same or different, and is independently selected from F, Cl, Br, CN, OH, methyl, ethyl, propyl, 3-membered cycloalkyl, 4-membered cycloalkyl, 4-membered saturated heterocyclyl, 5-membered saturated heterocyclyl, 6-membered saturated heterocyclyl, 5-membered heteroaryl, 6-membered heteroaryl, phenyl, methoxy, ethoxy, propoxy, 3-membered cycloalkyloxy, 4-membered cycloalkyloxy, 5-membered saturated heterocyclyloxy, and 6-membered saturated heterocyclyloxy.

As a preferred embodiment, the present disclosure also provides a compound of formula I or a pharmaceutically acceptable salt, wherein each RC is the same or different, and is independently selected from F, Cl, Br, CN, OH, methyl, ethyl, propyl, 3-membered cycloalkyl, 4-membered cycloalkyl, 4-membered saturated heterocyclyl, 5-membered saturated heterocyclyl, 6-membered saturated heterocyclyl, 5-membered heteroaryl, 6-membered heteroaryl, phenyl, methoxy, ethoxy, propoxy, 3-membered cycloalkyloxy, 4-membered cycloalkyloxy, 5-membered saturated heterocyclyloxy, and 6-membered saturated heterocyclyloxy.

As a preferred embodiment, the present disclosure also provides a compound of formula I or a pharmaceutically acceptable salt, wherein each heterocyclic ring, heterocyclyl and heteroaryl in D, E and $R^c$ have the same or different numbers and types of heteroatoms, and independently contain 1 or 2 heteroatoms selected from N and O.

As a preferred embodiment, the present disclosure also provides a compound of formula I or a pharmaceutically acceptable salt, wherein each heterocyclic ring, heterocyclyl and heteroaryl in D, E and $R^c$ have the same or different numbers and types of heteroatoms, and independently contain one N atom and/or one O atom.

As a preferred embodiment, the present disclosure also provides a compound of formula I or a pharmaceutically acceptable salt, wherein each $R^c$ is the same or different, and is independently selected from F, Cl, Br, OH, CN,

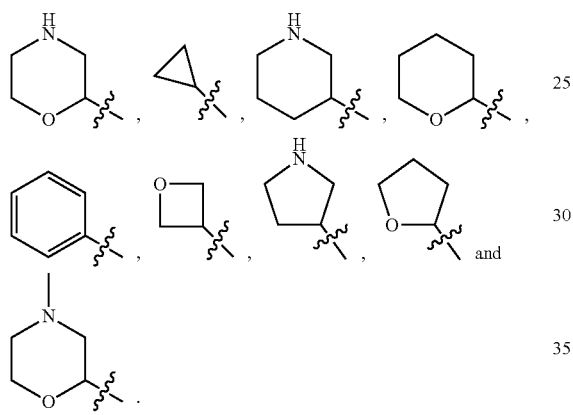

As a preferred embodiment, the present disclosure also provides a compound of formula I or a pharmaceutically acceptable salt, wherein D is selected from —H, —Br, —Cl, —CH₃, —NH₂,

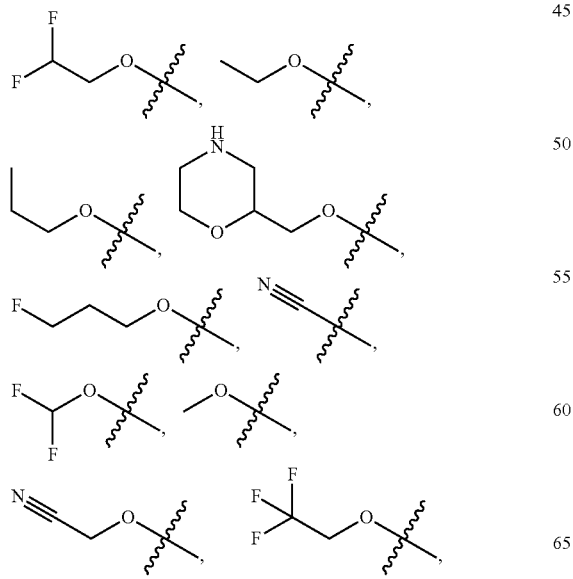

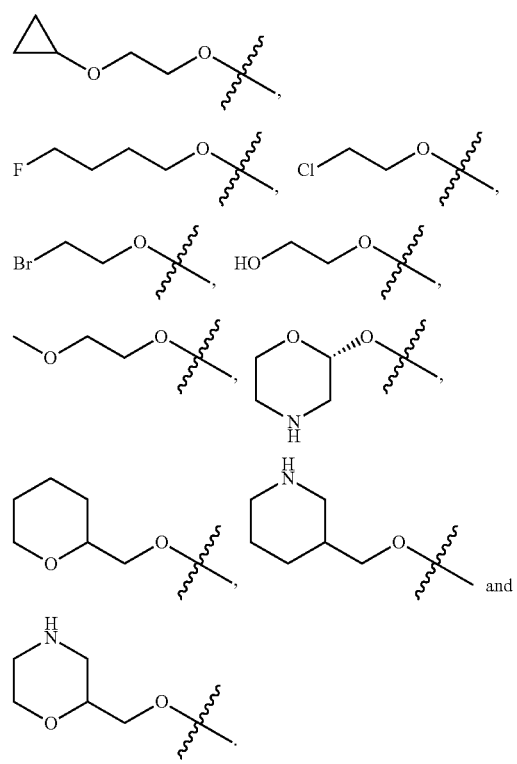

As a preferred embodiment, the present disclosure also provides a compound of formula I or a pharmaceutically acceptable salt, wherein E is selected from —H, —Br, —CN, NH₂, —CH₃, CF₃,

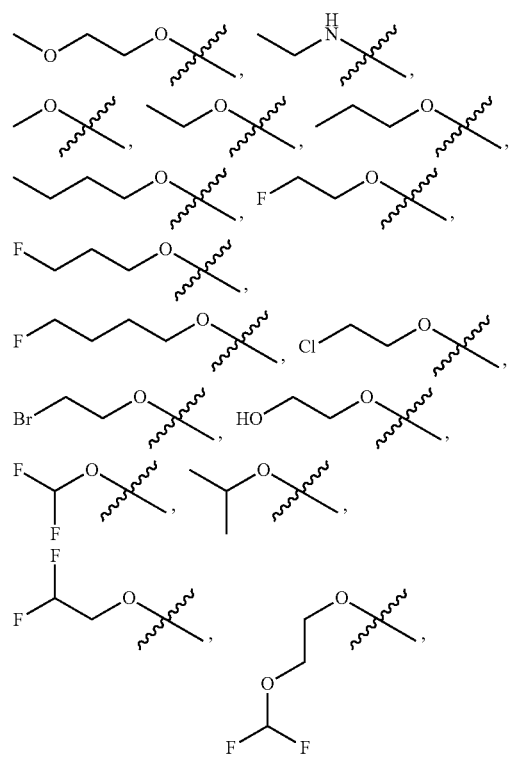

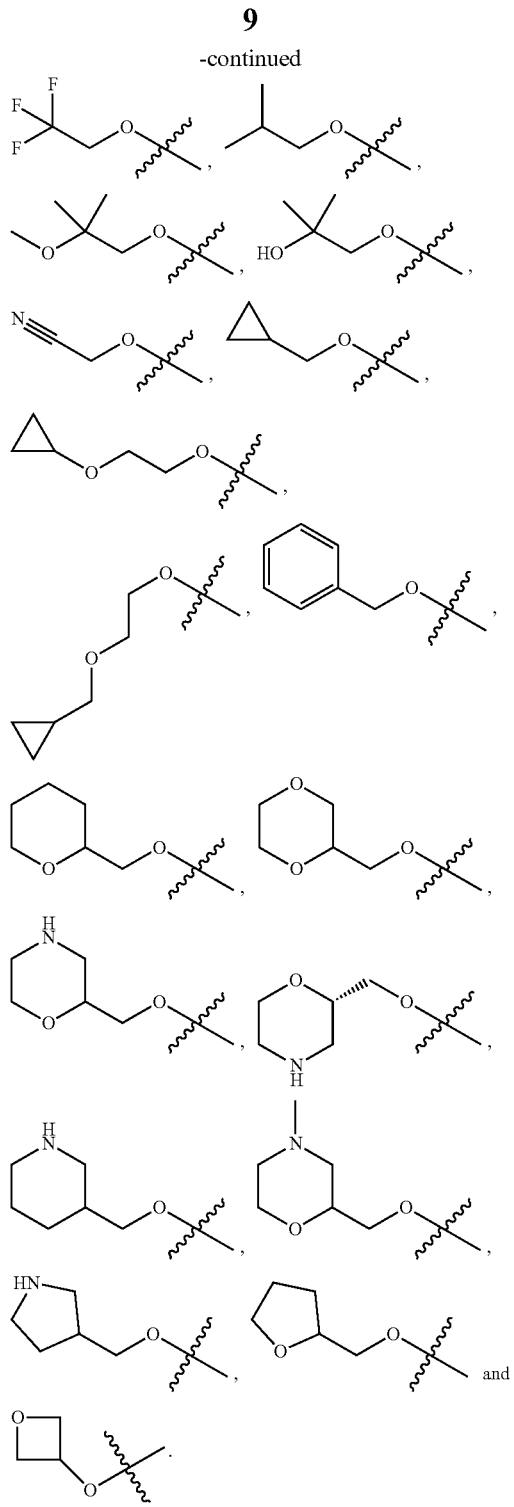

As a preferred embodiment, the present disclosure also provides a compound of formula I or a pharmaceutically acceptable salt, wherein E is selected from H, and D is selected from —H, —Br, —Cl, —

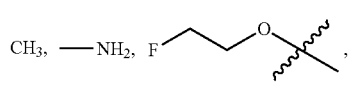

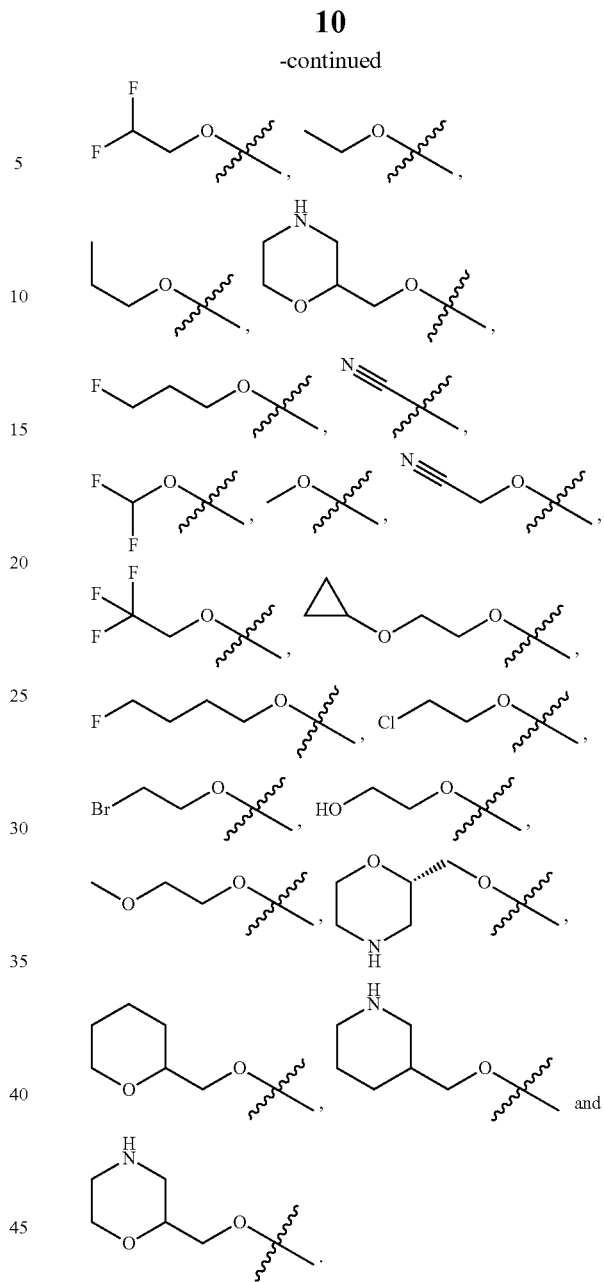

As a preferred embodiment, the present disclosure also provides a compound of formula I or a pharmaceutically acceptable salt, wherein G is selected from the following groups: saturated 5-, 6-, 7- and 8-membered heterocyclic rings containing two N atoms.

As a preferred embodiment, the present disclosure also provides a compound of formula I or a pharmaceutically acceptable salt, wherein G is selected from the following groups: saturated 5-membered heterocyclic ring containing two N atoms, saturated 6-membered heterocyclic ring containing two N atoms, saturated 7-membered heterocyclic ring containing two N atoms, and saturated 8-membered heterocyclic ring containing two N atoms.

As a preferred embodiment, the present disclosure also provides a compound of formula I or a pharmaceutically acceptable salt, wherein G is selected from the following groups:

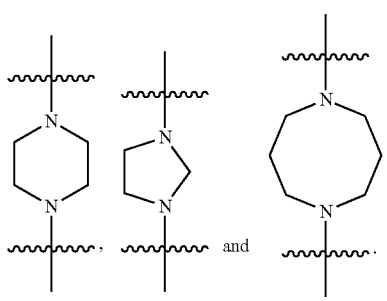

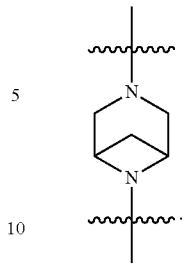

As a preferred embodiment, the present disclosure also provides a compound of formula I or a pharmaceutically acceptable salt, wherein G is selected from the following groups: saturated 7-, 8- and 9-membered bridged heterocyclic rings containing two N or O atoms.

As a preferred embodiment, the present disclosure also provides a compound of formula I or a pharmaceutically acceptable salt, wherein G is selected from the following groups: saturated 8-membered bridged heterocyclic ring containing two N or O atoms and saturated 9-membered bridged heterocyclic ring containing two N atoms.

As a preferred embodiment, the present disclosure also provides a compound of formula I or a pharmaceutically acceptable salt, wherein G is selected from the following groups: saturated 8-membered bridged heterocyclic ring containing two N atoms and saturated 9-membered bridged heterocyclic ring containing two N atoms.

As a preferred embodiment, the present disclosure also provides a compound of formula I or a pharmaceutically acceptable salt, wherein G is selected from the following groups:

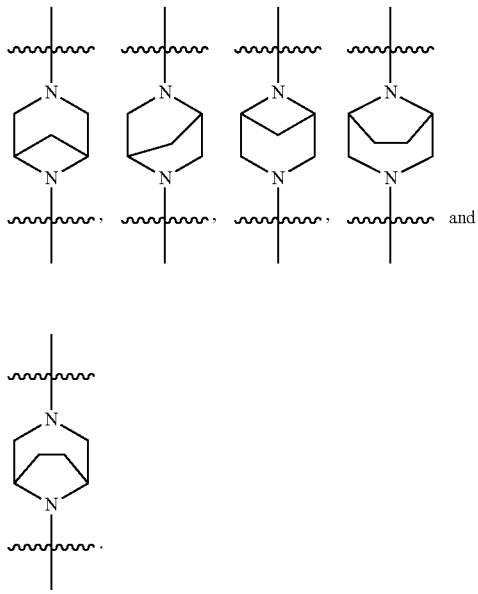

As a preferred embodiment, the present disclosure also provides a compound of formula I or a pharmaceutically acceptable salt, wherein G is selected from the following group:

As a preferred embodiment, the present disclosure also provides a compound of formula I or a pharmaceutically acceptable salt, wherein each $R^G$ is the same or different, and is independently selected from H, F, Cl, Br, OH, $NH_2$, $C_{1-3}$ alkyl, $C_{1-3}$ alkyl substituted with F or Cl, and $C_{1-3}$ alkoxy.

As a preferred embodiment, the present disclosure also provides a compound of formula I or a pharmaceutically acceptable salt, wherein each $R^G$ is the same or different, and is independently selected from H, $NH_2$, methyl, ethyl, propyl, F-substituted methyl, F-substituted ethyl, F-substituted propyl, methoxy, ethoxy and propoxy.

As a preferred embodiment, the present disclosure also provides a compound of formula I or a pharmaceutically acceptable salt, wherein each $R^G$ is the same or different, and is independently selected from H, $NH_2$, methyl, F-substituted methyl, and methoxy.

As a preferred embodiment, the present disclosure also provides a compound of formula I or a pharmaceutically acceptable salt, wherein K is selected from the following groups unsubstituted or optionally substituted with one, two or more $R^K$: K is selected from the following groups unsubstituted or optionally substituted with 1, 2 or 3 $R^K$: $C_{1-3}$ alkyl, $C_{5-6}$ cycloalkyl, phenyl, —$C_{1-3}$ alkylene phenyl ring, —$COC_{1-3}$ alkylene phenyl ring, —$COC_{1-3}$ alkylene biphenyl ring, —$C_{1-3}$ alkylene 5- to 8-membered aromatic heterocyclic ring, —$COC_{1-3}$ alkylene 5- to 8-membered aromatic heterocyclic ring, —$CONR^{K1}R^{K2}$, 5- to 6-membered heterocyclyl, $C_{1-3}$ alkoxy, $C_{3-6}$ cycloalkyloxy, $C_{6-10}$ aryloxy, 5- to 8-membered heteroaryloxy, and 5- to 8-membered heterocyclyloxy.

As a preferred embodiment, the present disclosure also provides a compound of formula I or a pharmaceutically acceptable salt, wherein K is selected from the following groups unsubstituted or optionally substituted with one, two or more $R^K$: K is selected from the following groups unsubstituted or optionally substituted with 1 or 2 $R^K$: $C_{1-3}$ alkyl, $C_{5-6}$ cycloalkyl, phenyl, —$C_{1-3}$ alkylene phenyl ring, —$COCH_2$ phenyl ring, —$COCH_2CH_2$ phenyl ring, —$COCH_2$ biphenyl ring, —$CH_2$-6-membered aromatic heterocyclic ring, —$CH_2CH_2$-6-membered aromatic heterocyclic ring, —$COCH_2$-6-membered aromatic heterocyclic ring, —$COCH_2CH_2$-6-membered aromatic heterocyclic ring, —$CONR^{K1}R^{K2}$, 5-membered heterocyclyl, 6-membered heterocyclyl, methoxy, $C_5$ cycloalkyloxy, phenyloxy, 6-membered heteroaryloxy, and 6-membered heterocyclyloxy.

As a preferred embodiment, the present disclosure also provides a compound of formula I or a pharmaceutically acceptable salt, wherein each aromatic heterocyclic ring, heterocyclic ring, heterocyclyl, aromatic ring, aryl and cycloalkyl in K are the same or different, and contain one N atom.

As a preferred embodiment, the present disclosure also provides a compound of formula I or a pharmaceutically acceptable salt, wherein each $R^K$ is independently selected from the following groups: —CN, OH, —NH$_2$, C$_{1-3}$ alkyl, C$_{1-3}$ alkoxy, C$_{3-6}$ cycloalkyl, F-substituted C$_{1-3}$ alkyl, Cl-substituted C$_{1-3}$ alkyl, F-substituted C$_{1-3}$ alkoxy and Cl-substituted C$_{1-3}$ alkoxy.

As a preferred embodiment, the present disclosure also provides a compound of formula I or a pharmaceutically acceptable salt, wherein each $R^K$ is independently selected from the following groups: —CN, OH, —NH$_2$, methyl, ethyl, methoxy and ethoxy.

As a preferred embodiment, the present disclosure also provides a compound of formula I or a pharmaceutically acceptable salt, wherein $R^{K1}$ and $R^{K2}$ are the same or different, and are independently selected from the following groups: —CN, C$_{1-3}$ alkyl, C$_{1-3}$ alkoxy, C$_{4-5}$ cycloalkyl, F-substituted C$_{1-3}$ alkyl, Cl-substituted C$_{1-3}$ alkyl, F-substituted C$_{1-3}$ alkoxy and Cl-substituted C$_{1-3}$ alkoxy.

As a preferred embodiment, the present disclosure also provides a compound of formula I or a pharmaceutically acceptable salt, wherein $R^{K1}$ and $R^{K2}$ are the same or different, and are independently selected from the following groups: —CN, OH, —NH$_2$, methyl, ethyl, methoxy and ethoxy.

As a preferred embodiment, the present disclosure also provides a compound of formula I or a pharmaceutically acceptable salt, wherein K is selected from the following groups:

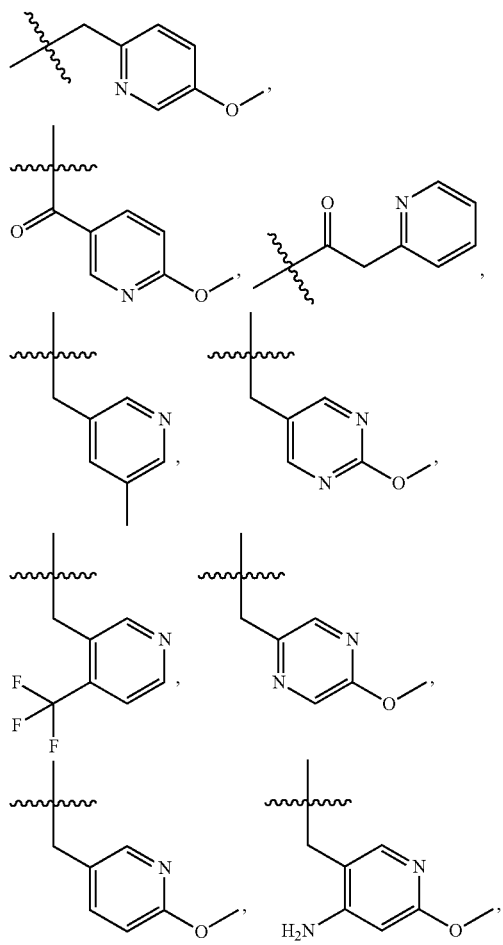

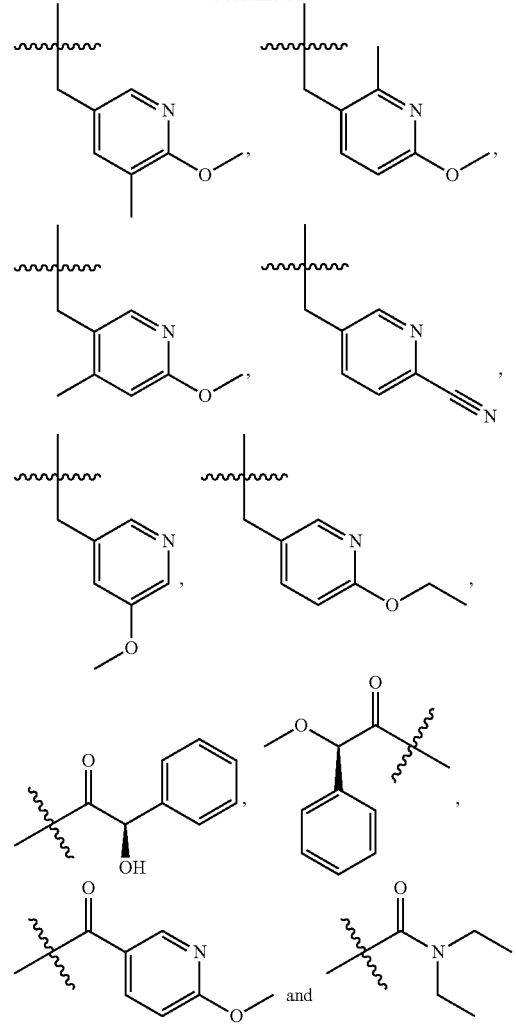

As a preferred embodiment, the present disclosure also provides a compound of formula I or a pharmaceutically acceptable salt, wherein the heterocyclyl, heterocyclic ring, aromatic heterocyclic ring, heteroaryl or aryl heterocyclyl contains 1, 2 or 3 heteroatoms selected from N and O.

As a preferred embodiment, the present disclosure also provides a compound of formula I or a pharmaceutically acceptable salt, wherein the heterocyclyl, heterocyclic ring, aromatic heterocyclic ring, heteroaryl or aryl heterocyclyl contains 1 or 2 heteroatoms selected from N and O.

As a preferred embodiment, the present disclosure also provides a compound of formula I or a pharmaceutically acceptable salt, wherein the heterocyclyl, heterocyclic ring, aromatic heterocyclic ring, heteroaryl or aryl heterocyclyl is a 4-, 5-, 6-, 7- or 8-membered ring containing 1 heteroatom selected from N and O.

As a preferred embodiment, the present disclosure also provides a compound of formula I or a pharmaceutically acceptable salt, wherein the heterocyclyl, heterocyclic ring, aromatic heterocyclic ring, heteroaryl or aryl heterocyclyl is a 4-, 5-, 6-, 7- or 8-membered heterocyclic ring containing 2 heteroatoms selected from N and O.

As a preferred embodiment, the present disclosure also provides a compound of formula I or a pharmaceutically acceptable salt, wherein the heterocyclyl, heterocyclic ring, aromatic heterocyclic ring, heteroaryl or aryl heterocyclyl is a 4-, 5-, 6-, 7- or 8-membered ring containing 2 heteroatoms selected from N.

As a preferred embodiment, the present disclosure also provides a compound of formula I or a pharmaceutically acceptable salt, wherein the heterocyclyl, heterocyclic ring, aromatic heterocyclic ring, heteroaryl or aryl heterocyclyl is a 5- or 6-membered ring containing 2 heteroatoms selected from N.

As a preferred embodiment, the present disclosure also provides a compound of formula I or a pharmaceutically acceptable salt, wherein the heterocyclyl, heterocyclic ring, aromatic heterocyclic ring, heteroaryl or aryl heterocyclyl is a 6-membered ring containing 2 heteroatoms selected from N.

As a preferred embodiment, the present disclosure also provides a compound of formula II or a pharmaceutically acceptable salt,

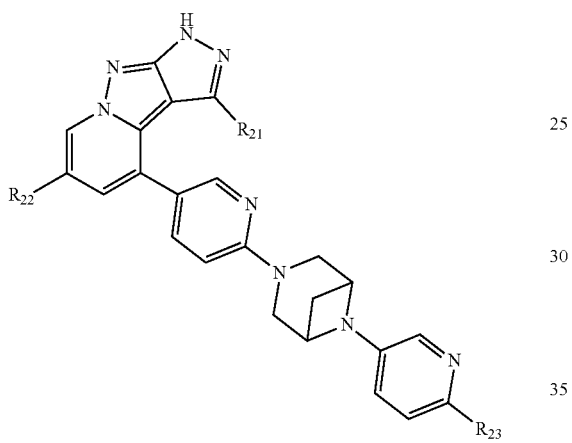

wherein $R_{22}$ is selected from H, halogen, CN, —$C_{1-6}$ alkyl, —$C_{1-6}$ alkoxy, —O(CH$_2$)$_m$—$C_{1-6}$ alkyl and —O(CH$_2$)$_m$—$C_{1-6}$ alkoxy, wherein each $C_{1-6}$ alkyl and $C_{1-6}$ alkoxy can be unsubstituted or substituted with halogen, $C_{1-6}$ alkyl or $C_{1-6}$ alkoxy, and m=0, 1 or 2;

$R_{21}$ is selected from H, NH$_2$ and —$C_{1-3}$ alkyl; and $R_{23}$ is selected from H, NH$_2$, —$C_{1-3}$ alkyl and —$C_{1-3}$ alkoxy.

As a preferred embodiment, the present disclosure also provides a compound of formula II or a pharmaceutically acceptable salt, wherein $R_{22}$ is selected from H, F, Cl, Br, CN, —$C_{1-3}$ alkyl, —$C_{1-3}$ alkoxy, —O(CH$_2$)$_m$—$C_{1-3}$ alkyl and —O(CH$_2$)$_m$—$C_{1-3}$ alkoxy, wherein each $C_{1-3}$ alkyl and $C_{1-3}$ alkoxy can be unsubstituted or substituted with F, Cl, Br, $C_{1-3}$ alkyl or $C_{1-3}$ alkoxy;

$R_{21}$ is selected from H, NH$_2$ and methyl; and $R_{23}$ is selected from H, NH$_2$, methyl and methoxy.

As a preferred embodiment, the present disclosure also provides a compound of formula II or a pharmaceutically acceptable salt, wherein $R_{22}$ is selected from H, F, Cl, Br, CN, —$C_{1-3}$ alkyl, —$C_{1-3}$ alkoxy, —O(CH$_2$)$_m$—$C_{1-3}$ alkyl and —O(CH$_2$)$_m$—$C_{1-3}$ alkoxy, wherein each $C_{1-3}$ alkyl and $C_{1-3}$ alkoxy can be unsubstituted or substituted with F, Cl, Br, $C_{1-3}$ alkyl or $C_{1-3}$ alkoxy;

$R_{21}$ is selected from H; and $R_{23}$ is selected from methoxy.

As a preferred embodiment, the present disclosure also provides a compound of formula II or a pharmaceutically acceptable salt, wherein $R_{22}$ is selected from H, F, Cl, CN, methyl, ethyl, methoxy, ethoxy, —O(CH$_2$)$_m$ methyl, —O(CH$_2$)$_m$ ethyl, —O(CH$_2$)$_m$ methoxy and —O(CH$_2$)$_m$ ethoxy, wherein each methyl, ethyl, methoxy and ethoxy can be unsubstituted or substituted with F, Cl, Br, methyl, ethyl, methoxy or ethoxy.

As a preferred embodiment, the present disclosure also provides a compound of formula II or a pharmaceutically acceptable salt, wherein m=1 or 2.

The present disclosure also provides the following compounds or pharmaceutically acceptable salts thereof:

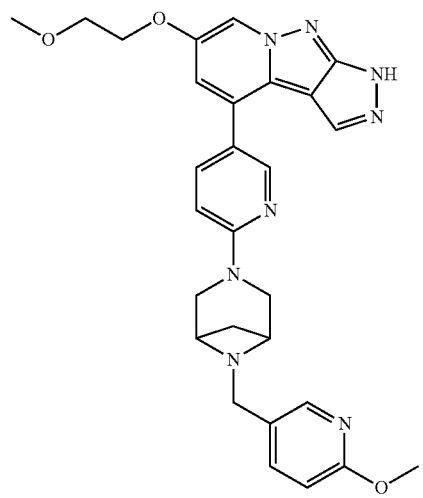

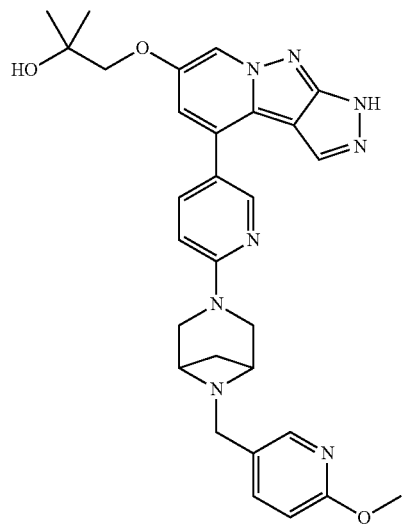

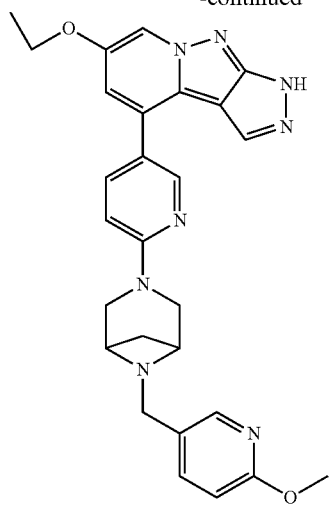
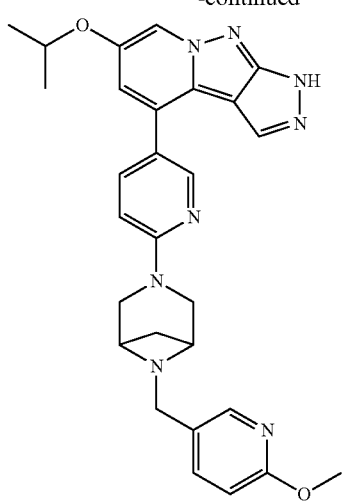
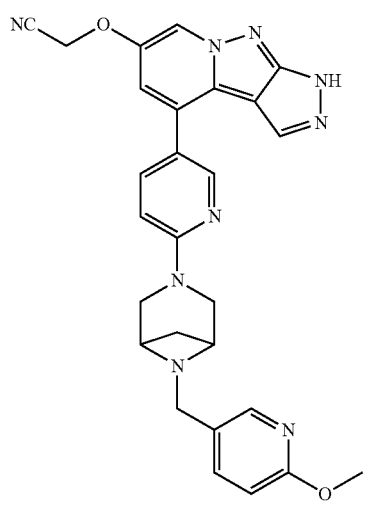
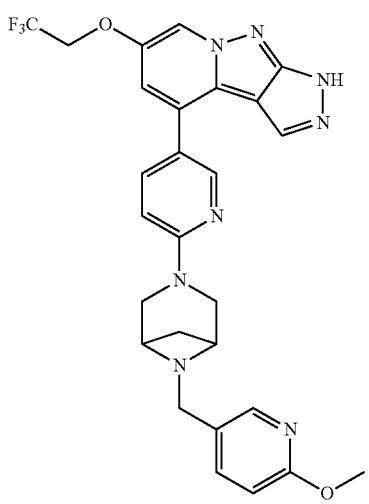
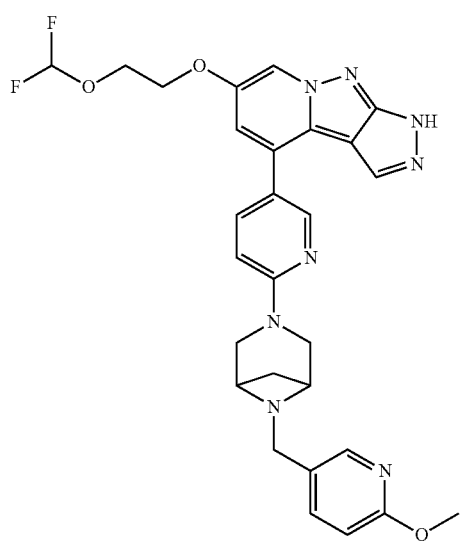
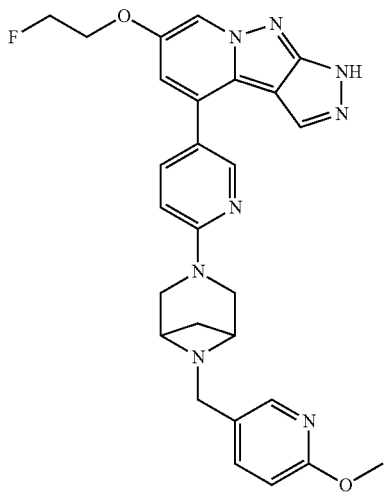

-continued
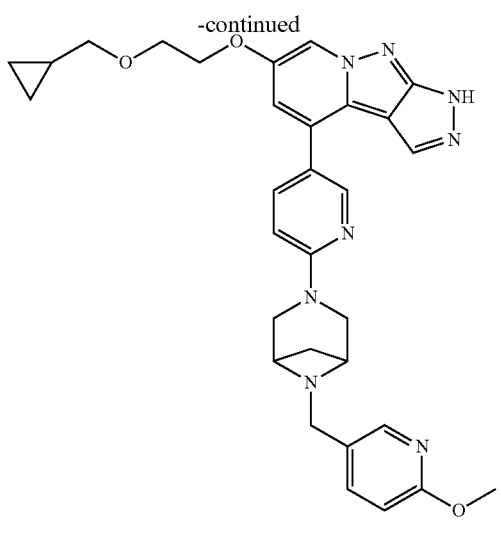
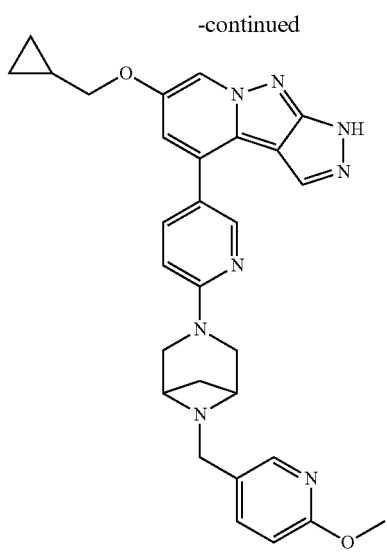
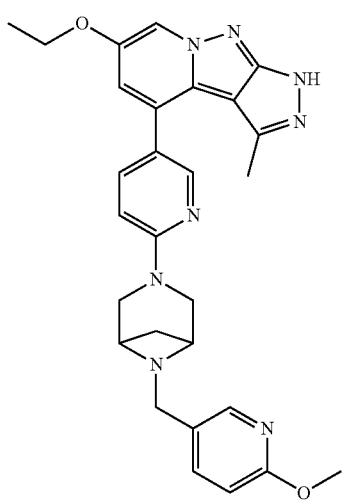
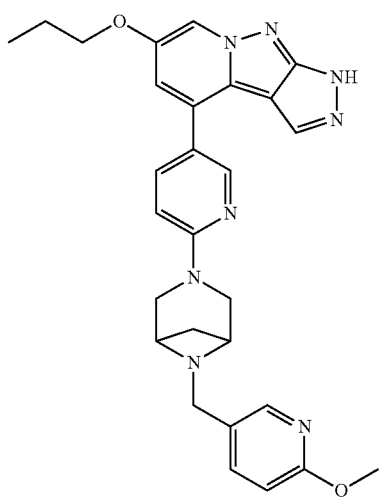
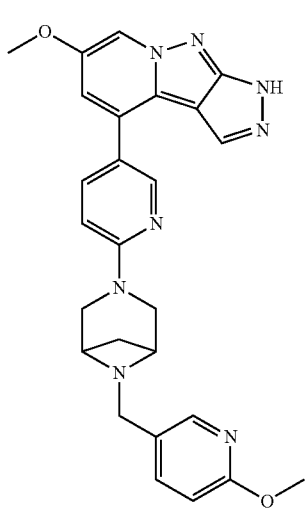
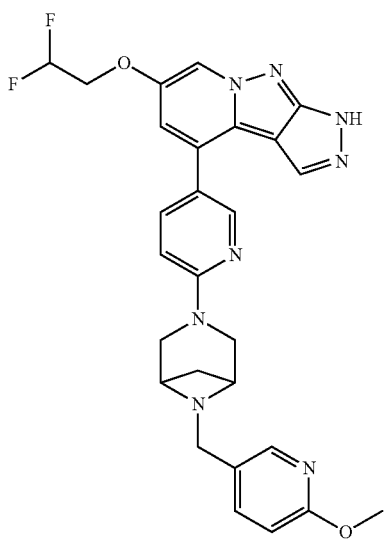

21
-continued
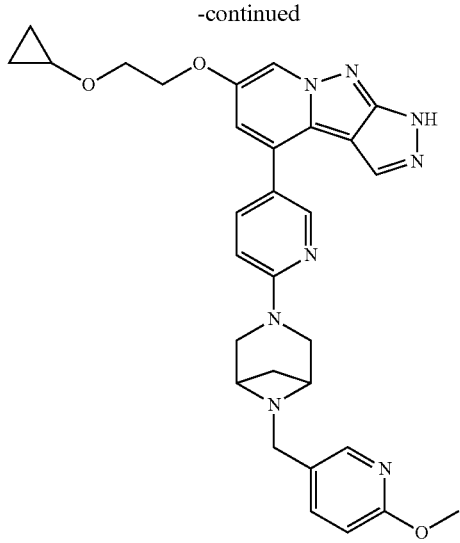
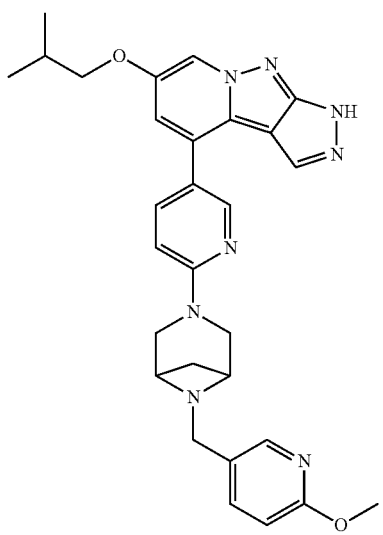
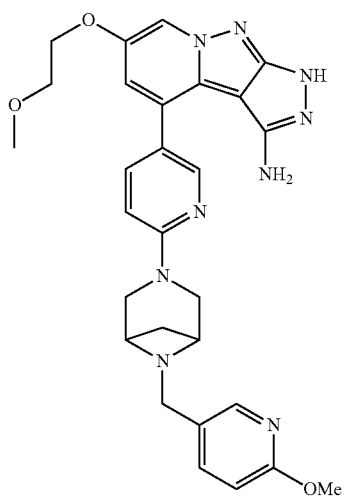
22
-continued
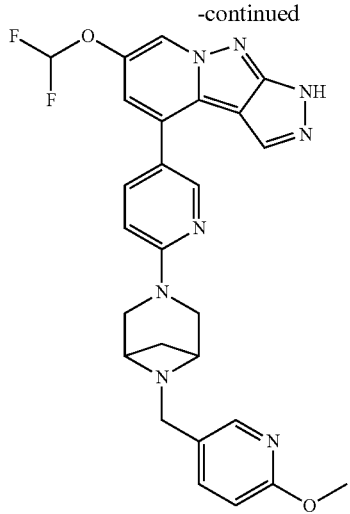
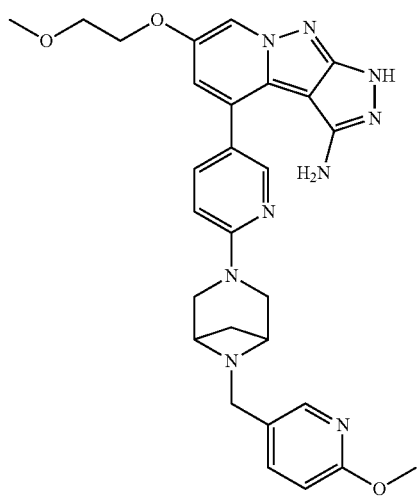
The present disclosure also provides the following compounds or pharmaceutically acceptable salts thereof:

23
-continued
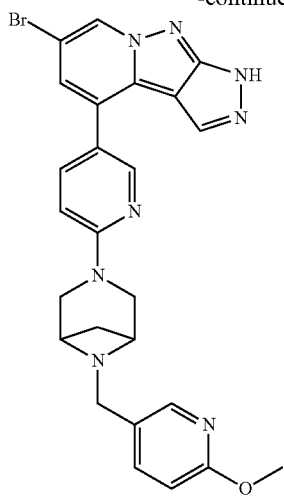
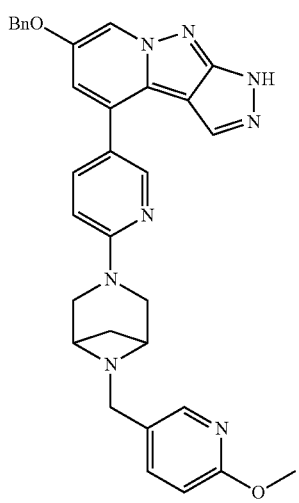
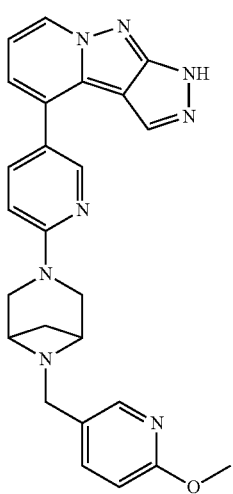
24
-continued
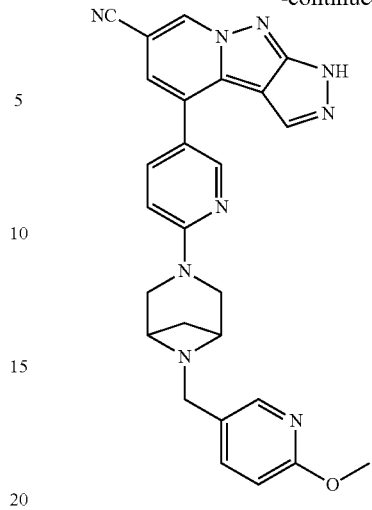
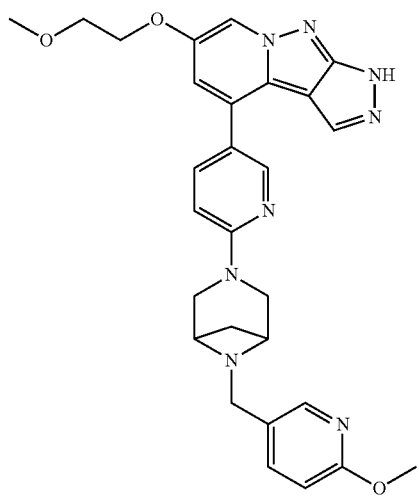

25
-continued
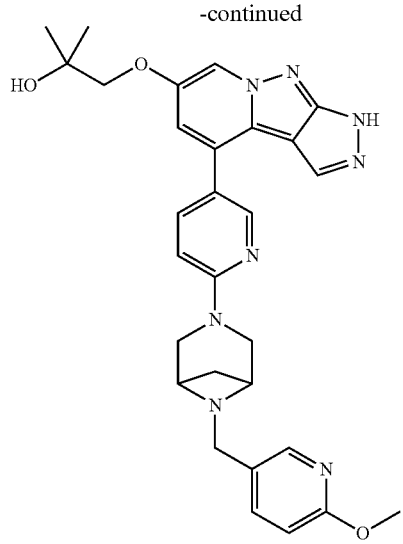
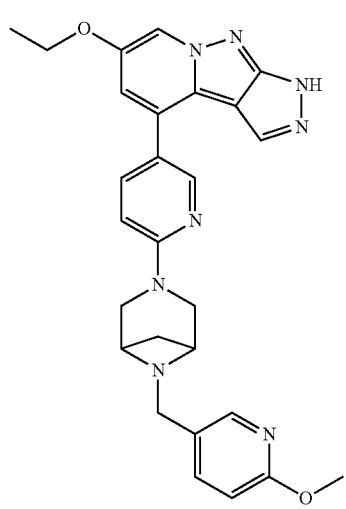
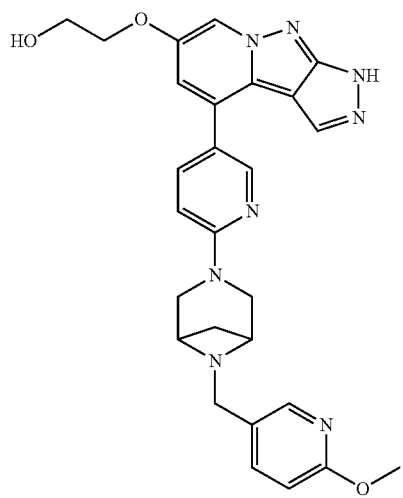
26
-continued
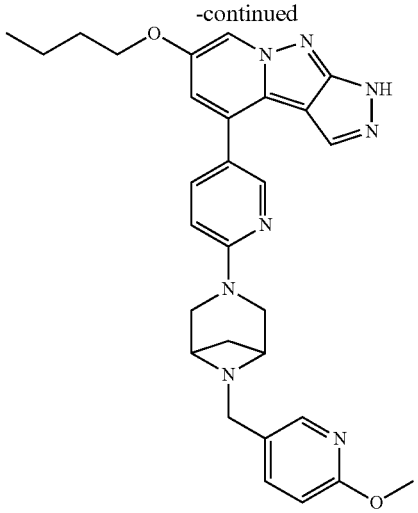
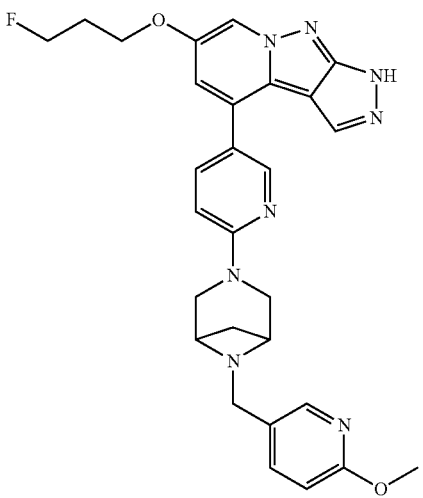
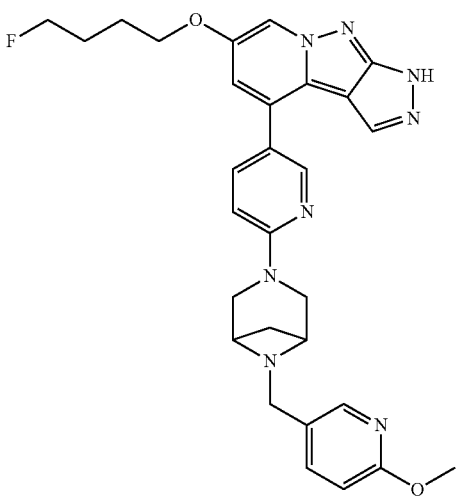

27
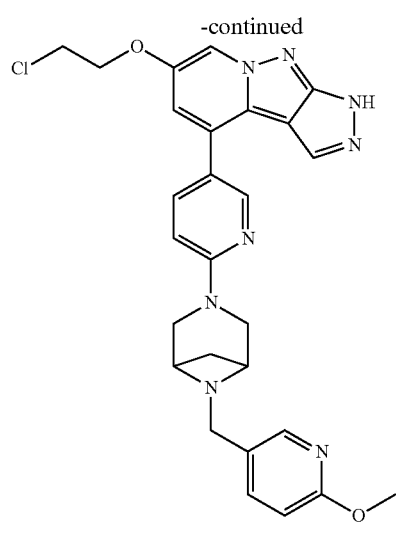
28
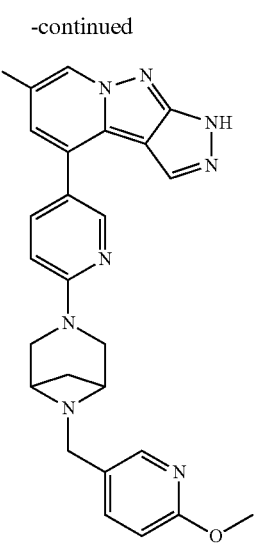
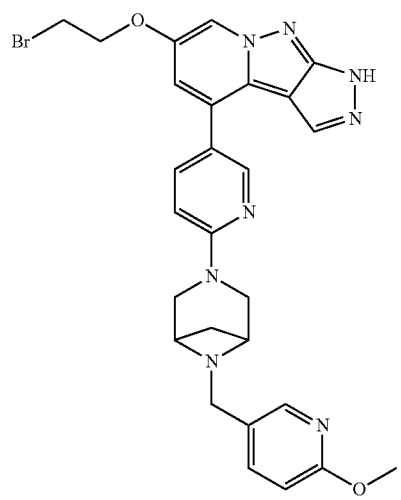
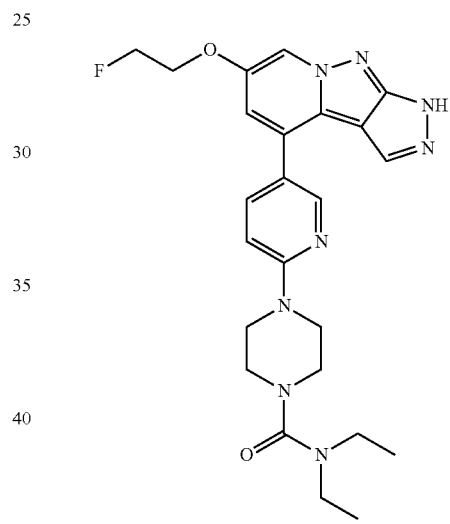
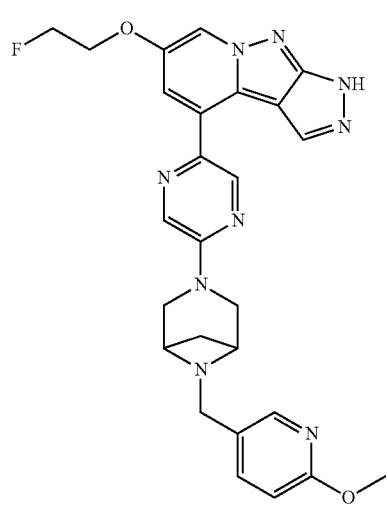
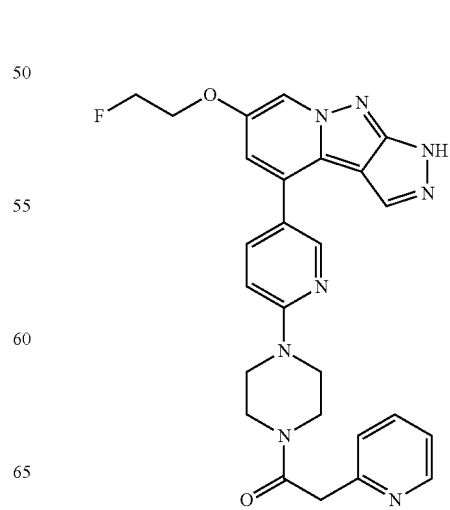

29
-continued
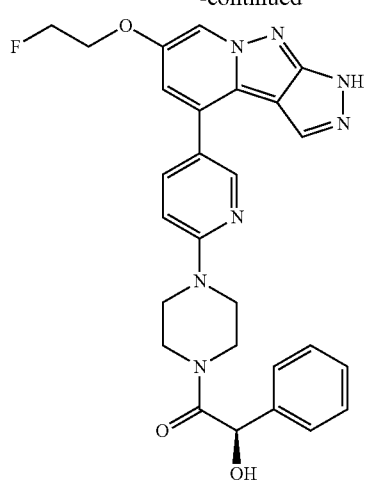
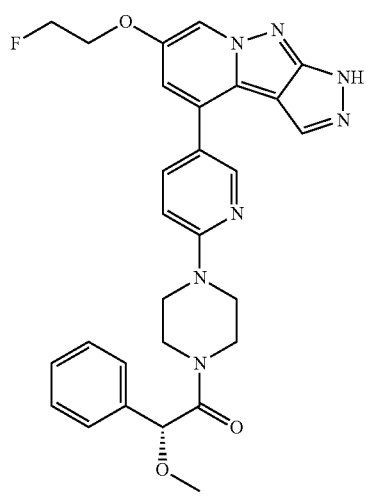
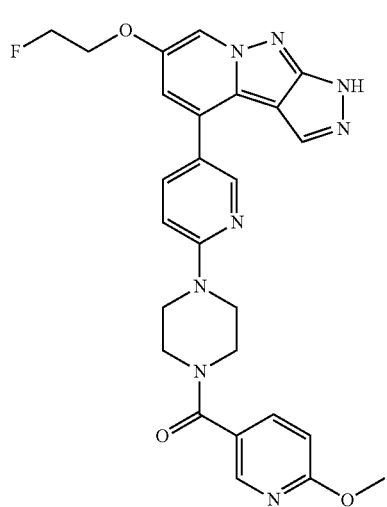
30
-continued
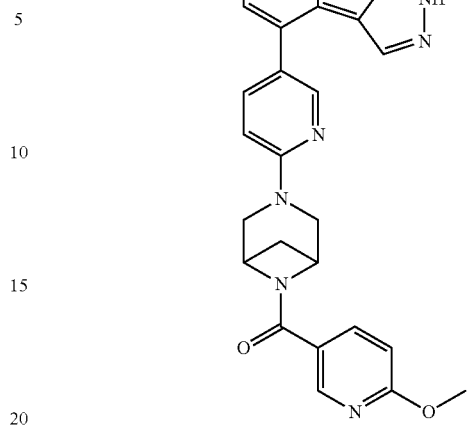
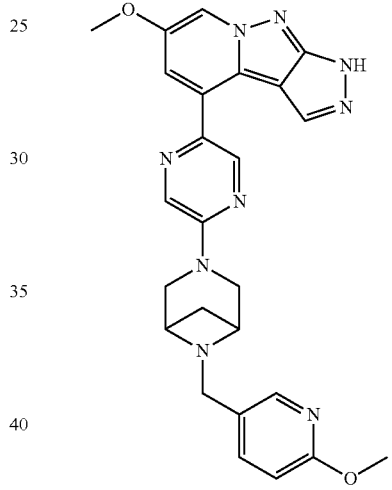
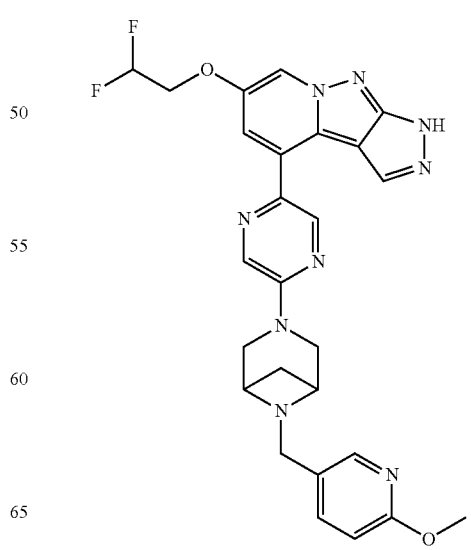

| 31 | 32 |
|---|---|
| -continued | -continued |
| 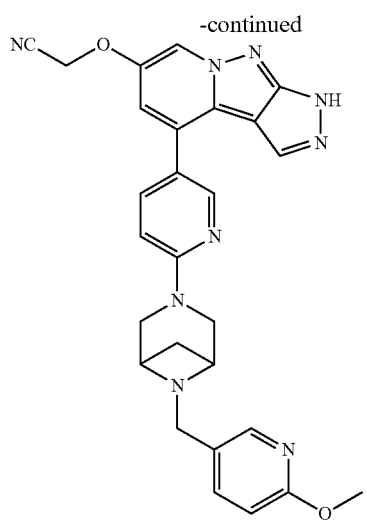 | 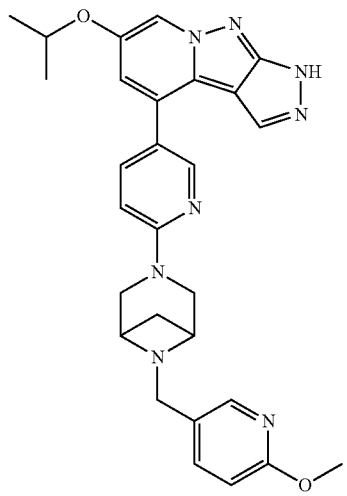 |
| 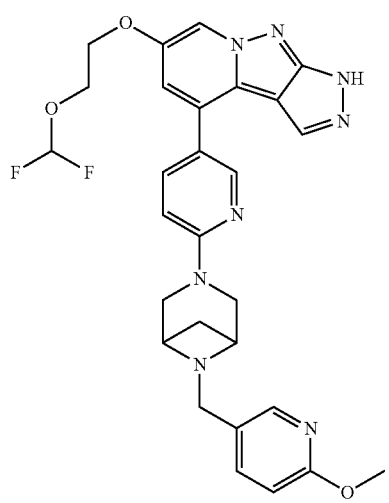 | 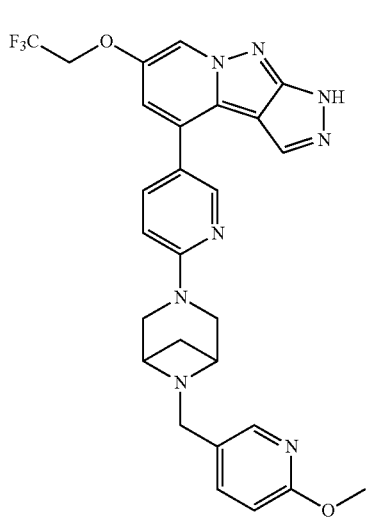 |
| 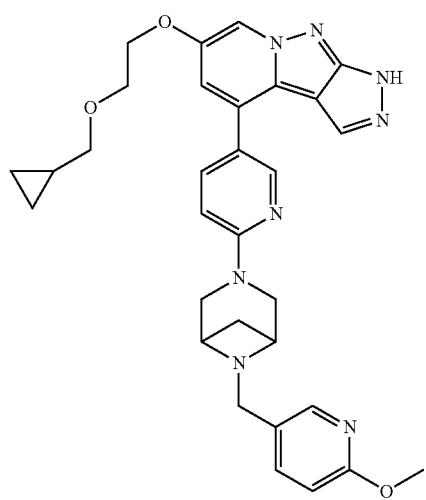 | 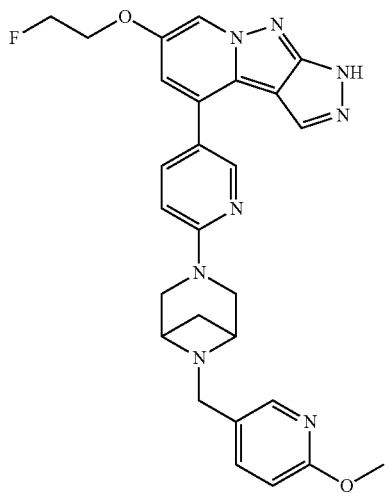 |

33
-continued
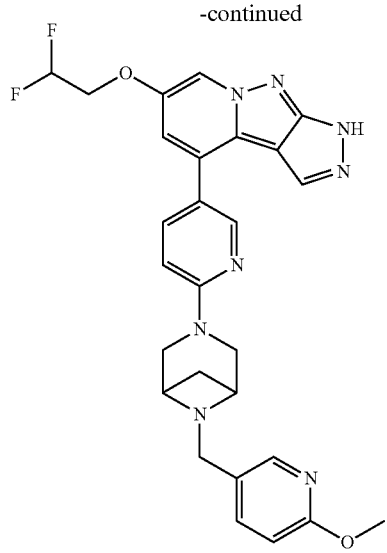
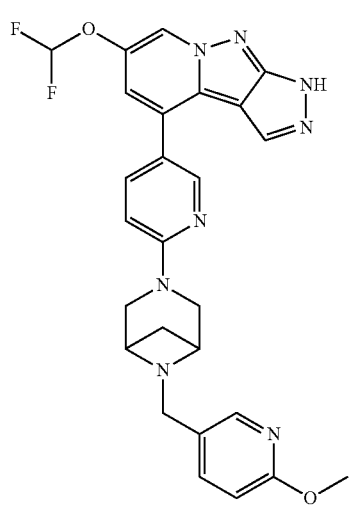
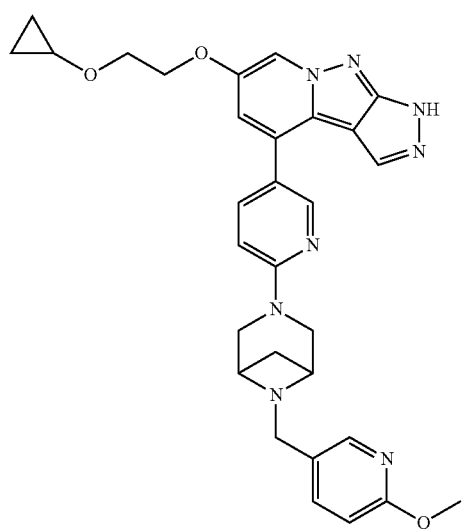
34
-continued
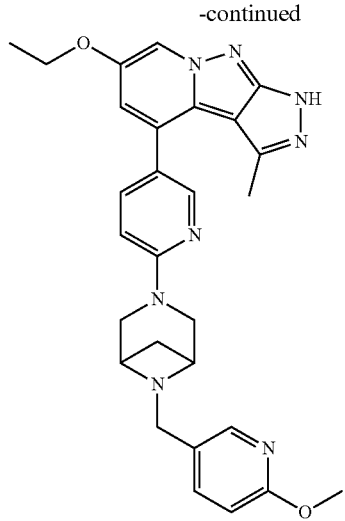
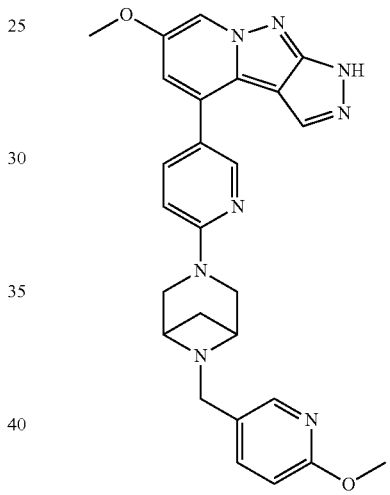
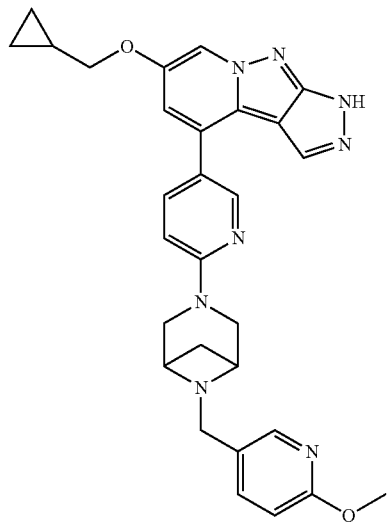

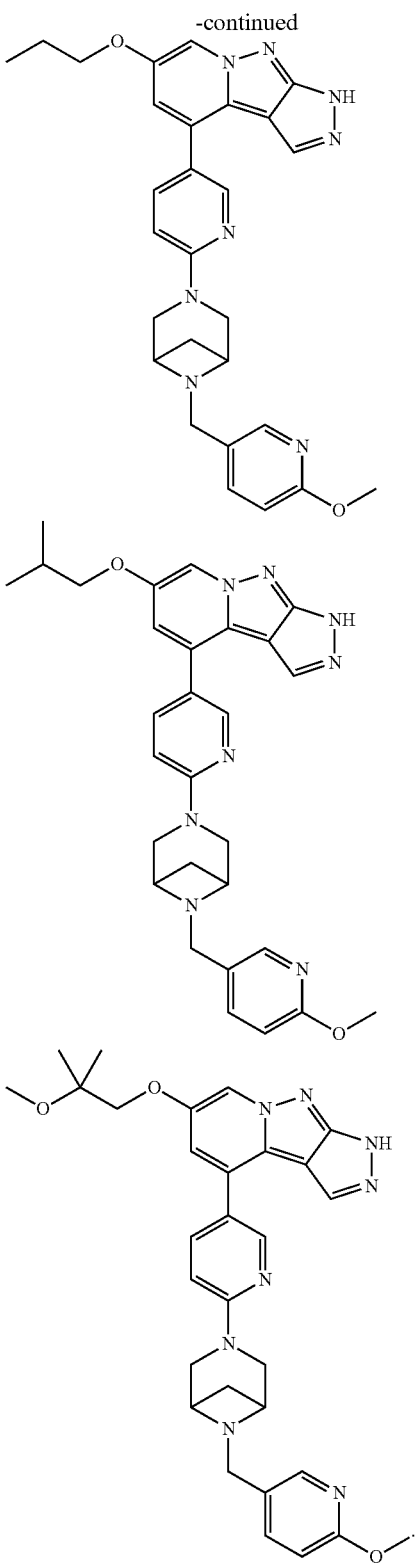

The present disclosure also provides a pharmaceutical composition, which comprises a therapeutically effective amount of the above compound or the pharmaceutically acceptable salt thereof, and at least one pharmaceutically acceptable excipient.

As a preferred embodiment, the present disclosure also provides use of the compound or the pharmaceutically acceptable salt thereof described above and the pharmaceutical composition described above in the preparation of a medicament.

As a preferred embodiment, the present disclosure also provides a preferred embodiment for the use, wherein the medicament is used for treating, arresting or preventing a disease or discomfort caused by the dysregulation of the mutation, expression, activity or level of a RET gene, a RET kinase protein or any one or more thereof.

As a preferred embodiment, the present disclosure also provides a preferred embodiment for the use, wherein one or more point mutations in the RET gene result in the translation of a RET protein with one or more amino acid substitutions at one or more of the following amino acid positions: 2, 3, 4, 5, 6, 7, 8, 11, 12, 13, 20, 32, 34, 40, 56, 64, 67, 114, 136, 145, 180, 200, 292, 294, 321, 330, 338, 360, 373, 393, 423, 432, 446, 505, 506, 510, 511, 513, 515, 525, 531, 532, 533, 550, 591, 593, 595, 600, 602, 603, 606, 609, 611, 616, 618, 619, 620, 623, 624, 630, 631, 632, 633, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 802, 804, 805, 806, 810, 818, 819, 823, 836, 841, 843, 844, 848, 852, 865, 870, 873, 876, 881, 882, 883, 884, 886, 891, 897, 898, 900, 901, 904, 905, 907, 908, 911, 912, 918, 919, 921, 922, 930, 961, 972, 981, 982, 1009, 1015, 1017, 1041, 1062, 1064 and 1096.

As a preferred embodiment, the present disclosure also provides a preferred embodiment for the use, wherein one or more point mutations in the RET gene result in the translation of a RET protein with one or more amino acid substitutions at one or more of the following amino acid positions: 32, 34, 40, 56, 64, 67, 114, 145, 292, 321, 330, 338, 360, 393, 423, 446, 510, 511, 513, 515, 525, 531, 532, 533, 550, 591, 593, 595, 600, 602, 603, 606, 609, 611, 616, 618, 619, 620, 623, 624, 630, 631, 632, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 804, 805, 806, 810, 818, 819, 823, 826, 833, 836, 841, 843, 844, 848, 852, 865, 870, 873, 876, 881, 883, 884, 886, 891, 897, 898, 900, 901, 904, 905, 907, 908, 911, 912, 918, 919, 921, 922, 930, 961, 972, 981, 982, 1009, 1015, 1017, 1041, 1064 and 1096.

As a preferred embodiment, the present disclosure also provides a preferred embodiment for the use, wherein one or more point mutations in the RET gene result in the translation of a RET protein containing one or more of the following amino acid substitutions: S32L, D34S, L40P, L56M, P64L, R67H, R114H, V145G, V292M, G321R, R330Q, T338I, R360W, F393L, G423R, G446R, A510V, E511K, G513D, C515S, C515W, R525W, C531R, G533C, G533S, G550E, V591I, G593E, E595D, E595A, R600Q, I602V, K603Q, K603E, Y606C, C609C, C609Y, C609S, C609G, C609R, C609F, C609W, C611R, C611S, C611G, C611Y, C611F, C611W, E616Q, C618S, C618Y, C618R, C618G, C618F, C618W, F619F, C620S, C620W, C620R, C620G, C620L, C620Y, C620F, E623K, D624N, C630A, C630R, C630S, C630Y, C630F, C630W, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, K666R, T675T, S686N, S689T, G691S, R694Q, M700L, V706M, V706A, E713K, E732K, G736R, G748C, A750P, S765P, P766S, P766M, E768Q, E768D, L769L, R770Q, D771N, N777S, V778I, Q781R, I788I, L790F, Y791F, Y791N, V804L, V804M, V804E, E805K, Y806E, Y806F, Y806S, Y806G, Y806C, Y806H, Y806N, Y806Y, G810R, G810S, G810A, E818K, S819I, G823E, Y826M, Y826S, R833C, S836S, P841L, P841P, E843D, R844W, R844Q, R844L, M848T, I852M, L865V, L870F, R873W, A876V, L881V, A883F, A883S, A883T, E884K, R886W, S891A, S891S, R897Q, D898V, Y900F, E901K, S904F, S904S, S904C, Y905F, K907E, K907M, R908K, G911D, R912P, R912Q, M918T, M918V, M918L, A919V, E921K, S922P, S922Y, T930M, F961L, R972G, Y981F, R982C, M1009V, Y1015F, D1017N, V1041G, M1064T and Y1096F.

As a preferred embodiment, the present disclosure also provides a preferred embodiment for the use, wherein one or more point mutations in the RET gene occur in one or more selected from exons 10, 11, 13, 14, 15 and 16 of a human RET gene.

As a preferred embodiment, the present disclosure also provides a preferred embodiment for the use, wherein the RET gene fusion is selected from: BCR-RET, CLIP1-RET, KIF5B-RET, CCDC6-RET, NCOA4-RET, TRIM33-RET, ERC1-RET, FGFR1OP-RET, RET-MBD1, RET-RAB61P2, RET-PRKAR1A, RET-TRIM24, RET-GOLGA5, HOOGA5, KIAA1217-RET, MPRIP-RET, HRH4-RET, RIA-RET, RET-PTC4, FRMD4A-RET, SQSTM1-RET, AFAP1L2-RET, PPFIBP2-RET, EML4-RET, PARD3-RET, MYH10-RET, HTIF1/RET, AFAP1-RET, RASGEF1A-RET and TEL-RET.

As a preferred embodiment, the present disclosure also provides a preferred embodiment for the use, wherein the dysregulation of the mutation, expression, activity or level of a RET gene, a RET kinase protein or any one or more thereof is RET gene fusion.

As a preferred embodiment, the present disclosure also provides a preferred embodiment for the use, wherein the disease or discomfort caused by the dysregulation of the expression, activity or level of a RET gene, a RET kinase protein or any one thereof is cancer or cancerometastasis.

As a preferred embodiment, the present disclosure also provides a preferred embodiment for the use, wherein the disease or discomfort caused by the dysregulation of the expression, activity or level of a RET gene, a RET kinase protein or any one thereof is selected from one or more of the following conditions: lung cancer, papillary thyroid cancer, medullary thyroid cancer, differentiated thyroid cancer, recurrent thyroid cancer, poorly differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, gastrointestinal gangliocytoma (MEN2A or MEN2B, respectively), pheochromocytoma, parathyroid hyperplasia, breast cancer, colorectal cancer, papillary renal cell carcinoma, gastrointestinal gangliocytoma and a combination thereof.

The present disclosure also provides a method for treating, arresting or preventing a disease or condition mediated by RET activity, which comprises: (1) determining whether the disease or discomfort is related to the dysregulation of the expression, activity or level of a RET gene, a RET kinase protein or any one or more thereof; and (2) if it is determined that the disease or discomfort is related to the dysregulation of the expression, activity or level of the RET gene, the RET kinase protein or any one or more thereof, administering to a patient an effective dose of the compound or the pharmaceutically acceptable salt thereof provided herein or the pharmaceutical composition provided herein.

As a preferred embodiment, the present disclosure also provides a preferred embodiment for the treatment method, wherein the disease or condition mediated by RET activity is cancer and/or cancerometastasis.

As a preferred embodiment, the present disclosure also provides a preferred embodiment for the treatment method, wherein one or more point mutations in the RET gene result in the translation of a RET protein with one or more amino acid substitutions at one or more of the following amino acid positions: 2, 3, 4, 5, 6, 7, 8, 11, 12, 13, 20, 32, 34, 40, 56, 64, 67, 114, 136, 145, 180, 200, 292, 294, 321, 330, 338, 360, 373, 393, 423, 432, 446, 505, 506, 510, 511, 513, 515, 525, 531, 532, 533, 550, 591, 593, 595, 600, 602, 603, 606, 609, 611, 616, 618, 619, 620, 623, 624, 630, 631, 632, 633, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 802, 804, 805, 806, 810, 818, 819, 823, 836, 841, 843, 844, 848, 852, 865, 870, 873, 876, 881, 882, 883, 884, 886, 891, 897, 898, 900, 901, 904, 905, 907, 908, 911, 912, 918, 919, 921, 922, 930, 961, 972, 981, 982, 1009, 1015, 1017, 1041, 1062, 1064 and 1096.

As a preferred embodiment, the present disclosure also provides a preferred embodiment for the treatment method, wherein one or more point mutations in the RET gene result in the translation of a RET protein with one or more amino acid substitutions at one or more of the following amino acid positions: 32, 34, 40, 56, 64, 67, 114, 145, 292, 321, 330, 338, 360, 393, 423, 446, 510, 511, 513, 515, 525, 531, 532, 533, 550, 591, 593, 595, 600, 602, 603, 606, 609, 611, 616, 618, 619, 620, 623, 624, 630, 631, 632, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 804, 805, 806, 810, 818, 819, 823, 826, 833, 836, 841, 843, 844, 848, 852, 865, 870, 873, 876, 881, 883, 884, 886, 891, 897, 898, 900, 901, 904, 905, 907, 908, 911, 912, 918, 919, 921, 922, 930, 961, 972, 981, 982, 1009, 1015, 1017, 1041, 1064 and 1096.

As a preferred embodiment, the present disclosure also provides a preferred embodiment for the treatment method, wherein one or more point mutations in the RET gene result in the translation of a RET protein containing one or more of the following amino acid substitutions: S32L, D34S, L40P, L56M, P64L, R67H, R114H, V145G, V292M, G321R, R330Q, T338I, R360W, F393L, G423R, G446R, A510V, E511K, G513D, C515S, C515W, R525W, C531R, G533C, G533S, G550E, V591I, G593E, E595D, E595A, R600Q, I602V, K603Q, K603E, Y606C, C609C, C609Y, C609S, C609G, C609R, C609F, C609W, C611R, C611S, C611G, C611Y, C611F, C611W, E616Q, C618S, C618Y, C618R, C618G, C618F, C618W, F619F, C620S, C620W, C620R, C620G, C620L, C620Y, C620F, E623K, D624N, C630A, C630R, C630S, C630Y, C630F, C630W, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, K666R, T675T, S686N, S689T, G691S, R694Q, M700L, V706M, V706A, E713K, E732K, G736R, G748C, A750P, S765P, P766S, P766M, E768Q, E768D, L769L, R770Q, D771N, N777S, V778I, Q781R, I788I, L790F, Y791F, Y791N, V804L, V804M, V804E, E805K, Y806E, Y806F, Y806S, Y806G, Y806C, Y806H, Y806N, Y806Y, G810R, G810S, G810A, E818K, S819I, G823E, Y826M, Y826S, R833C, S836S, P841L, P841P, E843D, R844W, R844Q, R844L, M848T, I852M, L865V, L870F, R873W, A876V, L881V, A883F, A883S, A883T, E884K, R886W, S891A, S891S, R897Q, D898V, Y900F, E901K, S904F, S904S, S904C, Y905F, K907E, K907M, R908K, G911D, R912P, R912Q, M918T, M918V, M918L, A919V, E921K, S922P, S922Y, T930M, F961L, R972G, Y981F, R982C, M1009V, Y1015F, D1017N, V1041G, M1064T and Y1096F.

As a preferred embodiment, the present disclosure also provides a preferred embodiment for the treatment method, wherein one or more point mutations in the RET gene occur in one or more exons 10, 11, 13, 14, 15 and 16 of a human RET gene.

As a preferred embodiment, the present disclosure also provides a preferred embodiment for the treatment method, wherein the RET gene fusion is selected from: BCR-RET, CLIP1-RET, KIF5B-RET, CCDC6-RET, NCOA4-RET, TRIM33-RET, ERC1-RET, FGFR1OP-RET, RET-MBD1, RET-RAB61P2, RET-PRKAR1A, RET-TRIM24, RET-GOLGA5, HOOGA5, KIAA1217-RET, MPRIP-RET, HRH4-RET, RIA-RET, RET-PTC4, FRMD4A-RET, SQSTM1-RET, AFAP1L2-RET, PPFIBP2-RET, EML4-RET, PARD3-RET, MYH10-RET, HTIF1/RET, AFAP1-RET, RASGEF1A-RET and TEL-RET.

As a preferred embodiment, the present disclosure also provides a preferred embodiment for the treatment method, wherein the dysregulation of the mutation, expression, activity or level of a RET gene, a RET kinase protein or any one or more thereof is RET gene fusion.

As a preferred embodiment, the present disclosure also provides a preferred embodiment for the treatment method, wherein the disease mediated by RET activity is selected from one or more of the following diseases: lung cancer, papillary thyroid cancer, medullary thyroid cancer, differentiated thyroid cancer, recurrent thyroid cancer, poorly differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, gastrointestinal gangliocytoma (MEN2A or MEN2B, respectively), pheochromocytoma, parathyroid hyperplasia, breast cancer, colorectal cancer, papillary renal cell carcinoma, gastrointestinal gangliocytoma and a combination thereof.

The present disclosure also provides a compound of the following formula I, or a stereoisomer, a racemate, a tautomer, an isotopically labeled compound, a nitrogen oxide or a pharmaceutically acceptable salt thereof:

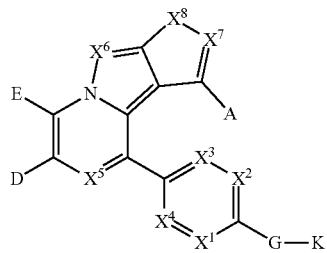

I wherein $X^1$, $X^2$, $X^3$, $X^4$, $X^5$, $X^6$ and $X^7$ are the same or different, and are independently selected from $CR^1$ and N;

$X^8$ is selected from $CR^1R^{1'}$ and $NR^1$;

wherein each $R^1$ and $R^{1'}$ are the same or different, and are independently selected from H, halogen, CN, OH, and the following groups unsubstituted or optionally substituted with one, two or more $R^a$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $NR^2R^3$, —$C(O)R^4$, —$OCR^5$, —$S(O)_2R^6$ and $OS(O)_2R^7$;

A is selected from H, halogen, CN, OH, $NH_2$, and the following groups unsubstituted or optionally substituted with one, two or more $R^b$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $NR^2R^3$, —$C(O)R^4$, —$OCR^5$, —$S(O)_2R^6$ and $OS(O)_2R^7$;

D and E are the same or different, and are independently selected from H, halogen, CN, OH, —O—$R^{21}$, and the following groups unsubstituted or optionally substituted with one, two or more $R^c$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, and $NH_2$, provided that at least one of D and E is selected from —O—$R^{21}$;

$R^{21}$ is selected from H, and the following groups unsubstituted or optionally substituted with one, two or more $R^d$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, and 3- to 20-membered heterocyclyl;

G is selected from the following groups unsubstituted or optionally substituted with one, two or more $R^e$: $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, and 3- to 20-membered heterocyclyloxy;

K is selected from the following groups unsubstituted or optionally substituted with one, two or more $R^f$: H, halogen, CN, OH, and the following groups unsubstituted or optionally substituted with one or more $R^g$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, $NR^2R^3$, —$C(O)R^4$, —$OCR^5$, —$S(O)_2R^6$ and $OS(O)_2R^7$;

each $R^2$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, —$C(O)R^4$ and —$S(O)_2R^6$;

each $R^3$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, —$C(O)R^4$ and —$S(O)_2R^6$; or, $R^2$ and $R^3$, together with a N atom connected thereto, form 5- to 20-membered heteroaryl or 3- to 20-membered heterocyclyl;

each $R^4$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, and $NR^2R^3$;

each $R^5$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkylcarbonyl, $C_{2-40}$ alkenylcarbonyl, $C_{2-40}$ alkynylcarbonyl, $C_{3-40}$ cycloalkylcarbonyl, $C_{3-40}$ cycloalkenylcarbonyl, $C_{3-40}$ cycloalkynylcarbonyl, $C_{6-20}$ arylcarbonyl, 5- to 20-membered heteroarylcarbonyl, and 3- to 20-membered heterocyclylcarbonyl;

each $R^6$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, and $NR^2R^3$;

each $R^7$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, and 3- to 20-membered heterocyclyl;

each $R^a$, $R^b$, $R^c$, $R^d$, $R^e$ and $R^f$ are the same or different, and are independently selected from halogen, CN, OH, SH, oxo (=O), $NO_2$, and the following groups unsubstituted or optionally substituted with one, two or more $R^g$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, $NR^2R^3$, —C(O)$R^4$, —OC$R^5$, —S(O)$_2R^6$ and OS(O)$_2R^7$;

each $R^g$ is the same or different, and is independently selected from halogen, CN, OH, SH, oxo (=O), $NO_2$, and the following groups unsubstituted or optionally substituted with one, two or more $R^h$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, $NR^2R^3$, —C(O)$R^4$, —OC$R^5$, —S(O)$_2R^6$ and OS(O)$_2R^7$; or, where a cyclic group (including but not limited to, $C_{3-40}$ cycloalkyl, $C_{3-40}$ cycloalkenyl, $C_{3-40}$ cycloalkynyl, 3- to 20-membered heterocyclyl, and the like) is substituted with two or more substituents at different positions, two of the substituents can also form a bridged ring with the cyclic group, wherein the bridge atoms other than the bridgehead atoms in the bridged ring can comprise 1, 2, 3, 4 or 5 divalent groups selected from $CH_2$, O and NH; and each $R^h$ is the same or different, and is independently selected from halogen, CN, OH, SH, oxo (=O), $NO_2$, and the following groups unsubstituted or optionally substituted with one or more $R^g$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, $NR^2R^3$, —C(O)$R^4$, —OC$R^5$, —S(O)$_2R^6$ and OS(O)$_2R^7$; or, where a cyclic group (including but not limited to, $C_{3-40}$ cycloalkyl, $C_{3-40}$ cycloalkenyl, $C_{3-40}$ cycloalkynyl, 3- to 20-membered heterocyclyl, and the like) is substituted with two or more substituents at different positions, two of the substituents can also form a bridged ring with the cyclic group, wherein the bridge atoms other than the bridgehead atoms in the bridged ring can comprise 1, 2, 3, 4 or 5 divalent groups selected from $CH_2$, O and NH; or, where one atom (such as carbon atom) is substituted with two or more substituents, two of the substituents can also, together with an atom connected thereto, form a cyclic group (including but not limited to, $C_{3-40}$ cycloalkyl, $C_{3-40}$ cycloalkenyl, $C_{3-40}$ cycloalkynyl, 3- to 20-membered heterocyclyl, and the like).

According to an embodiment of the present disclosure, $X^1$, $X^2$, $X^3$, $X^4$, $X^5$, $X^6$ and $X^7$ are the same or different, and are independently selected from $CR^1$ and N; for example, at least one, e.g. 1, 2, 3, 4, 5, 6 or 7, of $X^1$, $X^2$, $X^3$, $X^4$, $X^5$, $X^6$ and $X^7$ is N.

According to an embodiment of the present disclosure, $X^8$ is selected from $CR^1R^{1'}$ and $NR^1$.

According to an embodiment of the present disclosure, each $R^1$ and $R^{1'}$ are the same or different, and are independently selected from H, halogen, CN, OH, $C_{1-6}$ alkyl, $C_{3-10}$ cycloalkyl and $C_{1-6}$ alkoxy.

According to an embodiment of the present disclosure, A is selected from H, halogen, CN, OH, $C_{1-6}$ alkyl and $C_{1-6}$ alkyloxy.

According to an embodiment of the present disclosure, D and E are the same or different, and are independently selected from H, halogen, CN, $NH_2$ and —O—$R^{21}$, provided that at least one of D and E is selected from —O—$R^{21}$.

According to an embodiment of the present disclosure, $R^2$ is selected from $C_{1-6}$ alkyl unsubstituted or optionally substituted with one, two or more $R^d$.

According to an embodiment of the present disclosure, each $R^a$, $R^b$, $R^c$, $R^d$, $R^e$ and $R^f$ are the same or different, and are independently selected from halogen, CN, OH, and the following groups unsubstituted or optionally with one, two or more $R^g$: $C_{1-6}$ alkyl, $C_{1-6}$ alkyloxy, $C_{3-10}$ cycloalkyl and $C_{3-10}$ cycloalkyloxy.

According to an embodiment of the present disclosure, each $R^g$ is the same or different, and is independently selected from halogen and $C_{3-10}$ cycloalkyl.

According to the embodiment of the present disclosure, G is selected from $C_{3-10}$ cycloalkyl, $C_{6-14}$ aryl, 5- to 14-membered heteroaryl, and 3- to 10-membered heterocyclyl, for example, 6- to 7-membered heterocyclyl having a monocyclic, bicyclic or bridged ring structure containing 1, 2 or 3 heteroatoms independently selected from N, O and S.

According to an embodiment of the present disclosure, K is selected from —$C_{1-6}$ alkyl-$C_{3-10}$ cycloalkyl, —$C_{1-6}$ alkyl-$C_{6-14}$ aryl, —$C_{1-6}$ alkyl-5- to 14-membered heteroaryl, —$C_{1-6}$ alkyl-3- to 10-membered heterocyclyl, —C(O)$NH_2$, —C(O)—$C_{3-10}$ cycloalkyl, —C(O)—$C_{6-14}$ aryl, —C(O)-5- to 14-membered heteroaryl, —C(O)-3- to 10-membered heterocyclyl, —C(O)—$C_{1-6}$ alkyl-$C_{3-10}$ cycloalkyl, —C(O)—$C_{1-6}$ alkyl-$C_{6-14}$ aryl, —C(O)—$C_{1-6}$ alkyl-5- to 14-membered heteroaryl, and —C(O)—$C_{1-6}$ alkyl-3- to 10-membered heterocyclyl, wherein a cyclic or acyclic group of the $C_{3-10}$ cycloalkyl, $C_{6-14}$ aryl, 5- to 14-membered heteroaryl, 3- to 10-membered heterocyclyl, —C(O)—C$_{3-10}$ cycloalkyl, —C(O)—C$_{6-14}$ aryl, —C(O)-5- to 14-membered heteroaryl, —C(O)-3- to 10-membered heterocyclyl, —C(O)—C$_{1-6}$ alkyl-C$_{3-10}$ cycloalkyl, —C(O)—C$_{1-6}$ alkyl-C$_{6-14}$ aryl, —C(O)—C$_{1-6}$ alkyl-5- to 14-membered heteroaryl, or —C(O)—C$_{1-6}$ alkyl-3- to 10-membered heterocyclyl, or —C(O)NH$_2$ is optionally substituted with one, two or more groups selected from OH, halogen, CN, C$_{1-6}$ alkyl and C$_{1-6}$ alkyloxy; wherein the heterocyclyl can be pyridinyl (for example, pyridin-2-yl, pyridin-3-yl, pyridin-4-yl, pyridin-5-yl, and pyridin-6-yl), and the aryl can be phenyl.

According to an exemplary embodiment of the present disclosure, $X^1$, $X^2$, $X^3$, $X^4$, $X^5$, $X^6$ and $X^7$ are the same or different, and are independently selected from CH and N; for example, at least one, e.g. 1, 2, 3, 4, 5, 6 or 7, of $X1$, $X^2$, $X^3$, $X^4$, $X^5$, $X^6$ and $X^7$ is N.

According to an exemplary embodiment of the present disclosure, $X^8$ is selected from NR$^1$.

According to an exemplary embodiment of the present disclosure, $R^1$ is H.

According to an exemplary embodiment of the present disclosure, A is selected from H, NH$_2$, methyl, ethyl, propyl and isopropyl.

According to an exemplary embodiment of the present disclosure, E is H.

According to an exemplary embodiment of the present disclosure, D is selected from the following groups: halogen, BnO—, H, CN, NH$_2$, OCH$_3$,

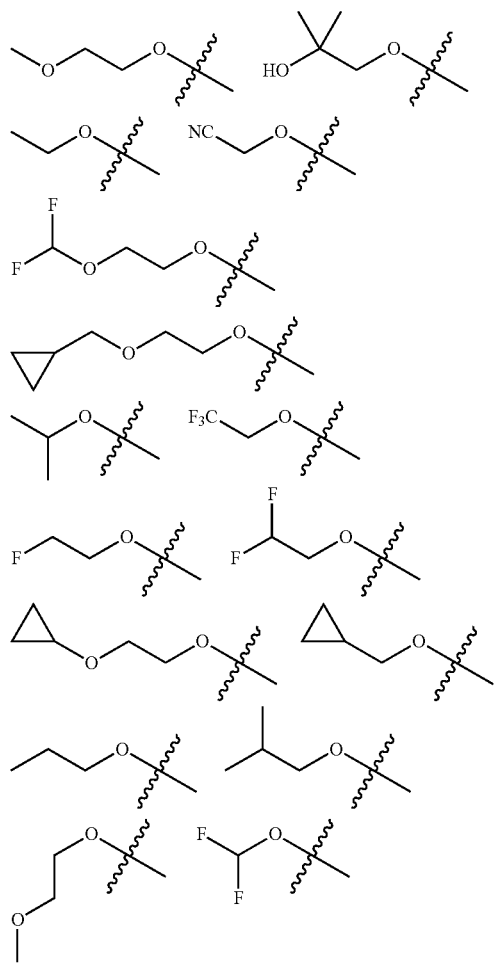

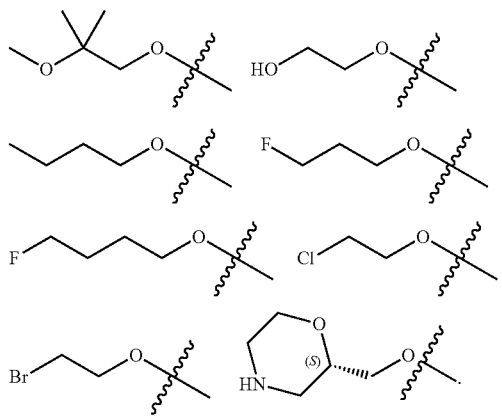

According to an exemplary embodiment of the present disclosure, G is selected from

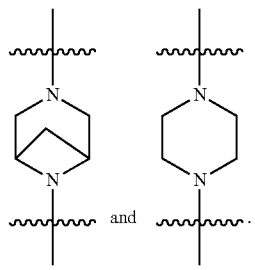 [SMILES: *N1CC2CC(C1)N2* ; *N1CCN(*)CC1]

and

According to an exemplary embodiment of the present disclosure, K is selected from

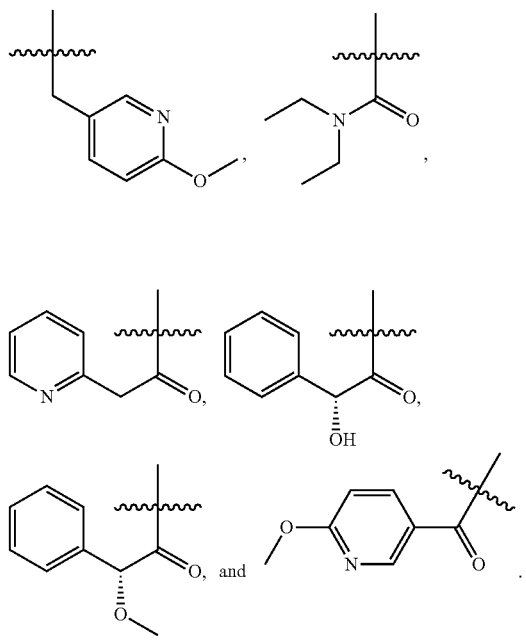

According to an embodiment of the present disclosure, the compound has a structure shown in the following formula:

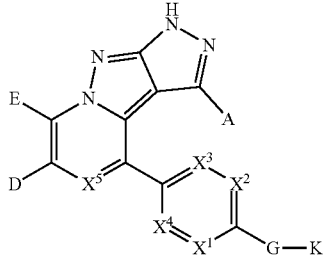
wherein $X^1$, $X^2$, $X^3$, $X^4$, $X^5$, A, D, E, G and K are defined as above.
As an example, the compound of formula I is selected from the following compounds,
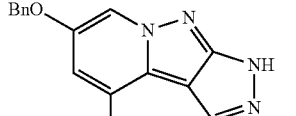
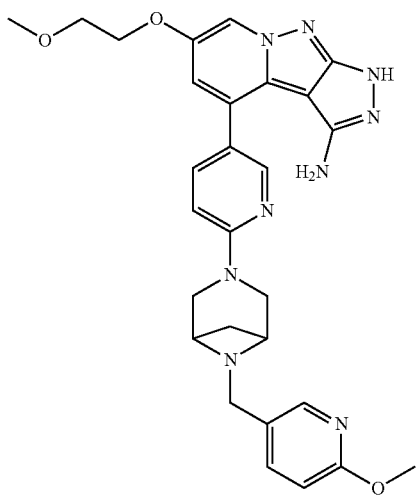
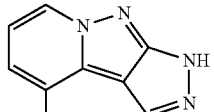
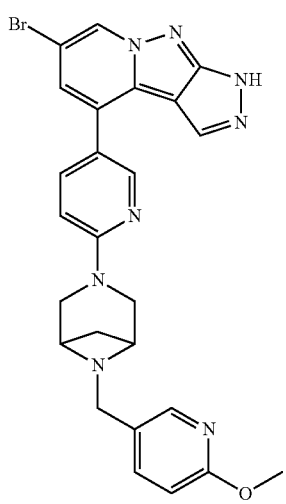
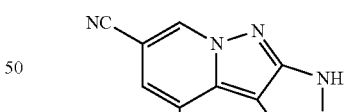

47
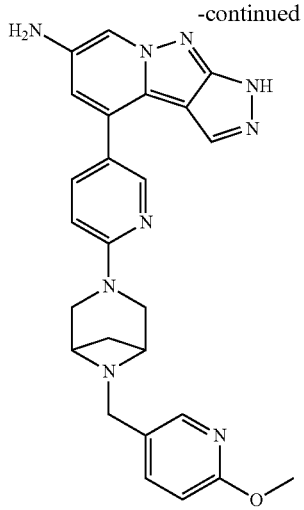
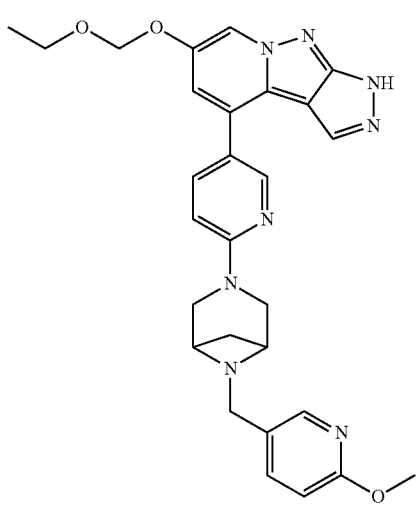
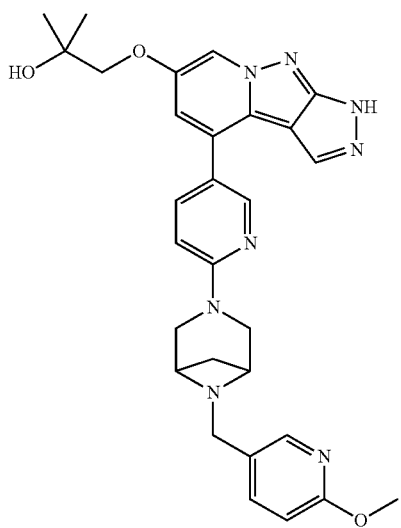
48
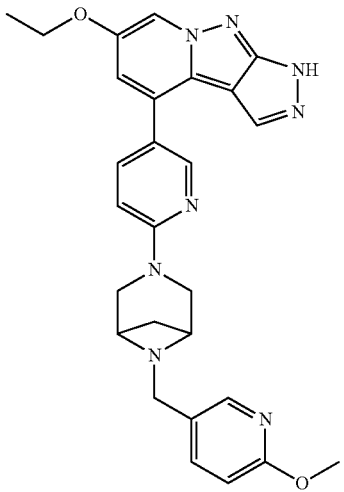
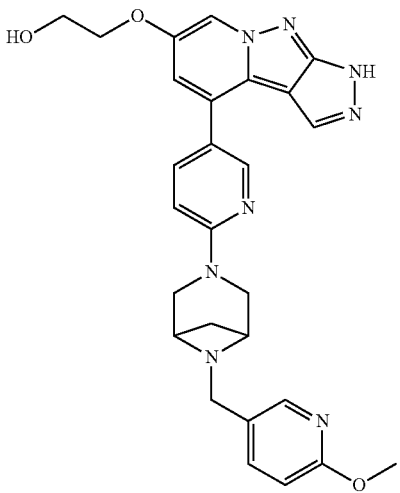
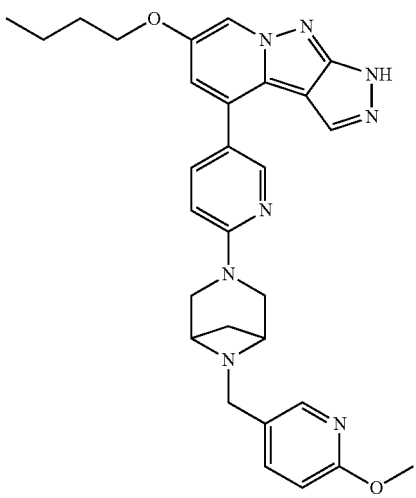

US 12,338,253 B2
49
-continued
50
-continued
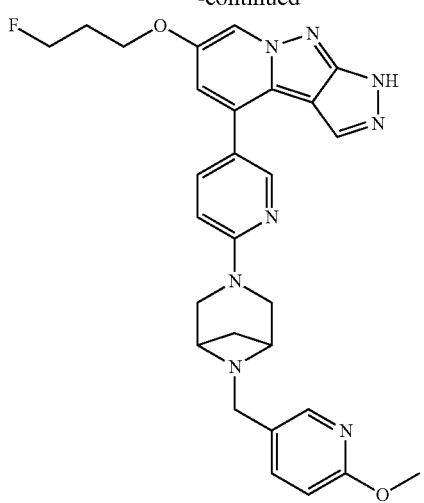
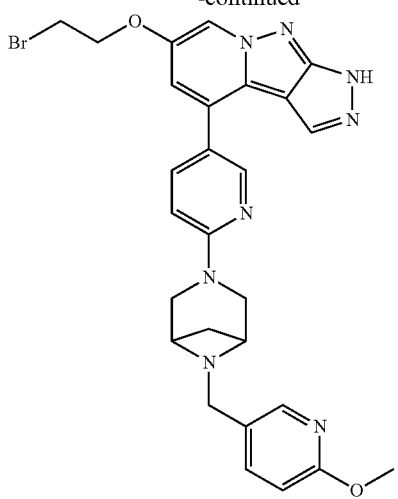

-continued
| 51 | 52 |
|---|---|
| 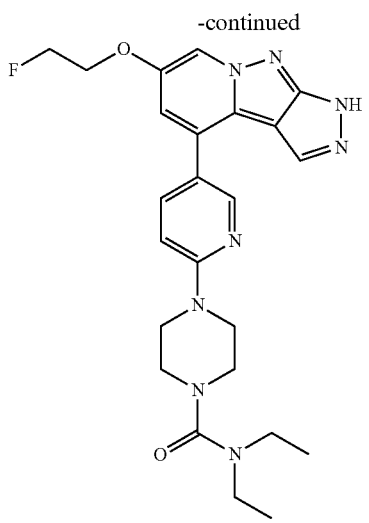 | 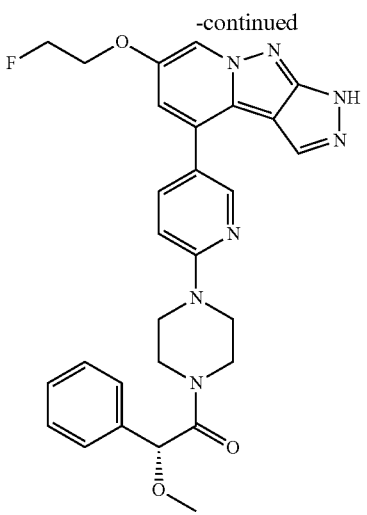 |
| 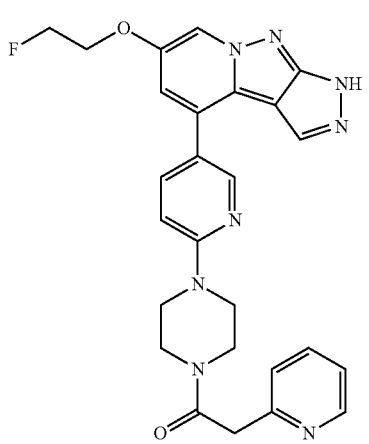 | 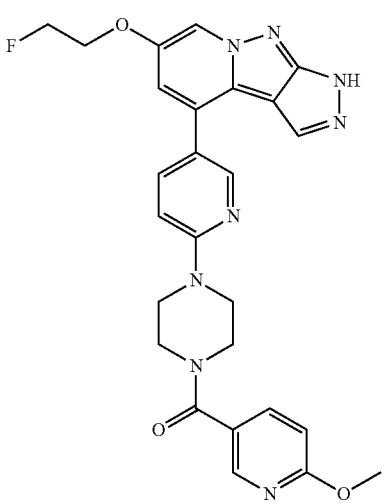 |
| 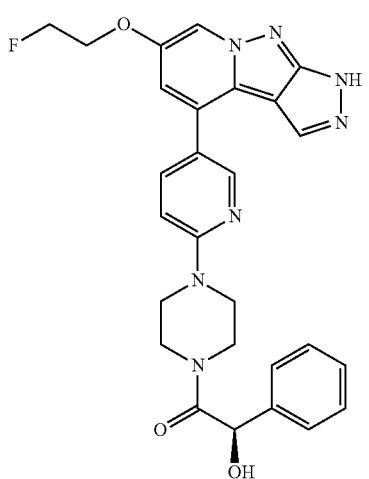 | 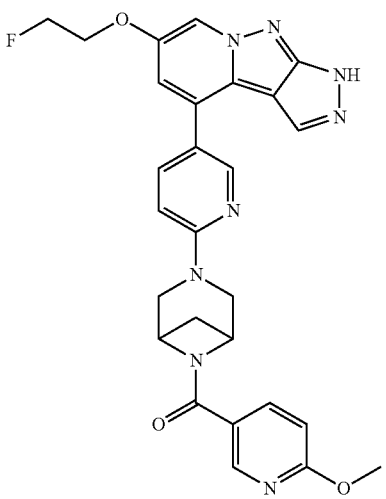 |

53
-continued
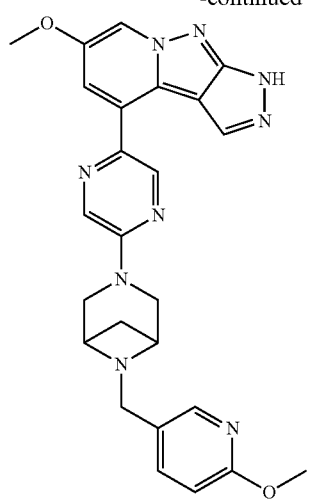
54
-continued
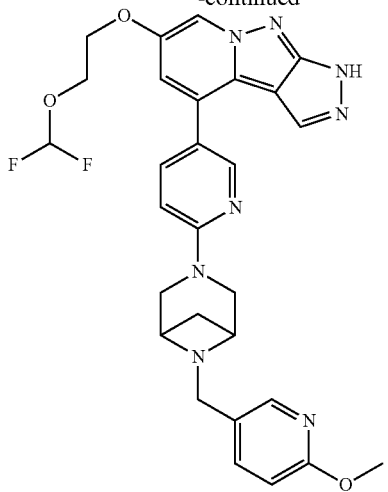
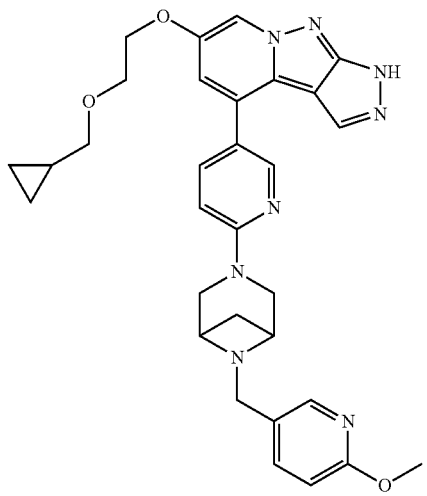
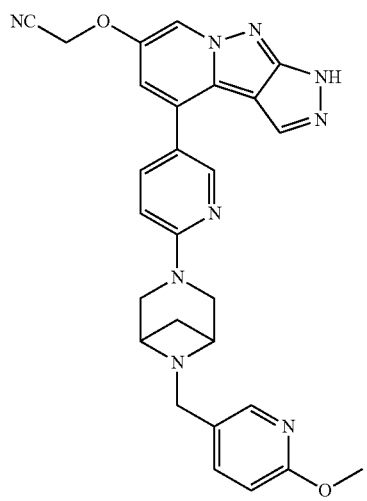
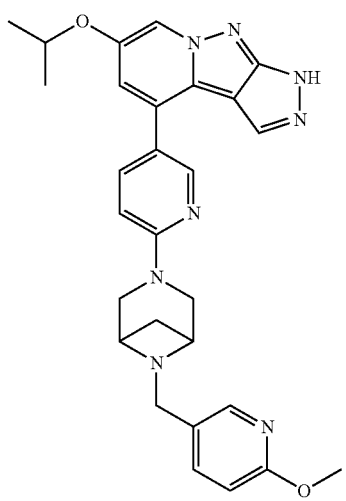

55
-continued
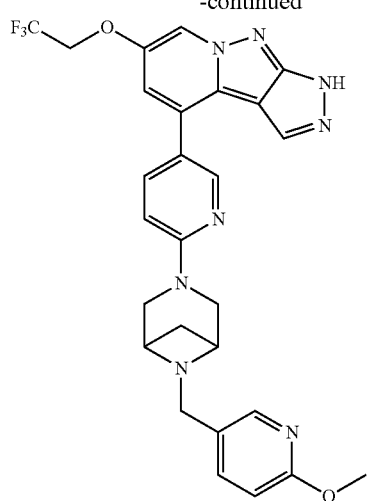
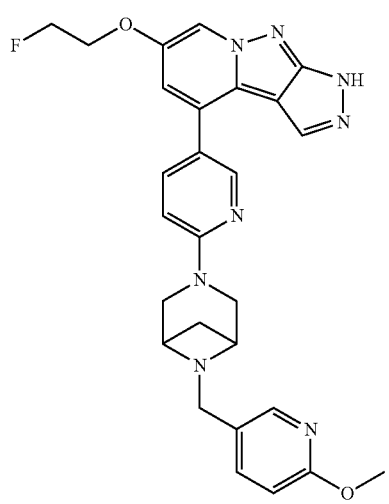
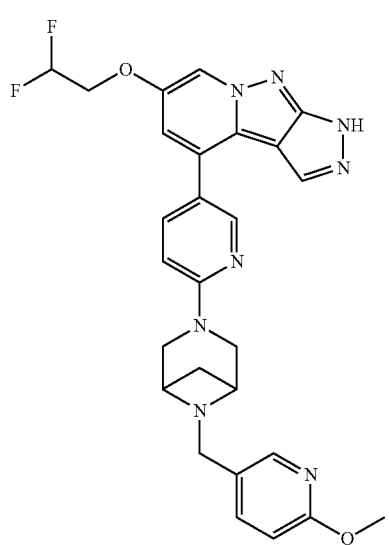
56
-continued
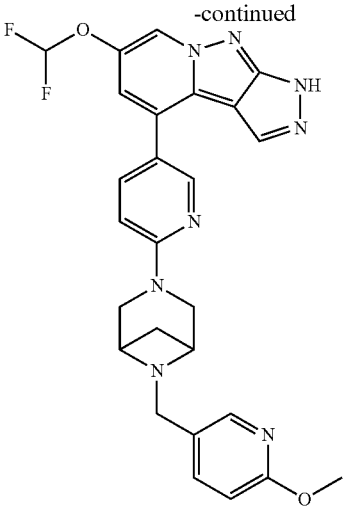
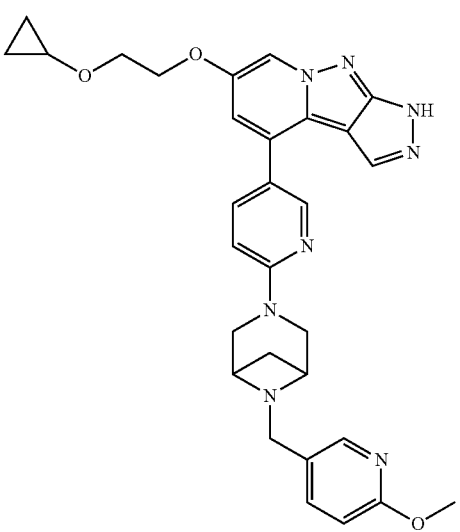
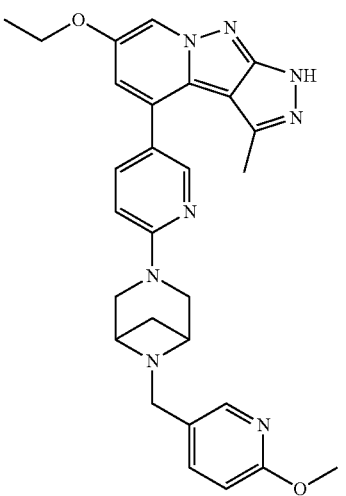

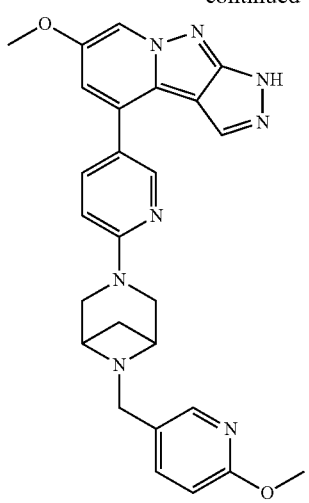
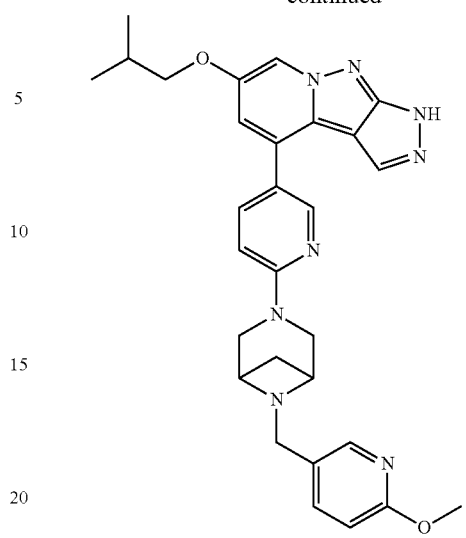
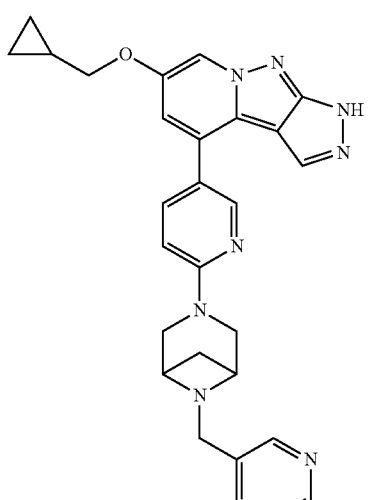
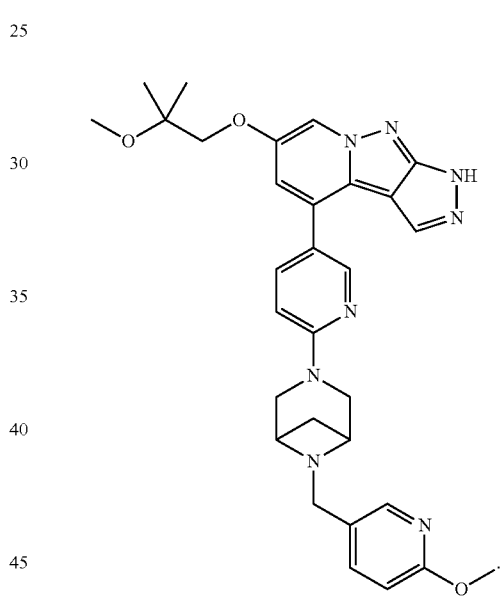
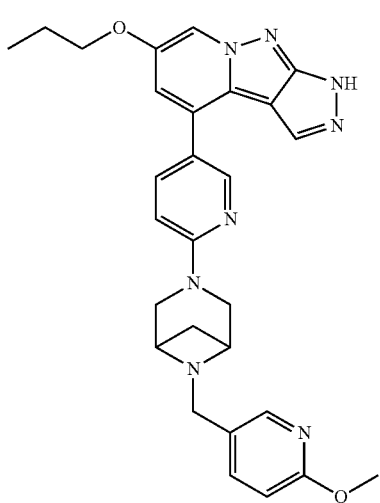
The present disclosure also provides a process for preparing the compound of formula I, which comprises the following steps:
reacting a compound of formula I-1 with a compound R²¹-L to obtain the compound of formula I,
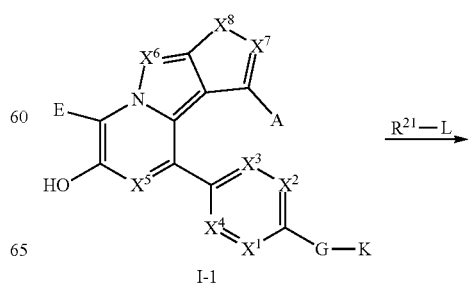
I-1

-continued

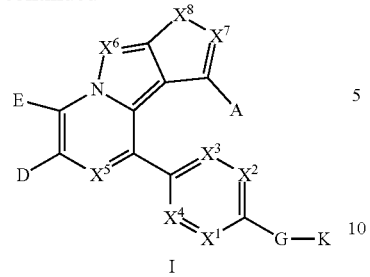

I wherein A, D, E, G, K, $X^1$, $X^2$, $X^3$, $X^4$, $X^5$, $X^6$, $X^7$, $X^8$ and $R^{21}$ are defined as above; and L is selected from leaving groups.

According to an embodiment of the present disclosure, the leaving group is selected from halogen and OTf.

According to an embodiment of the present disclosure, the reaction is performed in the presence of an alkaline, for example, potassium carbonate.

According to an embodiment of the present disclosure, the reaction is performed at a temperature of 50-100° C. for a period of 1-24 h.

According to an embodiment of the present disclosure, the reaction can be performed in the presence of an organic solvent (for example, DMF).

The present disclosure also provides a process for preparing the compound of formula I-1, which comprises reacting a compound of formula I-2 to obtain the compound of formula I-1:

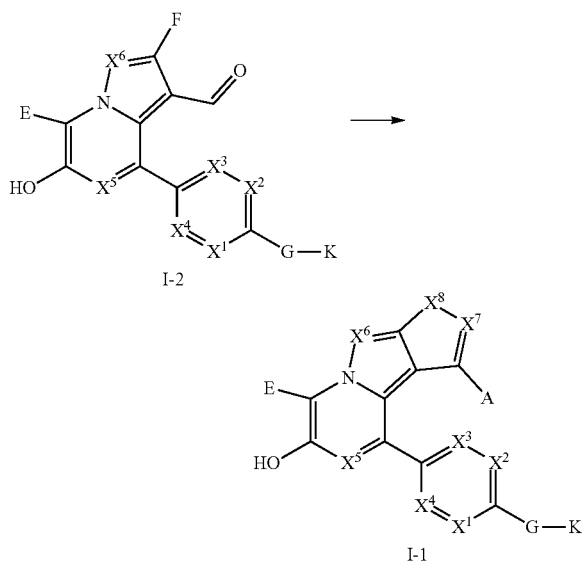

wherein A, D, E, G, K, $X^1$, $X^2$, $X^3$, $X^4$, $X^5$, $X^6$, $X^7$ and $X^8$ are defined as above.

According to an embodiment of the present disclosure, the reaction is performed in the presence of hydrazine hydrate, and $X^7$ is N and $X^8$ is NH.

According to an embodiment of the present disclosure, the reaction is performed in the presence of an organic solvent (for example, DMF).

According to an embodiment of the present disclosure, the reaction is performed under a heating condition.

The present disclosure also provides a compound of formula I-1 or formula I-2:

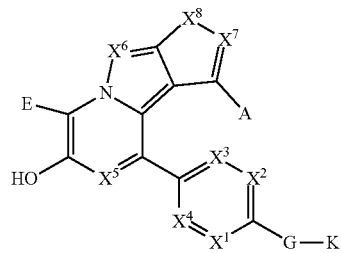

I-1

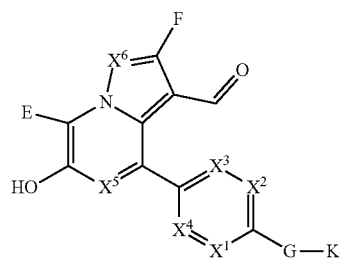

I-2

The present disclosure also provides use of the compound of formula I-1 or formula I-2 in the preparation of the compound of formula I.

The present disclosure also provides a pharmaceutical composition, which comprises a therapeutically effective amount of at least one of the compound of formula I, and the stereoisomer, the racemate, the tautomer, the isotopically labeled compound, the nitrogen oxide and the pharmaceutically acceptable salt thereof.

According to an embodiment of the present disclosure, the pharmaceutical composition also comprises one, two or more pharmaceutically acceptable carriers or excipients.

According to an embodiment of the present disclosure, the pharmaceutical composition also comprises one or more additional therapeutic agents.

The present disclosure also provides a method for inhibiting cell proliferation in vitro or in vivo, which comprises getting cells to contact with an effective amount of the compound of formula I, or the stereoisomer, the racemate, the tautomer, the isotopically labeled compound, the nitrogen oxide or the pharmaceutically acceptable salt thereof, or the pharmaceutical composition thereof disclosed herein.

The present disclosure also provides a method for treating a disease mediated by RET kinase, which comprises administering to a patient a therapeutically effective amount of at least one of the compound of formula I, and the stereoisomer, the racemate, the tautomer, the isotopically labeled compound, the nitrogen oxide and the pharmaceutically acceptable salt thereof.

The present disclosure also provides a method for treating a disease or condition related to RET in a patient in need of treatment, which comprises administering to the patient a therapeutically effective amount of the compound of formula I, or the stereoisomer, the racemate, the tautomer, the isotopically labeled compound, the nitrogen oxide or the pharmaceutically acceptable salt thereof, or the pharmaceutical composition thereof disclosed herein.

The present disclosure also provides a method for treating cancer and/or inhibiting metastasis related to the cancer in a patient in need of treatment, which comprises administering to the patient a therapeutically effective amount of the compound of formula I, or the stereoisomer, the racemate, the tautomer, the isotopically labeled compound, the nitrogen oxide or the pharmaceutically acceptable salt thereof, or the pharmaceutical composition thereof disclosed herein.

The present disclosure also provides a method for treating irritable bowel syndrome (IBS) and/or pain related to IBS in a patient in need of treatment, which comprises administering to the patient a therapeutically effective amount of the compound of formula I, or the stereoisomer, the racemate, the tautomer, the isotopically labeled compound, the nitrogen oxide or the pharmaceutically acceptable salt thereof, or the pharmaceutical composition thereof disclosed herein.

The present disclosure also provides a method for providing supportive care for a cancer patient, including preventing or minimizing a gastrointestinal disease (for example, diarrhea) related to treatment (including chemotherapy treatment), which comprises administering to the patient a therapeutically effective amount of the compound of formula I, or the stereoisomer, the racemate, the tautomer, the isotopically labeled compound, the nitrogen oxide or the pharmaceutically acceptable salt thereof, or the pharmaceutical composition thereof disclosed herein.

The present disclosure also provides use of at least one of the compound of formula I, and the stereoisomer, the racemate, the tautomer, the isotopically labeled compound, the nitrogen oxide and the pharmaceutically acceptable salt thereof in the preparation of a medicament for treating a disease mediated by RET kinase.

The present disclosure also provides use of at least one of the compound of formula I, and the stereoisomer, the racemate, the tautomer, the isotopically labeled compound, the nitrogen oxide and the pharmaceutically acceptable salt thereof in the preparation of a medicament for treating cancer and/or inhibiting metastasis related to the cancer.

The present disclosure also provides use of at least one of the compound of formula I, and the stereoisomer, the racemate, the tautomer, the isotopically labeled compound, the nitrogen oxide and the pharmaceutically acceptable salt thereof in the preparation of a medicament for treating irritable bowel syndrome (IBS) or pain related to IBS.

The present disclosure also provides use of at least one of the compound of formula I, and the stereoisomer, the racemate, the tautomer, the isotopically labeled compound, the nitrogen oxide and the pharmaceutically acceptable salt thereof in the preparation of a medicament for providing supportive care, including preventing or minimizing a gastrointestinal condition related to treatment (including chemotherapy treatment), for example, diarrhea, to a cancer patient.

The present disclosure also provides use of at least one of the compound of formula I, and the stereoisomer, the racemate, the tautomer, the isotopically labeled compound, the nitrogen oxide and the pharmaceutically acceptable salt thereof in the preparation of a medicament for inhibiting RET kinase activity.

The present disclosure also provides use of at least one of the compound of formula I, and the stereoisomer, the racemate, the tautomer, the isotopically labeled compound, the nitrogen oxide and the pharmaceutically acceptable salt thereof in the preparation of a medicament for treating a disease or condition related to RET.

The present disclosure also provides a method for treating cancer in a patient in need, which comprises (a) determining whether the cancer is related to the dysregulation of: the expression, activity or level of a RET gene, a RET kinase or any one thereof (for example, cancer related to RET); (b) if it is determined that the cancer is related to the dysregulation of: the expression, activity or level of the RET gene, the RET kinase or any one thereof (for example, cancer related to RET), administering to the patient a therapeutically effective amount of at least one of the compound of formula I, and the stereoisomer, the racemate, the tautomer, the isotopically labeled compound, the nitrogen oxide and the pharmaceutically acceptable salt thereof, or the pharmaceutical composition thereof.

The present disclosure also provides a method for reversing or preventing acquired resistance to an anticancer drug, which comprises administering to a patient at risk of developing or having the acquired resistance to the anticancer drug a therapeutically effective amount of at least one of the compound of formula I, and the stereoisomer, the racemate, the tautomer, the isotopically labeled compound, the nitrogen oxide and the pharmaceutically acceptable salt thereof.

The present disclosure also provides a method for delaying and/or preventing the development of resistance to an anticancer drug in an individual, which comprises administering to the individual an effective amount of at least one of the compound of formula I, and the stereoisomer, the racemate, the tautomer, the isotopically labeled compound, the nitrogen oxide and the pharmaceutically acceptable salt thereof before, during or after administering an effective amount of the anticancer drug.

The present disclosure also provides a method for treating an individual suffering from cancer and having an increased possibility of developing resistance to an anticancer drug, which comprises concomitantly administering to the individual (a) an effective amount of at least one of the compound of formula I, and the stereoisomer, the racemate, the tautomer, the isotopically labeled compound, the nitrogen oxide and the pharmaceutically acceptable salt thereof; and (b) an effective amount of the anticancer drug.

The present disclosure also provides a method for treating an individual suffering from cancer related to RET, wherein the cancer has one or more RET inhibitor resistance mutations, and the RET inhibitor resistance mutations increase the resistance of the cancer to a RET inhibitor that is not at least one of the compound of formula I, and the stereoisomer, the racemate, the tautomer, the isotopically labeled compound, the nitrogen oxide and the pharmaceutically acceptable salt thereof (for example, substitutions at amino acid positions 804, 810 and 904, e.g. V804M, V804L, V804E, G810R, G810S, G810C, G810V and S904F), the method comprising administering at least one of the compound of formula I, and the stereoisomer, the racemate, the tautomer, the isotopically labeled compound, the nitrogen oxide and the pharmaceutically acceptable salt thereof before, during or after administering another anticancer drug.

The present disclosure also provides a method for treating an individual suffering from cancer related to RET, which comprises administering at least one of the compound of formula I, and the stereoisomer, the racemate, the tautomer, the isotopically labeled compound, the nitrogen oxide and the pharmaceutically acceptable salt thereof before, during or after administering another anticancer drug.

The present disclosure provides a method for treating cancer (for example, cancer related to RET) in a patient in need, which comprises administering to the patient a therapeutically effective amount of at least one of the compound of formula I and the pharmaceutically acceptable salt thereof, or the pharmaceutical composition thereof.

Term Definition and Description

Unless otherwise stated, the definitions of groups and terms described in the specification and claims of the present application, including definitions thereof as examples, exemplary definitions, preferred definitions, definitions documented in tables, definitions of specific compounds in the examples, and the like, may be arbitrarily combined and incorporated with each other. The definitions of groups and the structures of the compounds in such combinations and incorporations should fall within the scope of the present specification.

Unless otherwise stated, the numerical ranges described in the specification and claims shall be construed as at least including each specific integer value therein. For example, the numerical range "1-40" shall be construed as at least including each integer value in the numerical range "1-10", i.e., 1, 2, 3, 4, 5, 6, 7, 8, 9 and 10, and each integer value in the numerical range "11-40", i.e., 11, 12, 13, 14, 15, ..., 35, 36, 37, 38, 39 and 40. It should be understood that where one, two or more are used to describe a substituent herein, "more" shall mean an integer ≥3, such as 3, 4, 5, 6, 7, 8, 9 or 10.

The term "halogen" refers to fluorine, chlorine, bromine and iodine.

The term "$C_{1-40}$ alkyl" preferably refers to a linear or branched saturated monovalent hydrocarbyl group having 1-40 carbon atoms. For example, "$C_{1-6}$ alkyl" refers to a linear or branched alkyl group having 1, 2, 3, 4, 5 or 6 carbon atoms. The alkyl is, for example, methyl, ethyl, propyl, butyl, pentyl, hexyl, isopropyl, isobutyl, sec-butyl, tert-butyl, isopentyl, 2-methylbutyl, 1-methylbutyl, 1-ethylpropyl, 1,2-dimethylpropyl, neopentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl, or isomers thereof.

The term "$C_{2-40}$ alkenyl" preferably refers to a linear or branched monovalent hydrocarbyl group comprising one or more double bonds and having 2-40 carbon atoms, and is preferably "$C_{2-6}$ alkenyl". "$C_{2-6}$ alkenyl" preferably refers to a linear or branched monovalent hydrocarbyl group comprising one or more double bonds and having 2, 3, 4, 5 or 6 carbon atoms, in particular 2 or 3 carbon atoms ("$C_{2-3}$alkenyl"); it should be understood that in the case where the alkenyl comprises more than one double bond, the double bonds can be separated from one another or conjugated. The alkenyl is, for example, ethenyl, allyl, (E)-2-methylethenyl, (Z)-2-methylethenyl, (E)-but-2-enyl, (Z)-but-2-enyl, (E)-but-1-enyl, (Z)-but-1-enyl, pent-4-enyl, (E)-pent-3-enyl, (Z)-pent-3-enyl, (E)-pent-2-enyl, (Z)-pent-2-enyl, (E)-pent-1-enyl, (Z)-pent-1-enyl, hex-5-enyl, (E)-hex-4-enyl, (Z)-hex-4-enyl, (E)-hex-3-enyl, (Z)-hex-3-enyl, (E)-hex-2-enyl, (Z)-hex-2-enyl, (E)-hex-1-enyl, (Z)-hex-1-enyl, isopropenyl, 2-methylprop-2-enyl, 1-methylprop-2-enyl, 2-methylprop-1-enyl, (E)-1-methylprop-1-enyl, (Z)-1-methylprop-1-enyl, 3-methylbut-3-enyl, 2-methylbut-3-enyl, 1-methylbut-3-enyl, 3-methylbut-2-enyl, (E)-2-methylbut-2-enyl, (Z)-2-methylbut-2-enyl, (E)-1-methylbut-2-enyl, (Z)-1-methylbut-2-enyl, (E)-3-methylbut-1-enyl, (Z)-3-methylbut-1-enyl, (E)-2-methylbut-1-enyl, (Z)-2-methylbut-1-enyl, (E)-1-methylbut-1-enyl, (Z)-1-methylbut-1-enyl, 1,1-dimethylprop-2-enyl, 1-ethylprop-1-enyl, 1-propylethenyl or 1-iso propylethenyl.

The term "$C_{2-40}$ alkynyl" refers to a linear or branched monovalent hydrocarbyl group comprising one or more triple bonds and having 2-40 carbon atoms, and is preferably "$C_2$-$C_6$ alkynyl". The term "$C_2$-$C_6$ alkynyl" refers to a linear or branched monovalent hydrocarbyl group comprising one or more triple bonds and having 2, 3, 4, 5 or 6 carbon atoms, in particular 2 or 3 carbon atoms ("$C_2$-$C_3$-alkynyl"). The $C_2$-$C_6$-alkynyl is, for example, ethynyl, prop-1-ynyl, prop-2-ynyl, but-1-ynyl, but-2-ynyl, but-3-ynyl, pent-1-alkynyl, pent-2-ynyl, pent-3-ynyl, pent-4-ynyl, hex-1-ynyl, hex-2-ynyl, hex-3-ynyl, hex-4-alkynyl, hex-5-ynyl, 1-methylprop-2-ynyl, 2-methylbut-3-ynyl, 1-methylbut-3-ynyl, 1-methylbut-2-ynyl, 3-methylbut-1-ynyl, 1-ethylprop-2-ynyl, 3-methylpent-4-ynyl, 2-methylpent-4-ynyl, 1-methylpent-4-ynyl, 2-methylpent-3-ynyl, 1-methylpent-3-ynyl, 4-methylpent-2-ynyl, 1-methylpent-2-nyl, 4-methylpent-1-ynyl, 3-methylpent-1-ynyl, 2-ethylbut-3-ynyl, 1-ethylbut-3-ynyl, 1-ethylbut-2-ynyl, 1-propylprop-2-ynyl, 1-isopropylprop-2-ynyl, 2,2-dimethylbut-3-ynyl, 1,1-dimethylbut-3-ynyl, 1,1-dimethylbut-2-ynyl or 3,3-dimethylbut-1-ynyl. In particular, the alkynyl is ethynyl, prop-1-ynyl or prop-2-ynyl.

The term "$C_{3-40}$ cycloalkyl" refers to a saturated or monovalent monocyclic or bicyclic hydrocarbon ring or bridged cycloalkane having 3-40 carbon atoms, and is preferably "$C_{3-10}$ cycloalkyl". The term "$C_{3-10}$ cycloalkyl" refers to a saturated monovalent monocyclic or bicyclic hydrocarbon ring or bridged cycloalkane having 3, 4, 5, 6, 7, 8, 9 or 10 carbon atoms. The $C_{3-10}$ cycloalkyl may be a monocyclic hydrocarbyl group such as cyclopropyl, cyclobutyl, cyclopentyl, cyclohexyl, cycloheptyl, cyclooctyl, cyclononyl or cyclodecyl, or may be a bicyclic hydrocarbyl such as a decahydronaphthalene ring.

The term "3- to 20-membered heterocyclyl" means a saturated monovalent monocyclic or bicyclic hydrocarbon ring or bridged cycloalkane, which is a non-aromatic cyclic group with the total number of ring atoms of 3-20 (such as 3, 4, 5, 6, 7, 8, 9 and 10) containing 1-5 heteroatoms independently selected from N, O and S, preferably a "3- to 10-membered heterocyclyl". The term "3- to 10-membered heterocyclyl" means a saturated monovalent monocyclic or bicyclic hydrocarbon ring or bridged cycloalkane, which contains 1-5, preferably 1-3 heteroatoms independently selected from N, O and S, for example, 1, 2 or 3 heteroatoms independently selected from N, 0 and S. The heterocyclyl may be connected to the rest of the molecule through any one of the carbon atoms or the nitrogen atom (if present). In particular, the heterocyclyl may include, but is not limited to: 4-membered rings such as azetidinyl and oxetanyl; 5-membered rings such as tetrahydrofuranyl, dioxolyl, pyrrolidinyl, imidazolidinyl, pyrazolidinyl and pyrrolinyl; 6-membered rings such as tetrahydropyranyl, piperidinyl, morpholinyl, dithianyl, thiomorpholinyl, piperazinyl and trithianyl; or 7-membered rings such as diazepanyl. Optionally, the heterocyclyl may be benzo-fused. The heterocyclyl may be bicyclic, such as but not limited to a 5,5-membered ring such as a hexahydrocyclopenta[c]pyrrol-2(1H)-yl ring, or a 5,6-membered bicyclic ring such as a hexahydropyrrolo[1,2-a]pyrazin-2(1H)-yl ring. The ring containing nitrogen atoms may be partially unsaturated, i.e., it may contain one or more double bonds, such as but not limited to 2,5-dihydro-1H-pyrrolyl, 4H-[1,3,4]thiadiazinyl, 4,5-dihydrooxazolyl or 4H-[1,4]thiazinyl, or it may be benzo-fused, such as but not limited to dihydroisoquinolyl. According to the present disclosure, the heterocyclyl is non-aromatic. Where the 3- to 20-membered heterocyclyl is connected to another group to form the compound disclosed herein, it may be that the carbon atom on the 3- to 20-membered heterocyclyl is connected to another group, or the heteroatom on the 3- to 20-membered heterocyclyl is connected to another group. For example, where the 3- to 20-membered heterocyclyl is selected from piperazinyl, it may be that the nitrogen atom on the piperazinyl is connected to another group. Alternatively, where the 3- to 20-membered heterocyclyl is selected from piperidinyl, it may be that the nitrogen atom on the piperidinyl and the carbon atom in the para position are connected to the other groups.

The term "$C_{6-20}$ aryl" preferably refers to an aromatic or partially aromatic monocyclic, bicyclic or tricyclic monovalent hydrocarbon ring having 6-20 carbon atoms, and is preferably "$C_{6-14}$ aryl". The term "$C_{6-14}$ aryl" preferably refers to an aromatic or partially aromatic monovalent monocyclic, bicyclic or tricyclic hydrocarbon ring having 6, 7, 8, 9, 10, 11, 12, 13 or 14 carbon atoms ("$C_{6-14}$ aryl"), in particular a ring having 6 carbon atoms ("$C_6$ aryl"), such as phenyl; or a biphenyl, a ring having 9 carbon atoms ("$C_9$ aryl") such as indanyl or indenyl, a ring having 10 carbon atoms ("$C_{10}$ aryl") such as tetrahydronaphthyl, dihydronaphthyl or naphthyl, a ring having 13 carbon atoms ("$C_{13}$ aryl") such as fluorenyl, or a ring having 14 carbon atoms ("$C_{14}$ aryl") such as anthracenyl. Where the $C_{6-20}$ aryl is substituted, it may be monosubstituted or polysubstituted. In addition, the substitution site is not limited, and may be, for example, ortho-, para- or meta-substitution.

The term "5- to 20-membered heteroaryl" refers to an aromatic monovalent monocyclic, bicyclic or tricyclic ring, which has 5-20 ring atoms, contains 1-5 heteroatoms independently selected from N, O and S, and is, for example, "5- to 14-membered heteroaryl". The term "5- to 14-membered heteroaryl" refers to an aromatic monovalent monocyclic, bicyclic or tricyclic ring, which has 5, 6, 7, 8, 9, 10, 11, 12, 13 or 14 ring atoms, in particular 5, 6, 9 or 10 carbon atoms, comprises 1-5, preferably 1-3 heteroatoms independently selected from N, O and S, and may be benzo-fused in each case. In particular, the heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl and the like, and benzo derivatives thereof such as benzofuranyl, benzothienyl, benzoxazolyl, benzoisoxazolyl, benzimidazolyl, benzotriazolyl, indazolyl, indolyl, and isoindolyl; or pyridinyl, pyridazinyl, pyrimidinyl, pyrazinyl, triazinyl and the like, and benzo derivatives thereof such as quinolyl, quinazolinyl, and isoquinolyl; or azocinyl, indolizinyl, purinyl and the like, and benzo derivatives thereof; or cinnolinyl, phthalazinyl, quinazolinyl, quinoxalinyl, naphthyridinyl, pteridinyl, carbazolyl, acridinyl, phenazinyl, phenothiazinyl, phenoxazinyl, and the like. Where the 5- to 20-membered heteroaryl is connected to another group to form the compound disclosed herein, it may be that the carbon atom on the 5- to 20-membered heteroaryl ring is connected to another group, or the heteroatom on the 5- to 20-membered heteroaryl ring is connected to another group. Where the 5- to 20-membered heteroaryl is substituted, it may be monosubstituted or polysubstituted. In addition, the substitution site is not limited. For example, it may that hydrogen connected to the carbon atom on the heteroaryl ring is substituted, or hydrogen connected to the heteroatom on the heteroaryl ring is substituted.

Unless otherwise stated, the heterocyclyl, heteroaryl or heteroarylene includes all possible isomeric forms thereof, e.g., positional isomers thereof. Thus, for some illustrative non-limiting examples, forms that involving substitutions at or bonding to other groups at one, two or more of positions 1, 2, 3, 4, 5, 6, 7, 8, 9, 10, 11, 12 and the like (if present) are included, including pyridin-2-yl, pyridinylene-2-yl, pyridin-3-yl, pyridinylene-3-yl, pyridin-4-yl and pyridinylene-4-yl; thienyl or thienylene, including thien-2-yl, thien-2-ylene, thien-3-yl, and thien-3-ylene; pyrazol-1-yl, pyrazol-3-yl, pyrazol-4-yl and pyrazol-5-yl.

The term "oxo" means that the carbon atom, nitrogen atom or sulfur atom in the substituent is substituted with an oxy group formed after oxidation (═O).

Unless otherwise stated, the definitions of terms used herein are also applicable to groups comprising the terms. For example, the definition of $C_{1-6}$ alkyl is also applicable to $C_{1-6}$ alkyloxy, —N($C_{1-6}$ alkyl)$_2$, —NH$C_{1-6}$ alkyl, —S(O)$_2$— $C_{1-6}$ alkyl and the like.

It will be understood by those skilled in the art that the compound of formula I may exist in the form of various pharmaceutically acceptable salts. If these compounds have basic centers, they can form acid addition salts; if these compounds have acidic centers, they can form base addition salts; if these compounds contain both acidic centers (e.g., carboxyl) and basic centers (e.g., amino), they can also form internal salts.

The compound disclosed herein may exist in the form of a solvate (e.g., hydrate), and the compound disclosed herein contains a polar solvent as a structural element of the crystal lattice of the compound, particularly, for example, water, methanol or ethanol. The amount of polar solvent, especially water, can exist in a stoichiometric or non-stoichiometric ratio.

According to the structure, the compound disclosed herein may be chiral and may therefore exist in various enantiomeric forms. These compounds may therefore exist in racemic or optically active form. The compound disclosed herein or intermediates thereof may be separated into enantiomers by chemical or physical methods well known to those skilled in the art, or used in this form for synthesis. In the case of racemic amines, diastereoisomers are prepared from mixtures by reaction with optically active resolving agents. Examples of suitable resolving agents are optically active acids such as R- or S-tartaric acid, diacetyltartaric acid, dibenzoyltartaric acid, mandelic acid, malic acid, lactic acid, suitable N-protected amino acids (e.g., N-benzoylproline or N-benzenesulfonylproline) or various optically active camphorsulfonic acids. Enantiomeric resolution by chromatography can be advantageously performed with the aid of optically active resolving agents, such as dinitrobenzoylphenylglycine, cellulose triacetate or other carbohydrate derivatives or chirally derivatized methacrylate polymers immobilized on silica gel. Suitable eluents for this purpose are mixtures of solvent containing water or alcohol, for example, hexane/isopropanol/acetonitrile.

The term "tautomer" refers to functional isomers resulting from the rapid movement of an atom in a molecule between two positions. The compound disclosed herein may exhibit the tautomerism. Tautomeric compounds may exist in two or more interconvertible forms. Prototropic tautomers result from the migration of a covalently bonded hydrogen atom between two atoms. Tautomers generally exist in an equilibrium form. Trying to separate a single tautomer usually leads to a mixture, the physicochemical properties of which are consistent with the mixture of the compound. The position of the equilibrium depends on the chemical properties of the molecule. For example, in many aliphatic aldehydes and ketones such as acetaldehyde, the keto form predominates; whereas in phenol, the enol form predominates. The present disclosure encompasses all tautomeric forms of the compound.

The corresponding stable isomers can be separated according to known methods, such as extraction, filtration or column chromatography.

The term "patient" refers to any animal including mammals, preferably mice, rats, other rodents, rabbits, dogs, cats, pigs, cattle, sheep, horses or primates, and most preferably humans.

The phrase "therapeutically effective amount" used herein refers to the amount of the active compound or drug that causes a biological or medical response that researchers, veterinarians, physicians or other clinicians are looking for in tissues, systems, animals, individuals or humans, including one or more of the following effects: (1) disease prevention: for example, the prevention of a disease, disorder or condition in an individual who is susceptible to the disease, disorder or condition but has not yet experienced or exhibited the pathology or symptoms of the disease; (2) disease inhibition: for example, the inhibition of a disease, disorder or condition in an individual who is experiencing or exhibiting the pathology or symptoms of the disease, disorder or condition. (i.e., the prevention of the further development of the pathology and/or symptoms); and (3) disease alleviation: for example, the alleviation of a disease, disorder or condition in an individual who is experiencing or exhibiting the pathology or symptoms of the disease, disorder or condition (i.e., the reverse of the pathology and/or symptoms).

ADVANTAGEOUS EFFECT

Figure 1:
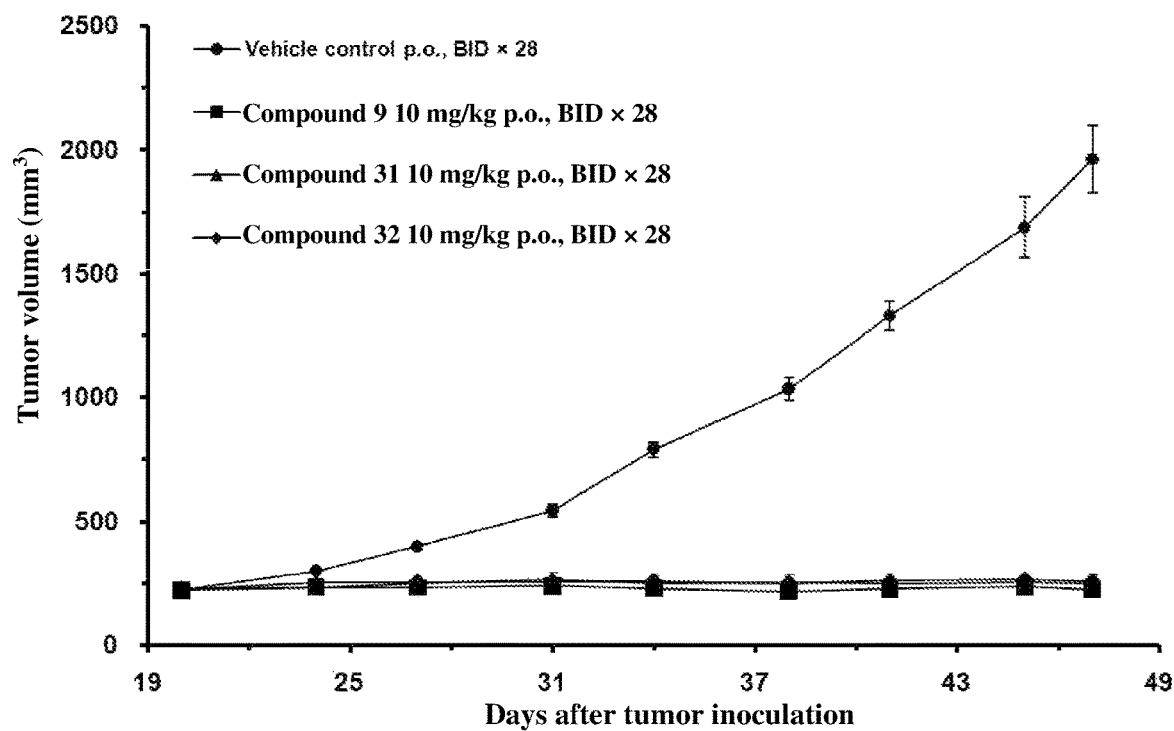
FIG. 1 shows the inhibitory effect of the compounds on the tumor of TT cell human medullary thyroid carcinoma xenograft model.

The compounds disclosed herein can be used as a highly selective and/or very effective RET inhibitor. Such compounds have strong inhibitory effect on the RET gatekeeper residue mutant RET V804M, RET solvent-front residue mutant G810R and other clinically relevant RET mutants, as well as wt-RET.

The compounds can also significantly inhibit the growth of TT cell line derived from thyroid cancer and Ba/F3 cells transformed with various RET mutants, and has a good inhibitory effect. In addition, the compound largely blocks cellular RET autophosphorylation and its downstream pathway, and can significantly induce TT cell death.

In addition, the representative example compounds disclosed herein also have particularly excellent pharmacokinetic properties, and can be administered to patients in smaller doses as active ingredients, thereby reducing the cost for treating patients.

DETAILED DESCRIPTION

The technical solution of the present disclosure will be further illustrated in detail with reference to the following specific examples. It should be understood that the following examples are merely exemplary illustration and explanation of the present disclosure, and should not be construed as limiting the protection scope of the present disclosure. All techniques implemented based on the aforementioned content of the present disclosure are encompassed within the protection scope of the present disclosure.

Unless otherwise specified, the starting materials and reagents used in the following examples are all commercially available products or can be prepared by known methods.

Example 1

6-(2-methoxyethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-3-amine (Compound 1)

Step A: 2-fluoro-6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridin-3-carbaldehyde oxime

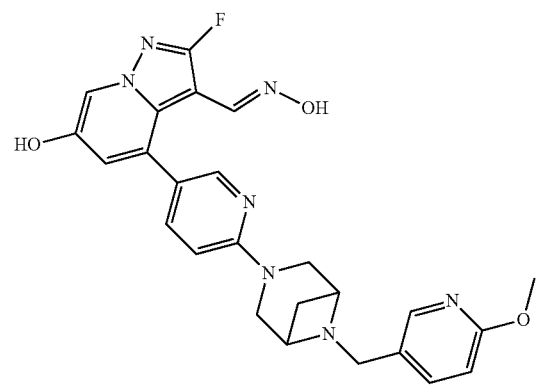 [SMILES: COc1ccc(CN2C3CC2CN(c2ccc(-c4cc(O)cn5nc(F)c(/C=N/O)c45)cn2)C3)cn1]

To a solution of 2-fluoro-6-hydroxy-4-(6-(6-(((6-methoxypyridin-3-yl)methyl)-3,6-diazabicyclo[3.1.1]heptane-3-yl)pyridin-3-yl)pyrazolo[1,5-a]pyridin-3-carbaldehyde (100 mg, 0.21 mmol) in ethanol (5.0 mL) was added hydroxylamine hydrochloride (15 mg, 0.21 mmol), and the mixture was heated to reflux for 12 h and concentrated to obtain the residue, which was directly used in the next step.

Step B: 2-fluoro-6-hydroxy-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-3-acetonitrile

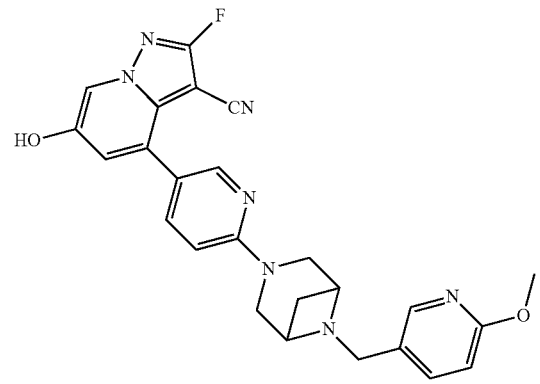 [SMILES: COc1ccc(CN2C3CC2CN(c2ccc(-c4cc(O)cn5nc(F)c(C#N)c45)cn2)C3)cn1]

Acetic anhydride (5.0 mL) was added to 2-fluoro-6-hydroxy-4-(6-(6-(((6-methoxypyridin-3-yl)methyl)-3,6-diazabicyclo[3.1.1]heptan-3-yl)pyridin-3-yl)pyrazolo[1,5-a]pyridin-3-carboxaldehyde oxime obtained in step A, and the mixture was heated to 80° C. and reacted for 2 h. The reaction solution was poured into ice water, stirred for 30 min and filtered to obtain a solid, which was separated by column chromatography to obtain the product (31 mg). m/z=472[M+1]⁺.

Step C: 2-fluoro-6-(2-methoxyethoxy)-4-(6-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-3-acetonitrile

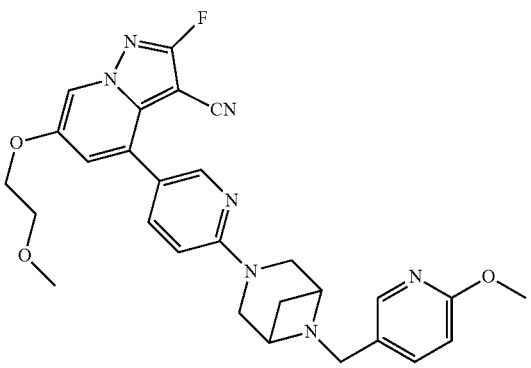 [SMILES: COCCOc1cc(-c2ccc(N3CC4CC(C3)N4Cc3ccc(OC)nc3)nc2)c2c(C#N)c(F)nn2c1]

To a solution of 2-fluoro-6-hydroxy-4-(6-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-3-acetonitrile (30 mg, 0.06 mmol) in DMF (2.0 mL) were added 2-bromoethyl methyl ether (9 mg, 0.06 mmol) and potassium carbonate (8.3 mg, 0.06 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (28 mg). $^1$HNMR (400 MHz, DMSO-$d_6$) δ 8.65 (d, 1H), 8.42 (d, 1H), 8.07 (d, 1H), 7.87 (d, 1H), 7.70 (d, 1H), 7.45 (d, 1H), 6.76-6.81 (m, 2H), 4.23-4.25 (m, 2H), 3.82 (s, 3H), 3.67-3.71 (m, 7H), 3.49-3.51 (m, 5H), 2.51 (d, 1H), 1.61 (d, 1H), 1.23 (s, 1H). m/z=530[M+1]⁺.

Step C: 6-(2-methoxyethoxy)-4-(6-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-3-amine

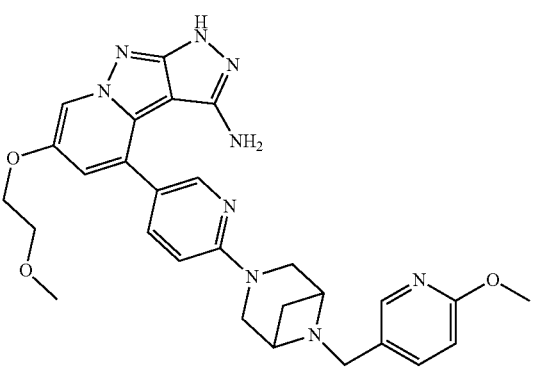 [SMILES: COCCOc1cc(-c2ccc(N3CC4CC(C3)N4Cc3ccc(OC)nc3)nc2)c2c3c(N)n[nH]c3nn2c1]

To a solution of 2-fluoro-6-(2-methoxyethoxy)-4-(6-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-3-acetonitrile (20 mg, 0.04 mmol) in DMF (2.0 mL) was added hydrazine hydrate (0.2 mL), and the mixture was heated to 100° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by reverse phase column chromatography to obtain the trifluoroacetate of the product (3.3 mg). $^1$HNMR (400 MHz, DMSO-$d_6$) δ 10.51 (brs, 2H), 9.56 (s, 1H), 9.37 (s, 1H), 8.38-8.49 (m, 3H), 7.86-7.89 (m, 2H), 7.32 (d, 1H), 6.92-6.94 (m, 1H), 6.80 (d, 1H), 4.64 (m, 3H), 4.46 (d, 2H), 4.22-4.25 (m, 4H), 3.87-3.90 (m, 5H), 3.70 (s, 2H), 3.32 (s, 3H), 2.09-2.10 (m, 1H). m/z=542[M+1]⁺.

Example 2

6-bromo-4-(6-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 2)

Step A: 4-(benzyloxy)-6-bromo-2-fluoropyrazolo[1,5-a]pyridine-3-carbaldehyde

To a solution of 4-(benzyloxy)-6-bromo-2-fluoropyrazolo[1,5-a]pyridine (380 mg, 1.2 mmol) in DMF (10 mL) was added dropwise with phosphorus oxychloride (1.0 g, 6.5 mmol) at 0° C., and after the addition, the mixture was warmed to room temperature and reacted overnight. The reaction solution was poured into ice water (100 mL), adjusted to pH 7 with 2 N NaOH solution, and extracted with ethyl acetate. The organic phases were combined, concentrated under reduced pressure, and separated by column chromatography to obtain the product (400 mg). m/z=350 [M+1]⁺.

Step B: 6-bromo-2-fluoro-4-hydroxypyrazolo[1,5-a]pyridine-3-carbaldehyde

To 4-(benzyloxy)-6-bromo-2-fluoropyrazolo[1,5-a]pyridine-3-carbaldehyde (100 mg, 0.28 mmol) and palladium on carbon (10 mg) was added methanol (10.0 mL) at room temperature, and the mixture was purged with a hydrogen balloon three times, and reacted at room temperature overnight. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product, m/z=259[M+1]⁺. ¹HNMR (400 MHz, DMSO-d₆) δ 11.96 (s, 1H), 10.03 (s, 1H), 8.76 (d, 1H), 7.13 (d, 1H).

Step C: 6-bromo-2-fluoro-3-formylpyrazolo[1,5-a]pyridin-4-yl trifluoromethanesulfonate

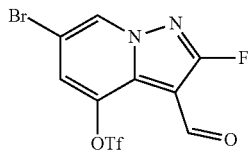 [SMILES: O=Cc1c(F)nn2cc(Br)cc(OS(=O)(=O)C(F)(F)F)c12]

To a solution of 6-bromo-2-fluoro-4-hydroxypyrazole[1,5-a]pyridine-3-carbaldehyde (52 mg, 0.2 mmol) in DMF (5 mL) were added N-phenyl-bis(trifluoromethanesulfonimide) (71 mg, 0.2 mmol) and diisopropylethylamine (78 mg, 0.6 mmol), and the mixture was reacted at room temperature for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (85 mg), m/z=392[M+1]⁺.

Step D: 6-bromo-2-fluoro-4-(6-(6-(((6-methoxypyridin-3-yl)methyl)-3,6-diazabicyclo[3.3.1]heptan-3-yl)pyridin-3-yl)pyrazolo[1,5-a]pyridine-3-carbaldehyde

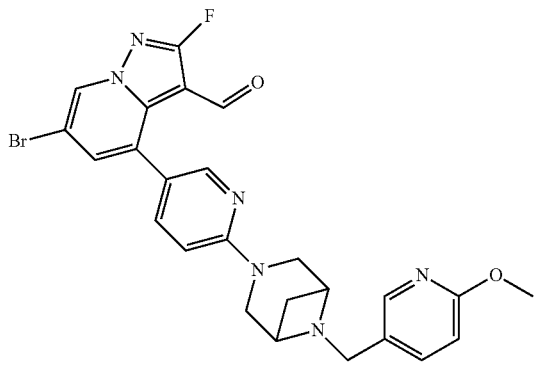 [SMILES: COc1ccc(CN2C3CC2CN(c2ccc(-c4cc(Br)cn5nc(F)c(C=O)c45)cn2)C3)cn1]

The operation was performed as in step F of Example 7 to obtain the product (10 mg). m/z=537[M+1]⁺.

Step E: 6-bromo-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine

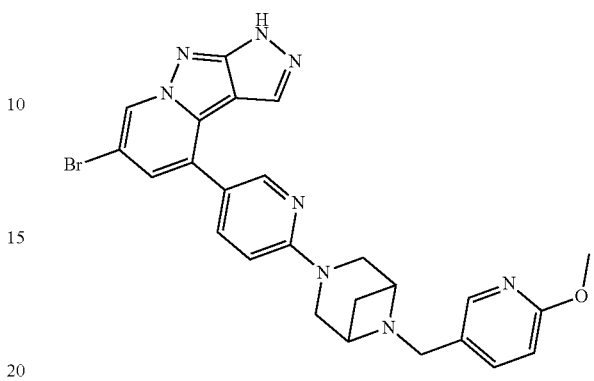

The operation was performed as in step H of Example 7 to obtain the product (5.4 mg). m/z=531[M+1]⁺. ¹H NMR (400 MHz, DMSO-d₆) δ 12.96 (s, 1H), 9.67 (d, 1H), 8.717 (d, 1H), 8.12-8.13 (m, 2H), 7.87-7.88 (m, 2H), 7.74 (dd, 1H), 6.92 (d, 1H), 6.71 (d, 1H), 3.74-3.88 (m, 5H), 3.72 (d, 2H), 3.48 (s, 2H), 3.34 (s, 2H), 2.49 (d, 1H), 1.58 (d, 1H).

Example 3

6-(benzyloxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 3)

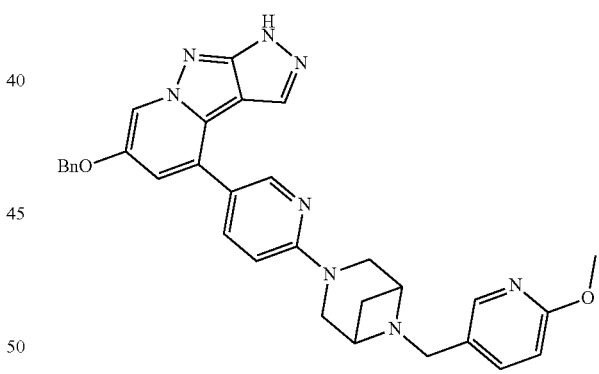

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added benzyl chloride (38 mg, 0.3 mmol) and potassium carbonate (83 mg, 0.6 mmol), and the mixture was heated to 60° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (35 mg). m/z=559[M+1]⁺. ¹H NMR (400 MHz, DMSO-d₆) δ 12.65 (s, 1H), 8.60-8.63 (dd, 2H), 8.08-8.10 (m, 2H), 7.69 (dd, 1H), 7.67 (s, 1H), 7.51-7.53 (m, 2H), 7.40-7.44 (m, 2H), 7.34-7.37 (m, 2H), 6.91 (d, 1H), 6.77 (d, 1H), 5.25 (s, 2H), 3.74-3.80 (m, 5H), 3.68 (brs, 2H), 3.51-3.58 (m, 4H), 2.51 (d, 1H), 1.58 (d, 1H).

Example 4

4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 4)

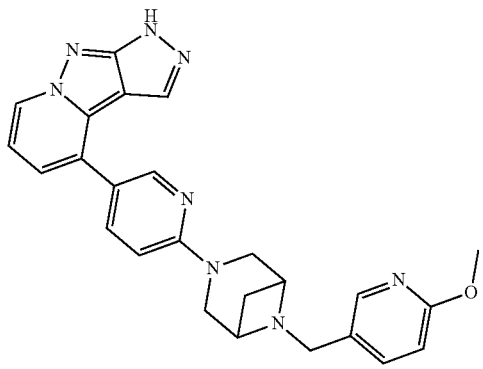 [SMILES: COc1ccc(CN2C3CC2CN(c2ccc(-c4cccn5nc6[nH]ncc6c45)cn2)C3)cn1]

To a solution of 6-bromo-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (30 mg, 0.056 mmol) in tetrahydrofuran was added palladium on carbon (3 mg), and the mixture was reacted under 1 atmosphere of hydrogen at room temperature, and filtered. The filtrate was concentrated under reduced pressure, and separated by column chromatography to obtain the product (1.6 mg). m/z=453[M+1]$^+$. $^1$H NMR (400 MHz, DMSO-d$_6$) δ 12.71 (s, 1H), 8.81 (d, 1H), 8.64 (d, 1H), 8.11 (d, 2H), 7.70 (s, 2H), 7.52 (d, 1H), 7.21 (m, 1H), 6.92 (d, 1H), 6.79 (d, 1H), 3.81 (s, 3H), 3.73-3.79 (m, 2H), 3.65-3.70 (m, 2H), 3.55-3.62 (m, 2H), 3.49-3.53 (s, 2H), 2.53 (d, 1H), 1.61 (d, 1H).

Example 5

4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine-6-carbonitrile (Compound 5)

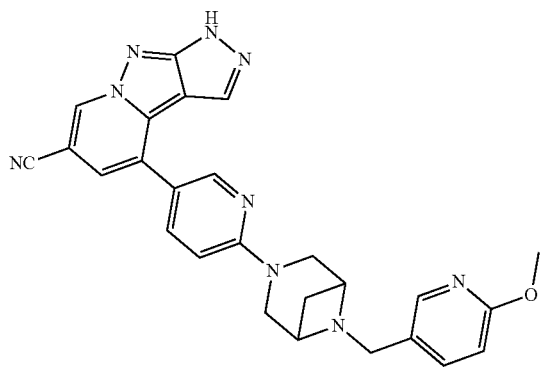 [SMILES: COc1ccc(CN2C3CC2CN(c2ccc(-c4cc(C#N)cn5nc6[nH]ncc6c45)cn2)C3)cn1]

To a solution of 6-bromo-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (30 mg, 0.057 mmol) in DMF (5 mL) were added tetrakis(triphenylphosphine)palladium (6.6 mg, 0.006 mol) and zinc cyanide (6.7 mg, 0.057 mol), and the mixture was heated to 100° C. and reacted for 12 h. The reaction solution was concentrated under reduced pressure, and separated by column chromatography to obtain the product (14 mg), m/z=478[M+1]$^+$. $^1$H NMR (400 MHz, DMSO-d$_6$) δ 13.01 (s, 1H), 9.66 (d, 1H), 8.67 (d, 1H), 8.10-8.15 (m, 2H), 7.81-7.82 (m, 2H), 7.72 (dd, 1H), 6.95 (d, 1H), 6.79 (d, 1H), 3.77-3.83 (m, 5H), 3.70 (d, 2H), 3.53 (s, 2H), 3.33 (s, 2H), 2.52 (d, 1H), 1.61 (d, 1H).

Example 6

4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-6-amine (Compound 6)

Step A: 6-((diphenylmethylene)amino)-2-fluoro-4-(6-(6-(((6-methoxypyridin-3-yl)methyl)-3,6-diazabicyclo[3.1.1]heptan-3-yl)pyridin-3-yl)pyrazolo[1,5-a]pyridine-3-carbaldehyde

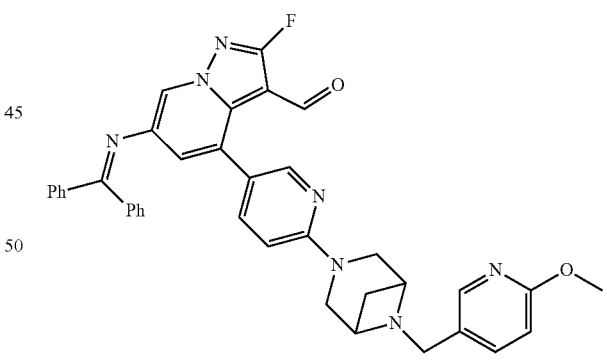

To a solution of 6-bromo-2-fluoro-4-(6-(((6-methoxypyridin-3-yl)methyl)-3,6-diazabicyclo[3.1.1]heptan-3-yl)pyridin-3-yl)pyrazolo[1,5-a]pyridine-3-carbaldehyde (180 mg, 0.34 mmol) in dioxane (30 mL) were added benzophenone imine (60 mg, 0.34 mmol), tris(dibenzylideneacetone)dipalladium-chloroform adduct (5.1 mg, 0.005 mmol), Xantphos (11 mg, 0.005 mmol) and cesium carbonate (330 mg, 1.0 mmol), and the mixture was heated to 100° C. and reacted for 12 h. The reaction solution was concentrated under reduced pressure, and separated by column chromatography to obtain the product (130 mg), m/z=638[M+1]$^+$.

Step B: 6-amino-2-fluoro-4-(6-(6-((6-methoxypyridin-3-yl)methyl)-3,6-diazabicyclo[3.1.1]heptan-3-yl)pyridin-3-yl)pyrazolo[1,5-a]pyridine-3-carbaldehyde

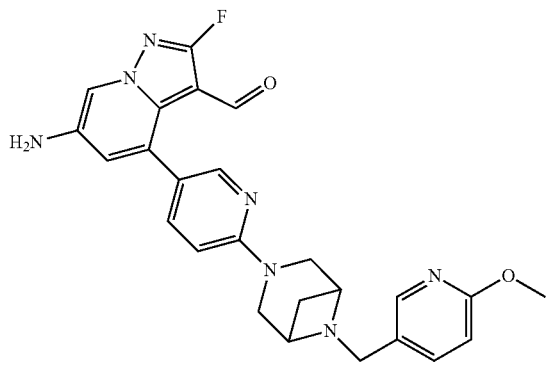 [SMILES: COc1ccc(CN2C3CC2CN(c2ccc(-c4cc(N)cn5nc(F)c(C=O)c45)cn2)C3)cn1]

To 6-((diphenylmethylene)amino)-2-fluoro-4-(6-((6-methoxypyridin-3-yl)methyl)-3,6-diazabicyclo[3.1.1]heptan-3-yl)pyridin-3-yl)pyrazolo[1,5-a]pyridine-3-carbaldehyde (30 mg, 0.05 mmol) in tetrahydrofuran (3 mL) was added hydrochloric acid (3 N, 2 mL), and the mixture was stirred at room temperature for 12 h. The reaction solution was concentrated under reduced pressure, and separated by column chromatography to obtain the product (22 mg), m/z=474[M+1]+.

Step C: 4-(6-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-6-amine

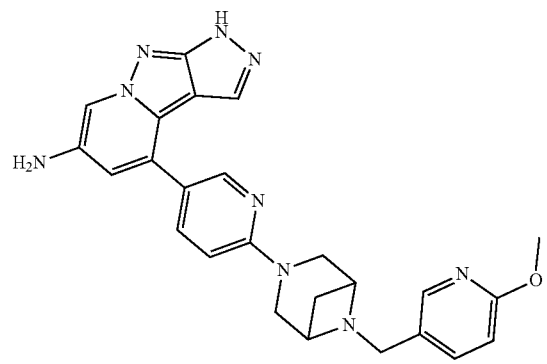 [SMILES: COc1ccc(CN2C3CC2CN(c2ccc(-c4cc(N)cn5nc6[nH]ncc6c45)cn2)C3)cn1]

The operation was performed as in step H of Example 7 to obtain the product (2.7 mg), m/z=468[M+1]+. 1H NMR (400 MHz, DMSO-d6) δ 12.43 (s, 1H), 8.56 (d, 1H), 8.11 (d, 1H), 8.03 (m, 2H), 7.69-7.72 (m, 1H), 7.50 (s, 1H), 7.01 (s, 1H), 6.92 (d, 1H), 6.79 (d, 1H), 5.24 (s, 2H), 3.75-3.83 (m, 5H), 3.70 (d, 2H), 3.53 (m, 4H), 2.51 (d, 1H), 1.61 (d, 1H).

Example 7

6-(2-methoxyethoxy)-4-(6-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 7)

Step A: tert-butyl((mesitylsulfonyl)oxy)carbamate

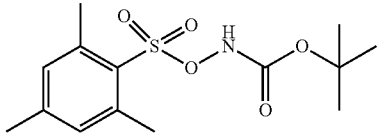 [SMILES: Cc1cc(C)c(S(=O)(=O)ONC(=O)OC(C)(C)C)c(C)c1]

To a solution of 2,4,6-trimethylbenzenesulfonyl chloride (20.0 g, 91.5 mmol) and tert-butyl N-hydroxycarbamate (12.2 g, 91.5 mmol) in methyl tert-butyl ether (500 mL) was slowly added dropwise with triethylamine (13.0 mL, 93.3 mmol) with a constant pressure dropping funnel in an ice bath with stirring, and the reaction system was kept at a temperature below 5° C. during the addition. The reaction solution was stirred in an ice bath for 4 h, filtered under reduced pressure to remove triethylamine hydrochloride, and rinsed with methyl tert-butyl ether three times. The filtrates were combined, and concentrated under reduced pressure in a water bath at a temperature below 15° C. to remove most of the methyl tert-butyl ether. The residue was added with n-hexane in an ice bath, stirred vigorously for 10 min to precipitate a large quantity of white solids, and filtered under reduced pressure. The filter cake was washed twice with n-hexane, and dried under vacuum to obtain the product (26.1 g). m/z=316[M+1]+.

Step B: 2-[(aminooxy)sulfonyl]-1,3,5-trimethylbenzene

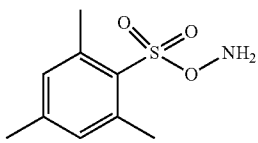

To trifluoroacetic acid (80 mL) was added tert-butyl ((mesitylsulfonyl)oxy)carbamate (10.0 g, 31.7 mmol) in batches at 0° C. After the addition, the reaction system was stirred at 0° C. for 3 h. After the reaction was completed as determined by TLC, the reaction system was poured into a large amount of ice water, stirred for 15 min to precipitate a large quantity of white solids, and filtered under reduced pressure. The filter cake was washed with a large amount of water until the pH of the solid was neutral, and filtered under reduced pressure to obtain the solid with a water content of about 20%, which can be directly used in the next step without further purification.

Step C: 2,4,6-trimethylbenzenesulfonate 1-amino-3-bromo-5-benzyloxypyridin-1-ium

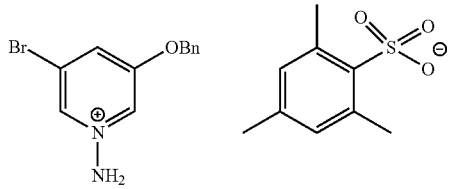 [SMILES: N[n+]1cc(Br)cc(OCc2ccccc2)c1 ; Cc1cc(C)c(S(=O)(=O)[O-])c(C)c1]

To a solution of 2-[(aminooxy)sulfonyl]-1,3,5-trimethylbenzene (6.8 g, 31.7 mmol) in dichloromethane (50 mL) was added 3-bromo-5-benzyloxypyridine (6.0 g, 32.0 mmol) at 0° C., and the mixture was stirred at 0° C. for 3 h to precipitate a large quantity of white solids. After the reaction was completed, the reaction system was added with ether (50 mL) at 0° C., stirred for 10 min, and filtered under reduced pressure. The filtrate was rinsed with ether, and dried under vacuum to obtain the product (15 g), which can be directly used in the next step without further purification. m/z=281[M+1]$^+$.

Step D: 6-(benzyloxy)-4-bromo-2-fluoropyrazolo[1,5-a]pyridine and 4-(benzyloxy)-6-bromo-2-fluoropyrazolo[1,5-a]pyridine

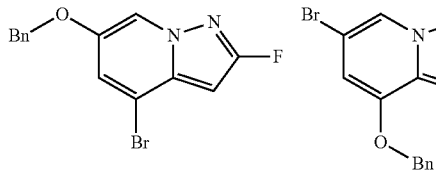

To a solution of 2,4,6-trimethylbenzenesulfonate 1-amino-3-bromo-5-benzyloxypyridin-1-ium (1.0 g, 2.3 mmol) in DMF (30 mL) was added potassium carbonate (1.4 g, 10.0 mmol). The reaction system was cooled to 0° C., added with 2,2-difluoroethenyl p-toluenesulfonate (0.5 g, 2.3 mmol) in batches, warmed to room temperature and stirred for 1 h, and stirred at 90° C. for another 1 h. After the reaction was completed, the reaction solution was cooled to room temperature, added with water to quench the reaction, and extracted with ethyl acetate. The organic phases were combined, washed with water, concentrated under reduced pressure, and separated by column chromatography to obtain 6-(benzyloxy)-4-bromo-2-fluoropyrazolo[1,5-a]pyridine (118 mg), $^1$HNMR (400 MHz, CDCl$_3$) δ 7.90 (s, 1H), 7.34-7.44 (m, 5H), 7.32 (s, 1H), 6.08 (d, 1H), 5.02 (s, 2H), m/z=322[M+1]$^+$, 4-(benzyloxy)-6-bromo-2-fluoropyrazolo[1,5-a]pyridine (280 mg), $^1$HNMR (400 MHz, CDCl$_3$) δ 8.07 (s, 1H), 7.80-7.82 (m, 5H), 6.61 (s, 1H), 6.18 (d, 1H), 5.15 (s, 2H), m/z=322[M+1]$^+$.

Step E: 6-(benzyloxy)-4-bromo-2-fluoropyrazolo[1,5-a]pyridine-3-carbaldehyde

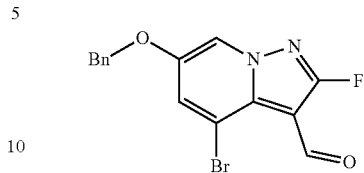

To a solution of 6-(benzyloxy)-4-bromo-2-fluoropyrazolo[1,5-a]pyridine (380 mg, 1.2 mmol) in DMF (10 mL) was added dropwise with phosphorus oxychloride (1.0 g, 6.5 mmol) at 0° C., and after the addition, the mixture was warmed to room temperature and reacted overnight. The reaction solution was poured into ice water (100 mL), adjusted to pH 7 with 2 N NaOH solution, and extracted with ethyl acetate. The organic phases were combined, concentrated under reduced pressure, and separated by column chromatography to obtain the product (400 mg). m/z=350 [M+1]$^+$; $^1$HNMR (400 MHz, DMSO-d$_6$) δ 10.49 (s, 1H), 8.80-8.87 (m, 1H), 8.09 (d, 1H), 7.45-7.58 (m, 2H), 7.36-7.44 (m, 3H), 5.20 (s, 2H).

Step F: 6-(benzyloxy)-2-fluoro-4-(6-((6-methoxypyridin-3-yl)methyl)-3,6-diazabicyclo[3.1.1]heptan-3-yl)pyridin-3-yl)pyrazolo[1,5-a]pyridine-3-carbaldehyde

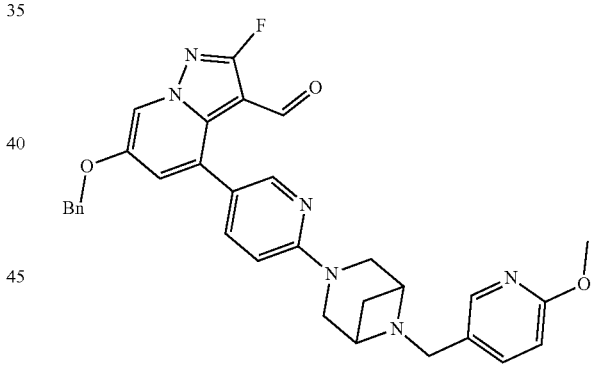

To 6-(benzyloxy)-4-bromo-2-fluoropyrazolo[1,5-a]pyridine (23 mg, 0.067 mmol) were added 6-((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane (28 mg, 0.067 mmol) (prepared by the method in reference WO2018/71447), tetrakis(triphenylphosphine)palladium (15 mg, 0.013 mol), potassium carbonate (36 mg, 0.264 mol) 1,4-dioxane (2 mL), and H$_2$O (1 mL), and the mixture was purged with nitrogen three times, and reacted at 90° C. for 2 h. After the reaction was completed, and the product was generated as determined by LCMS, the reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (25 mg). m/z=565[M+1]$^+$.

Step G: 2-fluoro-6-hydroxy-4-(6-(6-((6-methoxy-pyridin-3-yl)methyl)-3,6-diazabicyclo[3.1.1]heptan-3-yl)pyridin-3-yl)pyrazolo[1,5-a]pyridine-3-carbaldehyde

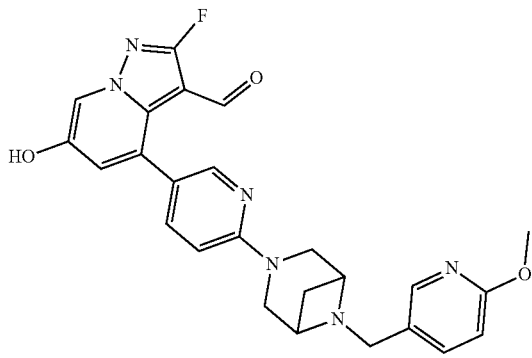 [SMILES: COc1ccc(CN2C3CC2CN(c2ccc(-c4cc(O)cn5nc(F)c(C=O)c45)cn2)C3)cn1]

To 6-(benzyloxy)-2-fluoro-4-(6-(6-((6-methoxypyridin-3-yl)methyl)-3,6-diazabicyclo[3.1.1]heptan-3-yl)pyridin-3-yl)pyrazolo[1,5-a]pyridine-3-carbaldehyde (100 mg, 0.18 mmol) and palladium on carbon (5 mg) was added methanol (10.0 mL), and the mixture was purged with a hydrogen balloon three times, and reacted at room temperature overnight. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product. $^1$HNMR (400 MHz, DMSO-d$_6$) δ 10.42 (s, 1H), 9.37 (s, 1H), 8.32 (s, 1H), 8.23 (s, 1H), 8.09 (s, 1H), 7.79 (d, 1H), 7.70 (d, 1H), 7.25 (s, 1H), 6.78 (t, 2H), 3.82 (s, 3H), 3.64-3.75 (m, 4H), 3.48-3.60 (m, 4H), 2.51 (d, 1H), 1.60 (d, 1H). m/z=475[M+1]$^+$.

Step H: 4-(6-(6-((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol

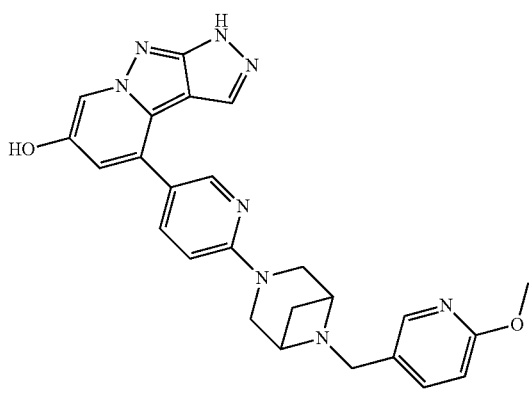 [SMILES: COc1ccc(CN2C3CC2CN(c2ccc(-c4cc(O)cn5nc6[nH]ncc6c45)cn2)C3)cn1]

To a solution of 2-fluoro-6-hydroxy-4-(6-(6-((6-methoxy-pyridin-3-yl)methyl)-3,6-diazabicyclo[3.1.1]heptan-3-yl)pyridin-3-yl)pyrazolo[1,5-a]pyridine-3-carbaldehyde (250 mg, 0.53 mmol) in DMF (5.0 mL) was added hydrazine hydrate (0.5 mL), and the mixture was heated to 100° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (170 mg). m/z=469[M+1]$^+$, $^1$HNMR (400 MHz, DMSO-d$_6$) δ 12.59 (s, 1H), 9.97 (s, 1H), 8.61 (s, 1H), 8.24 (d, 2H), 8.06-8.11 (m, 2H), 7.72 (dd, 1H), 7.58 (s, 1H), 7.15 (d, 1H), 6.93 (d, 1H), 6.79 (d, 1H), 3.72-3.83 (m, 5H), 3.69 (s, 2H), 3.35 (brs, 3H), 2.51 (d, 1H), 1.61 (d, 1H).

Step I: 6-(2-methoxyethoxy)-4-(6-(6-((6-methoxy-pyridin-3-yl)methyl)-3,6-diazabicyclo[3.3.1]heptan-3-yl)pyridin-3-yl)-1H-pyrazolo[3',4':3,4]pyrazolo[1,5-a]pyridine

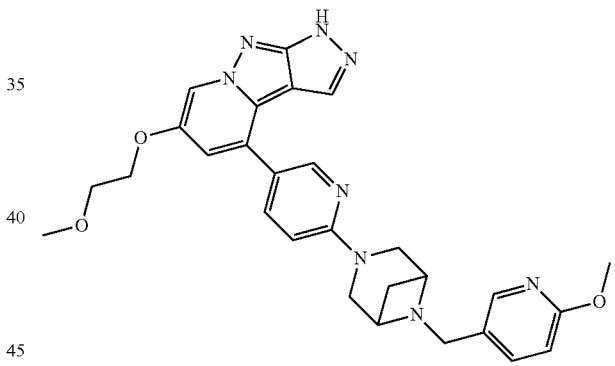

To a solution of 4-(6-(6-((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 2-bromoethyl methyl ether (40 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (84 mg). $^1$HNMR (400 MHz, DMSO-d$_6$) δ 12.66 (s, 1H), 8.65 (d, 1H), 8.56 (d, 1H), 8.13 (m, 2H), 7.69-7.72 (m, 1H), 7.63 (s, 1H), 7.30 (s, 1H), 6.93 (d, 1H), 6.79 (d, 1H), 4.26-4.28 (m, 2H), 3.83 (s, 3H), 3.72-3.79 (m, 6H), 3.47-3.70 (m, 7H), 2.51 (d, 1H), 1.61 (d, 1H), m/z=527 [M+1]$^+$.

Example 8

1-((4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-6-yl)oxy)-2-methylpropan-2-ol (Compound 8)

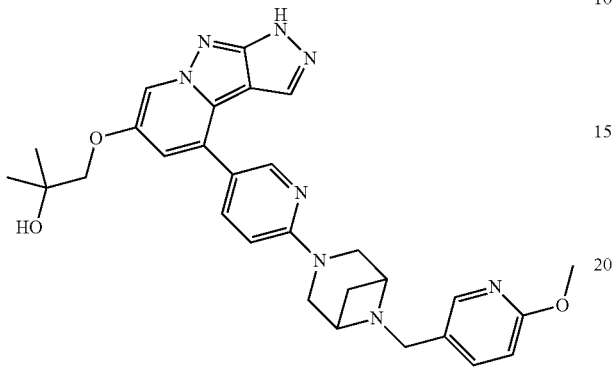

To 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.32 mmol), 2-methyl propylene oxide (350 mg, 4.8 mmol), and potassium carbonate (133 mg, 0.96 mmol) was added DMF (5.0 mL), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by reverse phase column chromatography to obtain the trifluoroacetate of the product (78 mg). m/z=541[M+1]$^+$.

Example 9

6-ethoxy-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 9)

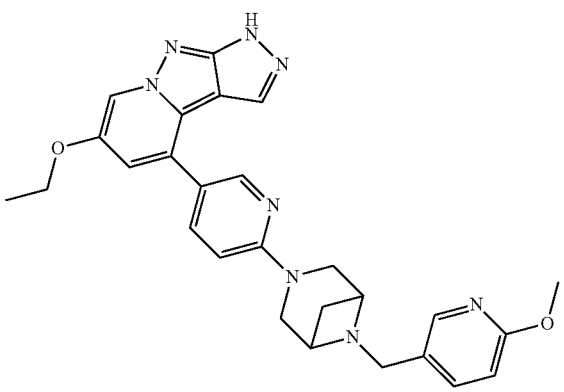 [SMILES: CCOc1cc(-c2ccc(N3CC4CC(C3)N4Cc3ccc(OC)nc3)nc2)c2c3cn[nH]c3nn2c1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 2-iodoethane (47 mg, 0.3 mmol) and potassium carbonate (83 mg, 0.6 mmol), and the mixture was heated to 60° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (125 mg). $^1$H NMR (400 MHz, DMSO-d$_6$) δ 12.66 (s, 1H), 8.65 (d, 1H), 8.53 (d, 1H), 8.10-8.12 (m, 2H), 7.62-7.72 (m, 2H), 7.27 (s, 1H), 6.93 (d, 1H), 6.79 (d, 1H), 4.16-4.21 (m, 2H), 3.82 (s, 3H), 3.77 (d, 2H), 3.67 (d, 2H), 3.56 (m, 2H), 3.51 (s, 2H), 2.51 (d, 1H), 1.61 (d, 1H), 1.39-1.42 (m, 3H), m/z=497[M+1]$^+$.

Example 10

2-((4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-6-yl)oxy)ethan-1-ol (Compound 10)

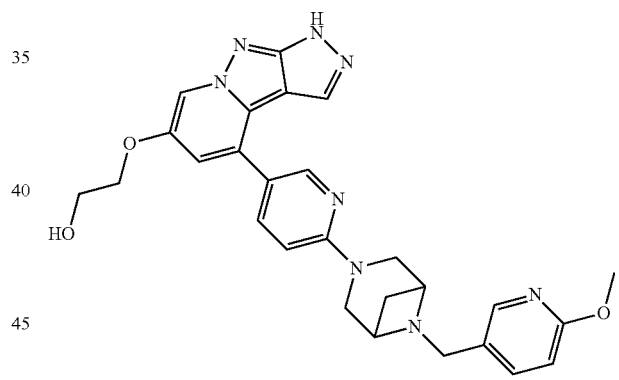

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added ethylene carbonate (26 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (30 mg), m/z=513[M+1]$^+$. $^1$H NMR (400 MHz, DMSO-d$_6$) δ 12.64 (s, 1H), 8.62 (d, 1H), 8.53 (d, 1H), 8.09 (dt, 2H), 7.72-7.63 (m, 1H), 7.60 (s, 1H), 7.26 (d, 1H), 6.90 (d, 1H), 6.75 (dd, 1H), 4.96 (t, 1H), 4.14 (t, 2H), 3.80 (s, 3H), 3.80-3.73 (m, 4H), 3.67 (d, 2H), 3.58 (s, 1H), 3.51 (s, 2H), 2.51 (d, 1H), 1.57 (t, 1H), 1.23 (d, 1H).

Example 11

6-butoxy-((4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-6-yl)oxy)ethan-1-ol (Compound 11)

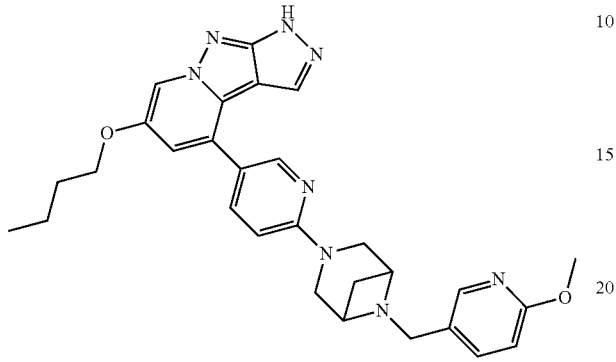

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added bromobutane (41 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (43 mg), m/z=525[M+1]$^+$, $^1$H NMR (400 MHz, DMSO-d$_6$) δ 12.63 (s, 1H), 8.63 (d, 1H), 8.51 (d, 1H), 8.09 (dt, 2H), 7.68 (dd, 1H), 7.60 (s, 1H), 7.25 (d, 1H), 6.89 (d, 1H), 6.76 (d, 1H), 4.11 (t, 2H), 3.81 (s, 3H), 3.80-3.79 (m, 2H), 3.76 (d, 1H), 3.67 (d, 2H), 3.51 (s, 2H), 2.51 (d, 1H), 1.79-1.69 (m, 2H), 1.58 (d, 1H), 1.53-1.42 (m, 2H), 1.22 (d, 1H), 0.95 (t, 3H).

Example 12

6-(3-fluoropropoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 12)

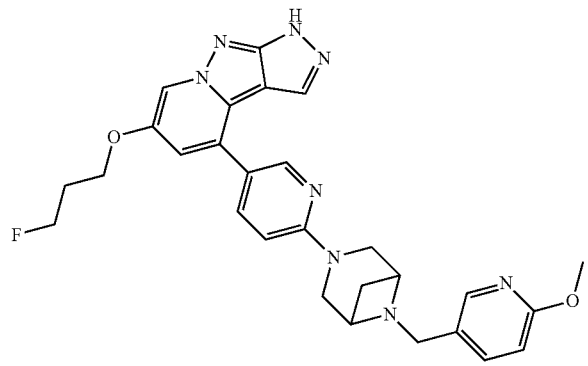 [SMILES: COc1ccc(CN2C3CC2CN(c2ccc(-c4cc(OCCCF)cn5nc6[nH]ncc6c45)cn2)C3)cn1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 1-bromo-3-fluoropropane (42 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (35 mg), m/z=529[M+1]$^+$, $^1$H NMR (400 MHz, DMSO-d$_6$) δ 12.65 (s, 1H), 8.63 (d, 1H), 8.57 (d, 1H), 8.09 (dd, 1H), 8.08 (s, 1H), 7.68 (dd, 1H), 7.61 (s, 1H), 7.28 (d, 1H), 6.90 (d, 1H), 6.76 (d, 1H), 4.71 (t, 1H), 4.59 (t, 1H), 4.23 (t, 2H), 3.81 (s, 3H), 3.80-3.72 (m, 2H), 3.67 (d, 2H), 3.57 (s, 2H), 3.51 (s, 2H), 2.51 (d, 1H), 2.16 (dt, 2H), 1.58 (d, 1H).

Example 13

6-(4-fluorobutoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 13)

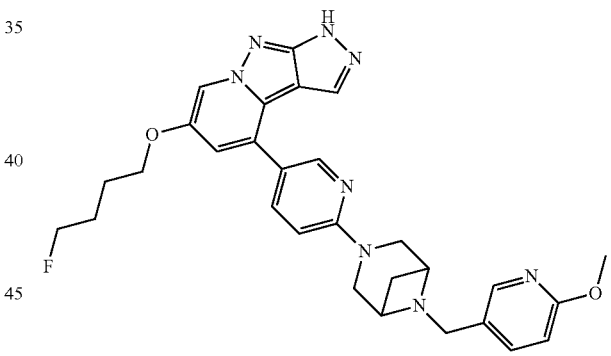

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 1-bromo-4-fluorobutane (47 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (60 mg), m/z=543[M+1]$^+$, $^1$H NMR (400 MHz, DMSO-d$_6$) δ 12.64 (s, 1H), 8.63 (d, 1H), 8.53 (d, 1H), 8.13-8.05 (m, 2H), 7.68 (dd, 1H), 7.61 (s, 1H), 7.27 (d, 1H), 6.90 (d, 1H), 6.76 (d, 1H), 4.59 (s, 1H), 4.47 (t, 1H), 4.20-4.12 (m, 2H), 3.81 (s, 3H), 3.80-3.71 (m, 2H), 3.67 (d, 2H), 3.58 (s, 2H), 3.51 (s, 2H), 2.52 (d, 1H), 1.87 (s, 2H), 1.86-1.76 (m, 2H), 1.58 (d, 1H).

Example 14

6-(2-chloroethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 14)

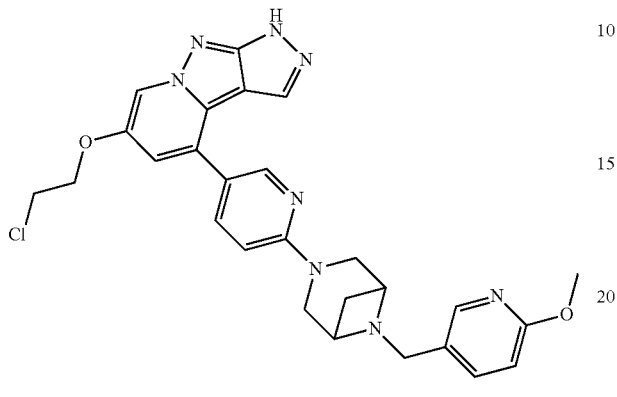

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 1-chloro-2-iodoethane (57 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (6 mg), m/z=531[M+1]$^+$, $^1$H NMR (400 MHz, DMSO-d$_6$) δ 12.67 (s, 1H), 8.62 (dd, 2H), 8.10 (dd, 1H), 8.09 (s, 1H), 7.68 (dd, 1H), 7.63 (s, 1H), 7.30 (d, 1H), 6.90 (d, 1H), 6.76 (d, 1H), 4.46-4.39 (m, 2H), 4.01 (dd, 2H), 3.81 (s, 3H), 3.76 (d, 2H), 3.67 (d, 2H), 3.57 (s, 2H), 3.51 (s, 2H), 2.58-2.50 (m, 1H), 1.58 (d, 1H).

Example 15

6-(2-bromoethoxy)-4-(6-(6-(((6-methoxypyridin-3-yl)methyl)-3,3.1]heptan-3-yl)pyridin-3-yl)-1H-pyrazolo[3',4':3,4]pyrazolo[1,5-a]pyridine (Compound 15)

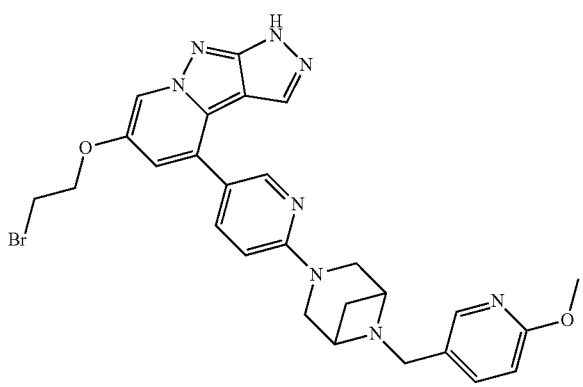 [SMILES: COc1ccc(CN2C3CC2CN(c2ccc(-c4cc(OCCCl)cn5nc6[nH]ncc6c45)cn2)C3)cn1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added (2-bromoethyl) trifluoromethanesulfonate (77 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (16 mg), m/z=575[M+1]$^+$, $^1$H NMR (400 MHz, DMSO-d$_6$) δ 12.68 (s, 1H), 8.61-8.67 (dd, 2H), 8.11-8.15 (m, 2H), 7.71 (d, 1H), 7.64 (s, 1H), 7.32 (d, 1H), 6.93 (d, 1H), 6.80 (d, 1H), 4.53 (t, 2H), 3.87-3.90 (m, 2H), 3.53-3.82 (m, 11H), 2.51 (d, 1H), 1.51-1.62 (m, 1H).

Example 16

6-(2-fluoroethoxy)-4-(5-(6-(((6-methoxypyridin-3-yl)methyl)-3,6-diazabicyclo[3.3.1]heptan-3-yl)pyrazin-2-yl)-1H-pyrazolo[3',4':3,4]pyrazolo[1,5-a]pyridine (Compound 16)

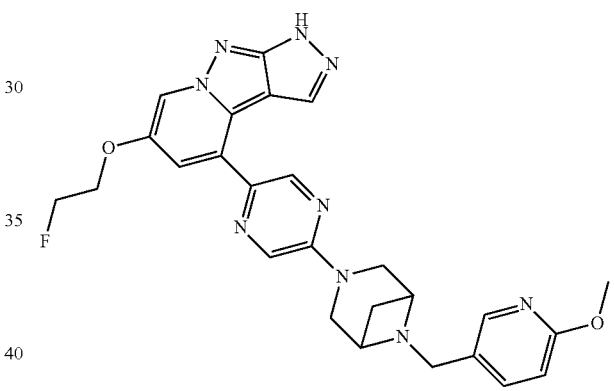

Step A: tert-butyl 3-(5-chloropyrazin-2-yl)-3,6-diazabicyclo[3.1.1]heptane-6-carboxylate

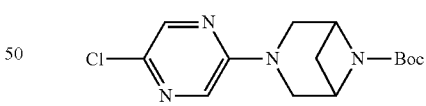

To a 250 mL single-necked flask were added tert-butyl 2-chloro-5-fluoropyrazine (6.9 g, 0.052 mol) and 3,6-diazabicyclo[3.1.1]heptane-6-carboxylate (11.5 g, 0.058 mol) at room temperature, and the mixture was added with DMSO (20 mL), and reacted at 120° C. overnight. The reaction solution was concentrated under reduced pressure to remove DMSO, dissolved with methanol, slowly added with saturated sodium hydroxide solution in an ice water bath to adjust the pH to about 13, and stirred for 2 h. The methanol was concentrated under reduced pressure, extracted with dichloromethane, dried over anhydrous sodium sulfate, concentrated under reduced pressure, and separated by column chromatography to obtain the product (12 g, 74% yield). m/z=311[M+1]$^+$.

Step B: 3-(5-chloropyrazin-2-yl)-3,6-diazabicyclo[3.1.1]heptane dihydrochloride

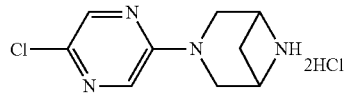 [SMILES: Clc1cnc(N2CC3CC(C2)N3)cn1]

To a 100 mL single-necked flask were added tert-butyl 3-(5-chloropyrazin-2-yl)-3,6-diazabicyclo[3.1.1]heptane-6-carboxylate (5.0 g, 14 mmol), and a solution of HCl in dioxane (15 mL), and the mixture was stirred at room temperature for 2 h, and concentrated to obtain the residue, which was directly used in the next step. m/z=211[M+1]$^+$.

Step C: 3-(5-chloropyrazin-2-yl)-6-((6-methoxypyridin-3-yl)methyl)-3,6-diazabicyclo[3.1.1]heptane

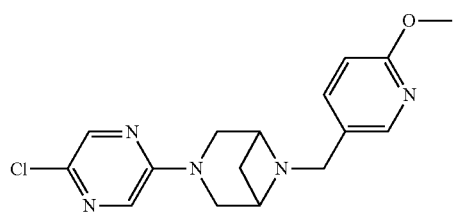 [SMILES: COc1ccc(CN2C3CC2CN(c2cnc(Cl)cn2)C3)cn1]

To a 100 mL single-neck flask were added 6-methoxynicotinaldehyde (0.21 g, 1.9 mmol), 3-(5-chloropyrazin-2-yl)-3,6-diazabicyclo[3.1.1]heptane dihydrochloride (0.4 g, 1.9 mmol), sodium acetate borohydride (1.2 g, 5.8 mmol), and dichloromethane (20 mL), and the mixture was stirred at room temperature for 12 h. After the reaction was completed as determined by TLC, the reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product 3-(5-chloropyrazin-2-yl)-6-((6-methoxypyridin-3-yl)methyl)-3,6-diazabicyclo[3.1.1]heptane (0.5 g, 80% yield). m/z=332[M+1]$^+$. $^1$HNMR (400 MHz, DMSO-d$_6$) δ 8.25 (d, 1H), 8.09 (s, 1H), 7.99 (d, 1H), 7.69 (dd, 1H), 6.78 (d, 1H), 3.83 (s, 3H), 3.71 (m, 4H), 3.51 (m, 4H), 2.51 (d, 1H), 1.59 (d, 1H).

Step D: 6-((6-methoxypyridin-3-yl)methyl)-3-(5-(4,4,5,5-tetramethyl-1,3,2-dioxaborolan-2-yl)pyrazin-2-yl)-3,6-diazabicyclo[3.1.1]heptane

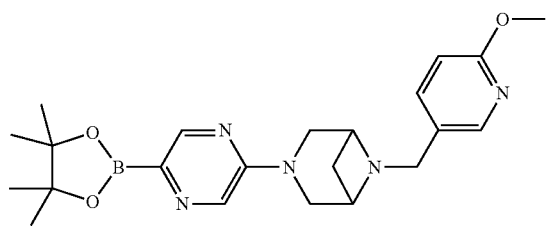

To a 10 mL sealed tube were added 3-(5-chloropyrazin-2-yl)-6-((6-methoxypyridin-3-yl)methyl)-3,6-diazabicyclo[3.1.1]heptane (44 mg, 0.132 mmol), bis(pinacolato)diboron (50 mg, 0.198 mmol), [1,1'-bis(diphenylphosphino)ferrocene]dichloropalladium(II) (10 mg, 0.013 mmol), potassium acetate (39 mg, 0.396 mmol), and 1,4-dioxane (20 mL), and the mixture was purged with nitrogen three times, and reacted at 100° C. for 3 h to obtain the product, which was directly used in the next step without post treatment.

Step E: 6-(benzyloxy)-2-fluoro-4-(5-(6-((6-methoxypyridin-3-yl)methyl)-3,6-diazabicyclo[3.1.1]heptan-3-yl)pyrazin-2-yl)pyrazolo[1,5-a]pyridine-3-carbaldehyde

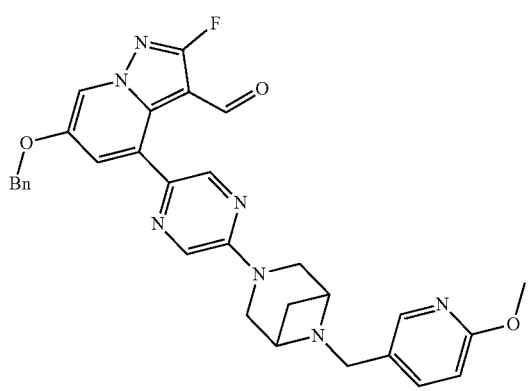 [SMILES: COc1ccc(CN2C3CC2CN(c2cnc(-c4cc(OCc5ccccc5)cn5nc(F)c(C=O)c45)cn2)C3)cn1]

To 6-(benzyloxy)-4-bromo-2-fluoropyrazolo[1,5-a]pyridine (23 mg, 0.067 mmol) were added 6-((6-methoxypyridin-3-yl)methyl)-3-(5-(4,4,5,5-tetramethyl-1,3,2-dioxaborolan-2-yl)pyrazin-2-yl)-3,6-diazabicyclo[3.1.1]heptane (28 mg, 0.067 mmol), tetrakis(triphenylphosphine)palladium (15 mg, 0.013 mol), potassium carbonate (36 mg, 0.264 mol) 1,4-dioxane (2 mL), and H$_2$O (1 mL), and the mixture was purged with nitrogen three times, and reacted at 90° C. for 2 h. After the reaction was completed, and the product was generated as determined by LCMS, the reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (20 mg). m/z=566[M+1]$^+$.

Step F: 2-fluoro-6-hydroxy-4-(5-(6-((6-methoxy-pyridin-3-yl)methyl)-3,6-diazabicyclo[3.1.1]heptan-3-yl)pyrazin-2-yl)pyrazolo[1,5-a]pyridine-3-carbaldehyde

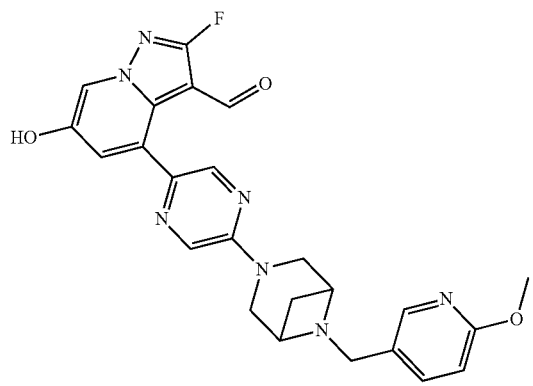 [SMILES: COc1ccc(CN2C3CC2CN(c2cnc(-c4cc(O)cn5nc(F)c(C=O)c45)cn2)C3)cn1]

To 6-(benzyloxy)-2-fluoro-4-(5-(6-((6-methoxypyridin-3-yl)methyl)-3,6-diazabicyclo[3.1.1]heptan-3-yl)pyrazin-2-yl)pyrazolo[1,5-a]pyridine-3-carbaldehyde (100 mg, 0.18 mmol) and palladium on carbon (5 mg) was added methanol (10.0 mL), and the mixture was purged with a hydrogen balloon three times, and reacted at room temperature overnight. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product, m/z=476[M+1]$^+$.

Step G: 4-(5-(6-((6-methoxypyridin-3-yl)methyl)-3,6-diazabicyclo[3.1.1]heptan-3-yl)pyrazin-2-yl)-1H-pyrazolo[3',4':3,4]pyrazolo[1,5-a]pyridin-6-ol

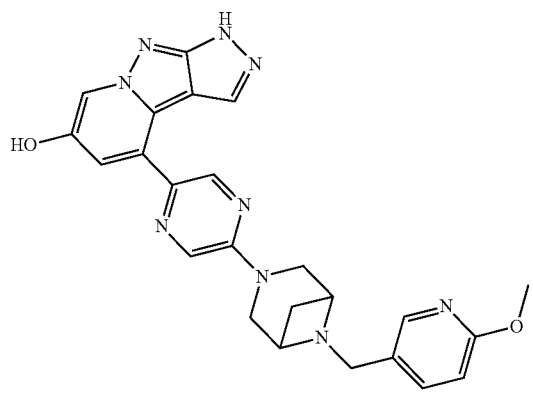 [SMILES: COc1ccc(CN2C3CC2CN(c2cnc(-c4cc(O)cn5nc6[nH]ncc6c45)cn2)C3)cn1]

To a solution of 2-fluoro-6-hydroxy-4-(5-(6-((6-methoxy-pyridin-3-yl)methyl)-3,6-diazabicyclo[3.1.1]heptan-3-yl)pyrazin-2-yl)pyrazolo[1,5-a]pyridine-3-carbaldehyde (250 mg, 0.53 mmol) in DMF (5.0 mL) was added hydrazine hydrate (0.5 mL), and the mixture was heated to 100° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (75 mg), m/z=470[M+1]$^+$.

Step H: 6-(2-fluoroethoxy)-4-(5-(6-((6-methoxy-pyridin-3-yl)methyl)-3,6-diazabicyclo[3.3.1]heptan-3-yl)pyrazin-2-yl)-1H-pyrazolo[3',4':3,4]pyrazolo[1,5-a]pyridine

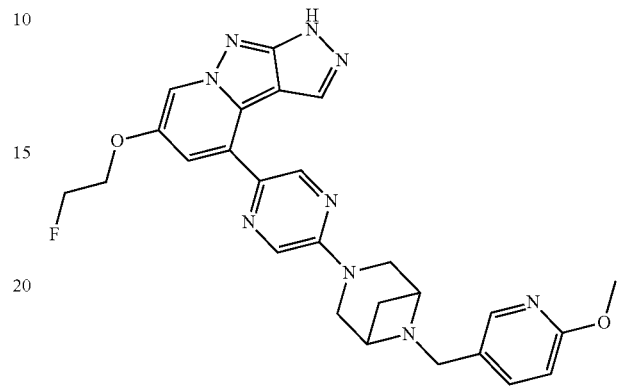

To a solution of 4-(5-(6-((6-methoxypyridin-3-yl)methyl)-3,6-diazabicyclo[3.1.1]heptan-3-yl)pyrazin-2-yl)-1H-pyrazolo[3',4':3,4]pyrazolo[1,5-a]pyridin-6-ol (150 mg, 0.3 mmol) in DMF (10.0 mL) were added 1-fluoro-2-iodoethane (52 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (34 mg), m/z=516[M+1]$^+$, H NMR (400 MHz, DMSO-$d_6$) δ 12.51 (s, 1H), 8.99 (s, 1H), 8.64 (d, 1H), 8.55 (s, 1H), 8.05-8.13 (m, 2H), 7.80 (d, 1H), 7.72 (dd, 1H), 6.79 (d, 1H), 4.90 (dd, 1H), 4.77 (d, 1H), 4.49 (dd, 2H), 3.83-3.87 (m, 5H), 3.65-3.71 (m, 4H), 3.56 (s, 2H), 2.56 (d, 1H), 1.62 (d, 1H).

Example 17

(2S)-2-(((4-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-6-yl)oxy)methyl)morpholine (Compound 17)

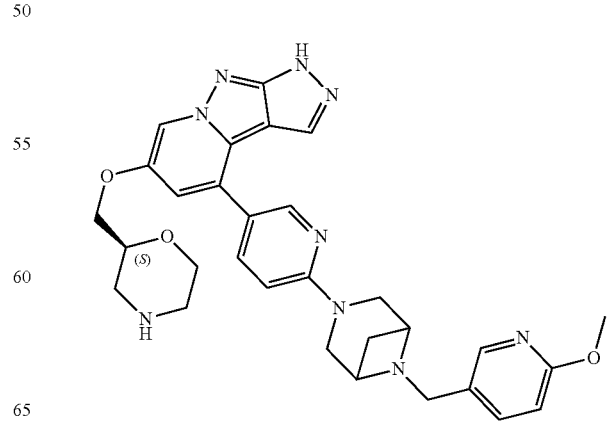

To a solution of 4-(5-(6-((6-methoxypyridin-3-yl)methyl)-3,6-diazabicyclo[3.1.1]heptan-3-yl)pyrazin-2-yl)-1H-pyrazolo[3',4':3,4]pyrazolo[1,5-a]pyridin-6-ol (150 mg, 0.3 mmol) in DMF (10.0 mL) were added tert-butyl (2S)-2-(bromomethyl)-4-morpholinocarboxylate (82 mg, 0.3 mmol) and potassium carbonate (83 mg, 0.6 mmol), and the mixture was heated to 80° C. and reacted for 12 h. The reaction solution was added with a solution of HCl in dioxane (1.5 mL, 4.0 M), and reacted for another 2 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (4.2 mg), m/z=567[M+1]⁺, ¹H NMR (400 MHz, DMSO-d₆): 12.65 (s, 1H), 8.65 (s, 1H), 8.54 (s, 1H), 8.10-8.12 (m, 2H), 7.63-7.72 (m, 2H), 7.30 (s, 1H), 6.90 (d, 1H), 6.76 (d, 1H), 4.10 (d, 2H), 3.76-3.83 (m, 8H), 3.64-3.72 (m, 3H), 3.48-3.63 (m, 6H), 2.58-2.76 (m, 2H), 1.58-1.61 (m, 1H).

Example 18

N,N-diethyl-4-(5-(6-(2-fluoroethoxy)-1H-pyrazolo[3',4':3,4]pyrazolo[1,5-a]pyridin-4-yl)pyridin-2-yl)piperazine-1-carboxamide (Compound 18)

Step A: tert-butyl 4-(5-(6-(benzyloxy)-2-fluoro-3-formylpyrazolo[1,5-a]pyridin-4-yl)pyridin-2-yl)piperazine-1-carboxylate

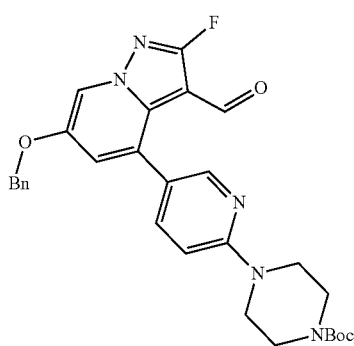 [SMILES: CC(C)(C)OC(=O)N1CCN(c2ccc(-c3cc(OCc4ccccc4)cn4nc(F)c(C=O)c34)cn2)CC1]

To 6-(benzyloxy)-4-bromo-2-fluoropyrazolo[1,5-a]pyridine (23 mg, 0.067 mmol) were added tert-butyl 4-(5-(4,4,5,5-tetramethyl-1,3,2-dioxaborolan-2-yl)pyridin-2-yl)piperazine-1-carboxylate (26 mg, 0.067 mmol), [1,1'-bis(diphenylphosphino)ferrocene]dichloropalladium(II) (10 mg, 0.013 mmol), potassium carbonate (36 mg, 0.264 mol), 1,4-dioxane (2 mL) and H₂O (1 mL), and the mixture was purged with nitrogen three times, and reacted at 90° C. for 2 h. After the reaction was completed, and the product was generated as determined by LCMS, the reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (18 mg), m/z=532[M+1]⁺.

Step B: tert-butyl 4-(5-(2-fluoro-3-formyl-6-hydroxypyrazolo[1,5-a]pyridin-4-yl)pyridin-2-yl)piperazine-1-carboxylate

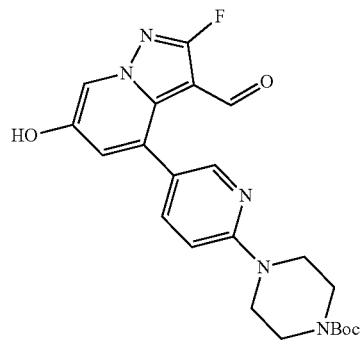 [SMILES: CC(C)(C)OC(=O)N1CCN(c2ccc(-c3cc(O)cn4nc(F)c(C=O)c34)cn2)CC1]

To tert-butyl 4-(5-(6-(benzyloxy)-2-fluoro-3-formylpyrazolo[1,5-a]pyridin-4-yl)pyridin-2-yl)piperazine-1-carboxylate (96 mg, 0.18 mmol) and palladium carbon (5 mg) was added methanol (10.0 mL) at room temperature, and the mixture was purged with a hydrogen balloon three times, and reacted at room temperature overnight. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product, m/z=442[M+1]⁺.

Step C: tert-butyl 4-(5-(6-hydroxy-1H-pyrazolo[3',4':3,4]pyrazolo[1,5-a]pyridin-4-yl)pyridin-2-yl)piperzine-1-carboxylate

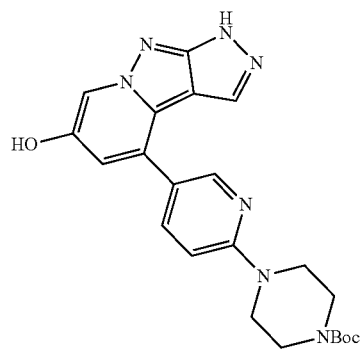 [SMILES: CC(C)(C)OC(=O)N1CCN(c2ccc(-c3cc(O)cn4nc5[nH]ncc5c34)cn2)CC1]

To a solution of tert-butyl 4-(5-(2-fluoro-3-carbaldehyde-6-hydroxypyrazolo[1,5-a]pyridin-4-yl)pyridin-2-yl)piperazine-1-carboxylate (234 mg, 0.53 mmol) in DMF (5.0 mL) was added hydrazine hydrate (0.5 mL), and the mixture was heated to 100° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (82 mg), m/z=436[M+1]⁺.

Step D: tert-butyl 4-(5-(6-(2-fluoroethoxy)-1H-pyrazolo[3',4':3,4]pyrazolo[1,5-a]pyridin-4-yl)pyridin-2-yl)piperazine-1-carboxylate

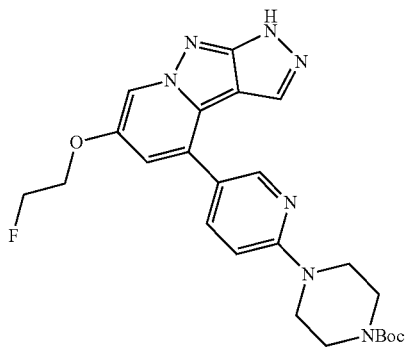 [SMILES: CC(C)(C)OC(=O)N1CCN(c2ccc(-c3cc(OCCF)cn4nc5[nH]ncc5c34)cn2)CC1]

To a solution of tert-butyl 4-(5-(6-hydroxy-1H-pyrazolo[3',4':3,4]pyrazolo[1,5-a]pyridin-4-yl)pyridin-2-yl)piperazine-1-carboxylate (130 mg, 0.3 mmol) in DMF (10.0 mL) were added 1-fluoro-2-iodoethane (52 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (60 mg), m/z=482[M+1]⁺, ¹HNMR (400 MHz, DMSO-d₆) δ 12.70 (brs, 1H), 8.61 (d, 2H), 8.11 (dd, 1H), 7.60 (s, 1H), 7.33 (d, 1H), 7.10 (d, 1H), 4.88 (q, 1H), 4.76 (q, 1H), 4.46 (t, 1H), 4.39 (t, 1H), 3.65 (t, 4H), 3.49 (d, 4H), 1.44 (d, 9H).

Step E: 6-(2-fluoroethoxy)-4-(6-(piperazin-1-yl)pyridin-3-yl)-1H-pyrazolo[3',4':3,4]pyrazolo[1,5-a]pyridine

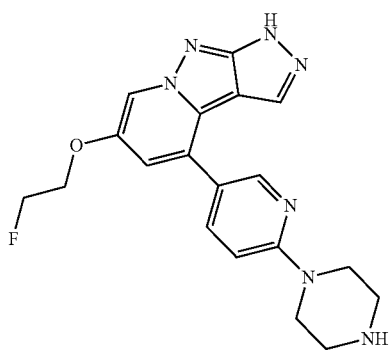 [SMILES: FCCOc1cc(-c2ccc(N3CCNCC3)nc2)c2c3cn[nH]c3nn2c1]

To a solution of tert-butyl 4-(5-(6-(2-fluoroethoxy)-1H-pyrazolo[3',4':3,4]pyrazolo[1,5-a]pyridin-4-yl)pyridin-2-yl)piperazine-1-carboxylate (63 mg, 0.13 mmol) in dioxane (2 mL) was added a solution of HCl in dioxane (0.5 mL, 4.0 M), and the mixture was reacted at room temperature for 12 h. The reaction solution was concentrated under reduced pressure to obtain the residue, which was directly used in the next step. m/z=382[M+1]⁺, ¹HNMR (400 MHz, DMSO-d₆) δ 12.68 (s, 1H), 8.61 (t, 2H), 8.09 (d, 1H), 7.59 (s, 1H), 7.33 (d, 1H), 7.08 (d, 1H), 4.88 (t, 1H), 4.76 (q, 1H), 4.47 (t, 1H), 4.39 (t, 1H), 3.62 (s, 4H), 2.93 (s, 4H), 1.15 (s, 1H).

Step F: N,N-diethyl-4-(5-(6-(2-fluoroethoxy)-1H-pyrazolo[3',4':3,4]pyrazolo[1,5-a]pyridin-4-yl)pyridin-2-yl)piperazine-1-carboxamide

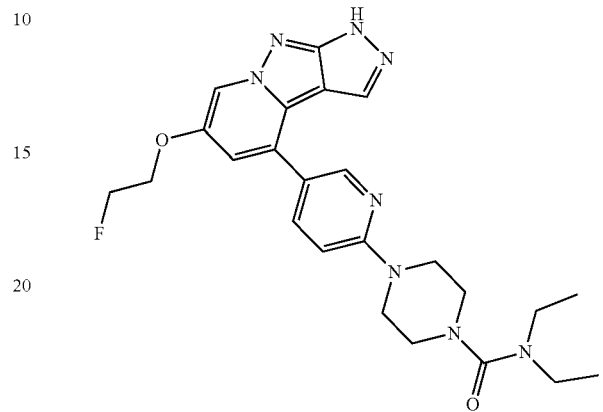

To a solution of 6-(2-fluoroethoxy)-4-(6-(piperazin-1-yl)pyridin-3-yl)-1H-pyrazolo[3',4':3,4]pyrazolo[1,5-a]pyridine (106 mg, 0.28 mmol) in dichloromethane (5 mL) were added diethylcarbamoyl chloride (40 mg, 0.3 mmol) and triethylamine (85 mg, 0.84 mmol), and the mixture was reacted at room temperature for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (32.4 mg), m/z=481[M+1]⁺, ¹H NMR (400 MHz, DMSO-d₆) δ 12.68 (s, 1H), 8.62 (d, 2H), 8.10 (dd, 1H), 7.58 (s, 1H), 7.34 (d, 1H), 7.09 (d, 1H), 4.88 (t, 1H), 4.76 (dd, 1H), 4.47 (t, 1H), 4.39 (t, 1H), 3.66 (t, 4H), 3.16-3.25 (m, 8H), 1.10 (t, 6H).

Example 19

1-(4-(5-(6-(2-fluoroethoxy)-1H-pyrazolo[3',4':3,4]pyrazolo[1,5-a]pyridin-4-yl)pyridin-2-yl)piperazin-1-yl)-2-(pyridin-2-yl)ethan-1-one (Compound 19)

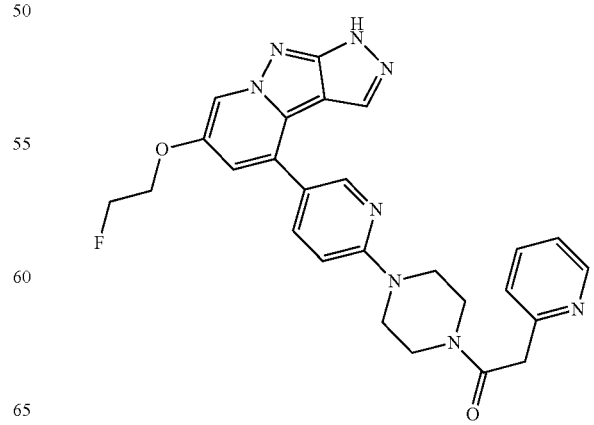

To a solution of 6-(2-fluoroethoxy)-4-(6-(piperazin-1-yl)pyridin-3-yl)-1H-pyrazolo[3',4':3,4]pyrazolo[1,5-a]pyridine (106 mg, 0.28 mmol) in dichloromethane (5 mL) were added 2-(pyridin-2-yl)acetic acid (41 mg, 0.3 mmol), 2-(7-azabenzotriazol-1-yl)-N,N,N',N'-tetramethyluronium hexafluorophosphate (114 mg, 0.3 mmol) and triethylamine (85 mg, 0.84 mmol), and the mixture was reacted at room temperature for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (32.4 mg), m/z=501[M+1]$^+$, $^1$H NMR (400 MHz, DMSO-d$_6$) δ 12.68 (s, 1H), 8.62 (d, 2H), 8.51 (t, 1H), 8.10 (dd, 1H), 7.73-7.78 (m, 1H), 7.58 (s, 1H), 7.34 (t, 2H), 7.28 (dd, 1H), 7.10 (d, 1H), 4.88 (t, 1H), 4.76 (t, 1H), 4.47 (d, 1H), 4.45 (d, 1H), 3.96 (s, 2H), 3.72 (m, 2H), 3.34 (s, 6H).

Example 20

(R)-1-(4-(5-(6-(2-fluoroethoxy)-1H-pyrazolo[3',4':3,4]pyrazolo[1,5-a]pyridin-4-yl)pyridin-2-yl)piperazin-1-yl)-2-hydroxy-2-phenylethan-1-one (Compound 20)

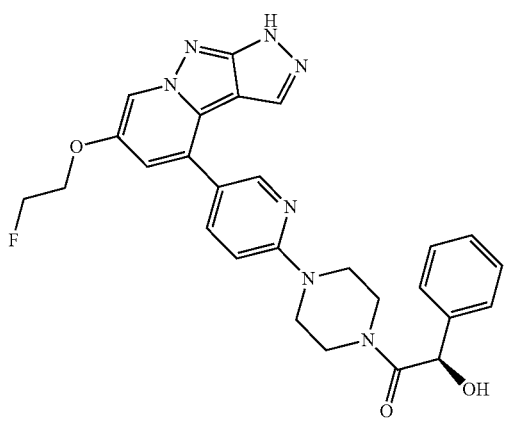 [SMILES: O=C([C@H](O)c1ccccc1)N1CCN(c2ccc(-c3cc(OCCF)cn4nc5[nH]ncc5c34)cn2)CC1]

To a solution of 6-(2-fluoroethoxy)-4-(6-(piperazin-1-yl)pyridin-3-yl)-1H-pyrazolo[3',4':3,4]pyrazolo[1,5-a]pyridine (106 mg, 0.28 mmol) in dichloromethane (5 mL) were added (R)-2-hydroxy-2-phenylacetic acid (46 mg, 0.3 mmol), 2-(7-azabenzotriazol-1-yl)-N,N,N',N'-tetramethyluronium hexafluorophosphate (114 mg, 0.3 mmol) and triethylamine (85 mg, 0.84 mmol), and the mixture was reacted at room temperature for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (33 mg), m/z=516[M+1]$^+$, $^1$H NMR (400 MHz, DMSO-d$_6$) δ 12.68 (s, 1H), 8.61 (dd, 2H), 8.07 (dd, 1H), 7.56 (s, 1H), 7.29-7.43 (m, 6H), 7.04 (d, 1H), 5.78 (d, 1H), 5.51 (d, 1H), 4.88 (t, 1H), 4.76 (t, 1H), 4.46 (t, 1H), 4.38 (t, 1H), 3.38-3.68 (m, 7H), 3.26-3.29 (m, 1H).

Example 21

(R)-1-(4-(5-(6-(2-fluoroethoxy)-1H-pyrazolo[3',4':3,4]pyrazolo[1,5-a]pyridin-4-yl)pyridin-2-yl)piperazin-1-yl)-2-methoxy-2-phenylethan-1-one (Compound 21)

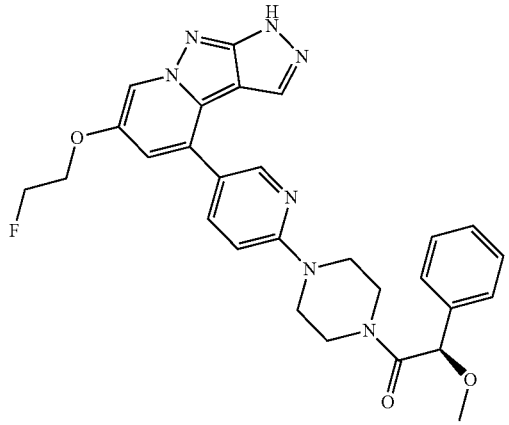 [SMILES: CO[C@@H](C(=O)N1CCN(c2ccc(-c3cc(OCCF)cn4nc5[nH]ncc5c34)cn2)CC1)c1ccccc1]

To a solution of 6-(2-fluoroethoxy)-4-(6-(piperazin-1-yl)pyridin-3-yl)-1H-pyrazolo[3',4':3,4]pyrazolo[1,5-a]pyridine (106 mg, 0.28 mmol) in dichloromethane (5 mL) were added (R)-2-methoxy-2-phenylacetic acid (46 mg, 0.3 mmol), 2-(7-azabenzotriazol-1-yl)-N,N,N',N'-tetramethyluronium hexafluorophosphate (114 mg, 0.3 mmol) and triethylamine (85 mg, 0.84 mmol), and the mixture was reacted at room temperature for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (35 mg), m/z=530[M+1]$^+$, $^1$H NMR (400 MHz, DMSO-d$_6$) δ 12.69 (s, 1H), 8.61 (dd, 2H), 8.08 (dd, 1H), 7.58 (s, 1H), 7.32-7.44 (m, 6H), 7.05 (d, 1H), 5.28 (s, 1H), 4.88 (t, 1H), 4.76 (t, 1H), 4.46 (t, 1H), 4.39 (d, 1H), 3.36-3.65 (m, 7H), 3.34 (s, 3H), 3.28 (brs, 1H).

Example 22

(4-(5-(6-(2-fluoroethoxy)-1H-pyrazolo[3',4':3,4]pyrazolo[1,5-a]pyridin-4-yl)pyridin-2-yl)piperazin-1-yl)(6-methoxypyridin-3-yl)methanone (Compound 22)

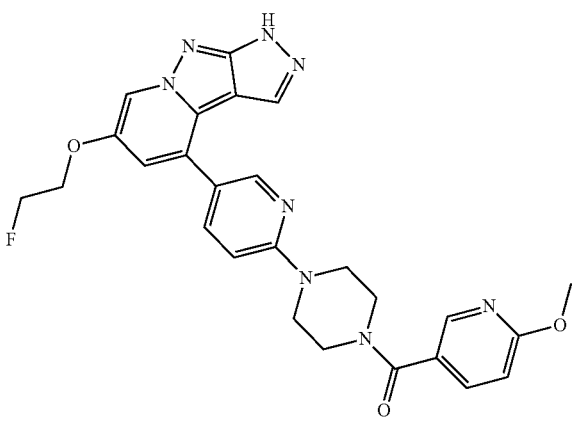 [SMILES: COc1ccc(C(=O)N2CCN(c3ccc(-c4cc(OCCF)cn5nc6[nH]ncc6c45)cn3)CC2)cn1]

To a solution of 6-(2-fluoroethoxy)-4-(6-(piperazin-1-yl)pyridin-3-yl)-1H-pyrazolo[3',4':3,4]pyrazolo[1,5-a]pyridine (106 mg, 0.28 mmol) in dichloromethane (5 mL) were added 6-methoxynicotinic acid (46 mg, 0.3 mmol), 2-(7-azabenzotriazol-1-yl)-N,N,N',N'-tetramethyluronium hexafluorophosphate (114 mg, 0.3 mmol) and triethylamine (85 mg, 0.84 mmol), and the mixture was reacted at room temperature for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (43 mg), m/z=517[M+1]$^+$, $^1$H NMR (400 MHz, DMSO-d$_6$) δ 12.69 (s, 1H), 8.63 (dd, 2H), 8.34 (d, 1H), 8.12 (dd, 1H), 7.86 (dd, 1H), 7.59 (s, 1H), 7.34 (d, 1H), 7.11 (d, 1H), 6.93 (d, 1H), 4.87 (d, 1H), 4.75 (d, 1H), 4.47 (d, 1H), 4.39 (d, 1H), 3.92 (s, 3H), 3.73 (m, 8H).

Example 23

(3-(5-(6-(2-fluoroethoxy)-1H-pyrazolo[3',4':3,4]pyrazolo[1,5-a]pyridin-4-yl)pyridin-2-yl)-3,6-diazabicyclo[3.3.1]heptan-6-yl)(6-methoxypyridin-3-yl)methanone (Compound 23)

Step A: tert-butyl 3-(5-bromopyridin-2-yl)-3,6-diazabicyclo[3.3.1]heptane-6-carboxylate

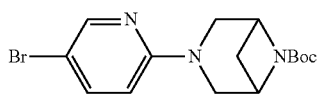

To a solution of 5-bromo-2-fluoropyridine (5.3 g, 30 mmol) in dimethylformamide (50 mL) were added 6-(tert-butylcarbonyl)-3,6-diazabicyclo[3,1,1]heptane (6.0 g, 30 mmol) and potassium carbonate (7.0 g, 50 mmol), and the mixture was heated to 120° C. and reacted for 16 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (6.0 g), m/z=354[M+1]$^+$.

Step B: tert-butyl 3-(5-(4,4,5,5-tetramethyl-1,3,2-dioxaborolan-2-yl)pyridin-2-yl)-3,6-diazabicyclo[3.3.1]heptane-6-carboxylate

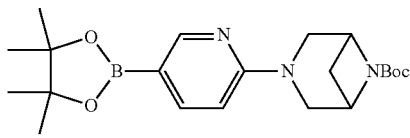 [SMILES: CC(C)(C)OC(=O)N1C2CC1CN(c1ccc(B3OC(C)(C)C(C)(C)O3)cn1)C2]

To a 10 mL sealed tube were added tert-butyl 3-(5-bromopyridin-2-yl)-3,6-diazabicyclo[3.3.1]heptane-6-carboxylate (47 mg, 0.132 mmol), bis(pinacolato)diboron (50 mg, 0.198 mmol), tetrakis(triphenylphosphine)palladium (15 mg, 0.013 mol), potassium acetate (39 mg, 0.396 mmol) and dimethyl sulfoxide (5 mL), and the mixture was purged with nitrogen three times, and reacted at 100° C. for 3 h. After the reaction was completed as determined by LCMS, the reaction solution was added with water, and extracted with ethyl acetate. The organic phases were combined, washed with water, dried over anhydrous sodium sulfate and filtered, and the filtrate was concentrated under reduced pressure to obtain the residue, which was directly used in the next step. $^1$H NMR (400 MHz, DMSO-d$_6$) δ 8.35 (d, 1H), 7.73 (q, 1H), 6.63 (d, 1H), 4.20 (d, 2H), 3.39-3.42 (m, 4H), 3.97 (s, 2H), 1.47 (d, 1H), 1.27-1.30 (m, 20H).

Step C: tert-butyl 3-(5-(6-(benzyloxy)-2-fluoro-3-formylpyrazolo[1,5-a]pyridin-4-yl)pyridin-2-yl)-3,6-diazabicyclo[3.3.1]heptane-6-carboxylate

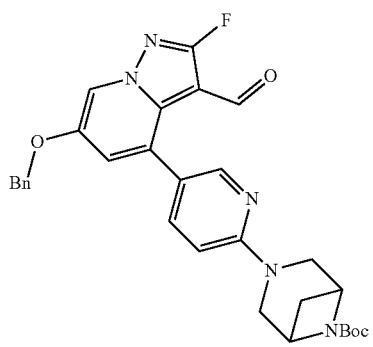 [SMILES: CC(C)(C)OC(=O)N1C2CC1CN(c1ccc(-c3cc(OCc4ccccc4)cn4nc(F)c(C=O)c34)cn1)C2]

To tert-butyl 6-(benzyloxy)-4-bromo-2-fluoropyrazolo[1,5-a]pyridine (23 mg, 0.067 mmol) were added 3-(5-(4,4,5,5-tetramethyl-1,3,2-dioxaborolan-2-yl)pyridin-2-yl)-3,6-diazabicyclo[3.3.1]heptane-6-carboxylate (27 mg, 0.067 mmol), [1,1'-bis(diphenylphosphino)ferrocene]dichloropalladium(II) (10 mg, 0.013 mmol), cesium carbonate (86 mg, 0.264 mol), 1,4-dioxane (2 mL) and H$_2$O (1 mL), and the mixture was purged with nitrogen three times, and reacted at 90° C. for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (21 mg). m/z=544[M+1]$^+$.

Step D: tert-butyl 3-(5-(2-fluoro-3-formyl-6-hydroxypyrazolo[1,5-a]pyridin-4-yl)pyridin-2-yl)-3,6-diazabicyclo[3.3.1]heptane-6-carboxylate

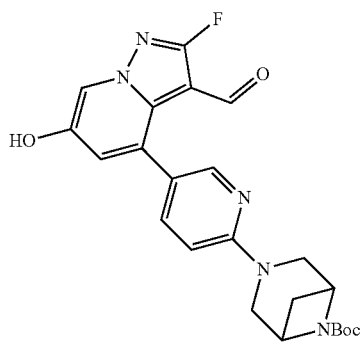 [SMILES: CC(C)(C)OC(=O)N1C2CC1CN(c1ccc(-c3cc(O)cn4nc(F)c(C=O)c34)cn1)C2]

To tert-butyl 3-(5-(6-(benzyloxy)-2-fluoro-3-formylpyrazolo[1,5-a]pyridin-4-yl)pyridin-2-yl)-3,6-diazabicyclo[3.3.1]heptane-6-carboxylate (98 mg, 0.18 mmol) and palladium on carbon (5 mg) was added methanol (10.0 mL) at room temperature, and the mixture was purged with a hydrogen balloon three times, and reacted at room temperature overnight. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product, m/z=454[M+1]$^+$.

Step E: tert-butyl 3-(5-(6-hydroxy-1H-pyrazolo[3',4':3,4]pyrazolo[1,5-a]pyridin-4-yl)pyridin-2-yl)-3,6-diazabicyclo[3.1.1]heptane-6-carboxylate

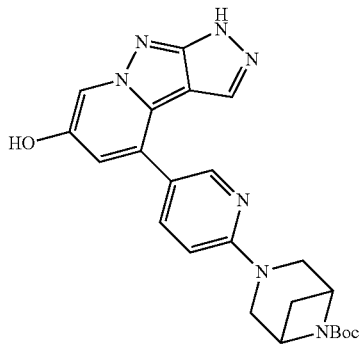 [SMILES: CC(C)(C)OC(=O)N1C2CC1CN(c1ccc(-c3cc(O)cn4nc5[nH]ncc5c34)cn1)C2]

To a solution of tert-butyl 3-(5-(2-fluoro-3-formyl-6-hydroxypyrazolo[1,5-a]pyridin-4-yl)pyridin-2-yl)-3,6-diazabicyclo[3.3.1]heptane-6-carboxylate (240 mg, 0.53 mmol) in DMF (5.0 mL) was added hydrazine hydrate (0.5 mL), and the mixture was heated to 100° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (92 mg), m/z=448[M+1]$^+$.

Step F: tert-butyl 3-(5-(6-(2-fluoroethoxy)-1H-pyrazolo[3',4':3,4]pyrazolo[1,5-a]pyridin-4-yl)pyridin-2-yl)-3,6-diazabicyclo[3.1.1]heptane-6-carboxylate

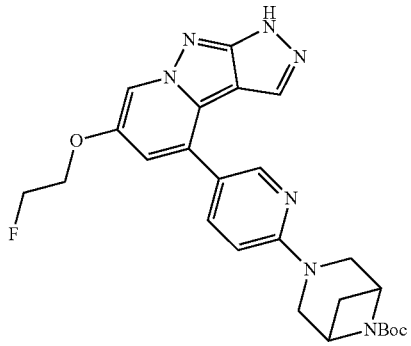 [SMILES: CC(C)(C)OC(=O)N1C2CC1CN(c1ccc(-c3cc(OCCF)cn4nc5[nH]ncc5c34)cn1)C2]

To a solution of tert-butyl 3-(5-(6-hydroxy-1H-pyrazolo[3',4':3,4]pyrazolo[1,5-a]pyridin-4-yl)pyridin-2-yl)-3,6-diazabicyclo[3.1.1]heptane-6-carbonate (134 mg, 0.3 mmol) in DMF (10.0 mL) was added 1-fluoro-2-iodoethane (52 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (60 mg), m/z=494[M+1]$^+$, $^1$H NMR (400 MHz, DMSO-$d_6$) δ 12.67 (s, 1H), 8.60-8.63 (m, 2H), 8.07-8.10 (m, 1H), 7.57 (s, 1H), 7.33 (d, 1H), 6.92 (d, 1H), 4.86-4.88 (q, 1H), 4.74-4.76 (t, 1H), 4.37-4.39 (t, 1H), 4.26 (d, 2H), 4.00-4.07 (m, 2H), 3.54 (d, 2H), 2.59 (d, 1H), 1.99 (s, 1H), 1.53 (d, 1H), 1.29 (s, 9H).

Step H: 4-(6-(3,6-diazabicyclo[3.1.1]heptan-3-yl)pyridin-3-yl)-6-(2-fluoroethoxy)-1H-pyrazolo[3',4':3,4]pyrazolo[1,5-a]pyridine

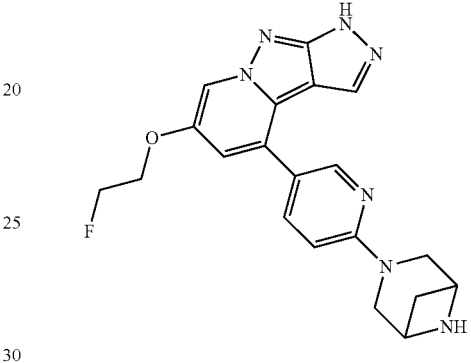

To a solution of tert-butyl 4-(5-(6-(2-fluoroethoxy)-1H-pyrazolo[3',4':3,4]pyrazolo[1,5-a]pyridin-4-yl)pyridin-2-yl)piperazine-1-carbonate (63 mg, 0.13 mmol) in dioxane (2 mL) was added a solution of HCl in dioxane (0.5 mL, 4.0 M), and the mixture was reacted at room temperature for 12 h. The reaction solution was concentrated under reduced pressure to obtain the residue, which was directly used in the next step, m/z=394[M+1]$^+$, $^1$H NMR (400 MHz, DMSO-$d_6$) δ 12.70 (s, 1H), 8.68 (s, 1H), 8.63 (s, 1H), 8.17 (s, 1H), 7.58 (s, 1H), 7.35 (s, 1H), 6.96 (s, 1H), 4.75-4.89 (m, 2H), 4.39-4.47 (m, 2H), 3.91-4.05 (m, 4H), 2.91 (brs, 2H), 1.92 (s, 1H), 1.15 (s, 2H).

Step I: (3-(5-(6-(2-fluoroethoxy)-1H-pyrazolo[3',4':3,4]pyrazolo[1,5-a]pyridin-4-yl)pyridin-2-yl)-3,6-diazabicyclo[3.1.1]heptan-6-yl)(6-methoxypyridin-3-yl)methanone

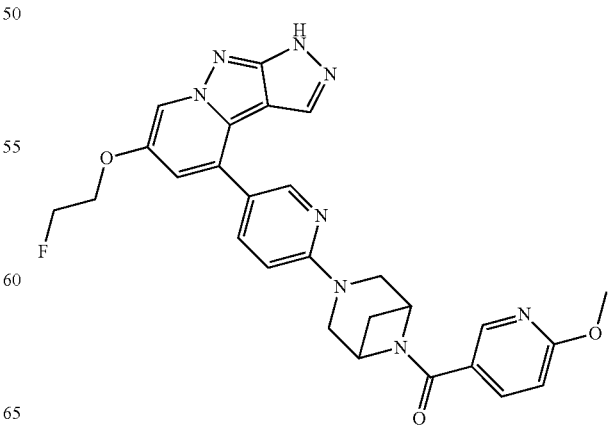

To a solution of 4-(6-(3,6-diazabicyclo[3.1.1]heptan-3-yl)pyridin-3-yl)-6-(2-fluoroethoxy)-1H-pyrazolo[3',4':3,4]pyrazolo[1,5-a]pyridine (110 mg, 0.28 mmol) in dichloromethane (5 mL) were added 6-methoxynicotinic acid (46 mg, 0.3 mmol), 2-(7-azabenzotriazol-1-yl)-N,N,N',N'-tetramethyluronium hexafluorophosphate (114 mg, 0.3 mmol) and triethylamine (85 mg, 0.84 mmol), and the mixture was reacted at room temperature for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (3 mg), m/z=529[M+1]+, 1HNMR (400 MHz, DMSO-d6) δ 12.66 (s, 1H), 8.55-8.60 (m, 3H), 8.08 (dd, 1H), 8.00 (dd, 1H), 7.58 (s, 1H), 7.31 (d, 1H), 6.84-6.90 (m, 2H), 4.94 (brs, 1H), 4.86 (dd, 1H), 4.74 (dd, 1H), 4.61 (brs, 1H), 4.42-4.44 (m, 1H), 4.35-4.36 (m, 1H), 4.20 (d, 1H), 3.71 (d, 3H), 3.57 (m, 3H), 2.84 (q, 1H), 1.72 (d, 1H).

Example 24

6-methoxy-4-(5-(6-((6-methoxypyridin-3-yl)methyl)-3,6-diazabicyclo[3.3.1]heptan-3-yl)pyrazin-2-yl)-1H-pyrazolo[3',4':3,4]pyrazolo[1,5-a]pyridine (Compound 24)

Step A: 2,4,6-trimethylbenzenesulfonate 1-amino-3-bromo-5-methoxypyridin-1-ium

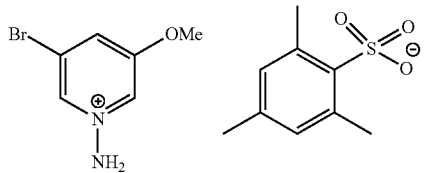

To a solution of 2-[(aminooxy)sulfonyl]-1,3,5-trimethylbenzene (6.8 g, 31.7 mmol) in dichloromethane (50 mL) was added 3-bromo-5-methoxypyridine (6.0 g, 32.0 mmol) at 0° C., and the mixture was stirred at 0° C. for 3 h to precipitate a large quantity of white solids. After the reaction was completed, the reaction system was added with ether (50 mL) at 0° C., stirred for 10 min, and filtered under reduced pressure. The filtrate was rinsed with ether, and dried under vacuum to obtain the product (15 g), which can be directly used in the next step without further purification. m/z=204 [M+1]+.

Step B: 4-bromo-2-fluoro-6-methoxypyrazolo[1,5-a]pyridine

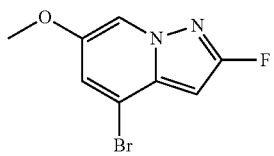

To a solution of 2,4,6-trimethylbenzenesulfonate 1-amino-3-bromo-5-methoxypyridin-1-ium (1.0 g, 2.3 mmol) in DMF (30 mL) was added potassium carbonate (1.4 g, 10.0 mmol). The reaction system was cooled to 0° C., added with 2,2-difluoroethenyl p-toluenesulfonate (0.5 g, 2.3 mmol) in batches, warmed to room temperature and stirred for 1 h, and stirred at 90° C. for another 1 h. After the reaction was completed, the reaction solution was cooled to room temperature, added with water to quench the reaction, and extracted with ethyl acetate. The organic phases were combined, washed with water, concentrated under reduced pressure, and separated by column chromatography to obtain the product (80 mg), m/z=245[M+1]+, 1HNMR (400 MHz, CDCl3) δ 8.07 (s, 1H), 6.61 (s, 1H), 6.18 (d, 1H), 3.85 (s, 3H).

Step C: 4-bromo-2-fluoro-6-methoxypyrazolo[1,5-a]pyridine-3-carbaldehyde

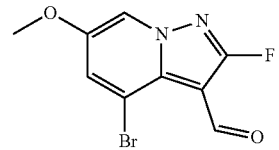

To a solution of 4-bromo-2-fluoro-6-methoxypyrazolo[1,5-a]pyridine (294 mg, 1.2 mmol) in DMF (10 mL) was added dropwise with phosphorus oxychloride (1.0 g, 6.5 mmol) at 0° C., and after the addition, the mixture was warmed to room temperature and reacted overnight. The reaction solution was poured into ice water (100 mL), adjusted to pH 7 with 2 N NaOH solution, and extracted with ethyl acetate. The organic phases were combined, concentrated under reduced pressure, and separated by column chromatography to obtain the product (240 mg). m/z=273 [M+1]+. 1HNMR (400 MHz, DMSO-d6) δ 10.51 (s, 1H), 8.72 (d, 1H), 8.04 (d, 1H), 3.87 (s, 3H).

Step D: 4-bromo-6-methoxy-1H-pyrazolo[3',4':3,4]pyrazolo[1,5-a]pyridine

The operation was performed as in step E of Example 22, m/z=267 [M+1]+, 1HNMR (400 MHz, DMSO-d6) δ 12.82 (s, 1H), 8.67 (d, 1H), 7.92 (s, 1H), 7.62 (d, 1H), 3.89 (s, 3H).

Step E: 6-methoxy-4-(5-(6-(((6-methoxypyridin-3-yl)methyl)-3,6-diazabicyclo[3.1.1]heptan-3-yl)pyrazin-2-yl)-1H-pyrazolo[3',4':3,4]pyrazolo[1,5-a]pyridine

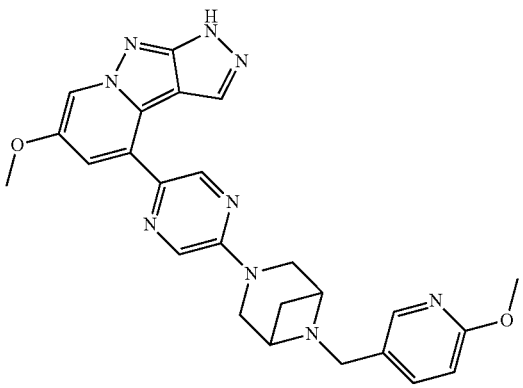

The operation was performed as in step E of Example 16, m/z=484[M+1]$^+$, $^1$H NMR (400 MHz, DMSO-d$_6$) δ 12.50 (s, 1H), 8.98 (d, 1H), 8.59 (dd, 2H), 8.13 (d, 1H), 8.03 (s, 1H), 7.70-7.74 (m, 2H), 6.79 (d, 1H), 3.94 (s, 3H), 3.82-3.87 (m, 5H), 3.65-3.71 (m, 4H), 3.56 (s, 2H), 2.49-2.56 (m, 1H), 1.64 (d, 1H).

Example 25

6-(2,2-difluoroethoxy)-4-(5-(6-(((6-methoxypyridin-3-yl)methyl)-3,6-diazabicyclo[3.3.1]heptan-3-yl)pyrazin-2-yl)-1H-pyrazolo[3',4':3,4]pyrazolo[1,5-a]pyridine (Compound 25)

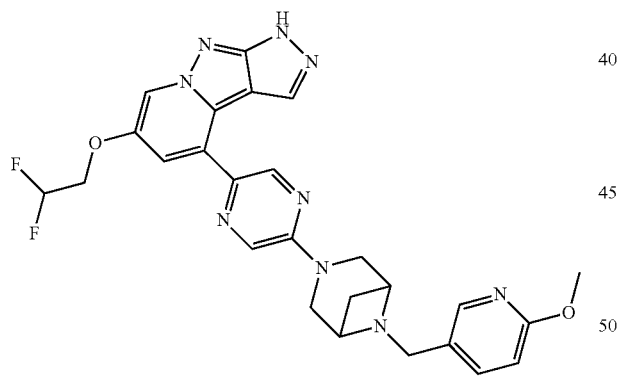

To a solution of 4-(5-(6-(((6-methoxypyridin-3-yl)methyl)-3,6-diazabicyclo[3.1.1]heptan-3-yl)pyrazin-2-yl)-1H-pyrazolo[3',4':3,4]pyrazolo[1,5-a]pyridin-6-ol (150 mg, 0.3 mmol) in DMF (10.0 mL) were added 1,1-difluoro-2-iodoethane (58 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (12 mg). m/z=534[M+1]$^+$, H NMR (400 MHz, DMSO-d$_6$) δ 12.55 (s, 1H), 9.01 (s, 1H), 8.73 (s, 1H), 8.55 (s, 1H), 8.12 (s, 1H), 8.07 (s, 1H), 7.83 (s, 1H), 7.72 (d, 1H), 6.77 (d, 1H), 6.35-6.66 (m, 1H), 4.50-4.57 (m, 2H), 3.82-3.87 (m, 5H), 3.65-3.84 (m, 4H), 3.56-3.64 (m, 2H), 1.62-1.64 (m, 1H).

Example 26

2-((4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridin-6-yl)oxy)acetonitrile (Compound 26)

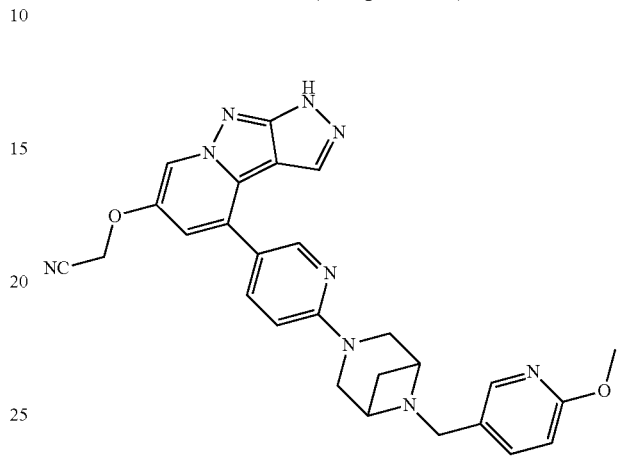

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added bromoacetonitrile (36 mg, 0.3 mmol) and potassium carbonate (83 mg, 0.6 mmol), and the mixture was heated to 90° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (62 mg). m/z=508[M+1]$^+$, $^1$H NMR (400 MHz, DMSO-d$_6$) δ 12.76 (s, 1H), 8.81 (s, 1H), 8.67 (s, 1H), 8.10-8.14 (m, 2H), 7.68-7.71 (m, 2H), 7.43 (s, 1H), 6.92 (d, 1H), 6.76 (d, 1H), 5.37 (s, 2H), 3.68-3.82 (m, 8H), 3.53-3.68 (m, 3H), 2.51 (d, 1H), 1.58-1.61 (m, 1H).

Example 27

6-(2-(difluoromethoxy)ethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 27)

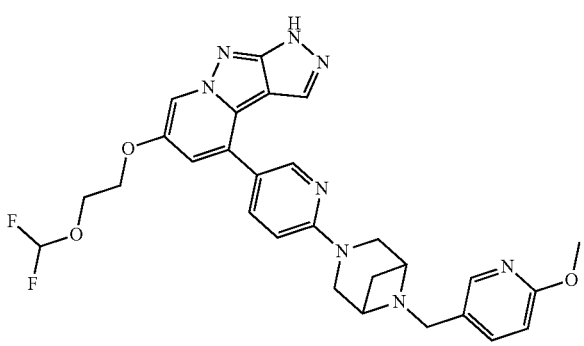 [SMILES: COc1ccc(CN2C3CC2CN(c2ccc(-c4cc(OCCOC(F)F)cn5nc6[nH]ncc6c45)cn2)C3)cn1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 2-(difluoromethoxy)ethyl p-toluenesulfonate (80 mg, 0.3 mmol, prepared by the method in reference WO2016/123706) and potassium carbonate (83 mg, 0.6 mmol), and the mixture was heated to 90° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (143 mg). m/z=563[M+1]$^+$. $^1$H NMR (400 MHz, DMSO-d$_6$) δ 12.67 (s, 1H), 8.60-8.66 (dd, 2H), 8.10-8.13 (m, 2H), 7.63-7.72 (m, 2H), 7.32 (s, 1H), 6.91 (d, 1H), 6.76-6.80 (m, 1H), 4.37 (d, 2H), 4.23 (d, 2H), 3.76-3.83 (m, 5H), 3.68-3.70 (m, 3H), 3.53-3.69 (m, 4H), 2.51 (d, 1H), 1.61 (d, 1H).

Example 28

6-(2-(cyclopropylmethoxy)ethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 28)

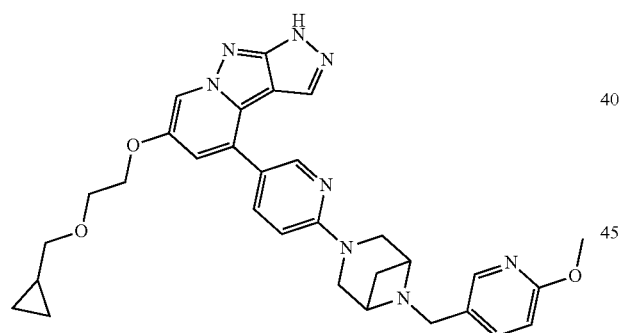

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 2-(cyclopropylmethoxy)ethyl p-toluenesulfonate (81 mg, 0.3 mmol, prepared by the method in reference U.S. Pat. No. 4,406,907) and potassium carbonate (83 mg, 0.6 mmol), and the mixture was heated to 90° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (127 mg). m/z=567[M+1]$^+$.

Example 29

6-isopropoxy-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 29)

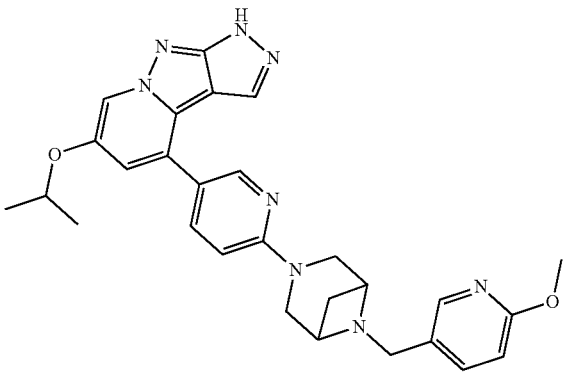 [SMILES: COc1ccc(CN2C3CC2CN(c2ccc(-c4cc(OC(C)C)cn5nc6[nH]ncc6c45)cn2)C3)cn1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added iodoisopropane (51 mg, 0.3 mmol) and potassium carbonate (83 mg, 0.6 mmol), and the mixture was heated to 80° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (133 mg). m/z=511[M+1]$^+$. $^1$H NMR (400 MHz, DMSO-d$_6$) δ 12.65 (s, 1H), 8.65 (d, 1H), 8.55 (d, 1H), 8.11 (d, 2H), 7.63-7.72 (m, 1H), 7.62 (s, 1H), 7.26 (d, 1H), 6.92 (d, 1H), 6.79 (d, 1H), 4.75 (m, 1H), 3.72-3.83 (m, 5H), 3.70 (d, 2H), 3.53-3.60 (m, 4H), 2.51 (d, 1H), 1.59 (d, 1H), 1.36 (d, 6H).

Example 30

4-(6-(6-(((6-methoxypyridin-3-yl)methyl)-3,6-diazabicyclo[3.3.1]heptan-3-yl)pyridin-3-yl)-6-(2,2,2-trifluoroethoxy)-1H-pyrazolo[3',4':3,4]pyrazolo[1,5-a]pyridine (Compound 30)

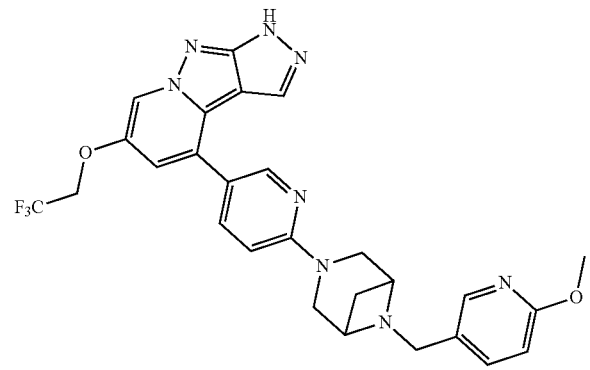 [SMILES: COc1ccc(CN2C3CC2CN(c2ccc(-c4cc(OCC(F)(F)F)cn5nc6[nH]ncc6c45)cn2)C3)cn1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added trifluoroethyl p-toluenesulfonate (76 mg, 0.3 mmol) and potassium carbonate (83 mg, 0.6 mmol), and the mixture was heated to 120° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (20 mg). m/z=551[M+1]$^+$. $^1$HNMR (400 MHz, DMSO-d$_6$) δ 12.72 (s, 1H), 8.75 (d, 1H), 8.66 (d, 1H), 8.08-8.13 (m, 2H), 7.65-7.71 (m, 2H), 7.41 (d, 1H), 6.92 (d, 1H), 6.74-6.77 (m, 1H), 4.92-4.98 (m, 2H), 3.75-3.81 (m, 5H), 3.64-3.68 (m, 2H), 3.52-3.68 (m, 4H), 2.51 (d, 1H), 1.55-1.59 (m, 1H).

Example 31

6-(2-fluoroethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 31)

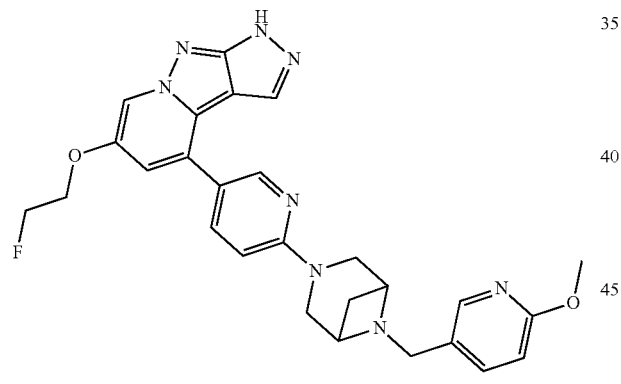

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 1-bromo-2-fluoroethane (38 mg, 0.3 mmol) and potassium carbonate (83 mg, 0.6 mmol), and the mixture was heated to 70° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (139 mg). $^1$HNMR (400 MHz, DMSO-d$_6$) δ 12.68 (s, 1H), 8.61-8.66 (d, 2H), 8.10-8.13 (m, 2H), 7.64-7.12 (m, 2H), 7.33 (d, 1H), 6.93 (d, 2H), 6.79 (d, 2H), 4.89 (t, 1H), 4.76 (t, 1H), 4.47 (t, 1H), 4.39 (t, 1H), 3.76-3.83 (m, 5H), 3.70 (d, 2H), 3.53-3.60 (m, 4H), 2.51 (d, 1H), 1.61 (d, 1H). m/z=515 [M+1]$^+$.

Example 32

6-(2,2-difluoroethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 32)

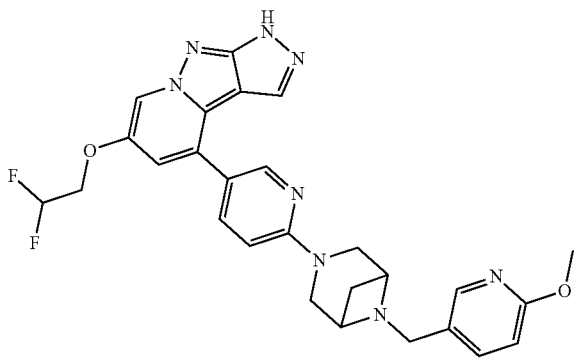 [SMILES: COc1ccc(CN2C3CC2CN(c2ccc(-c4cc(OCC(F)F)cn5nc6[nH]ncc6c45)cn2)C3)cn1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 1,1-difluoro-2-iodoethane (58 mg, 0.3 mmol) and potassium carbonate (83 mg, 0.6 mmol), and the mixture was heated to 70° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (118 mg). $^1$HNMR (400 MHz, DMSO-d$_6$) δ 12.69 (s, 1H), 8.69 (d, 1H), 8.66 (d, 1H), 8.10-8.13 (m, 2H), 7.71 (d, 1H), 7.65 (s, 1H), 7.57 (s, 1H), 6.91 (d, 1H), 6.76 (d, 1H), 6.38-6.62 (m, 1H), 4.52 (t, 2H), 3.80-3.83 (m, 5H), 3.68 (m, 2H), 3.53-3.62 (m, 4H), 2.51 (d, 1H), 1.58 (d, 1H), m/z=533 [M+1]$^+$.

Example 33

6-(difluoromethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 33)

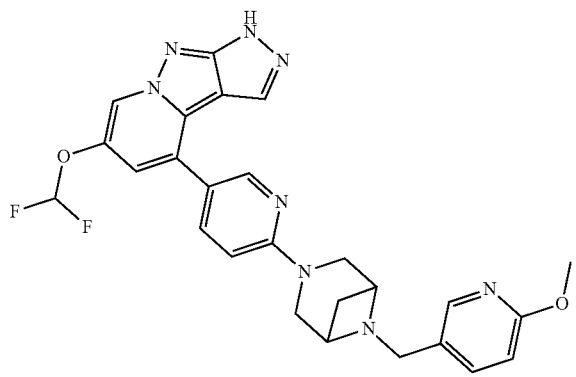 [SMILES: COc1ccc(CN2C3CC2CN(c2ccc(-c4cc(OC(F)F)cn5nc6[nH]ncc6c45)cn2)C3)cn1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added sodium difluorochloroacetate (46 mg, 0.3 mmol) and potassium carbonate (83 mg, 0.6 mmol), and the mixture was heated to 80° C. and reacted for 12 h. The reaction was added with water, and extracted with ethyl acetate. The organic phases were combined, washed with water, dried over anhydrous sodium sulfate and filtered, and the filtrate was concentrated under reduced pressure, and separated by reverse phase column chromatography to obtain the trifluoroacetate of the product (118 mg), m/z=519 [M+1]$^+$, $^1$H NMR (400 MHz, DMSO-$d_6$): 8.64 (s, 1H), 8.54 (s, 1H), 8.10-8.26 (m, 2H), 7.80-7.89 (m, 2H), 7.56 (s, 1H), 7.28-7.34 (m, 1H), 7.06-7.09 (m, 1H), 6.89-6.97 (m, 1H), 3.76-3.93 (m, 11H), 2.51 (d, 1H), 2.02-2.08 (m, 1H).

Example 34

6-(2-cyclopropoxyethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 34)

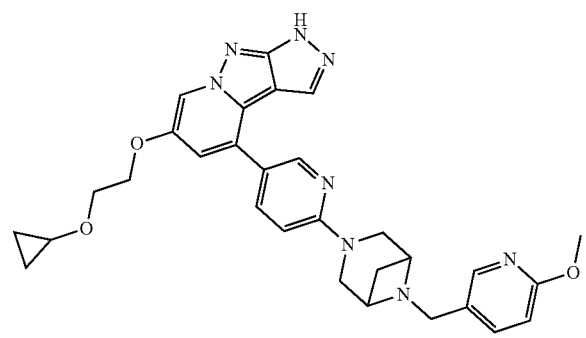 [SMILES: COc1ccc(CN2C3CC2CN(c2ccc(-c4cc(OCCOC5CC5)cn5nc6[nH]ncc6c45)cn2)C3)cn1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 2-(cyclopropyloxy)ethyl p-toluenesulfonate (77 mg, 0.3 mmol) and potassium carbonate (83 mg, 0.6 mmol), and the mixture was heated to 70° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by reverse phase column chromatography to obtain the trifluoroacetate of the product (132 mg). m/z=553[M+1]$^+$. $^1$H NMR (400 MHz, DMSO-$d_6$): 8.73 (s, 1H), 8.69 (s, 1H), 8.15-8.19 (m, 2H), 7.85-7.89 (m, 2H), 7.48-7.52 (m, 1H), 6.93-6.98 (m, 2H), 4.61-4.65 (m, 2H), 4.48-4.50 (m, 2H), 4.02-4.12 (m, 4H), 3.79-3.98 (m, 8H), 3.48-3.53 (m, 1H), 2.08-2.12 (m, 2H), 1.68-1.80 (m, 1H).

Example 35

6-ethoxy-4-(6-(6-(((6-methoxypyridin-3-yl)methyl)-3,6-diazabicyclo[3.3.1]heptan-3-yl)pyridin-3-yl)-3-methyl-1H-pyrazolo[3',4':3,4]pyrazolo[1,5-a]pyridine (Compound 35)

Step A: 1-(6-(benzyloxy)-4-bromo-2-fluoropyrazolo[1,5-a]pyridin-3-yl)ethan-1-one

To 6-(benzyloxy)-4-bromo-2-fluoropyrazolo[1,5-a]pyridine (220 mg, 0.69 mmol) was added acetic anhydride (2.0 mL), followed by phosphoric acid (0.2 mL) at 0° C., and the mixture was stirred at room temperature for 12 h, directly concentrated under reduced pressure, and separated by column chromatography to obtain the product (100 mg). m/z=364[M+1]$^+$.

Step B: 1-(4-bromo-2-fluoro-6-hydroxypyrazolo[1,5-a]pyridin-3-yl)ethan-1-one

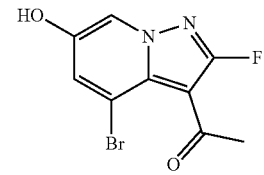

To 1-(6-(benzyloxy)-4-bromo-2-fluoropyrazolo[1,5-a]pyridin-3-yl)ethan-1-one (100 mg, 0.28 mmol) and palladium on carbon (5 mg) was added methanol (10.0 mL) at room temperature, and the mixture was purged with a hydrogen balloon three times, and reacted at room temperature overnight. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (65 mg). m/z=274[M+1]$^+$.

Step C: 1-(4-bromo-6-ethoxy-2-fluoropyrazolo[1,5-a]pyridin-3-yl)ethan-1-one

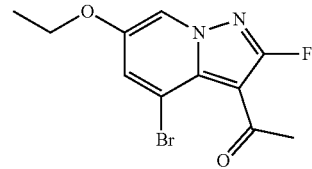 [SMILES: CCOc1cc(Br)c2c(C(C)=O)c(F)nn2c1]

To 1-(4-bromo-2-fluoro-6-hydroxypyrazolo[1,5-a]pyridin-3-yl)ethan-1-one (110 mg, 0.36 mmol), iodoethane (56 mg, 0.4 mmol) and potassium carbonate (167 mg, 1.2 mmol) was added DMF (2.0 mL), and the mixture was heated to 60° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (100 mg). m/z=302[M+1]⁺.

Step D: 4-bromo-6-ethoxy-3-methyl-1H-pyrazolo[3',4':3,4]pyrazolo[1,5-a]pyridine

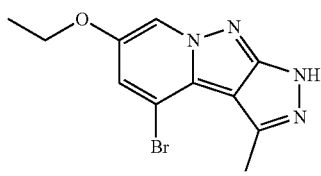 [SMILES: CCOc1cc(Br)c2c3c(C)n[nH]c3nn2c1]

1-(4-bromo-6-ethoxy-2-fluoropyrazolo[1,5-a]pyridin-3-yl)ethan-1-one (110 mg, 0.37 mmol) was dissolved in DMF (5.0 mL), followed by the addition of hydrazine hydrate (0.5 mL), and the mixture was heated to 120° C. and reacted. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (72 mg). m/z=296[M+1]⁺.

Step E: 6-ethoxy-4-(6-(6-(((6-methoxypyridin-3-yl)methyl)-3,6-diazabicyclo[3.3.1]heptan-3-yl)pyridin-3-yl)-3-methyl-1H-pyrazolo[3',4':3,4]pyrazolo[1,5-a]pyridine

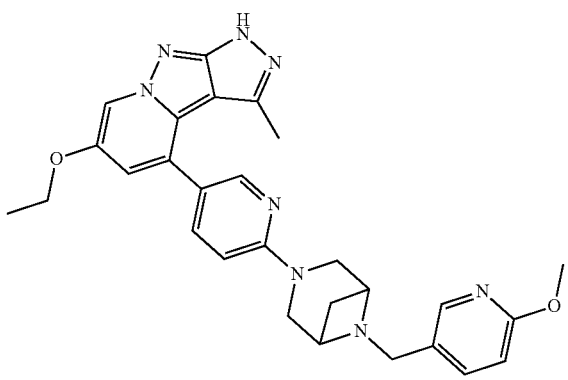 [SMILES: CCOc1cc(-c2ccc(N3CC4CC(C3)N4Cc3ccc(OC)nc3)nc2)c2c3c(C)n[nH]c3nn2c1]

To 4-bromo-6-ethoxy-3-methyl-1H-pyrazolo[3',4':3,4]pyrazolo[1,5-a]pyridine (72 mg, 0.24 mmol) were added 6-(((6-methoxypyridin-3-yl)methyl)-3-(5-(4,4,5,5-tetramethyl-1,3,2-dioxaborolan-2-yl)pyridin-2-yl)-3,6-diazabicyclo[3.1.1]heptane (101 mg, 0.24 mmol) (prepared by the method in reference WO2018/71447), tetrakis(triphenylphosphine)palladium (18 mg, 0.013 mol), potassium carbonate (66 mg, 0.48 mol) 1,4-dioxane (2 mL), and H₂O (1 mL), and the mixture was purged with nitrogen three times, and reacted at 90° C. for 2 h. After the reaction was completed, and the product was generated as determined by LCMS, the reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (36 mg). ¹HNMR (400 MHz, DMSO-d₆) δ 12.11 (s, 1H), 8.49 (d, 2H), 8.06 (s, 1H), 7.88 (d, 1H), 7.69 (d, 1H), 7.03 (s, 1H), 6.85 (dd, 2H), 4.17 (d, 2H), 3.67-3.82 (m, 3H), 3.49-3.56 (m, 4H), 3.44-3.54 (m, 4H), 2.51 (d, 1H), 1.98 (s, 3H), 1.60 (d, 1H), 1.40 (t, 3H). m/z=511[M+1]⁺.

Example 36

6-methoxy-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 36)

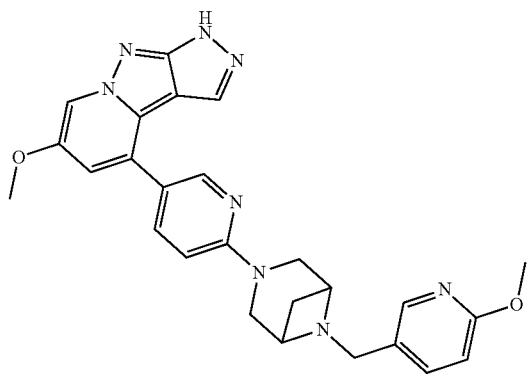

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added iodomethane (43 mg, 0.3 mmol) and potassium carbonate (83 mg, 0.6 mmol), and the mixture was heated to 60° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (137 mg). ¹HNMR (400 MHz, DMSO-d₆) δ 12.66 (s, 1H), 8.64-8.65 (m, 1H), 8.55 (d, 1H), 7.63-7.71 (m, 3H), 7.28 (d, 1H), 6.93 (d, 1H), 6.79 (d, 2H), 3.88-3.96 (m, 3H), 3.76-3.82 (m, 5H), 3.71 (brs, 2H), 3.49-3.55 (m, 4H), 2.51 (d, 1H), 1.61 (d, 1H). m/z=483[M+1]⁺.

Example 37

6-(cyclopropylmethoxy)-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 37)

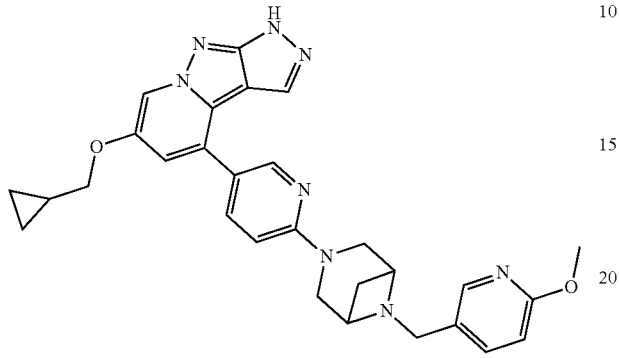

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added cyclopropyl bromomethane (41 mg, 0.3 mmol) and potassium carbonate (83 mg, 0.6 mmol), and the mixture was heated to 60° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (66 mg), 1H NMR (400 MHz, DMSO-d$_6$) δ 12.63 (s, 1H), 8.63 (s, 1H), 8.47 (s, 1H), 8.10 (m, 2H), 7.65 (m, 1H), 7.60 (s, 1H), 7.29 (s, 1H), 6.90 (d, 1H), 6.77 (d, 1H), 3.96 (d, 2H), 3.81 (s, 3H), 3.4-3.75 (m, 8H), 2.51 (d, 1H), 1.60 (d, 1H), 0.75-0.85 (m, 1H), 0.59 (m, 2H), 0.36 (m, 2H), m/z=523[M+1]$^+$.

Example 38

4-(6-(6-(((6-methoxypyridin-3-yl)methyl)-3,6-diazabicyclo[3.3.1]heptan-3-yl)pyridin-3-yl)-6-propoxy-1H-pyrazolo[3',4':3,4]pyrazolo[1,5-a]pyridine (Compound 38)

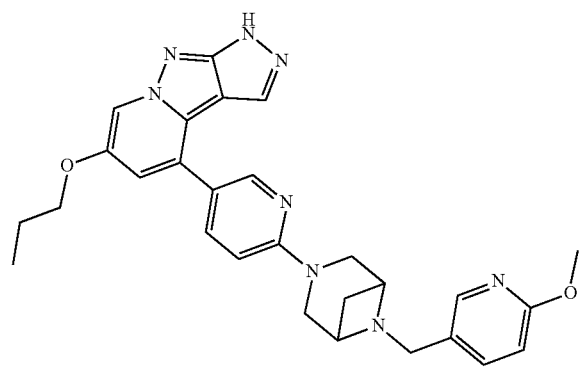 [SMILES: CCCOc1cc(-c2ccc(N3CC4CC(C3)N4Cc3ccc(OC)nc3)nc2)c2c3cn[nH]c3nn2c1]

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 1-bromopropane (37 mg, 0.3 mmol) and potassium carbonate (83 mg, 0.6 mmol), and the mixture was heated to 60° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (96 mg). m/z=511[M+1]$^+$. $^1$H NMR (400 MHz, DMSO-d$_6$) δ 12.63 (s, 1H), 8.63 (d, 1H), 8.51 (d, 1H), 8.08 (s, 2H), 7.77-7.65 (m, 1H), 7.60 (s, 1H), 7.26 (d, 1H), 6.90 (d, 1H), 6.76 (d, 1H), 4.08 (t, 2H), 3.81 (s, 3H), 3.76 (d, 2H), 3.67 (d, 2H), 3.58 (s, 1H), 3.52 (s, 2H), 2.51 (d, 1H), 1.78 (p, 2H), 1.58 (d, 1H), 1.22 (s, 1H), 1.02 (t, 3H).

Example 39

6-isobutoxy-4-(6-(6-(((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 39)

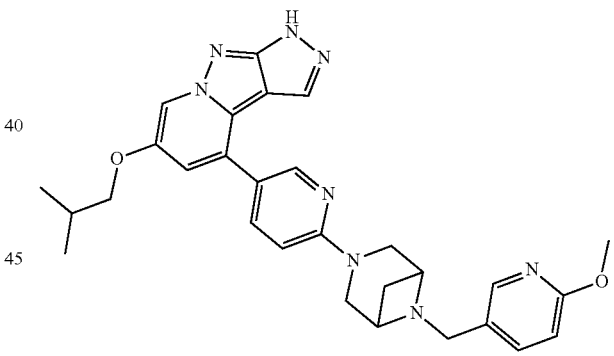

To a solution of 4-(6-(6-(((6-methoxypyridin-3-yl)methyl)-3,6-diazabicyclo[3.1.1]heptan-3-yl)pyridin-3-yl)-1H-pyrazolo[3',4':3,4]pyrazolo[1,5-a]pyridin-6-ol (150 mg, 0.3 mmol) in DMF (10.0 mL) were added 1-bromo-2-methylpropane (41 mg, 0.3 mmol) and potassium carbonate (83 mg, 0.6 mmol), and the mixture was heated to 60° C. and reacted for 12 h. The reaction solution was added with water, and extracted with ethyl acetate. The organic phases were combined, washed with water, dried over anhydrous sodium sulfate and filtered, and the filtrate was concentrated under reduced pressure, and separated by column chromatography to obtain the product (33 mg). m/z=525[M+1]$^+$. $^1$H NMR (400 MHz, DMSO-d$_6$) δ 12.63 (s, 1H), 8.64 (d, 1H), 8.51 (d, 1H), 8.12-8.07 (m, 2H), 7.69 (dd, 1H), 7.60 (s, 1H), 7.27 (d, 1H), 6.90 (d, 1H), 6.76 (d, 1H), 3.90 (d, 2H), 3.81 (s, 3H), 3.76 (d, 2H), 3.67 (d, 2H), 3.51 (s, 2H), 2.51 (d, 1H), 2.07 (dq, 1H), 1.58 (d, 1H), 1.24 (d, 2H), 1.02 (d, 6H).

Example 40

6-(2-methoxy-2-methylpropoxy)-4-(6-(6-((6-methoxypyridin-3-yl)methyl)-3,6-diazabicyclo[3.3.1]heptan-3-yl)pyridin-3-yl)-1H-pyrazolo[3',4':3,4]pyrazolo[1,5-a]pyridine (Compound 40)

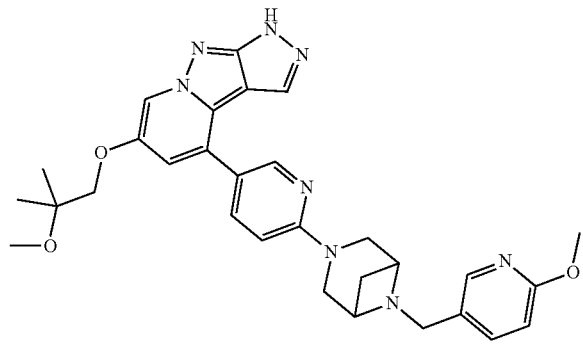

BIOACTIVITY TEST EXAMPLE

Test Example 1

Rearranged during transfection (RET) is an identified proto-oncogene. It encodes a single transmembrane receptor tyrosine kinase that is necessary for the development, maturation and maintenance of many tissues and cell types. Under normal conditions, the binding of the ligand of glial cell line-derived neurotrophic factor (GDNF) family to RET on the cell surface leads to the dimerization and autophosphorylation of tyrosine residues in the cell, which in turn leads to the activation of downstream RAS-MAPK, PI3K-AKT and phospholipase Cγ (PLCγ) pathways, and increases the survival and proliferation of cells. Examples of mutations that activate RET include C634W, M918T, gatekeeper mutations V804L and V804M, and solvent-front mutation G810R.

This test combines peptide substrates and a single proprietary monoclonal antibody with HTRF technology, which is a highly sensitive and stable technology for detecting molecular interactions of proteins. The enzyme phosphorylates the substrates, and then the Eu-labeled antibody binds to the phosphorylated substrates, and streptavidin-XL665 binds to all of the substrates. The TR-FRET signal is generated according to the HTRF principle. Once the inhibitor (test compound) is added, a weaker TR-FRET signal is obtained. Based on this, the inhibitory effect is evaluated.

TABLE 1

Reagents and consumables for kinase activity test

| Materials and reagents | Supplier | Model |
|---|---|---|
| HTRF KinEASE-TK kit | Cisbio | 62TK0PEC |
| Ret wt | Carna | 08-159 |
| RET (V804M), activation | Signalchem | R02-12GG |
| RET G810R | Proqinase | 1724-0000-1 |
| DMSO | Sigma | D8418-1L |
| ATP | Promega | A769 |
| DTT | Sigma | D0632 |
| MgCl$_2$ | Sigma | M1028 |
| Cabozantinib | MCE | HY-13016 |
| Plate shaker | Thermo | 4625-1CECN/THZ Q |
| Centrifuge | Eppendorf | 5810R |
| Envision 2104 multilable plate reader | PerkinElmer | 2104-0010 |
| Echo | Labcyte | 550 |
| 384 polystyrene Shallow flat white | Greiner | 784075 |
| Microplate low speed centrifuge | Xiangzhi | TD5B |
| Biotek microplate reader | Biotek | Synergy 4 |

1.2 Preparation of Solution

All the test compounds were dissolved in DMSO to prepare a 10 mM stock solution respectively.

Cabozantinib was subjected to serial 3-fold dilution with DMSO from 2 mM and 0.2 mM, respectively, for a total of 10 concentrations.

Other compounds were subjected to serial 3-fold dilution with DMSO from 10 mM (stock solution) for a total of 10 concentrations.

1000× positive control (0.1 mM cabozantinib) and 1000× negative control (100% DMSO) were prepared, and shaken on a plate shaker for 5 min.

1.3 Preparation of 1× Kinase Buffer 4 volume of distilled water was added to 1 volume of enzyme buffer 5×; 5 mM MgCl$_2$; 1 mM DTT.

1.4 Screening Method a) 1 µL of compound dilution was transferred to each well of the test plate;

b) the compound plate was centrifuged at 1000 g for 1 min;

c) the test plate was sealed;

d) 2× Ret wt (0.04 ng/µL), 2× Ret V804M (0.2 ng/µL) and 2×RET G810R (2 ng/µL) in 1× kinase buffer were prepared;

e) 5 µL of 2× Ret wt, Ret V804M or RET G810R was added to a 384-well test plate;

f) the sample plate was centrifuged at 1000 g for 30 s, and left to stand at room temperature for 10 min;

g) a solution of 5× TK-substrate-biotin (5 µM) in kinase buffer and a solution of 5×ATP (50 µM) in kinase buffer were prepared with 1× kinase buffer;

h) the reaction was initiated by adding 2 µL of STK-substrate-biotin and 2 µL of ATP (prepared in step g);

i) the sample plate was centrifuged at 1000 g for 30 s, and the test plate was sealed and left to stand at room temperature for 30 min;

j) 4× Sa-XL 665 (250 nM) in HTRF detection buffer was prepared;

k) 5 µL of Sa-XL 665 and 5 µL of TK-antibody-Cryptate (prepared in step i) were added to each well of the test plate;

l) the plate was centrifuged at 1000 g for 30 s, and left to stand at room temperature for 1 h; and m) the plate was read for the fluorescence signal values of 620 nm (Cryptate) and 665 nm (XL665) on Envision 2104 plate reader or BioTek microplate reader.

1.5 Data Analysis

The ratio (665 nm/620 nm) of each well was calculated. The inhibition rate % was calculated as follows:

Inhibition rate %=[1−(ratio of test compound−average ratio of positive control)/(average ratio of negative control−average ratio of positive control)]*100%

Ratio: generated from the measured fluorescence signal value

The average ratio of positive control is the average ratio of positive control (20 μM cabozantinib) in the sample plate.

The average ratio of negative controls is the average ratio of negative control (0.1% DMSO) in the sample plate.

Some nonlinear fitting formulas were used to obtain the $IC_{50}$ values (half maximal inhibitory concentration) of the compounds: GraphPad 6.0 software was used for data analysis.

$$Y=Bottom+(Top-Bottom)/(1+10^{\wedge}((Log\ IC_{50}-X)*Hill\ Slope))$$

X: Log value of compound concentration Y: Inhibition rate (% inhibition)

Z' factor equation:

$$Z'=1-3(SD\ min+SD\ max)/(AVE\ max-AVE\ min)$$

Min is the positive control 20 μM Cabozantinib Ratio (665/620 nM*10000), and Max is the negative control DMSO Ration(665/620 nM*10000).

SD is the standard error, and AVE is the average value of Ration(665/620 nM*10000).

The Kinase Test Results are Shown in Table 2, Table 3 and Table 4:

TABLE 2

| Compound No. | RET wt $IC_{50}$ (nM) |
|---|---|
| Compound 1 | 4.1 |
| Compound 7 | 0.1 |
| Compound 9 | 0.2 |
| Compound 12 | 0.1 |
| Compound 27 | 0.1 |
| Compound 31 | 0.1 |
| Compound 32 | 0.1 |
| Compound 36 | 0.2 |
| Compound 38 | 0.2 |
| Compound 39 | 0.4 |
| Cabozantinib | 20.2 |

TABLE 3

| Compound No. | RET V804M $IC_{50}$ (nM) |
|---|---|
| Compound 1 | 2.9 |
| Compound 7 | 0.1 |
| Compound 9 | 0.1 |
| Compound 12 | 0.1 |
| Compound 16 | 0.1 |
| Compound 17 | 0.1 |
| Compound 23 | 0.1 |
| Compound 27 | 0.1 |
| Compound 31 | 0.1 |
| Compound 32 | 0.1 |
| Compound 36 | 0.1 |
| Compound 38 | 0.1 |
| Compound 39 | 0.3 |
| Cabozantinib | 89.3 |

TABLE 4

| Compound No. | RET G810R $IC_{50}$ (nM) |
|---|---|
| Compound 3 | 16.2 |
| Compound 5 | 38.4 |
| Compound 7 | 2.7 |
| Compound 9 | 1.9 |
| Compound 10 | 3.8 |
| Compound 11 | 10.1 |
| Compound 12 | 3.9 |
| Compound 13 | 3.1 |
| Compound 14 | 2.2 |
| Compound 15 | 7.9 |
| Compound 16 | 2.9 |
| Compound 18 | 18.9 |
| Compound 19 | 4.8 |
| Compound 20 | 1.6 |
| Compound 21 | 0.6 |
| Compound 22 | 1.7 |
| Compound 24 | 2.3 |
| Compound 25 | 4.3 |
| Compound 26 | 2.1 |
| Compound 27 | 4.8 |
| Compound 30 | 5.9 |
| Compound 31 | 1.0 |
| Compound 32 | 2.3 |
| Compound 36 | 1.7 |
| Compound 38 | 2.9 |
| Compound 39 | 30.5 |
| Cabozantinib | 325.5 |
| Selpercatinib(LOXO-292) | 43.2 |

The experimental results shown in Table 2, Table 3 and Table 4 show that the inhibitory activity of compounds 1, 7, 9, 12, 27, 31, 32, 36, 38 and 39 on RET wt is significantly better than that of cabozantinib. Among them, the inhibitory activity of compounds 1, 7, 9, 12, 16, 17, 23, 27, 31, 32, 36, 38 and 39 on RET V804M is significantly better than that of cabozantinib; and the inhibitory activity of compounds 3, 5, 7, 9, 10, 11, 12, 13, 14, 15, 16, 18, 19, 20, 21, 22, 24, 25, 26, 27, 30, 31, 32, 36, 38 and 39 on RET G810R is significantly better than that of cabozantinib and selpercatinib (LOXO-292).

Test Example 2

TABLE 2.1

| Reagents and consumables for cell activity test | | |
|---|---|---|
| Reagents and consumables | Supplier | Model |
| Ham's F-12K | Procell | PM150910 |
| FBS | Invitrogen | 10099141 |
| Penicillin-streptomycin | Invitrogen | 15140-122 |
| DMSO | Sigma | D8418-1L |
| Cabozantinib | MCE | HY-13016 |
| 384 well cell seeding plate | Corning | 3570 |
| CelltiterGlo assay kit (CTG) | Promega | G7573 |
| Instrumentation: | Vendor | Model |
| Echo550 | Echo | 550 |
| Biological Safety Cabinet (Class II) | Thermo Scientific | 1300 Series A2 |
| Centrifuge | Eppendorf | 5702 |
| $CO_2$ Incubator | Thermo Scientific | 1300 SERIES A2 |
| EnVision | PerkinElmer | EnVision 2104 |

2.2 Experimental Steps a) cabozantinib and test compounds (10 mM stock solution) were subjected to 5-fold dilution to 2 mM with 100% DMSO, and diluted at a ratio of 1:3 in a 384-well dilution plate for 10 concentrations respectively;

b) 200 nL of the solution (prepared in step a) was transferred to a 384-well cell culture plate with Echo; the gradient concentrations of cabozantinib and the test compounds were 10000 nM, 3333.3 nM, 1111.1 nM, 370.4 nM, 123.4 nM, 41.1 nM, 13.7 nM, 4.5 nM, 1.5 nM and 0.5 nM, respectively, and the final concentration of DMSO was 0.5%;

c) the TT cell line medium contained 10% FBS and 1% penicillin-streptomycin;

d) the cell suspension was added to a 384-well plate containing the compound (prepared in step b), each well containing 800 cells with a volume of 40 μL, and incubated in a cell incubator for 72 h;

e) the 384-well cell culture plate was taken out and added with 20 μL of CTG reagent;

f) the plate was shaken in a fast shaker for 2 min, and left to stand at room temperature for 30 min; and the plate was read for the fluorescence signal value using Envision instrument.

2.3 Data Processing

% Inhibition (inhibition rate)=100*(HC−test compound well reading)/(HC−LC)

High control (HC, reading control without inhibition): 0.5% DMSO

Low control (LC, control with compound inhibition): 1 μM CEP-32496

The $IC_{50}$ values were calculated using GraphPad Prism 6 software.

Y=Bottom+(Top−Bottom)/(1+10^((Log $IC_{50}$−X)*Hill-Slope));

X: log of cpd concentration;
Y: % inhibition;
Top and Bottom: plateaus in same units as Y;
Log $IC_{50}$: same log units as X; and
HillSlope: slope factor The Cell Results are Shown in Table 5:

TABLE 5

| Compound No | TT Cell $IC_{50}$ (nM) |
|---|---|
| Compound 1 | 319.4 |
| Compound 2 | 42.2 |
| Compound 3 | 32.8 |
| Compound 5 | 11.8 |
| Compound 6 | 19.4 |
| Compound 7 | 2.5 |
| Compound 8 | 14.4 |
| Compound 9 | 5.5 |
| Compound 10 | 12.3 |
| Compound 11 | 16.8 |
| Compound 12 | 1.5 |
| Compound 13 | 10.7 |
| Compound 16 | 12.8 |
| Compound 17 | 11.3 |
| Compound 18 | 78.2 |
| Compound 19 | 31.2 |
| Compound 20 | 27.8 |
| Compound 21 | 15.8 |
| Compound 22 | 39.5 |
| Compound 23 | 7.9 |
| Compound 24 | 22.4 |
| Compound 25 | 23.4 |
| Compound 26 | 22.7 |
| Compound 27 | 27.9 |
| Compound 28 | 64.3 |
| Compound 29 | 60.8 |
| Compound 30 | 48.6 |
| Compound 31 | 12.7 |
| Compound 32 | 6.5 |
| Compound 33 | 350.4 |
| Compound 34 | 81.8 |
| Compound 35 | 296.4 |
| Compound 36 | 10.7 |
| Compound 37 | 29.2 |
| Compound 38 | 10.6 |
| Compound 39 | 12.3 |
| Cabozantinib | 142.9 |

The experimental results shown in Table 5 show that the inhibitory activity of compounds 2, 3, 5, 6, 7, 8, 9, 10, 11, 12, 13, 16, 17, 18, 19, 20, 21, 22, 23, 24, 25, 26, 27, 28, 29, 30, 31, 32, 34, 36, 37, 38 and 39 on TT cells is significantly better than that of cabozantinib.

Test Example 3. Pharmacodynamic Test on TT Cell Human Medullary Thyroid Carcinoma Xenograft Model 3.1 Cell Culturing TT tumor cells were cultured in F12K medium containing inactivated 10% fetal bovine serum, 100 U/mL penicillin, 100 μg/mL streptomycin and 2 mM glutamine in an incubator at 37° C. and 5% $CO_2$. The cells were cultured at a starting concentration of $1\times10^6$ cells/mL, and divided and transferred to flasks for sub-culture every 3 to 4 days when they were overgrown. The tumor cells in the logarithmic growth phase were used for tumor inoculation in vivo.

3.2 Inoculation and Grouping of Tumor Cells

The TT tumor cells resuspended in serum-free F12K medium at a concentration of $1\times10^7$ cells+gel/100 μL were inoculated subcutaneously into the right flank of experimental animals. When the tumor grew to about 224 $mm^3$, the compounds were administered in groups, with 6 animals in each group.

3.3 Administration, Tumor Measurement and Experimental Indicators

The mice were orally administered with the test compound twice a day for 28 consecutive days.

Tumor volume: the long and short diameters of the tumor were measured using a vernier caliper. The volume was calculated by the formula: volume=0.5×long diameter×short $diameter^2$. Animals were required to have their body weight and tumor size measured twice a week during the administration.

Reaction of animals after the administration: the experimental animals were weighed while measuring the tumors. The relationship between the change in the animal weight and the time of administration was recorded. At the same time, the survival and health of the mice, such as animal activity, feeding and other general states during the administration were observed.

Relative tumor proliferation rate T/C (%)=TRTV/CRTV× 100% (TRTV: treatment group RTV; CRTV: negative control group RTV), where the relative tumor volume (RTV) is calculated as: RTV=Vt/V0, where V0 is the tumor volume measured at the time of group administration (that is, day 1 of the administration), and Vt is the tumor volume at each measurement. Tumor growth inhibition rate TGI (%)=(1−T/C)×100%.

In the TT cell human medullary thyroid carcinoma xenograft model, compound 9, compound 31 and compound 32 were administered at a dose of 10 mg/kg, and they all exhibit very significant tumor inhibitory effects (TGI=88.5%, TGI=87.4% and TGI=86.9%), with the efficacy among the three groups being comparable. During the administration, the experimental animals in all groups are in good activity, feeding and other general states without significant weight loss or adverse reactions. The test results are shown in FIG. 1.

Test Example 4. Pharmacodynamic Test on Ba/F3 Cell KIF5B-RET-V804M Fusion Xenograft Model 4.1 Cell Culturing Ba/F3 KIF5B-RET-V804M tumor cells were cultured in RPMI-1640 medium containing inactivated 10% fetal bovine serum, 100 U/mL penicillin, 100 μg/mL streptomycin and 2 mM glutamine in an incubator at 37° C. and 5% $CO_2$. The cells were divided and transferred to flasks for sub-culture every 3 to 4 days when they were overgrown, and the tumor cells in the logarithmic growth phase were used for tumor inoculation in vivo.

4.2 Inoculation and Grouping of Tumor Cells

Ba/F3 KIF5B-RET-V804M tumor cells resuspended in equal volume of PBS and Matrigel at a concentration of $5 \times 10^7$ cells/mL were inoculated subcutaneously into the right flank of BALB/c nude mice at 100 μL/mouse. When the tumor grew to about 194 mm³, the compounds were administered in groups, with 6 animals in each group.

4.3 Administration, Tumor Measurement and Experimental Indicators

The mice were orally administered with the test compound twice a day for 14 consecutive days.

Tumor volume: the long and short diameters of the tumor were measured using a vernier caliper. The volume was calculated by the formula: volume=0.5×long diameter×short diameter². Animals were required to have their body weight and tumor size measured twice a week during the administration.

Reaction of animals after the administration: the experimental animals were weighed while measuring the tumors. The relationship between the change in the animal weight and the time of administration was recorded. At the same time, the survival and health of the mice, such as animal activity, feeding and other general states during the administration were observed.

Relative tumor proliferation rate T/C (%)=TRTV/CRTV× 100% (TRTV: treatment group RTV; CRTV: negative control group RTV), where the relative tumor volume (RTV) is calculated as: RTV=Vt/V0, where V0 is the tumor volume measured at the time of group administration (that is, day 1 of the administration), and Vt is the tumor volume at each measurement. Tumor growth inhibition rate TGI (%)=(1−T/C)×100%.

Figure 2:
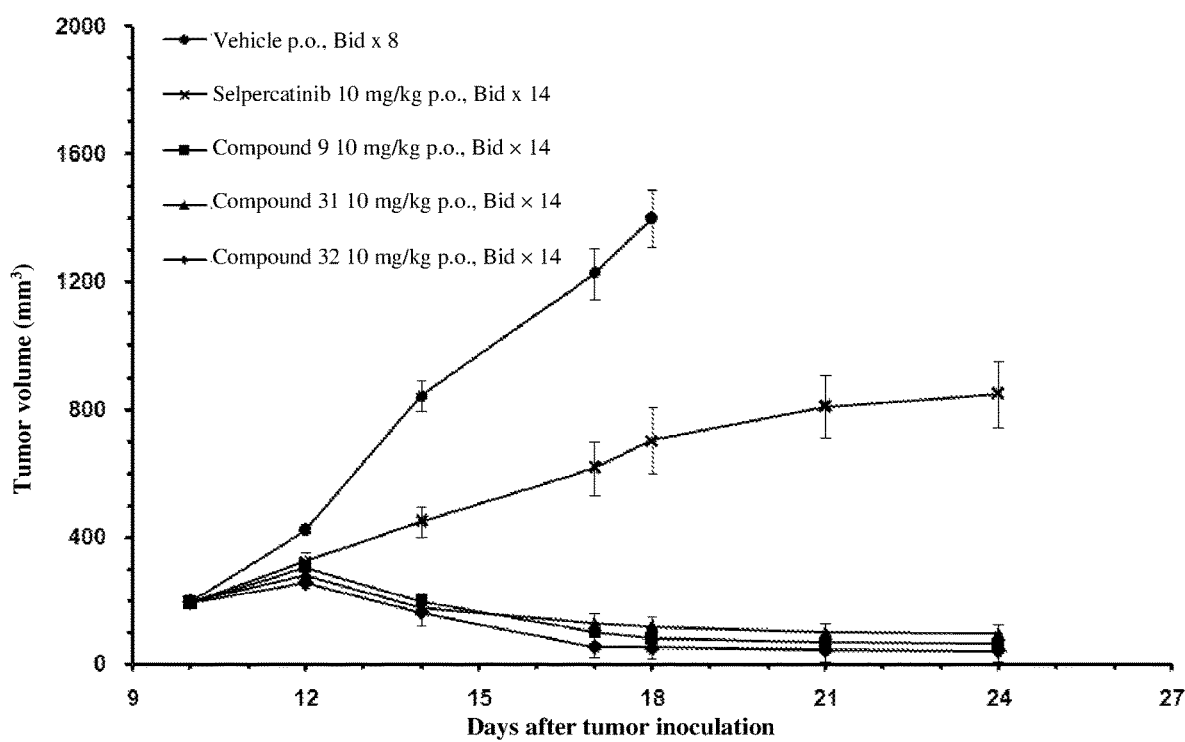
FIG. 2 shows the inhibitory effect of the compounds on the tumor of Ba/F3 cell KIF5B-RET-V804M fusion xenograft model.

Selpercatinib, compound 9, compound 31 and compound 32 were all administered at a dose of 10 mg/kg, and had the tumor growth inhibition rates of 49%, 94%, 92%, 96%, respectively, at the end of the control experiment (on day 8 of the administration). The tumor volume of each treatment group was significantly lower than that of the control group (p<0.05); and the tumor volume of the compound 9, compound 31 and compound 32 groups were significantly lower than that of the selpercatinib group (p<0.05). At the end of the experiment (on day 14 of the administration), the tumor volume of the compound 9, compound 31, and compound 32 groups was significantly lower than that of the selpercatinib group (p<0.05). During the treatment, the tumor-bearing mice all showed good tolerance to the test compounds. The mice in each group had normal body weight and no abnormal performance, and were in good general state. The test results are shown in FIG. 2.

The present disclosure relates to the field of medicinal chemistry, in particular to a nitrogen-containing polycyclic fused ring compound of formula I, a pharmaceutical composition thereof, a preparation method therefor and use thereof. The compound disclosed herein can be used as a highly selective and very effective RET inhibitor. Such a compound has strong inhibitory effect on the RET gatekeeper residue mutant RET V804M, RET solvent-front residue mutant RET G810R and other clinically relevant RET mutants, as well as RET wt. The compound can also significantly inhibit the growth of TT cell line derived from thyroid cancer and Ba/F3 cells transformed with various RET mutants, and significantly induce the death of TT cells.

The exemplary embodiments of the present disclosure have been described herein. However, it should be understood that the protection scope of the present disclosure is not limited to the foregoing embodiments. Any modifications, equivalents, improvements and the like made without departing from the spirit and principle of the present disclosure shall fall within the protection scope of the present disclosure.

The invention claimed is:

1. A compound of formula I or a pharmaceutically acceptable salt thereof:

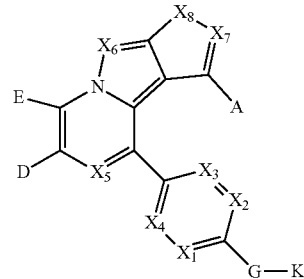

wherein $X^1$, $X^2$, $X^3$, $X^4$, $X^5$, $X^6$ and $X^7$ are the same or different, and are independently selected from $CR^1$ and N;

$X^8$ is selected from $CR^1R^{1'}$ and $NR^1$; wherein each $R^1$ and $R^{1'}$ are the same or different, and are independently selected from H, halogen, CN, $NH_2$ and OH, or each $R^1$ and $R^{1'}$ are the same or different, and are independently selected from the following groups unsubstituted or optionally substituted with 1, 2 or 3 $R^a$: $C_{1-6}$ alkyl, $C_{3-6}$ cycloalkyl, $C_{1-6}$ alkoxy and $C_{3-6}$ cycloalkyloxy; and each $R^a$ is the same or different, and is independently selected from halogen, CN, OH, $C_{1-6}$ alkyl, $C_{3-6}$ cycloalkyl and $C_{1-6}$ alkoxy;

A is selected from H, halogen, CN, OH and $NH_2$, or

A is selected from the following groups unsubstituted or optionally substituted with 1, 2 or 3 $R^b$: $C_{1-6}$ alkyl, $C_{2-6}$ alkenyl, $C_{3-6}$ cycloalkyl, $C_{1-6}$ alkoxy and $C_{3-6}$ cycloalkyloxy; wherein each $R^b$ is the same or different, and is independently selected from halogen, CN, OH, $C_{1-6}$ alkyl, $C_{3-6}$ cycloalkyl and $C_{1-6}$ alkoxy;

D and E are the same or different, and are independently selected from H, halogen, CN, OH and $NH_2$, or D and E are the same or different, and are independently selected from the following groups unsubstituted or optionally substituted with 1, 2 or 3 $R^c$: —$C_{1-6}$ alkyl, —$C_{1-6}$ alkoxy, —O($CH_2$)$_n$O($CH_2$)$_n$$C_{3-6}$ carbocyclic ring, —O(CH²)ₙ-3- to 8-membered heterocyclic ring, and —O(CH²)ₙC₆₋₁₀ aromatic ring; wherein
   each $R^c$ is the same or different, and is independently selected from halogen, CN, OH, oxo (=O), $C_{1-6}$ alkyl, $C_{1-6}$ alkoxy, $C_{3-6}$ cycloalkyl, 3- to 10-membered heterocyclyl, 5- to 7-membered heteroaryl, 6- to 10-membered aryl, $C_{1-6}$ alkoxy, 3- to 6-membered cycloalkyloxy and 3- to 8-membered heterocyclyloxy;
   each n is the same or different, and is independently selected from 0, 1, 2 and 3; and
   each heterocyclic ring, heterocyclyl and heteroaryl in D, E and $R^c$ have the same or different numbers and types of heteroatoms, and independently contain 1, 2 or 3 heteroatoms selected from N, O and S;
G is selected from the following groups: (1) saturated 4- to 8-membered heterocyclic ring containing 2 heteroatoms; (2) saturated 7- to 10-membered heterocyclic ring containing 2 heteroatoms; (3) saturated 7- to 11-membered heterospiro ring containing 2 heteroatoms; and (4) saturated 7- to 10-membered bicyclic fused heterocyclic ring containing 2 heteroatoms; wherein the above heteroatoms are selected from N and O respectively, and each ring is independently unsubstituted or optionally substituted with 1, 2, 3 or 4 $R^G$;
   each $R^G$ is the same or different, and is independently selected from H, halogen, OH, $NH_2$, $C_{1-6}$ alkyl, halogen-substituted $C_{1-6}$ alkyl, $C_{1-6}$ alkoxy and halogen-substituted $C_{1-6}$ alkoxy; and
K is selected from the following groups unsubstituted or optionally substituted with 1, 2, 3 or 4 $R^K$: $C_{1-6}$ alkyl, $C_{3-6}$ cycloalkyl, $C_{6-10}$ aryl, —$C_{1-6}$ alkylene $C_{6-10}$ aromatic ring, —$COC_{1-6}$ alkylene $C_{6-10}$ aromatic ring, —$C_{1-6}$ alkylene 5- to 10-membered aromatic heterocyclic ring, —$COC_{1-6}$ alkylene 5- to 10-membered aromatic heterocyclic ring, —$CONR^{K1}R^{K2}$, 3- to 10-membered heterocyclyl, $C_{1-6}$ alkoxy, $C_{3-6}$ cycloalkyloxy, $C_{6-10}$ aryloxy, 5- to 10-membered heteroaryloxy, and 3- to 10-membered heterocyclyloxy; wherein
   each $R^K$ is the same or different, and is independently selected from the following groups: —CN, OH, —$NH_2$, $C_{1-6}$ alkyl, $C_{1-6}$ alkoxy, $C_{3-6}$ cycloalkyl, halogen-substituted $C_{1-6}$ alkyl and halogen-substituted $C_{1-6}$ alkoxy;
   $R^{K1}$ and $R^{K2}$ are the same or different, and are independently selected from the following groups: —CN, $C_{1-6}$ alkyl, $C_{1-6}$ alkoxy, $C_{3-6}$ cycloalkyl, halogen-substituted $C_{1-6}$ alkyl and halogen-substituted $C_{1-6}$ alkoxy; and
   each aromatic heterocyclic ring, heterocyclic ring and heterocyclyl in K is the same or different, and independently contains one or two N.

2. The compound of formula I or the pharmaceutically acceptable salt according to claim 1, wherein $X^1$, $X^3$ and $X^4$ are all independently selected from $CR^1$.

3. The compound of formula I or the pharmaceutically acceptable salt according to claim 1, wherein $X^5$ is selected from $CR^1$.

4. The compound of formula I or the pharmaceutically acceptable salt according to claim 1, wherein $X^8$ is selected from $NR^1$.

5. The compound of formula I or the pharmaceutically acceptable salt according to claim 1, wherein each $R^1$ and $R^{1'}$ are the same or different, and are independently selected from H, F, Cl, Br, CN, $NH_2$ and OH, or each $R^1$ and $R^{1'}$ are the same or different, and are independently selected from the following groups unsubstituted or optionally substituted with 1, 2 or 3 $R^a$: $C_{1-3}$ alkyl, $C_{4-6}$ cycloalkyl, $C_{1-3}$ alkoxy and $C_{4-6}$ cycloalkyloxy.

6. The compound of formula I or the pharmaceutically acceptable salt according to claim 1, wherein each $R^1$ and $R^{1'}$ are the same or different, and are independently selected from H, F, Cl, Br, CN and $NH_2$, or
   each $R^1$ and $R^{1'}$ are the same or different, and are independently selected from the following groups unsubstituted or optionally substituted with 1, 2 or 3 $R^a$: methyl, ethyl, propyl, 5-membered cycloalkyl, 6-membered cycloalkyl, methoxy, ethoxy, propoxy, 5-membered cycloalkyloxy and 6-membered cycloalkyloxy.

7. The compound of formula I or the pharmaceutically acceptable salt according to claim 1, wherein each $R^a$ is the same or different, and is independently selected from F, Cl, Br, CN, OH, $C_{1-3}$ alkyl, $C_{4-6}$ cycloalkyl and $C_{1-3}$ alkoxy.

8. The compound of formula I or the pharmaceutically acceptable salt according to claim 1, wherein each $R^a$ is the same or different, and is independently selected from F, Cl, CN, OH, methyl, ethyl, propyl, 5-membered cycloalkyl, 6-membered cycloalkyl, methoxy, ethoxy, propoxy, 5-membered cycloalkyloxy and 6-membered cycloalkyloxy.

9. The compound of formula I or the pharmaceutically acceptable salt according to claim 1, wherein $X^1$ is selected from CH.

10. The compound of formula I or the pharmaceutically acceptable salt according to claim 1, wherein $X^3$ is selected from CH.

11. The compound of formula I or the pharmaceutically acceptable salt according to claim 1, wherein $X^5$ is selected from CH.

12. The compound of formula I or the pharmaceutically acceptable salt according to claim 1, wherein $X^5$ is selected from CH.

13. The compound of formula I or the pharmaceutically acceptable salt according to claim 1, wherein $X^8$ is selected from NH.

14. The compound of formula I or the pharmaceutically acceptable salt according to claim 1, wherein $X^1$, $X^3$, $X^4$ and $X^5$ are all selected from CH, and $X^8$ is selected from NH.

15. The compound of formula I or the pharmaceutically acceptable salt according to claim 1, wherein $X^2$ is selected from N.

16. The compound of formula I or the pharmaceutically acceptable salt according to claim 1, wherein $X^6$ is selected from N.

17. The compound of formula I or the pharmaceutically acceptable salt according to claim 1, wherein $X^7$ is selected from N.

18. The compound of formula I or the pharmaceutically acceptable salt according to claim 1, wherein $X^1$, $X^3$, $X^4$ and $X^5$ are all selected from CH, $X^2$, $X^6$ and $X^7$ are all selected from N, and $X^8$ is selected from NH.

19. The compound of formula I or the pharmaceutically acceptable salt according to claim 1, wherein A is selected from H, F, Cl, Br, CN, OH and $NH_2$, or
   A is selected from the following groups unsubstituted or optionally substituted with 1, 2 or 3 $R^b$: $C_{1-3}$ alkyl, $C_{4-6}$ cycloalkyl, $C_{1-3}$ alkoxy and $C_{4-6}$ cycloalkyloxy; wherein each $R^b$ is the same or different, and is independently selected from F, Cl, Br, CN, OH, $C_{1-3}$ alkyl and $C_{1-3}$ alkoxy.

20. The compound of formula I or the pharmaceutically acceptable salt according to claim 1, wherein A is selected from H, F, Cl, CN, OH and $NH_2$, or
   A is selected from the following groups unsubstituted or optionally substituted with 1, 2 or 3 $R^b$: methyl, ethyl, propyl, 5-membered cycloalkyl, 6-membered cycloalkyl, methoxy, ethoxy, propoxy, 5-membered cycloalkyloxy and 6-membered cycloalkyloxy; wherein each $R^b$ is the same or different, and is independently selected from F, Cl, methyl, ethyl, methoxy and ethoxy.

21. The compound of formula I or the pharmaceutically acceptable salt according to claim 1, wherein A is selected from H, —F, —Cl, —CN, —OH, $NH_2$ and —$CH_3$.

22. The compound of formula I or the pharmaceutically acceptable salt according to claim 1, wherein D and E are the same or different, and are independently selected from H, F, Cl, Br, CN, OH and $NH_2$, or D and E are the same or different, and are independently selected from the following groups unsubstituted or optionally substituted with 1, 2 or 3 $R^c$: —$C_{1-3}$ alkyl, —$C_{1-3}$ alkoxy, —$O(CH^2)_nO(CH^2)_nC_{3-6}$ carbocyclic ring, —$O(CH^2)_n$-4- to 6-membered heterocyclic ring, —$O(CH^2)_nC_6$ aromatic ring, and —$O(CH^2)_nC_{10}$ aromatic ring.

23. The compound of formula I or the pharmaceutically acceptable salt according to claim 1, wherein D and E are the same or different, and are independently selected from H, F, Cl, Br, CN, OH and $NH_2$, or D and E are the same or different, and are independently selected from the following groups unsubstituted or optionally substituted with 1, 2 or 3 $R^c$: methyl, ethyl, propyl, methoxy, ethoxy, propoxy, —$O(CH^2)_nO(CH^2)_n$-3-membered carbocyclic ring, —$O(CH^2)_nO(CH^2)_n$-4-membered carbocyclic ring, —$O(CH^2)_nO(CH^2)_n$-5-membered carbocyclic ring, —$O(CH^2)_n$-5-membered heterocyclic ring, —$O(CH^2)_n$-6-membered heterocyclic ring, and —$O(CH^2)_n$-phenyl ring.

24. The compound of formula I or the pharmaceutically acceptable salt according to claim 1, wherein D and E are the same or different, and are independently selected from H, F, Cl, Br, CN, OH and $NH_2$, or D and E are the same or different, and are independently selected from the following groups unsubstituted or optionally substituted with 1, 2 or 3 $R^c$: methyl, methoxy, —$O(CH^2)_nO(CH^2)_n$-3-membered carbocyclic ring, —$O(CH^2)_n$-6-membered heterocyclic ring, and —$O(CH^2)_n$-phenyl ring.

25. The compound of formula I or the pharmaceutically acceptable salt according to claim 1, wherein each n is the same or different, and is independently selected from 0, 1 and 2.

26. The compound of formula I or the pharmaceutically acceptable salt according to claim 1, wherein each n is the same or different, and is independently selected from 1 and 2.

27. The compound of formula I or the pharmaceutically acceptable salt according to claim 1, wherein each $R^c$ is the same or different, and is independently selected from F, Cl, Br, CN, OH, $C_{1-3}$ alkyl, $C_{3-5}$ cycloalkyl, 4- to 6-membered heterocyclyl, 5- to 6-membered heteroaryl, phenyl, $C_{1-3}$ alkoxy, 3- to 5-membered cycloalkyloxy, and 4- to 6-membered saturated heterocyclyloxy.

28. The compound of formula I or the pharmaceutically acceptable salt according to claim 1, wherein each $R^c$ is the same or different, and is independently selected from F, Cl, Br, CN, OH, methyl, ethyl, propyl, 3-membered cycloalkyl, 4-membered cycloalkyl, 4-membered saturated heterocyclyl, 5-membered saturated heterocyclyl, 6-membered saturated heterocyclyl, 5-membered heteroaryl, 6-membered heteroaryl, phenyl, methoxy, ethoxy, propoxy, 3-membered cycloalkyloxy, 4-membered cycloalkyloxy, 5-membered saturated heterocyclyloxy, and 6-membered saturated heterocyclyloxy.

29. The compound of formula I or the pharmaceutically acceptable salt according to claim 1, wherein each $R^c$ is the same or different, and is independently selected from F, Cl, Br, CN, OH, methyl, ethyl, propyl, 3-membered cycloalkyl, 4-membered cycloalkyl, 4-membered saturated heterocyclyl, 5-membered saturated heterocyclyl, 6-membered saturated heterocyclyl, 5-membered heteroaryl, 6-membered heteroaryl, phenyl, methoxy, ethoxy, propoxy, 3-membered cycloalkyloxy, 4-membered cycloalkyloxy, 5-membered saturated heterocyclyloxy, and 6-membered saturated heterocyclyloxy.

30. The compound of formula I or the pharmaceutically acceptable salt according to claim 1, wherein each heterocyclic ring, heterocyclyl and heteroaryl in D, E and $R^c$ have the same or different numbers and types of heteroatoms, and independently contain 1 or 2 heteroatoms selected from N and O.

31. The compound of formula I or the pharmaceutically acceptable salt according to claim 1, wherein each heterocyclic ring, heterocyclyl and heteroaryl in D, E and $R^c$ have the same or different numbers and types of heteroatoms, and independently contain one N atom and/or one O atom.

32. The compound of formula I or the pharmaceutically acceptable salt according to claim 1, wherein each $R^c$ is the same or different, and is independently selected from F, Cl, Br, OH, CN,

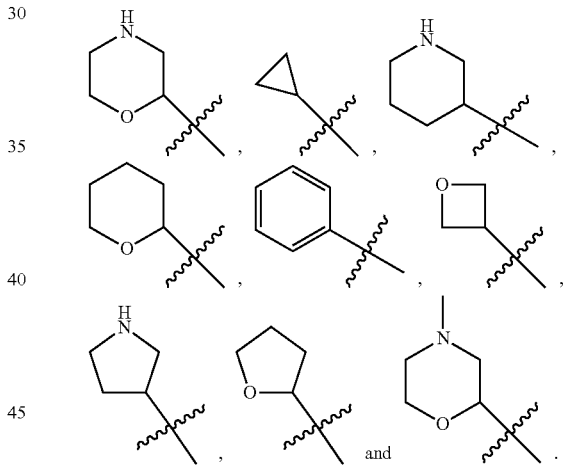

33. The compound of formula I or the pharmaceutically acceptable salt according to claim 1, wherein D is selected from —H, —Br, —Cl, —$CH_3$, —$NH_2$,

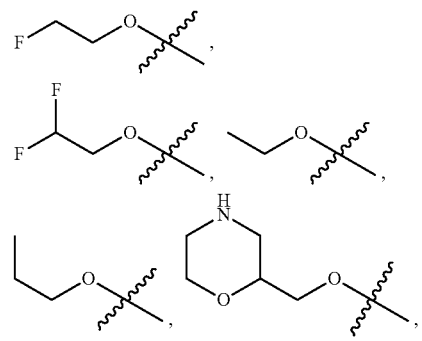

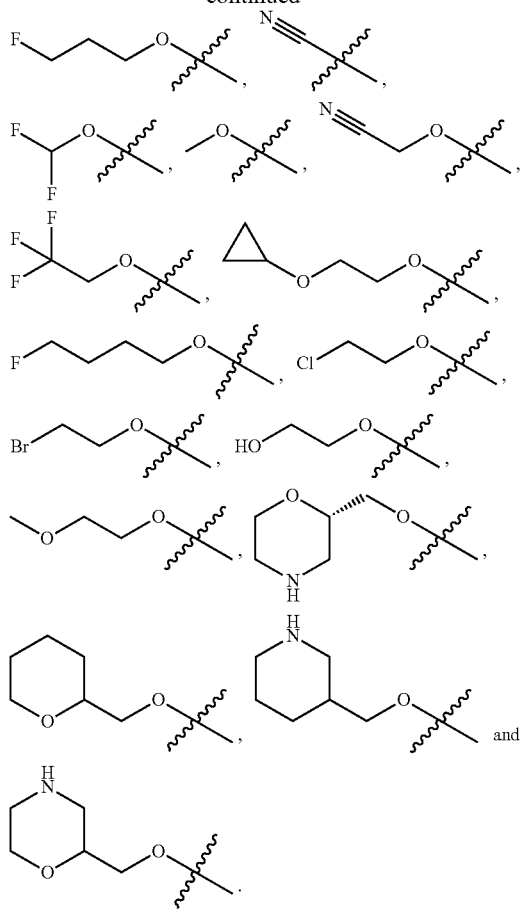
34. The compound of formula I or the pharmaceutically acceptable salt according to claim 1, wherein E is selected from —H, —Br, —CN, NH₂, —CH₃, CF₃,
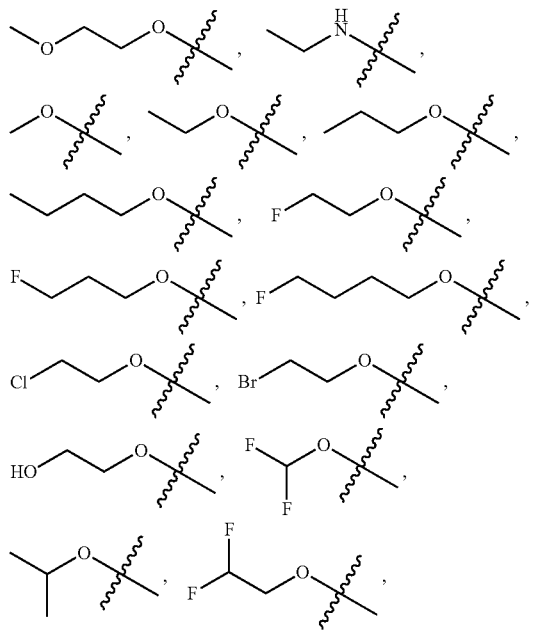
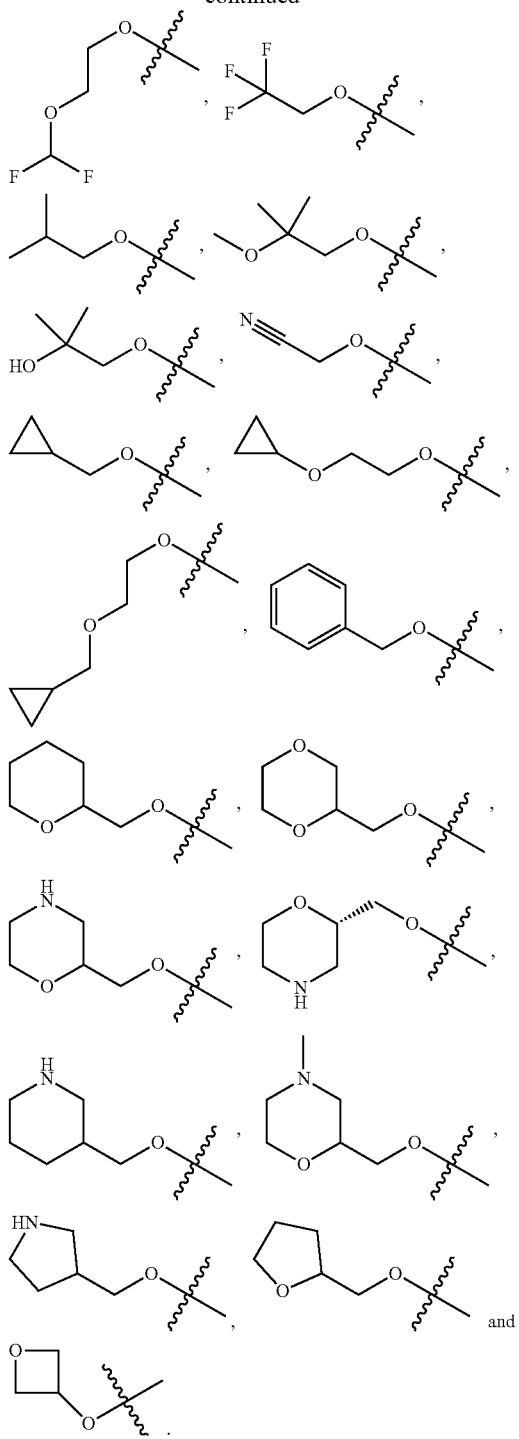
35. The compound of formula I or the pharmaceutically acceptable salt according to claim 1, wherein E is selected from H, and D is selected from —H, —Br, —Cl, —CH₃, —NH₂,
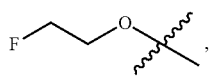

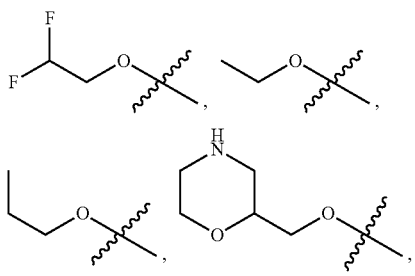

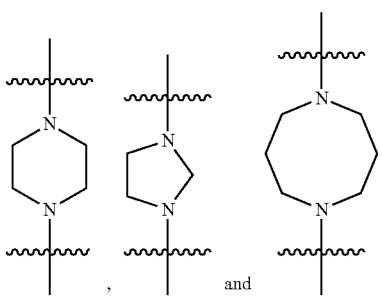

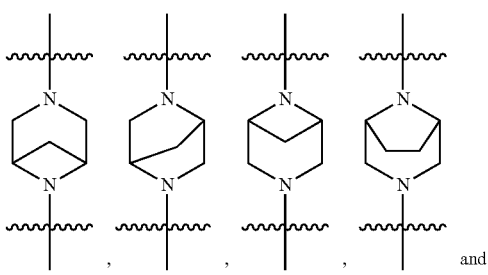

39. The compound of formula I or the pharmaceutically acceptable salt according to claim 1, wherein G is selected from the following groups: saturated 7-, 8- and 9-membered bridged heterocyclic rings containing two N or O atoms.

40. The compound of formula I or the pharmaceutically acceptable salt according to claim 1, wherein G is selected from the following groups: saturated 8-membered bridged heterocyclic ring containing two N or O atoms and saturated 9-membered bridged heterocyclic ring containing two N atoms.

41. The compound of formula I or the pharmaceutically acceptable salt according to claim 1, wherein G is selected from the following groups: saturated 8-membered bridged heterocyclic ring containing two N atoms and saturated 9-membered bridged heterocyclic ring containing two N atoms.

42. The compound of formula I or the pharmaceutically acceptable salt according to claim 1, wherein G is selected from the following groups:

36. The compound of formula I or the pharmaceutically acceptable salt according to claim 1, wherein G is selected from the following groups: saturated 5-, 6-, 7- and 8-membered heterocyclic rings containing two N atoms.

37. The compound of formula I or the pharmaceutically acceptable salt according to claim 1, wherein G is selected from the following groups: saturated 5-membered heterocyclic ring containing two N atoms, saturated 6-membered heterocyclic ring containing two N atoms, saturated 7-membered heterocyclic ring containing two N atoms, and saturated 8-membered heterocyclic ring containing two N atoms.

38. The compound of formula I or the pharmaceutically acceptable salt according to claim 1, wherein G is selected from the following groups:

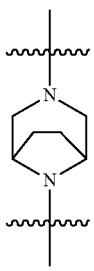

43. The compound of formula I or the pharmaceutically acceptable salt according to claim 1, wherein G is selected from the following group:

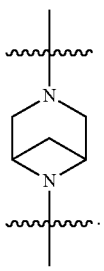

44. The compound of formula I or the pharmaceutically acceptable salt according to claim 1, wherein each $R^G$ is the same or different, and is independently selected from H, F, Cl, Br, OH, $NH_2$, $C_{1-3}$ alkyl, $C_{1-3}$ alkyl substituted with F or Cl and $C_{1-3}$ alkoxy.

45. The compound of formula I or the pharmaceutically acceptable salt according to claim 1, wherein each $R^G$ is the same or different, and is independently selected from H, $NH_2$, methyl, ethyl, propyl, F-substituted methyl, F-substituted ethyl, F-substituted propyl, methoxy, ethoxy and propoxy.

46. The compound of formula I or the pharmaceutically acceptable salt according to claim 1, wherein each $R^G$ is the same or different, and is independently selected from H, $NH_2$, methyl, F-substituted methyl, and methoxy.

47. The compound of formula I or the pharmaceutically acceptable salt according to claim 1, wherein K is selected from the following groups unsubstituted or optionally substituted with one, two or more $R^K$: K is selected from the following groups unsubstituted or optionally substituted with 1, 2 or 3 $R^K$: $C_{1-3}$ alkyl, $C_{5-6}$ cycloalkyl, phenyl, —$C_{1-3}$ alkylene phenyl ring, —$COC_{1-3}$ alkylene phenyl ring, —$COC_{1-3}$ alkylene biphenyl ring, —$C_{1-3}$ alkylene 5- to 8-membered aromatic heterocyclic ring, —$COC_{1-3}$ alkylene 5- to 8-membered aromatic heterocyclic ring, —$CONR^{K1}R^{K2}$, 5- to 6-membered heterocyclyl, $C_{1-3}$ alkoxy, $C_{3-6}$ cycloalkyloxy, $C_{6-10}$ aryloxy, 5- to 8-membered heteroaryloxy, and 5- to 8-membered heterocyclyloxy.

48. The compound of formula I or the pharmaceutically acceptable salt according to claim 1, wherein K is selected from the following groups unsubstituted or optionally substituted with one, two or more $R^K$: K is selected from the following groups unsubstituted or optionally substituted with 1 or 2 $R^K$: $C_{1-3}$ alkyl, $C_{5-6}$ cycloalkyl, phenyl, —$C_{1-3}$ alkylene phenyl ring, —$COCH_2$ phenyl ring, —$COCH_2CH_2$ phenyl ring, —$COCH_2$ biphenyl ring, —$CH_{2-6}$-membered aromatic heterocyclic ring, —$CH_2CH_{2-6}$-membered aromatic heterocyclic ring, —$COCH_{2-6}$-membered aromatic heterocyclic ring, —$COCH_2CH_{2-6}$-membered aromatic heterocyclic ring, —$CONR^{K1}R^{K2}$, 5-membered heterocyclyl, 6-membered heterocyclyl, methoxy, $C_5$ cycloalkyloxy, phenyloxy, 6-membered heteroaryloxy, and 6-membered heterocyclyloxy.

49. The compound of formula I or the pharmaceutically acceptable salt according to claim 1, wherein each aromatic heterocyclic ring, heterocyclic ring, heterocyclyl, aromatic ring, aryl and cycloalkyl in K are the same or different, and contain one N atom.

50. The compound of formula I or the pharmaceutically acceptable salt according to claim 1, wherein each $R^K$ is independently selected from the following groups: —CN, OH, —$NH_2$, $C_{1-3}$ alkyl, $C_{1-3}$ alkoxy, $C_{3-6}$ cycloalkyl, F-substituted $C_{1-3}$ alkyl, Cl-substituted $C_{1-3}$ alkyl, F-substituted $C_{1-3}$ alkoxy and Cl-substituted $C_{1-3}$ alkoxy.

51. The compound of formula I or the pharmaceutically acceptable salt according to claim 1, wherein each $R^K$ is independently selected from the following groups: —CN, OH, —$NH_2$, methyl, ethyl, methoxy and ethoxy.

52. The compound of formula I or the pharmaceutically acceptable salt according to claim 1, wherein $R^{K1}$ and $R^{K2}$ are the same or different, and are independently selected from the following groups: —CN, $C_{1-3}$ alkyl, $C_{1-3}$ alkoxy, $C_{4-5}$ cycloalkyl, F-substituted $C_{1-3}$ alkyl, Cl-substituted $C_{1-3}$ alkyl, F-substituted $C_{1-3}$ alkoxy and Cl-substituted $C_{1-3}$ alkoxy.

53. The compound of formula I or the pharmaceutically acceptable salt according to claim 1, wherein $R^{K1}$ and $R^{K2}$ are the same or different, and are independently selected from the following groups: —CN, OH, —$NH_2$, methyl, ethyl, methoxy and ethoxy.

54. The compound of formula I or the pharmaceutically acceptable salt according to claim 1, wherein K is selected from the following groups:

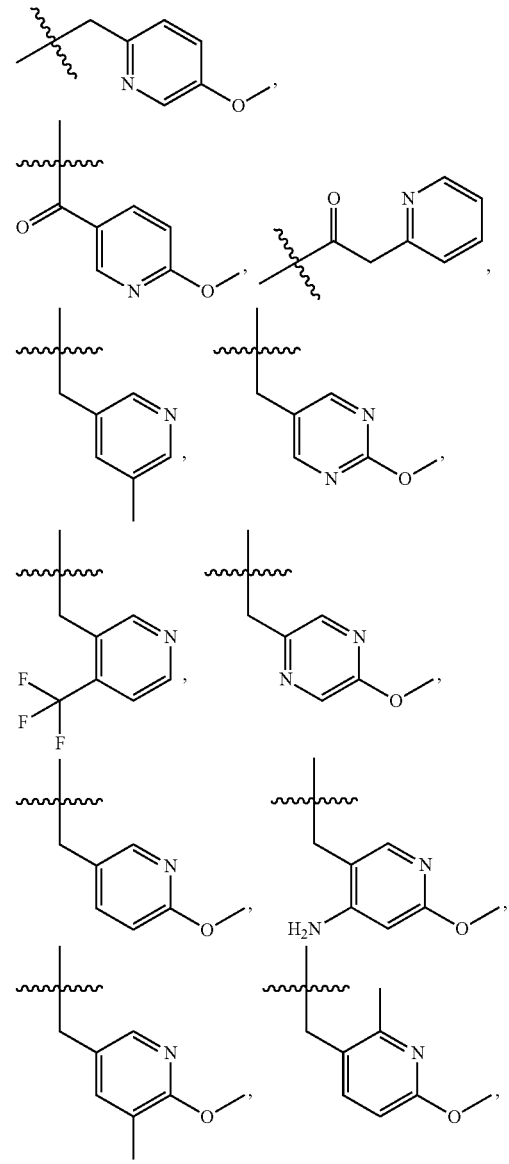

133
-continued

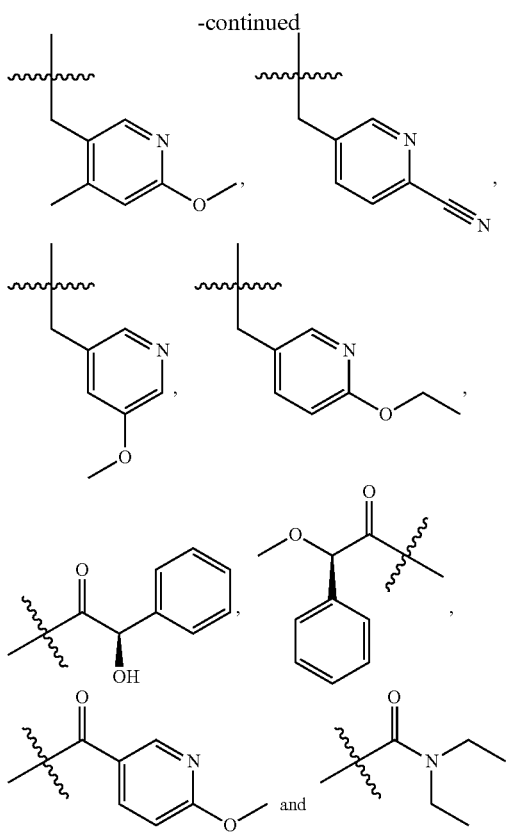

55. The compound of formula I or the pharmaceutically acceptable salt according to claim 1, wherein the heterocyclyl, heterocyclic ring, aromatic heterocyclic ring, heteroaryl or aryl heterocyclyl contains 1, 2 or 3 heteroatoms selected from N and O.

56. The compound of formula I or the pharmaceutically acceptable salt according to claim 1, wherein the heterocyclyl, heterocyclic ring, aromatic heterocyclic ring, heteroaryl or aryl heterocyclyl contains 1 or 2 heteroatoms selected from N and O.

57. The compound of formula I or the pharmaceutically acceptable salt according to claim 1, wherein the heterocyclyl, heterocyclic ring, aromatic heterocyclic ring, heteroaryl or aryl heterocyclyl is a 4-, 5-, 6-, 7- or 8-membered ring containing 1 heteroatom selected from N and O.

58. The compound of formula I or the pharmaceutically acceptable salt according to claim 1, wherein the heterocyclyl, heterocyclic ring, aromatic heterocyclic ring, heteroaryl or aryl heterocyclyl is a 4-, 5-, 6-, 7- or 8-membered ring containing 2 heteroatoms selected from N and O.

59. The compound of formula I or the pharmaceutically acceptable salt according to claim 1, wherein the heterocyclyl, heterocyclic ring, aromatic heterocyclic ring, heteroaryl or aryl heterocyclyl is a 4-, 5-, 6-, 7- or 8-membered ring containing 2 heteroatoms selected from N.

60. The compound of formula I or the pharmaceutically acceptable salt according to claim 1, wherein the heterocyclyl, heterocyclic ring, aromatic heterocyclic ring, heteroaryl or aryl heterocyclyl is a 5- or 6-membered ring containing 2 heteroatoms selected from N.

61. The compound of formula I or the pharmaceutically acceptable salt according to claim 1, wherein the heterocyclyl, heterocyclic ring, aromatic heterocyclic ring, heteroaryl or aryl heterocyclyl is a 6-membered ring containing 2 heteroatoms selected from N.

62. A compound of formula II or a pharmaceutically acceptable salt thereof:

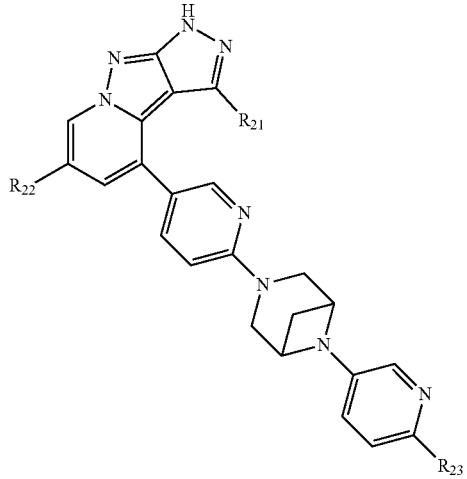

wherein $R_{22}$ is selected from H, halogen, CN, —$C_{1-6}$ alkyl, —$C_{1-6}$ alkoxy, —$O(CH^2)_m$—$C_{1-6}$ alkyl and —$O(CH^2)_m$—$C_{1-6}$ alkoxy, wherein each $C_{1-6}$ alkyl and $C_{1-6}$ alkoxy can be unsubstituted or substituted with halogen, $C_{1-6}$ alkyl or $C_{1-6}$ alkoxy, and m=0, 1 or 2;

$R_{21}$ is selected from H, $NH_2$ and —$C_{1-3}$ alkyl; and $R_{23}$ is selected from H, $NH_2$, —$C_{1-3}$ alkyl and —$C_{1-3}$ alkoxy.

63. The compound of formula II or the pharmaceutically acceptable salt according to claim 62, wherein $R_{22}$ is selected from H, F, Cl, Br, CN, —$C_{1-3}$ alkyl, —$C_{1-3}$ alkoxy, —$O(CH^2)_m$—$C_{1-3}$ alkyl and —$O(CH^2)_m$—$C_{1-3}$ alkoxy, wherein each $C_{1-3}$ alkyl and $C_{1-3}$ alkoxy can be unsubstituted or substituted with F, Cl, Br, $C_{1-3}$ alkyl or $C_{1-3}$ alkoxy;

$R_{21}$ is selected from H, $NH_2$ and methyl; and $R_{23}$ is selected from H, $NH_2$, methyl and methoxy.

64. The compound of formula II or the pharmaceutically acceptable salt according to claim 62, wherein $R_{22}$ is selected from H, F, Cl, Br, CN, —$C_{1-3}$ alkyl, —$C_{1-3}$ alkoxy, —$O(CH^2)_m$—$C_{1-3}$ alkyl and —$O(CH^2)_m$—$C_{1-3}$ alkoxy, wherein each $C_{1-3}$ alkyl and $C_{1-3}$ alkoxy can be unsubstituted or substituted with F, Cl, Br, $C_{1-3}$ alkyl or $C_{1-3}$ alkoxy;

$R_{21}$ is selected from H; and $R_{23}$ is selected from methoxy.

65. The compound of formula II or the pharmaceutically acceptable salt according to claim 62, wherein $R_{22}$ is selected from H, F, Cl, CN, methyl, ethyl, methoxy, ethoxy, —$O(CH^2)_m$-methyl, —$O(CH^2)_m$-ethyl, —$O(CH^2)_m$-methoxy and —$O(CH^2)_m$-ethoxy, wherein each methyl, ethyl, methoxy and ethoxy can be unsubstituted or substituted with F, Cl, Br, methyl, ethyl, methoxy or ethoxy.

66. The compound of formula II or the pharmaceutically acceptable salt according to claim 62, wherein m=1 or 2.

67. A compound selected from the following formulas or pharmaceutically acceptable salts thereof:

135
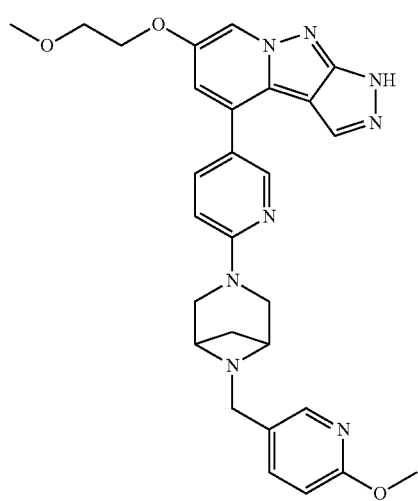
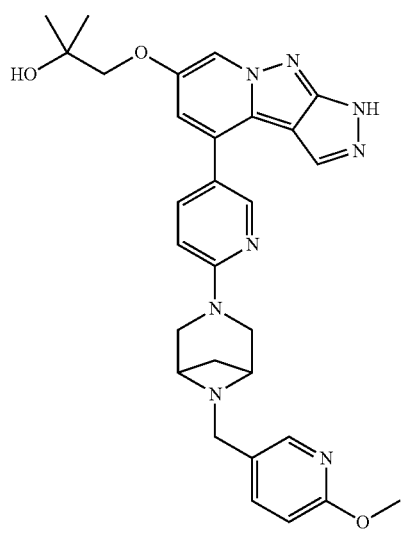
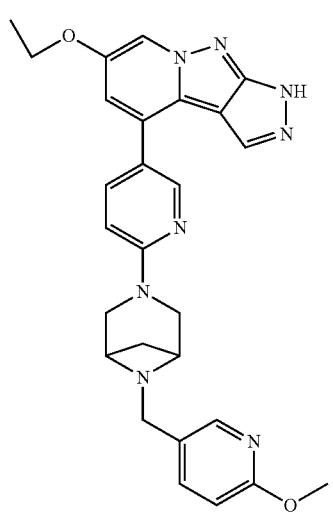
136
-continued
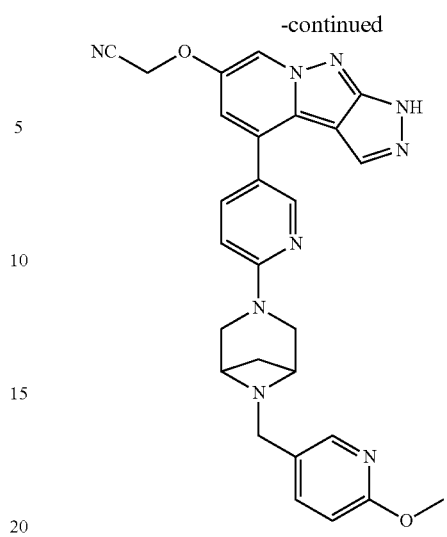
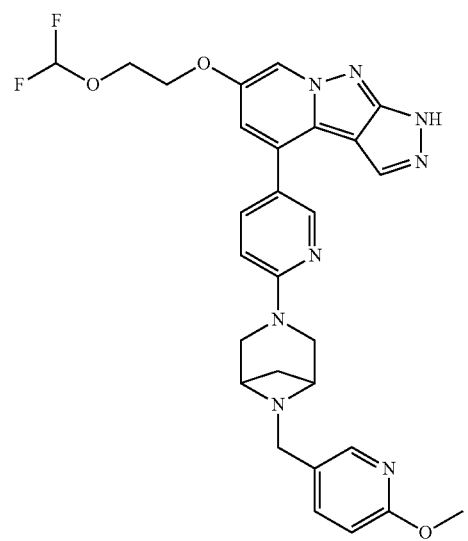
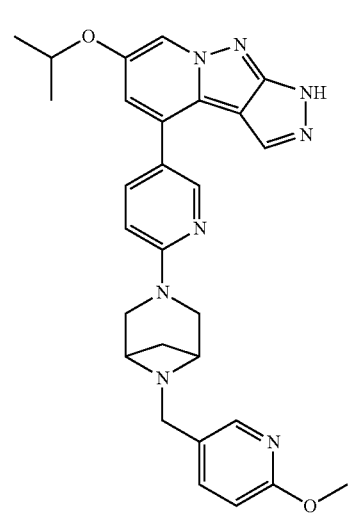

137
-continued
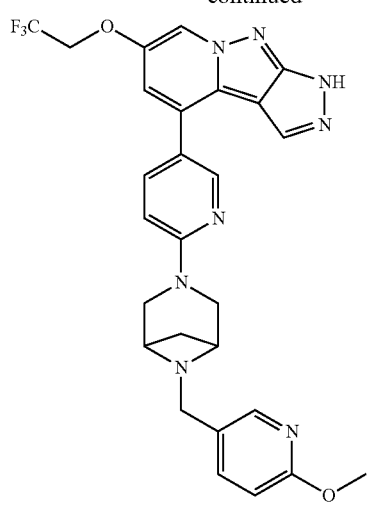
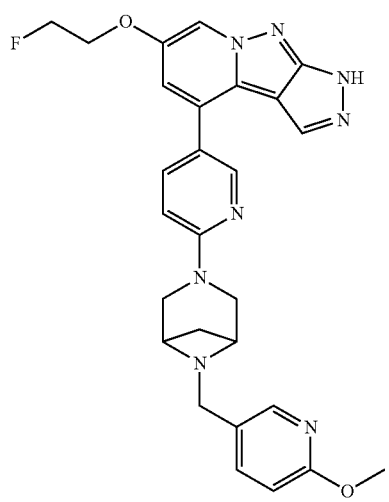
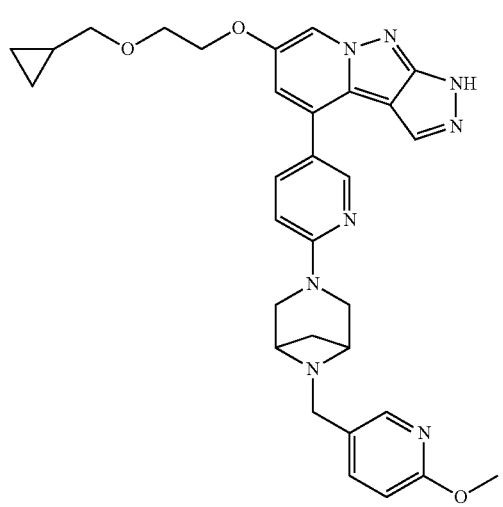
138
-continued
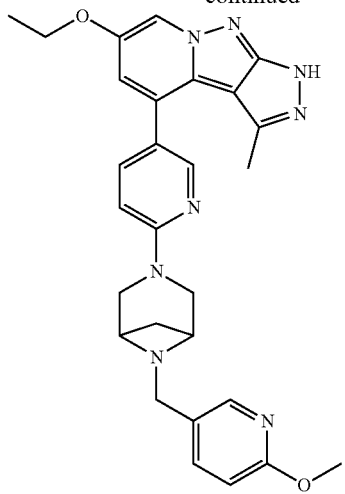
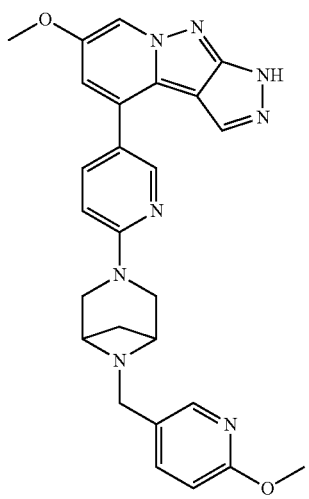
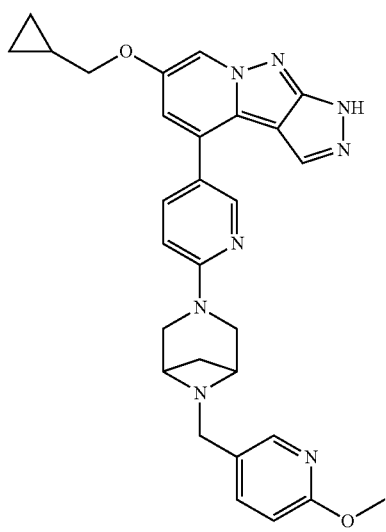

139
-continued
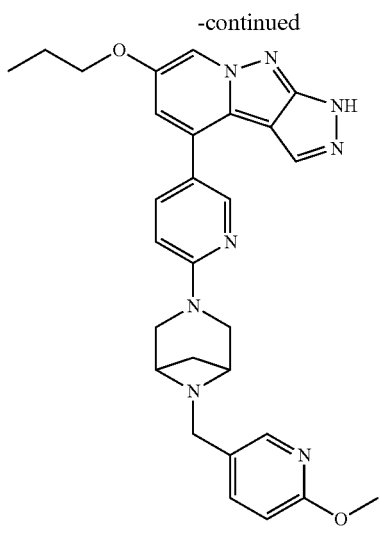
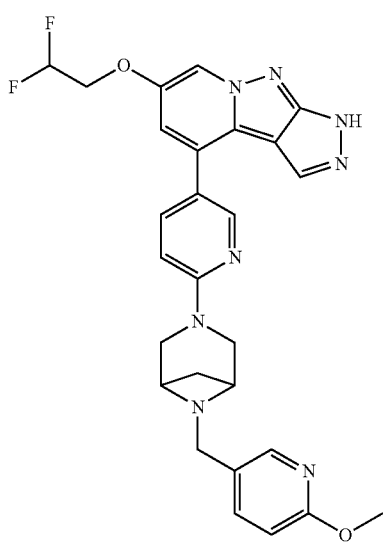
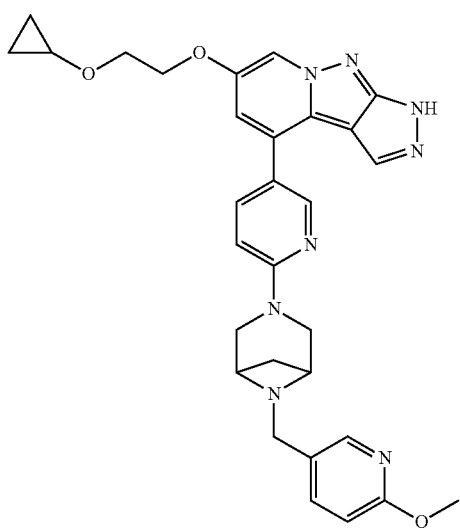
140
-continued
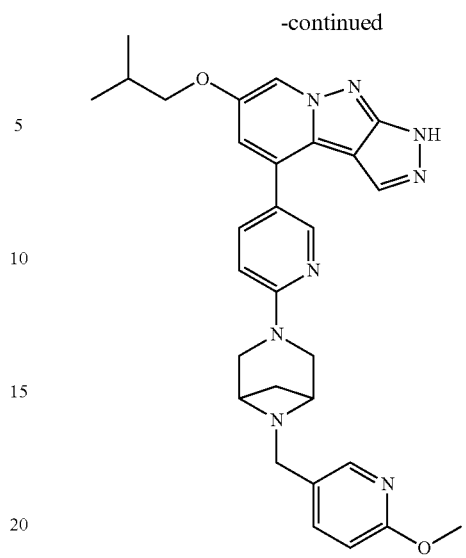
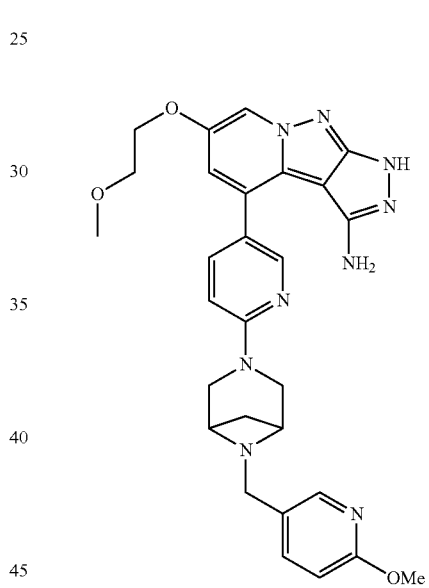
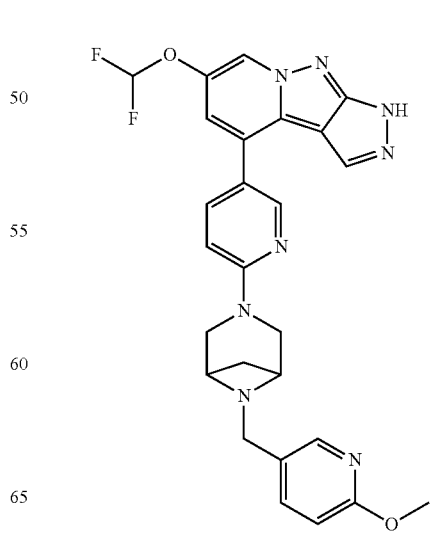

141
-continued
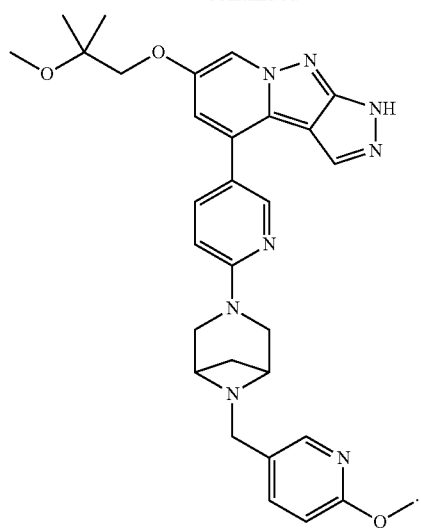
142
-continued
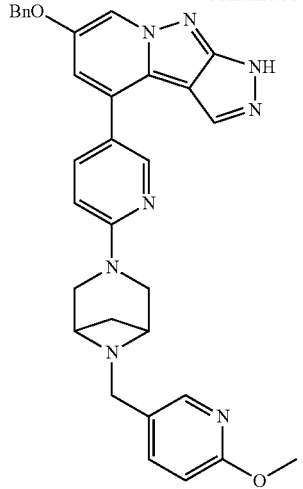
68. A compounds selected from the following formulas or pharmaceutically acceptable salts thereof:
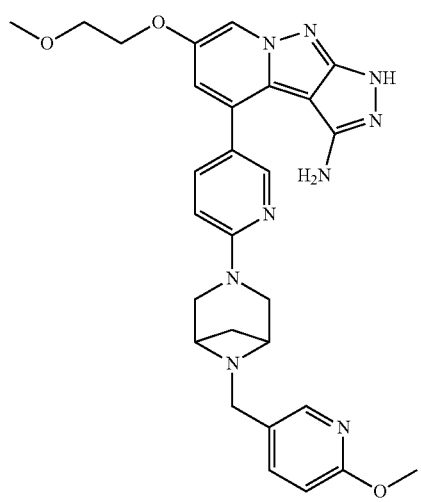
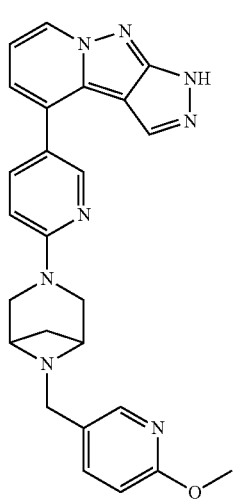
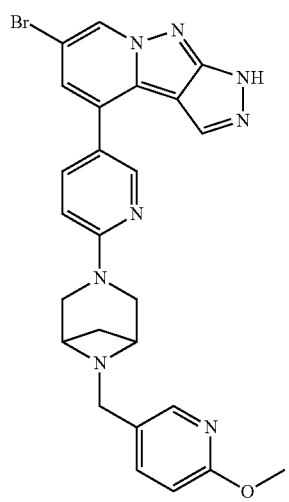
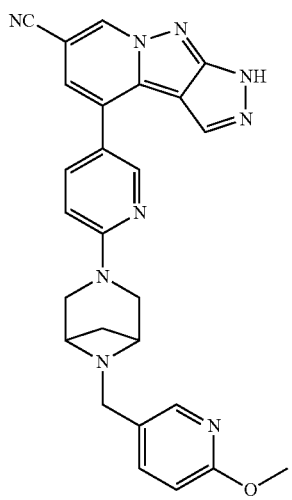

143
-continued
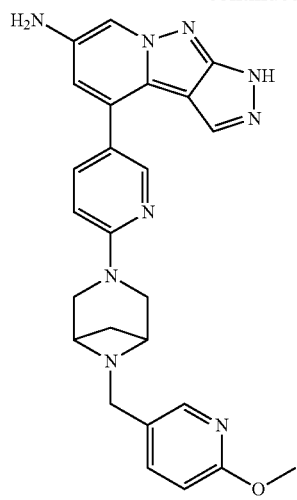
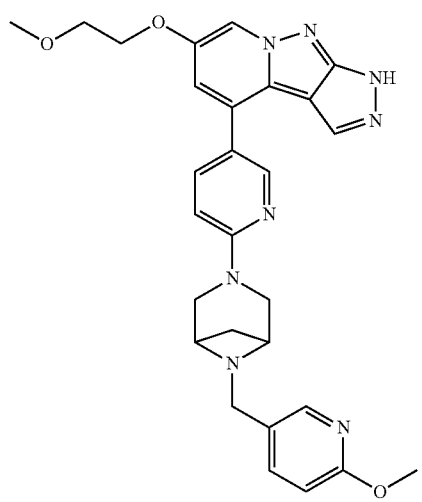
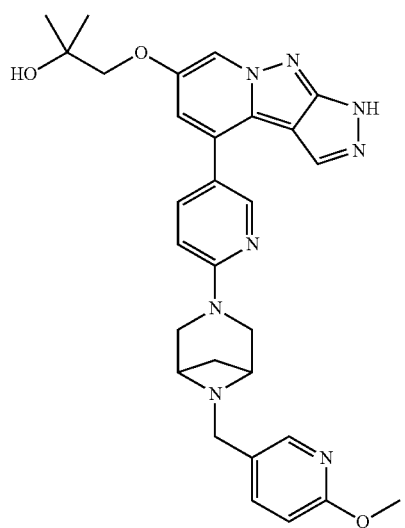
144
-continued
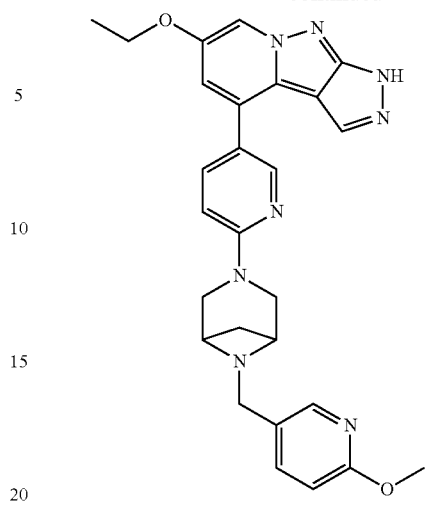
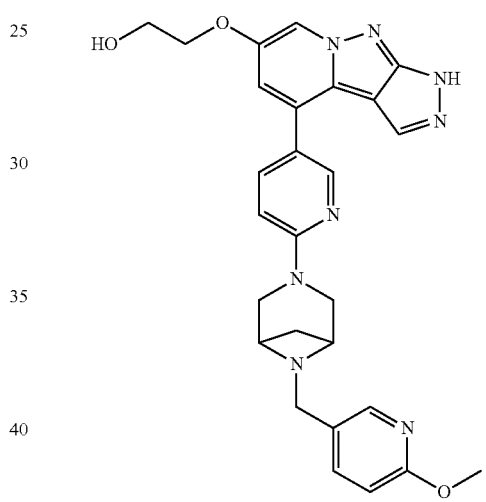
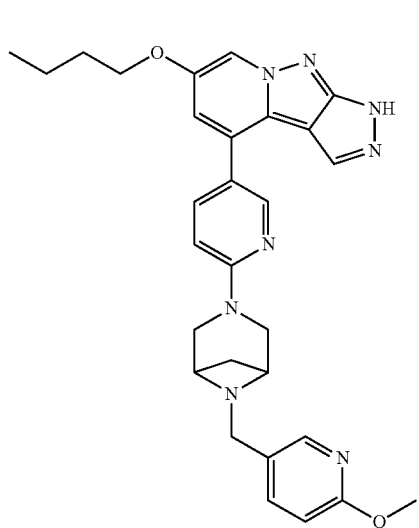

145
-continued
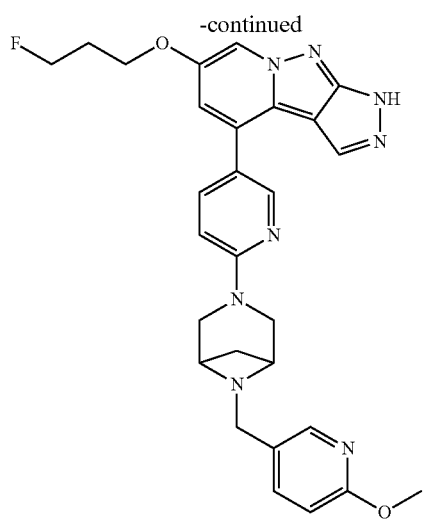
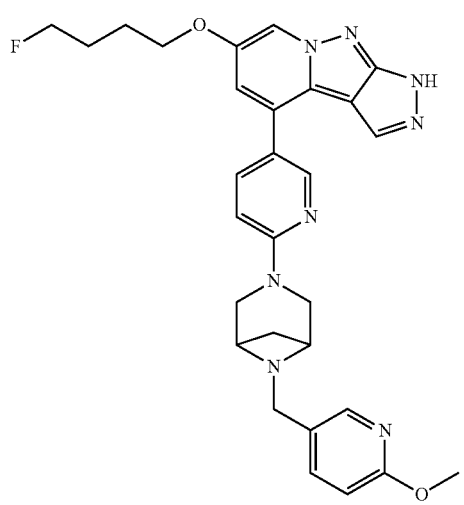
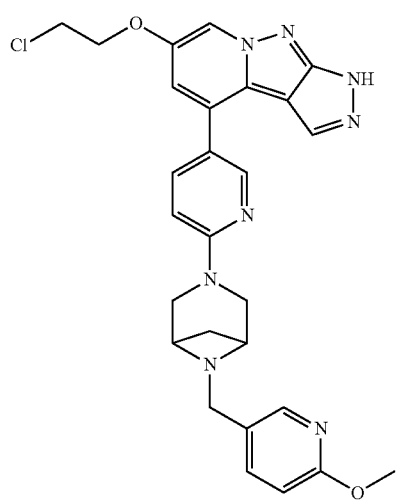
146
-continued
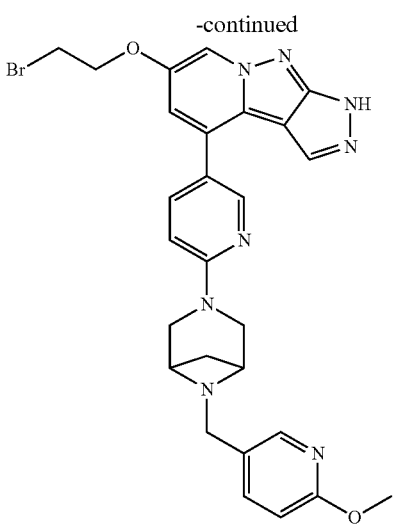
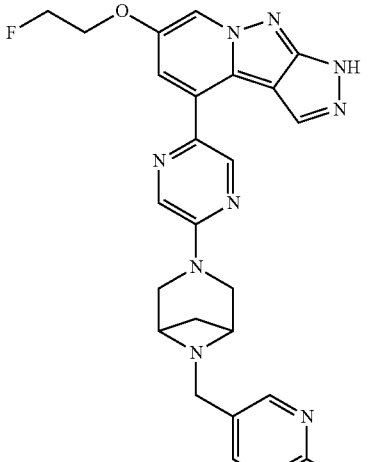
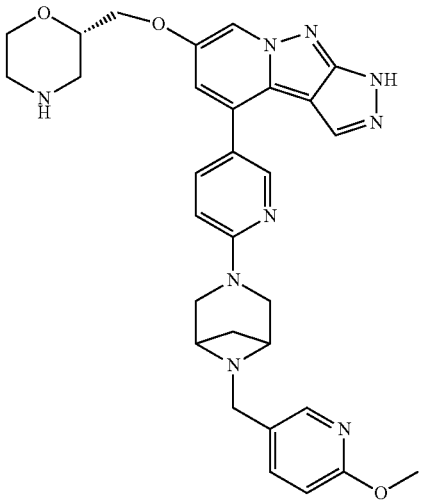

147
-continued
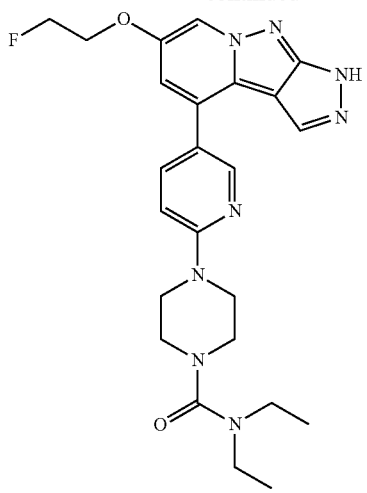
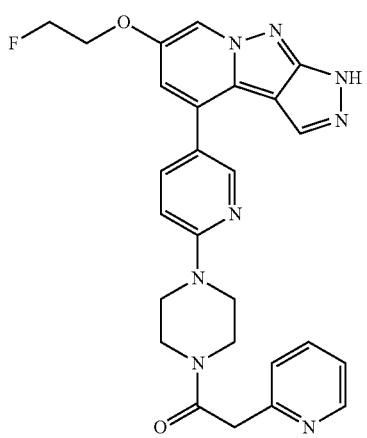
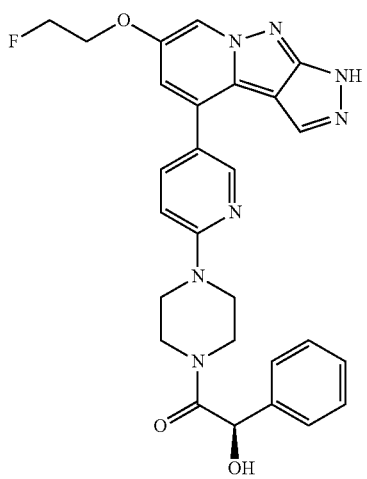
148
-continued
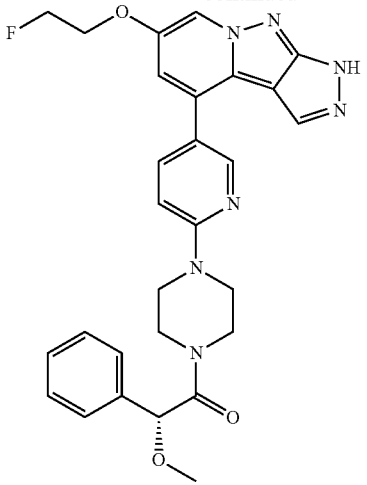
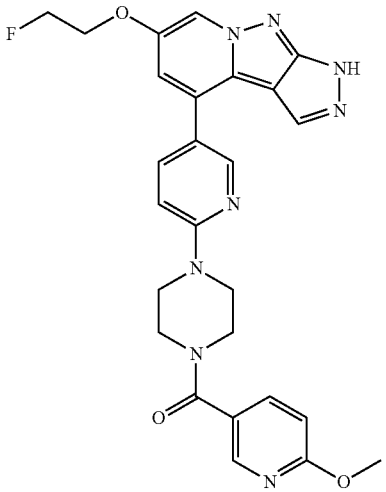
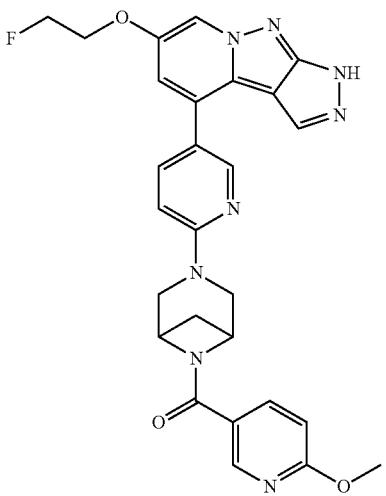

149
-continued
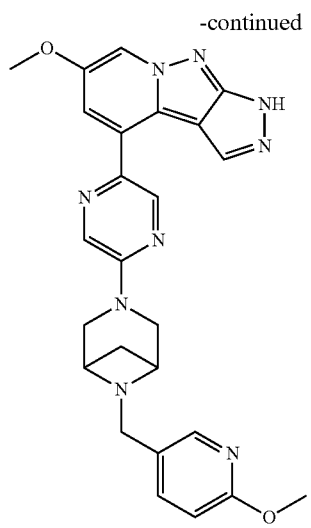
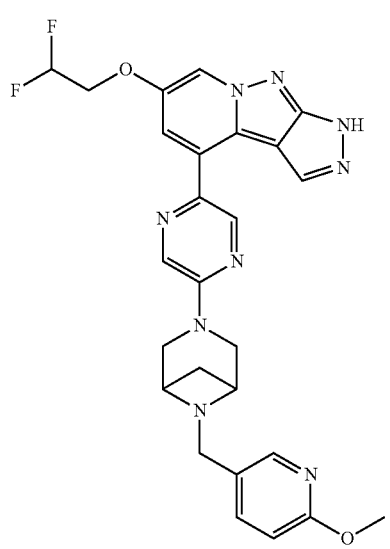
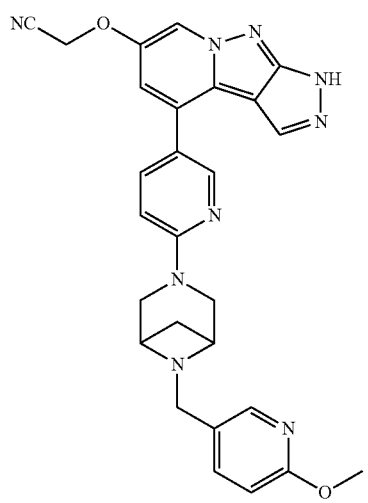
150
-continued
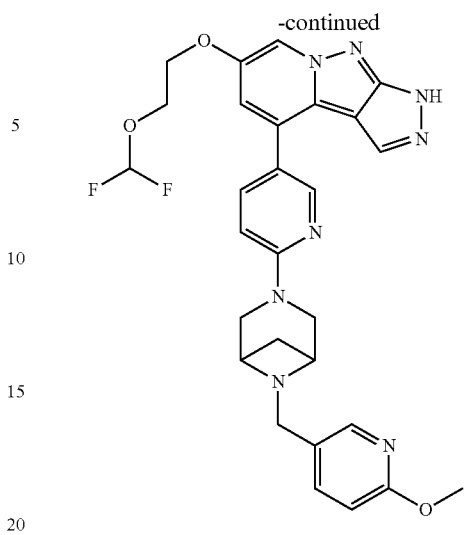
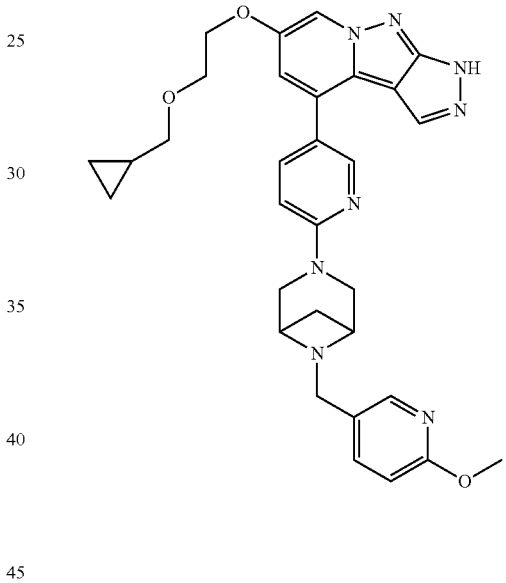
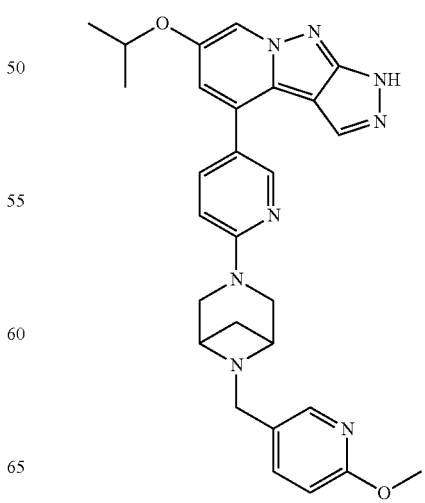

151
-continued
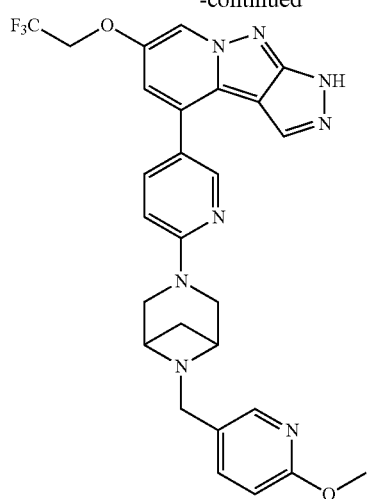
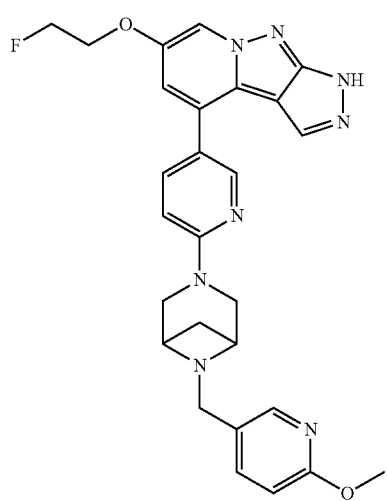
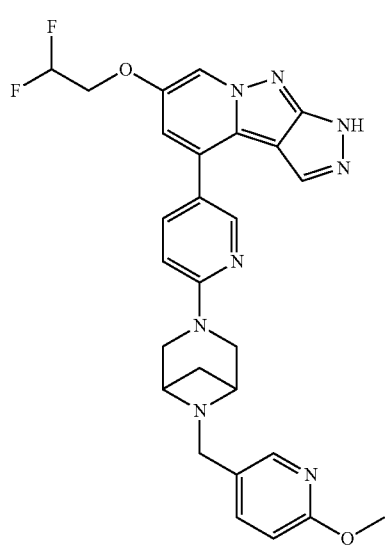
152
-continued
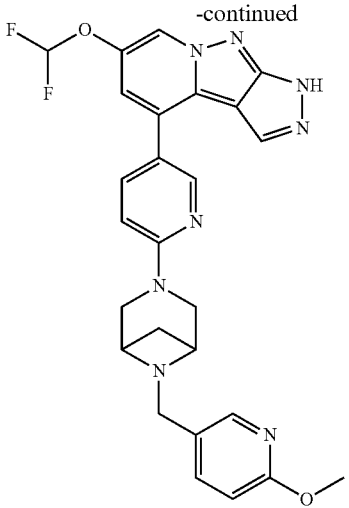
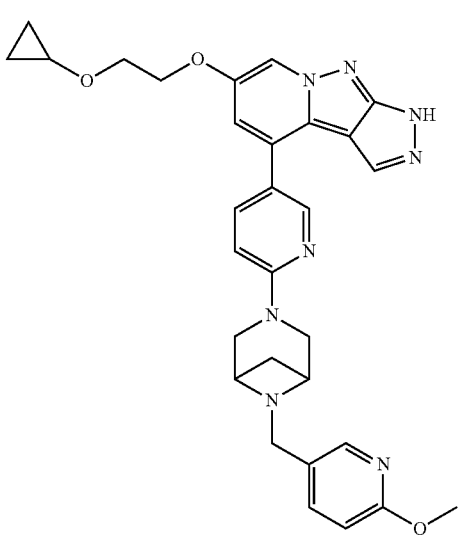
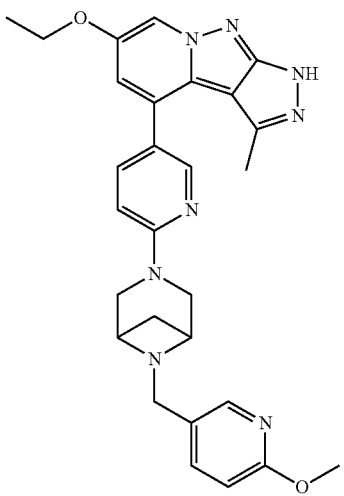

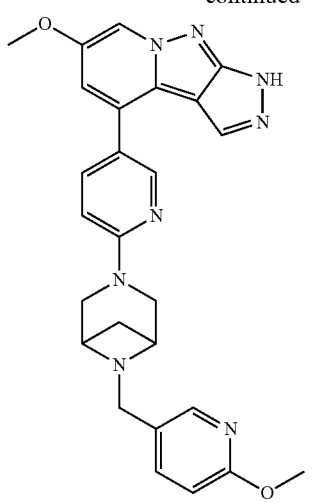

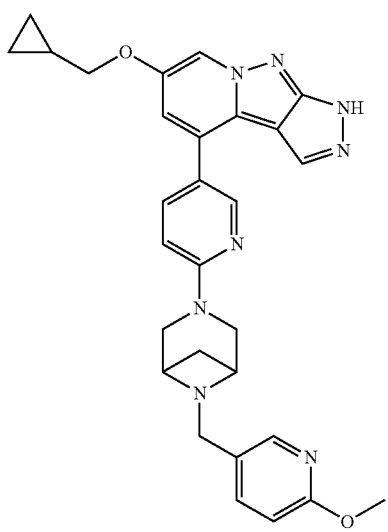

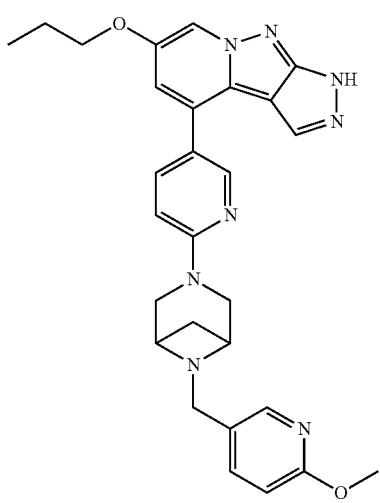

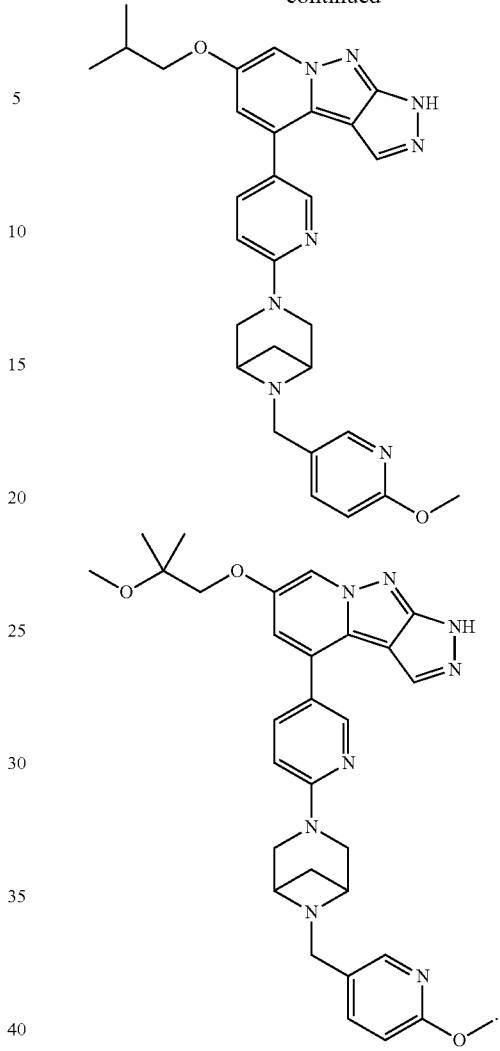

69. A pharmaceutical composition, comprising a therapeutically effective amount of the compound or the pharmaceutically acceptable salt thereof according to claim 1, and at least one pharmaceutically acceptable excipient.

70. A method for treating or arresting a disease or condition mediated by RET activity, comprising: (1) determining whether the disease or discomfort is related to the dysregulation of the expression, activity or level of a RET gene, a RET kinase protein or any one or more thereof; and (2) if it is determined that the disease or discomfort is related to the dysregulation of the expression, activity or level of the RET gene, the RET kinase protein or any one or more thereof, administering to a patient an effective dose of the compound or the pharmaceutically acceptable salt thereof according to claim 1, wherein the disease or condition mediated by RET activity is cancer and/or cancer metastasis.

71. The method according to claim 70, wherein one or more point mutations in the RET gene result in the translation of a RET protein with one or more amino acid substitutions at one or more of the following amino acid positions: 2, 3, 4, 5, 6, 7, 8, 11, 12, 13, 20, 32, 34, 40, 56, 64, 67, 114, 136, 145, 180, 200, 292, 294, 321, 330, 338, 360, 373, 393, 423, 432, 446, 505, 506, 510, 511, 513, 515, 525, 531, 532, 533, 550, 591, 593, 595, 600, 602, 603, 606, 609, 611, 616, 618, 619, 620, 623, 624, 630, 631, 632, 633, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 802, 804, 805, 806, 810, 818, 819, 823, 836, 841, 843, 844, 848, 852, 865, 870, 873, 876, 881, 882, 883, 884, 886, 891, 897, 898, 900, 901, 904, 905, 907, 908, 911, 912, 918, 919, 921, 922, 930, 961, 972, 981, 982, 1009, 1015, 1017, 1041, 1062, 1064 and 1096.

72. The method according to claim 70, wherein one or more point mutations in the RET gene result in the translation of a RET protein with one or more amino acid substitutions at one or more of the following amino acid positions: 32, 34, 40, 56, 64, 67, 114, 145, 292, 321, 330, 338, 360, 393, 423, 446, 510, 511, 513, 515, 525, 531, 532, 533, 550, 591, 593, 595, 600, 602, 603, 606, 609, 611, 616, 618, 619, 620, 623, 624, 630, 631, 632, 634, 635, 636, 640, 641, 648, 649, 664, 665, 666, 675, 686, 689, 691, 694, 700, 706, 713, 732, 736, 748, 750, 765, 766, 768, 769, 770, 771, 777, 778, 781, 788, 790, 791, 804, 805, 806, 810, 818, 819, 823, 826, 833, 836, 841, 843, 844, 848, 852, 865, 870, 873, 876, 881, 883, 884, 886, 891, 897, 898, 900, 901, 904, 905, 907, 908, 911, 912, 918, 919, 921, 922, 930, 961, 972, 981, 982, 1009, 1015, 1017, 1041, 1064 and 1096.

73. The method according to claim 70, wherein one or more point mutations in the RET gene result in the translation of a RET protein containing one or more of the following amino acid substitutions: S32L, D34S, L40P, L56M, P64L, R67H, R114H, V145G, V292M, G321R, R330Q, T338I, R360W, F393L, G423R, G446R, A510V, E511K, G513D, C515S, C515W, R525W, C531R, G533C, G533S, G550E, V591I, G593E, E595D, E595A, R600Q, I602V, K603Q, K603E, Y606C, C609C, C609Y, C609S, C609G, C609R, C609F, C609W, C611R, C611S, C611G, C611Y, C611F, C611W, E616Q, C618S, C618Y, C618R, C618G, C618F, C618W, F619F, C620S, C620W, C620R, C620G, C620L, C620Y, C620F, E623K, D624N, C630A, C630R, C630S, C630Y, C630F, C630W, D631N, D631Y, D631A, D631G, D631V, D631E, E632K, E632G, C634W, C634Y, C634S, C634R, C634F, C634G, C634L, C634A, C634T, R635G, T636P, T636M, A640G, A641S, A641T, V648I, S649L, A664D, H665Q, K666E, K666M, K666N, K666R, T675T, S686N, S689T, G691S, R694Q, M700L, V706M, V706A, E713K, E732K, G736R, G748C, A750P, S765P, P766S, P766M, E768Q, E768D, L769L, R770Q, D771N, N777S, V778I, Q781R, I788I, L790F, Y791F, Y791N, V804L, V804M, V804E, E805K, Y806E, Y806F, Y806S, Y806G, Y806C, Y806H, Y806N, Y806Y, G810R, G810S, G810A, E818K, S819I, G823E, Y826M, Y826S, R833C, S836S, P841L, P841P, E843D, R844W, R844Q, R844L, M848T, I852M, L865V, L870F, R873W, A876V, L881V, A883F, A883S, A883T, E884K, R886W, S891A, S891S, R897Q, D898V, Y900F, E901K, S904F, S904S, S904C, Y905F, K907E, K907M, R908K, G911D, R912P, R912Q, M918T, M918V, M918L, A919V, E921K, S922P, S922Y, T930M, F961L, R972G, Y981F, R982C, M1009V, Y1015F, D1017N, V1041G, M1064T and Y1096F.

74. The method according to claim 70, wherein one or more point mutations in the RET gene occur in one or more exons 10, 11, 13, 14, 15 and 16 of a human RET gene.

75. The method according to claim 70, wherein the RET gene fusion is selected from: BCR-RET, CLIP1-RET, KIF5B-RET, CCDC6-RET, NCOA4-RET, TRIM33-RET, ERC1-RET, FGFR1OP-RET, RET-MBD1, RET-RAB61P2, RET-PRKAR1A, RET-TRIM24, RET-GOLGA5, HOOGA5, KIAA1217-RET, MPRIP-RET, HRH4-RET, RIA-RET, RET-PTC4, FRMD4A-RET, SQSTM1-RET, AFAP1L2-RET, PPFIBP2-RET, EML4-RET, PARD3-RET, MYH10-RET, HTIF1/RET, AFAP1-RET, RASGEF1A-RET and TEL-RET.

76. The method according to claim 70, wherein the dysregulation of the mutation, expression, activity or level of a RET gene, a RET kinase protein or any one or more thereof is RET gene fusion.

77. The method according to claim 70, wherein the disease mediated by RET activity is selected from one or more of the following diseases: lung cancer, papillary thyroid cancer, medullary thyroid cancer, differentiated thyroid cancer, recurrent thyroid cancer, poorly differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, gastrointestinal gangliocytoma (MEN2A or MEN2B, respectively), pheochromocytoma, parathyroid hyperplasia, breast cancer, colorectal cancer, papillary renal cell carcinoma, gastrointestinal gangliocytoma and a combination thereof.

78. A compound of the following formula I, or a stereoisomer, a racemate, a tautomer, an isotopically labeled compound, a nitrogen oxide or a pharmaceutically acceptable salt thereof:

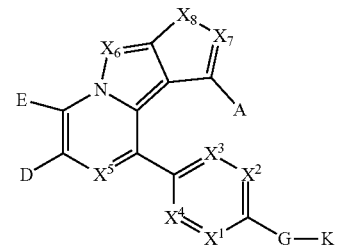

I wherein $X^1$, $X^2$, $X^3$, $X^4$, $X^5$, $X^6$ and $X^7$ are the same or different, and are independently selected from $CR^1$ and N;

$X^8$ is selected from $CR^1R^{1'}$ and $NR^1$;

wherein each $R^1$ and $R^{1'}$ are the same or different, and are independently selected from H, halogen, CN, OH, and the following groups unsubstituted or optionally substituted with one, two or more $R^a$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $NR^2R^3$, —$C(O)R^4$, —$OCR^5$, —$S(O)_2R^6$ and $OS(O)_2R^7$;

A is selected from H, halogen, CN, OH, $NH_2$, and the following groups unsubstituted or optionally substituted with one, two or more $R^b$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $NR^2R^3$, —$C(O)R^4$, —$OCR^5$, —$S(O)_2R^6$ and $OS(O)^2R^7$;

D and E are the same or different, and are independently selected from H, halogen, CN, OH, —O—$R^2$, and the following groups unsubstituted or optionally substituted with one, two or more $R^c$: $C_{1-40}$ alkenyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, and 3- to 20-membered heterocyclyl, provided that at least one of D and E is selected from —O—$R^2$;

R² is selected from H, and the following groups unsubstituted or optionally substituted with one, two or more R$^d$: C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, and 3- to 20-membered heterocyclyl;

G is selected from the following groups unsubstituted or optionally substituted with one, two or more R$^e$: C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, C$_{3-40}$ cycloalkyloxy, C$_{3-40}$ cycloalkenyloxy, C$_{3-40}$ cycloalkynyloxy, C$_{6-20}$ aryloxy, 5- to 20-membered heteroaryloxy, and 3- to 20-membered heterocyclyloxy;

K is selected from the following groups unsubstituted or optionally substituted with one, two or more R$^f$: H, halogen, CN, OH, and the following groups unsubstituted or optionally substituted with one or more R$^g$: C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, C$_{1-40}$ alkyloxy, C$_{2-40}$ alkenyloxy, C$_{2-40}$ alkynyloxy, C$_{3-40}$ cycloalkyloxy, C$_{3-40}$ cycloalkenyloxy, C$_{3-40}$ cycloalkynyloxy, C$_{6-20}$ aryloxy, 5- to 20-membered heteroaryloxy, 3- to 20-membered heterocyclyloxy, NR²R³, —C(O)R⁴, —OCR⁵, —S(O)$_2$R⁶ and OS(O)²R⁷;

each R² is the same or different, and is independently selected from H, C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, —C(O)R⁴ and —S(O)$_2$R⁶;

each R³ is the same or different, and is independently selected from H, C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, —C(O)R⁴ and —S(O)$_2$R⁶; or, R² and R³, together with a N atom connected thereto, form 5- to 20-membered heteroaryl or 3- to 20-membered heterocyclyl;

each R⁴ is the same or different, and is independently selected from H, C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, C$_{1-40}$ alkyloxy, C$_{2-40}$ alkenyloxy, C$_{2-40}$ alkynyloxy, C$_{3-40}$ cycloalkyloxy, C$_{3-40}$ cycloalkenyloxy, C$_{3-40}$ cycloalkynyloxy, C$_{6-20}$ aryloxy, 5- to 20-membered heteroaryloxy, 3- to 20-membered heterocyclyloxy, and NR²R³;

each R⁵ is the same or different, and is independently selected from H, C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, C$_{1-40}$ alkylcarbonyl, C$_{2-40}$ alkenylcarbonyl, C$_{2-40}$ alkynylcarbonyl, C$_{3-40}$ cycloalkylcarbonyl, C$_{3-40}$ cycloalkenylcarbonyl, C$_{3-40}$ cycloalkynylcarbonyl, C$_{6-20}$ arylcarbonyl, 5- to 20-membered heteroarylcarbonyl, and 3- to 20-membered heterocyclylcarbonyl;

each R⁶ is the same or different, and is independently selected from H, C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, C$_{1-40}$ alkyloxy, C$_{2-40}$ alkenyloxy, C$_{2-40}$ alkynyloxy, C$_{3-40}$ cycloalkyloxy, C$_{3-40}$ cycloalkenyloxy, C$_{3-40}$ cycloalkynyloxy, C$_{6-20}$ aryloxy, 5- to 20-membered heteroaryloxy, 3- to 20-membered heterocyclyloxy, and NR²R³;

each R⁷ is the same or different, and is independently selected from H, C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, and 3- to 20-membered heterocyclyl;

each R$^a$, R$^b$, R$^c$, R$^d$, R$^e$ and R$^f$ are the same or different, and are independently selected from halogen, CN, OH, SH, oxo (=O), NO$_2$, and the following groups unsubstituted or optionally substituted with one, two or more R$^g$: C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, C$_{1-40}$ alkyloxy, C$_{2-40}$ alkenyloxy, C$_{2-40}$ alkynyloxy, C$_{3-40}$ cycloalkyloxy, C$_{3-40}$ cycloalkenyloxy, C$_{3-40}$ cycloalkynyloxy, C$_{6-20}$ aryloxy, 5- to 20-membered heteroaryloxy, 3- to 20-membered heterocyclyloxy, NR²R³, —C(O)R⁴, —OCR⁵, —S(O)$_2$R⁶ and OS(O)²R⁷;

each R$^h$ is the same or different, and is independently selected from halogen, CN, OH, SH, oxo (=O), NO$_2$, and the following groups unsubstituted or optionally substituted with one, two or more R$^h$: C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, C$_{1-40}$ alkyloxy, C$_{2-40}$ alkenyloxy, C$_{2-40}$ alkynyloxy, C$_{3-40}$ cycloalkyloxy, C$_{3-40}$ cycloalkenyloxy, C$_{3-40}$ cycloalkynyloxy, C$_{6-20}$ aryloxy, 5- to 20-membered heteroaryloxy, 3- to 20-membered heterocyclyloxy, NR²R³, —C(O)R⁴, —OCR⁵, —S(O)$_2$R⁶ and OS(O)²R⁷; or, where a cyclic group (including but not limited to, C$_{3-40}$ cycloalkyl, C$_{3-40}$ cycloalkenyl, C$_{3-40}$ cycloalkynyl, 3- to 20-membered heterocyclyl, and the like) is substituted with two or more substituents at different positions, two of the substituents can also form a bridged ring with the cyclic group, wherein the bridge atoms other than the bridgehead atoms in the bridged ring can comprise 1, 2, 3, 4 or 5 divalent groups selected from CH², O and NH; and each R$^h$ is the same or different, and is independently selected from halogen, CN, OH, SH, oxo (=O), NO$_2$, and the following groups unsubstituted or optionally substituted with one or more R$^g$: C$_{1-40}$ alkyl, C$_{2-40}$ alkenyl, C$_{2-40}$ alkynyl, C$_{3-40}$ cycloalkyl, C$_{3-40}$ cycloalkenyl, C$_{3-40}$ cycloalkynyl, C$_{6-20}$ aryl, 5- to 20-membered heteroaryl, 3- to 20-membered heterocyclyl, C$_{1-40}$ alkyloxy, C$_{2-40}$ alkenyloxy, C$_{2-40}$ alkynyloxy, C$_{3-40}$ cycloalkyloxy, C$_{3-40}$ cycloalkenyloxy, C$_{3-40}$ cycloalkynyloxy, C$_{6-20}$ aryloxy, 5- to 20-membered heteroaryloxy, 3- to 20-membered heterocyclyloxy, NR²R³, —C(O)R⁴, —OCR⁵, —S(O)$_2$R⁶ and OS(O)²R⁷; or, where a cyclic group (including but not limited to, C$_{3-40}$ cycloalkyl, C$_{3-40}$ cycloalkenyl, C$_{3-40}$ cycloalkynyl, 3- to 20-membered heterocyclyl, and the like) is substituted with two or more substituents at different positions, two of the substituents can also form a bridged ring with the cyclic group, wherein the bridge atoms other than the bridgehead atoms in the bridged ring can comprise 1, 2, 3, 4 or 5 divalent groups selected from CH², O and NH; or, where one atom (such as carbon atom) is substituted with two or more substituents, two of the substituents can also, together with an atom connected thereto, form a cyclic group (including but not limited to, $C_{3-40}$ cycloalkyl, $C_{3-40}$ cycloalkenyl, $C_{3-40}$ cycloalkynyl, 3- to 20-membered heterocyclyl, and the like).

79. The compound according to claim 78, wherein $X^1$, $X^2$, $X^3$, $X^4$, $X^5$, $X^6$ and $X^7$ are the same or different, and are independently selected from $CR^1$ and N; for example, at least one of $X^1$, $X^2$, $X^3$, $X^4$, $X^5$, $X^6$ and $X^1$ is N;

$X^8$ is selected from $CR^1R^{1'}$ and $NR^1$;

each $R^1$ and $R^{1'}$ are the same or different, and are independently selected from H, halogen, CN, OH, $C_{1-6}$ alkyl, $C_{3-10}$ cycloalkyl and $C_{1-6}$ alkoxy;

A is selected from H, halogen, CN, OH, $C_{1-6}$ alkyl and $C_{1-6}$ alkyloxy;

D and E are the same or different, and are independently selected from H and —O—$R^2$, provided that at least one of D and E is selected from —O—$R^2$;

$R^2$ is selected from $C_{1-6}$ alkyl unsubstituted or optionally substituted with one, two or more $R^d$;

each $R^a$, $R^b$, $R^c$, $R^d$, $R^e$ and $R^f$ are the same or different, and are independently selected from halogen, CN, OH, and the following groups unsubstituted or optionally with one, two or more $R^g$: $C_{1-6}$ alkyl, $C_{1-6}$ alkyloxy, $C_{3-10}$ cycloalkyl and $C_{3-10}$ cycloalkyloxy;

each $R^g$ is the same or different, and is independently selected from halogen and $C_{3-10}$ cycloalkyl;

G is selected from $C_{3-10}$ cycloalkyl, $C_{6-14}$ aryl, 5- to 14-membered heteroaryl, and 3- to 10-membered heterocyclyl; and K is selected from —$C_{1-6}$ alkyl-$C_{3-10}$ cycloalkyl, —$C_{1-6}$ alkyl-$C_{6-14}$ aryl, —$C_{1-6}$ alkyl-5- to 14-membered heteroaryl, and —$C_{1-6}$ alkyl-3- to 10-membered heterocyclyl, wherein a cyclic group of the $C_{3-10}$ cycloalkyl, $C_{6-14}$ aryl, 5- to 14-membered heteroaryl, or 3- to 10-membered heterocyclyl is optionally further substituted with one, two or more $C_{1-6}$ alkyl or $C_{1-6}$ alkoxy.

80. The compound according to claim 78, wherein $X^1$, $X^2$, $X^3$, $X^4$, $X^5$, $X^6$ and $X^7$ are the same or different, and are independently selected from CH and N; for example, at least one of $X^1$, $X^2$, $X^3$, $X^4$, $X^5$, $X^6$ and $X^7$ is N;

$X^8$ is selected from $NR^1$;

$R^1$ is H;

A is selected from H, $NH_2$, methyl, ethyl, propyl and isopropyl;

E is H;

D is selected from the following groups:

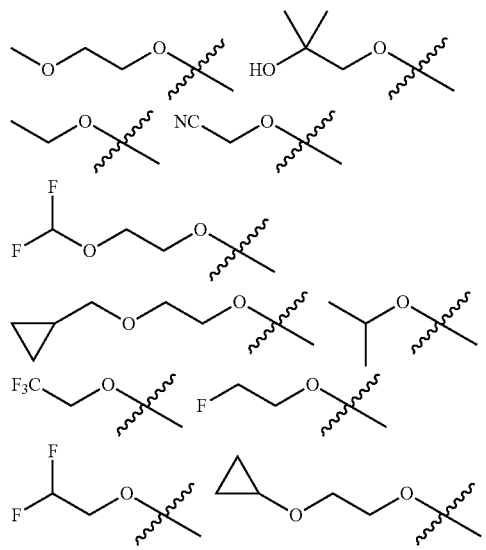

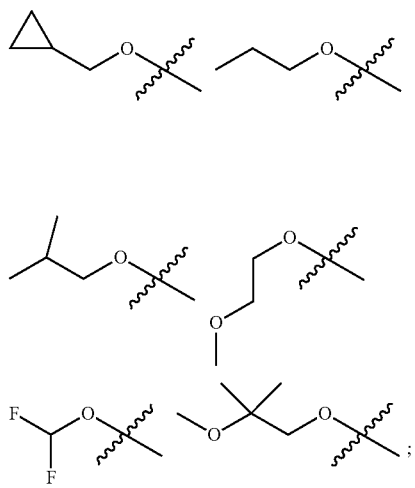

G is selected from

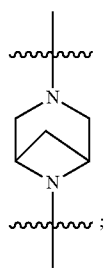

and

K is selected from

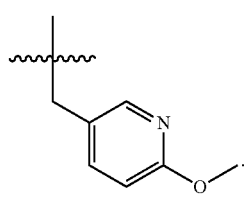 [SMILES: *Cc1ccc(OC)nc1]

81. A process for preparing the compound according to claim 78, comprising the following steps:

reacting a compound of formula I-1 with a compound $R^2$-L to obtain the compound of formula I,

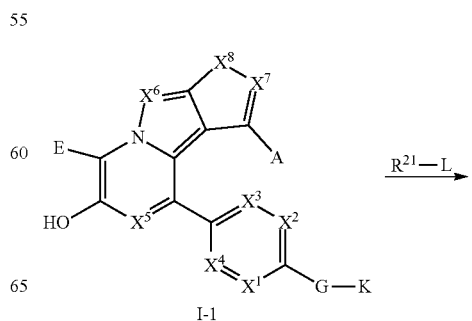

I-1

-continued

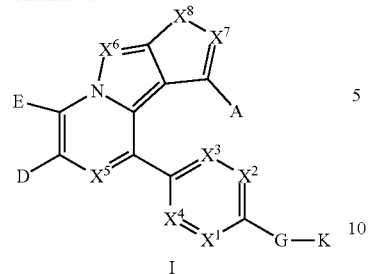

I wherein A, D, E, G, K, $X^1$, $X^2$, $X^3$, $X^4$, $X^5$, $X^6$, $X^7$, $X^8$ and $R^2$ are defined as in claim 78; and L is selected from leaving groups.

82. A process for preparing the compound of formula I-1, comprising reacting a compound of formula I-2 to obtain the compound of formula I-1:

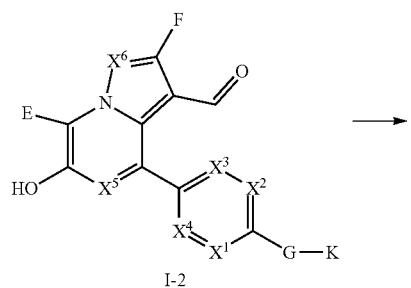

I-2

→

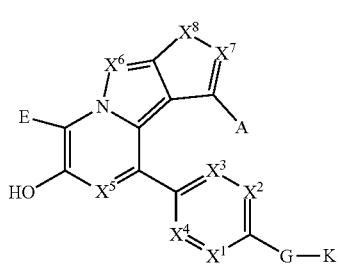

I-1 wherein A, D, E, G, K, $X^1$, $X^2$, $X^3$, $X^4$, $X^5$, $X^6$, $X^7$ and $X^8$ are defined as in claim 78.

83. A compound of formula I-1 or formula I-2:

I-1

-continued

I-2

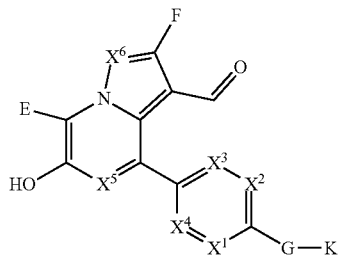

wherein A, E, G, K, $X^1$, $X^2$, $X^3$, $X^4$, $X^5$, $X^6$, $X^7$ and $X^8$ are defined as in claim 78.

84. A pharmaceutical composition, comprising a therapeutically effective amount of at least one of the compound of formula I, and the stereoisomer, the racemate, the tautomer, the isotopically labeled compound, the nitrogen oxide and the pharmaceutically acceptable salt thereof according to claim 78.

85. A compound of the following formula I, or a stereoisomer, a racemate, a tautomer, an isotopically labeled compound, a nitrogen oxide or a pharmaceutically acceptable salt thereof:

I

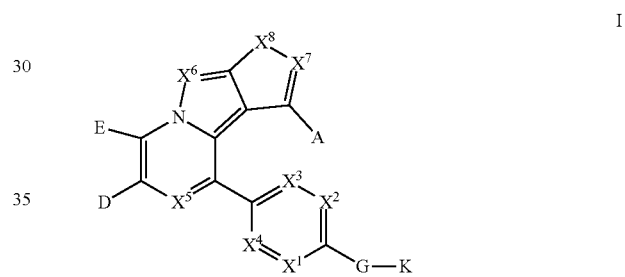

wherein $X^1$, $X^2$, $X^3$, $X^4$, $X^5$, $X^6$ and $X^7$ are the same or different, and are independently selected from $CR^1$ and N;

$X^8$ is selected from $CR^1R^{1'}$ and $NR^1$;

wherein each $R^1$ and $R^{1'}$ are the same or different, and are independently selected from H, halogen, CN, OH, and the following groups unsubstituted or optionally substituted with one, two or more $R^a$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $NR^2R^3$, —C(O)$R^4$, —OC$R^5$, —S(O)$_2R^6$ and OS(O)$^2R^7$;

A is selected from H, halogen, CN, OH, $NH_2$, and the following groups unsubstituted or optionally substituted with one, two or more $R^b$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $NR^2R^3$, —C(O)$R^4$, —OC$R^5$, —S(O)$_2R^6$ and OS(O)$^2R^7$;

D and E are the same or different, and are independently selected from H, halogen, CN, OH, —O—$R^{21}$, and the following groups unsubstituted or optionally substituted with one, two or more $R^c$: $C_{1-40}$ alkenyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, and $NH_2$, provided that at least one of D and E is selected from —O—$R^{21}$;

$R^{21}$ is selected from H, and the following groups unsubstituted or optionally substituted with one, two or more $R^d$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, and 3- to 20-membered heterocyclyl;

G is selected from the following groups unsubstituted or optionally substituted with one, two or more $R^e$: $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, and 3- to 20-membered heterocyclyloxy;

K is selected from the following groups unsubstituted or optionally substituted with one, two or more $R^f$: H, halogen, CN, OH, and the following groups unsubstituted or optionally substituted with one or more $R^g$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, $NR^2R^3$, —C(O)$R^4$, —OCR$^5$, —S(O)$_2R^6$ and OS(O)$^2R^7$;

each $R^2$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, —C(O)$R^4$ and —S(O)$_2R^6$;

each $R^3$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, —C(O)$R^4$ and —S(O)$_2R^6$; or, $R^2$ and $R^3$, together with a N atom connected thereto, form 5- to 20-membered heteroaryl or 3- to 20-membered heterocyclyl;

each $R^4$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, and $NR^2R^3$;

each $R^5$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkylcarbonyl, $C_{2-40}$ alkenylcarbonyl, $C_{2-40}$ alkynylcarbonyl, $C_{3-40}$ cycloalkylcarbonyl, $C_{3-40}$ cycloalkenylcarbonyl, $C_{3-40}$ cycloalkynylcarbonyl, $C_{6-20}$ arylcarbonyl, 5- to 20-membered heteroarylcarbonyl, and 3- to 20-membered heterocyclylcarbonyl;

each $R^6$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, and $NR^2R^3$;

each $R^7$ is the same or different, and is independently selected from H, $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, and 3- to 20-membered heterocyclyl;

each $R^a$, $R^b$, $R^c$, $R^d$, $R^e$ and $R^f$ are the same or different, and are independently selected from halogen, CN, OH, SH, oxo (=O), $NO_2$, and the following groups unsubstituted or optionally substituted with one, two or more $R^g$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, $NR^2R^3$, —C(O)$R^4$, —OCR$^5$, —S(O)$_2R^6$ and OS(O)$^2R^7$;

each $R^g$ is the same or different, and is independently selected from halogen, CN, OH, SH, oxo (=O), $NO_2$, and the following groups unsubstituted or optionally substituted with one, two or more $R^h$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, $NR^2R^3$, —C(O)$R^4$, —OCR$^5$, —S(O)$_2R^6$ and OS(O)$^2R^7$; or, where a cyclic group (including but not limited to, $C_{3-40}$ cycloalkyl, $C_{3-40}$ cycloalkenyl, $C_{3-40}$ cycloalkynyl, 3- to 20-membered heterocyclyl, and the like) is substituted with two or more substituents at different positions, two of the substituents can also form a bridged ring with the cyclic group, wherein the bridge atoms other than the bridgehead atoms in the bridged ring can comprise 1, 2, 3, 4 or 5 divalent groups selected from $CH^2$, O and NH; and each $R^h$ is the same or different, and is independently selected from halogen, CN, OH, SH, oxo (=O), $NO_2$, and the following groups unsubstituted or optionally substituted with one or more $R^g$: $C_{1-40}$ alkyl, $C_{2-40}$ alkenyl, $C_{2-40}$ alkynyl, $C_{3-40}$ cycloalkyl, $C_{3-40}$ cycloalkenyl, $C_{3-40}$ cycloalkynyl, $C_{6-20}$ aryl, 5- to 20-membered heteroaryl, 3- to 20-membered heterocyclyl, $C_{1-40}$ alkyloxy, $C_{2-40}$ alkenyloxy, $C_{2-40}$ alkynyloxy, $C_{3-40}$ cycloalkyloxy, $C_{3-40}$ cycloalkenyloxy, $C_{3-40}$ cycloalkynyloxy, $C_{6-20}$ aryloxy, 5- to 20-membered heteroaryloxy, 3- to 20-membered heterocyclyloxy, $NR^2R^3$, —C(O)$R^4$, —OCR$^5$, —S(O)$_2R^6$ and OS(O)$^2R^7$; or, where a cyclic group (including but not limited to, $C_{3-40}$ cycloalkyl, $C_{3-40}$ cycloalkenyl, $C_{3-40}$ cycloalkynyl, 3- to 20-membered heterocyclyl, and the like) is substituted with two or more substituents at different positions, two of the substituents can also form a bridged ring with the cyclic group, wherein the bridge atoms other than the bridgehead atoms in the bridged ring can comprise 1, 2, 3, 4 or 5 divalent groups selected from $CH^2$, O and NH; or, where one atom (such as carbon atom) is substituted with two or more substituents, two of the substituents may also, together with an atom connected thereto, form a cyclic group (including but not limited to, $C_{3-40}$ cycloalkyl, $C_{3-40}$ cycloalkenyl, $C_{3-40}$ cycloalkynyl, 3- to 20-membered heterocyclyl, and the like).

86. The compound according to claim 85, wherein $X^1$, $X^2$, $X^3$, $X^4$, $X^5$, $X^6$ and $X^7$ are the same or different, and are independently selected from $CR^1$ and N; for example, at least one of $X^1$, $X^2$, $X^3$, $X^4$, $X^5$, $X^6$ and $X^1$ is N;

$X^8$ is selected from $CR^1R^{1'}$ and $NR^1$;

each $R^1$ and $R^{1'}$ are the same or different, and are independently selected from H, halogen, CN, OH, $C_{1-6}$ alkyl, $C_{3-10}$ cycloalkyl and $C_{1-6}$ alkoxy;

A is selected from H, halogen, CN, OH, $C_{1-6}$ alkyl and $C_{1-6}$ alkyloxy;

D and E are the same or different, and are independently selected from H, halogen, CN, $NH_2$ and —O—$R^{21}$, provided that at least one of D and E is selected from —O—$R^2$;

$R^{21}$ is selected from $C_{1-6}$ alkyl unsubstituted or optionally substituted with one, two or more $R^d$;

each $R^a$, $R^b$, $R^c$, $R^d$, $R^e$ and $R^f$ are the same or different, and are independently selected from halogen, CN, OH, and the following groups unsubstituted or optionally with one, two or more $R^g$: $C_{1-6}$ alkyl, $C_{1-6}$ alkyloxy, $C_{3-10}$ cycloalkyl and $C_{3-10}$ cycloalkyloxy;

each $R^g$ is the same or different, and is independently selected from halogen and $C_{3-10}$ cycloalkyl;

G is selected from $C_{3-10}$ cycloalkyl, $C_{6-14}$ aryl, 5- to 14-membered heteroaryl, and 3- to 10-membered heterocyclyl, for example, 6- to 7-membered heterocyclyl having a monocyclic, bicyclic or bridged ring structure containing 1, 2 or 3 heteroatoms independently selected from N, O and S; and K is selected from —$C_{1-6}$ alkyl-$C_{3-10}$ cycloalkyl, —$C_{1-6}$ alkyl-$C_{6-14}$ aryl, —$C_{1-6}$ alkyl-5- to 14-membered heteroaryl, —$C_{1-6}$ alkyl-3- to 10-membered heterocyclyl, —C(O) $NH_2$, —C(O)—$C_{3-10}$ cycloalkyl, —C(O)—$C_{6-14}$ aryl, —C(O)-5- to 14-membered heteroaryl, —C(O)-3- to 10-membered heterocyclyl, —C(O)—$C_{1-6}$ alkyl-$C_{3-10}$ cycloalkyl, —C(O)—$C_{1-6}$ alkyl-$C_{6-14}$ aryl, —C(O)—$C_{1-6}$ alkyl-5- to 14-membered heteroaryl, and —C(O)—$C_{1-6}$ alkyl-3- to 10-membered heterocyclyl, wherein a cyclic or acyclic group of the $C_{3-10}$ cycloalkyl, $C_{6-14}$ aryl, 5- to 14-membered heteroaryl, 3- to 10-membered heterocyclyl, —C(O)—$C_{3-10}$ cycloalkyl, —C(O)—$C_{6-14}$ aryl, —C(O)-5- to 14-membered heteroaryl, —C(O)-3- to 10-membered heterocyclyl, —C(O)—$C_{1-6}$ alkyl-$C_{3-10}$ cycloalkyl, —C(O)—$C_{1-6}$ alkyl-$C_{6-14}$ aryl, —C(O)—$C_{1-6}$ alkyl-5- to 14-membered heteroaryl, or —C(O)—$C_{1-6}$ alkyl-3- to 10-membered heterocyclyl, or —C(O)$NH_2$ is optionally substituted with one, two or more groups selected from OH, halogen, CN, $C_{1-6}$ alkyl and $C_{1-6}$ alkyloxy; wherein the heterocyclyl can be pyridinyl, and the aryl can be phenyl.

87. The compound according to claim 85, wherein $X^1$, $X^2$, $X^3$, $X^4$, $X^5$, $X^6$ and $X^7$ are the same or different, and are independently selected from CH and N; for example, at least one of $X^1$, $X^2$, $X^3$, $X^4$, $X^5$, $X^6$ and $X^7$ is N;

$X^8$ is selected from $NR^1$;

$R^1$ is H;

A is selected from H, $NH_2$, methyl, ethyl, propyl and isopropyl;

E is H;

D is selected from the following groups: halogen, BnO—, H, CN, $NH_2$, $OCH_3$,

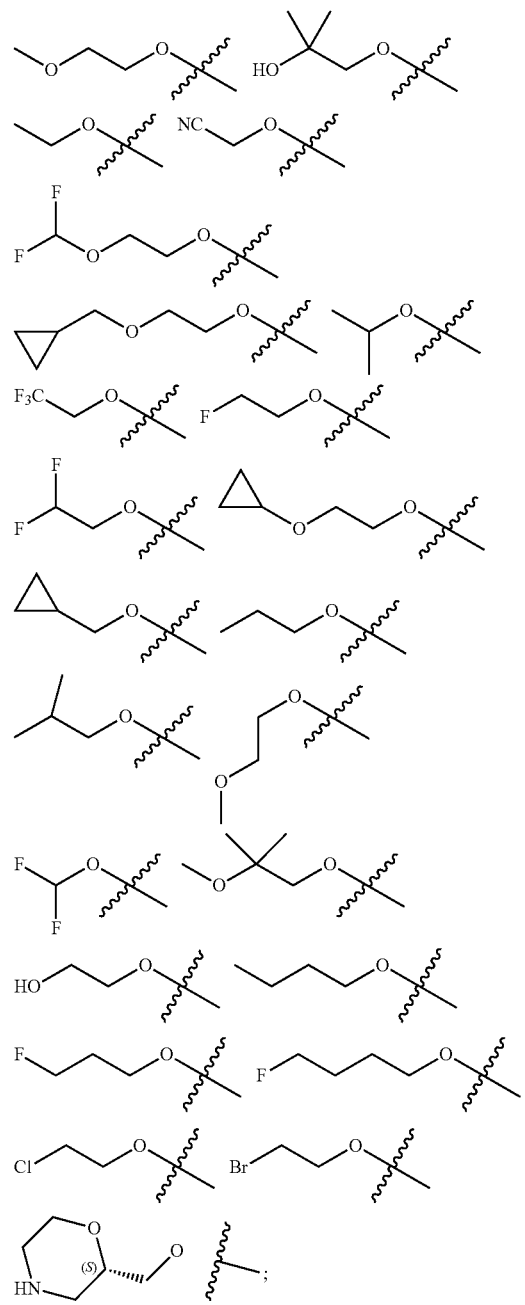

G is selected from

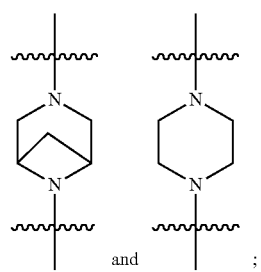 [SMILES: *N1CC2CC(C1)N2* ; *N1CCN(*)CC1]

and
K is selected from
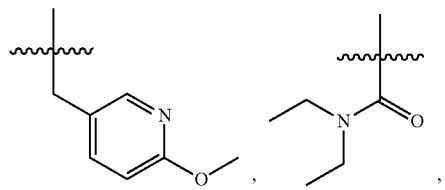
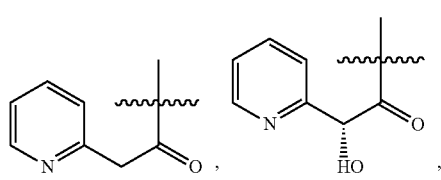
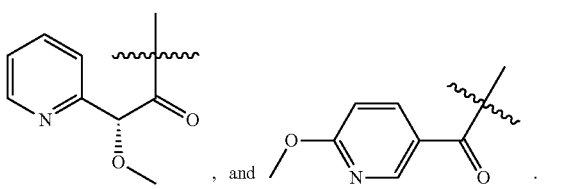
88. The compound according to claim 85, wherein the compound of formula I is selected from the following compounds:
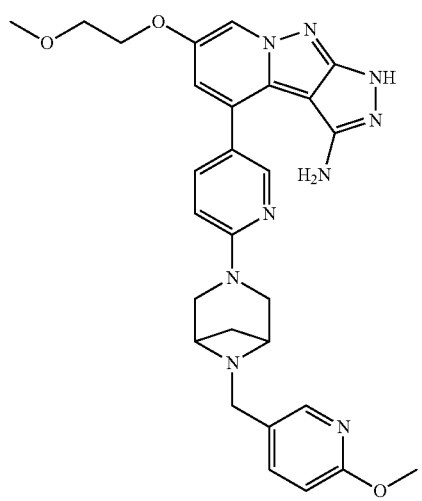
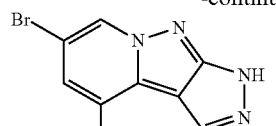
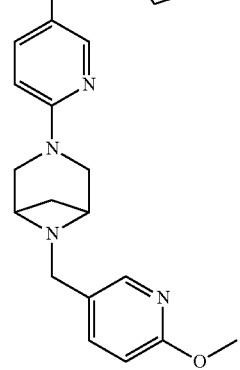
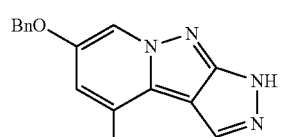
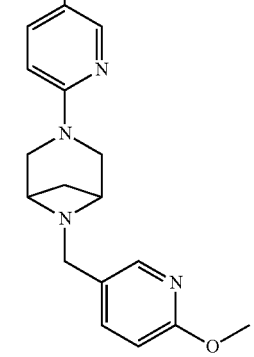

169
-continued
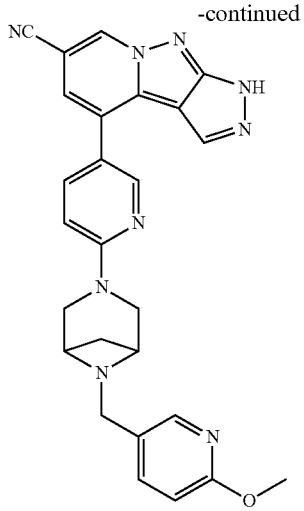
170
-continued
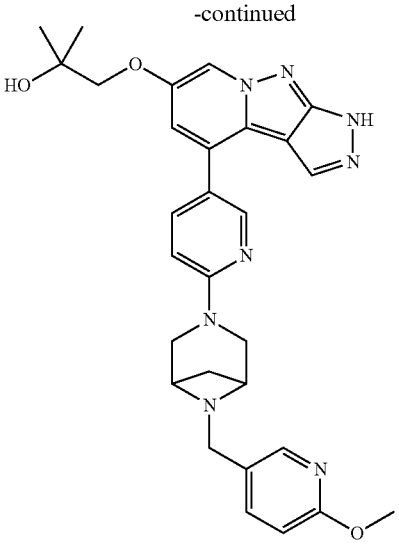
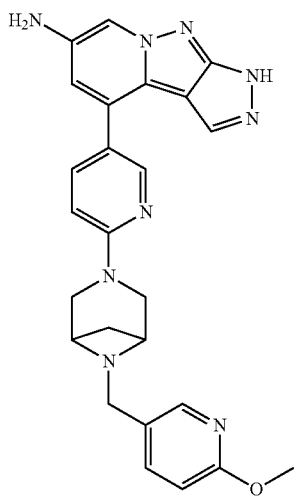
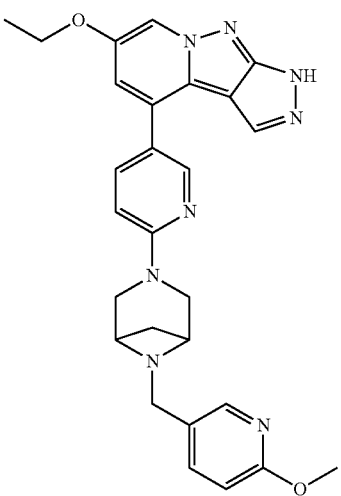
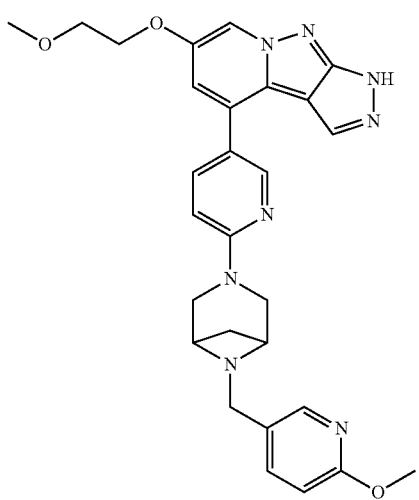
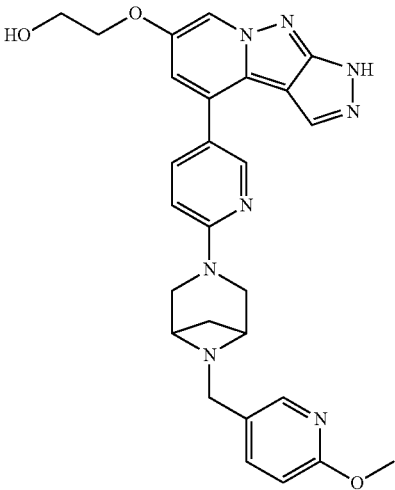

171
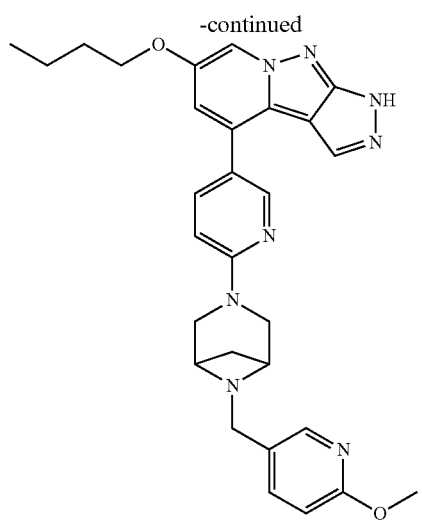
172
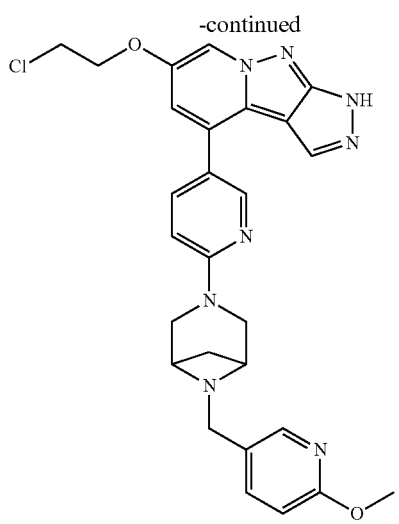
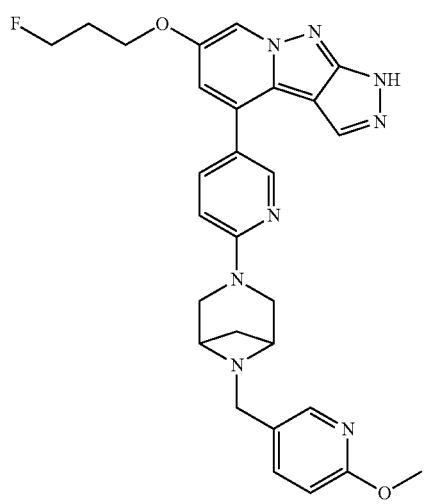
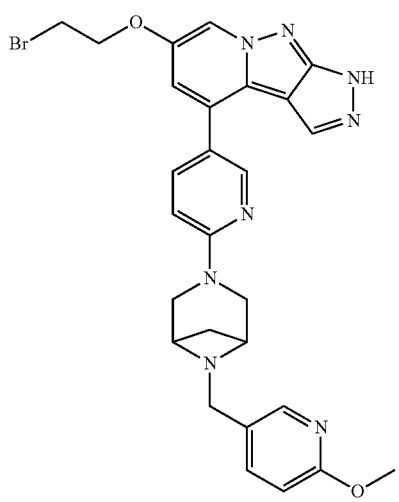
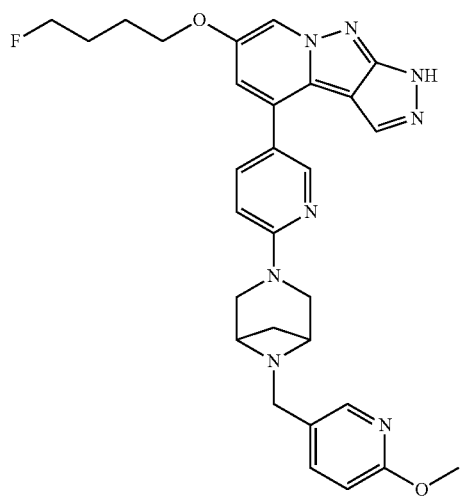
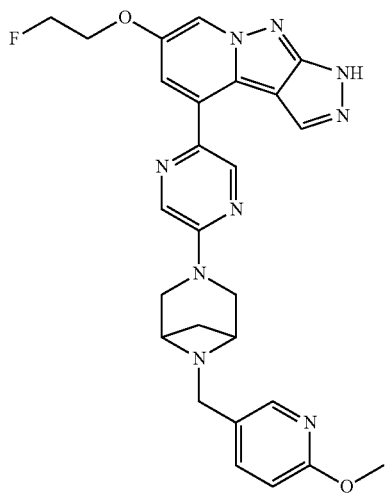

173
-continued
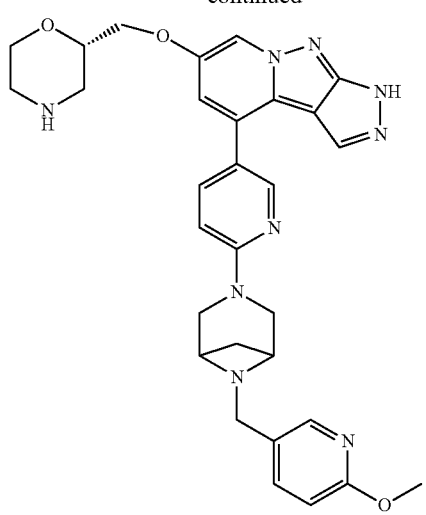
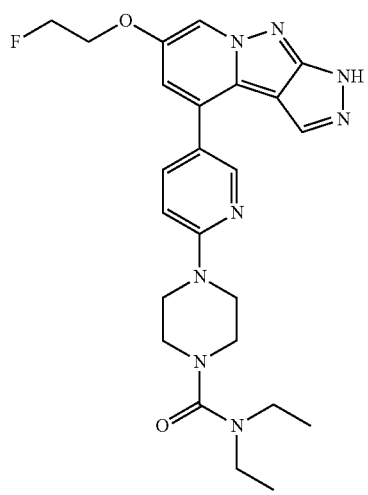
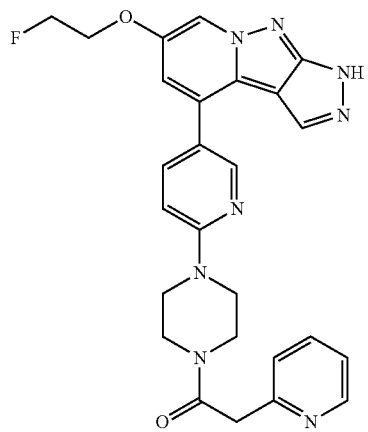
174
-continued
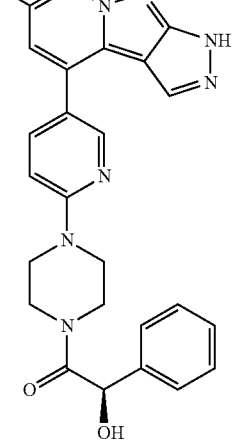
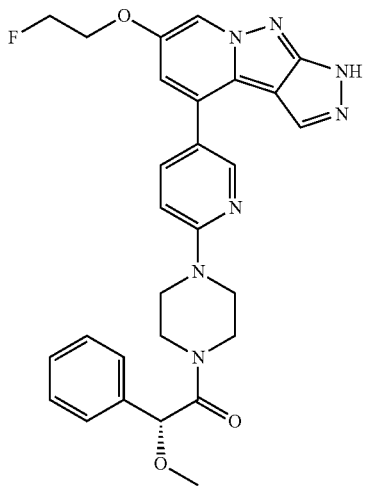
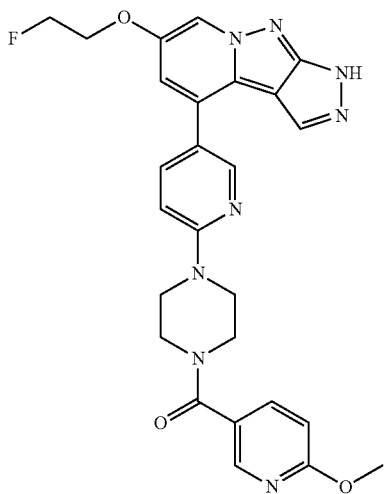

175
-continued
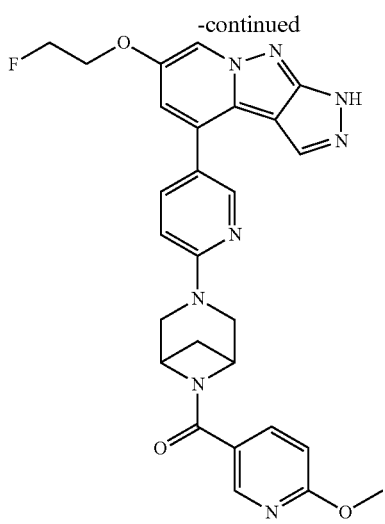
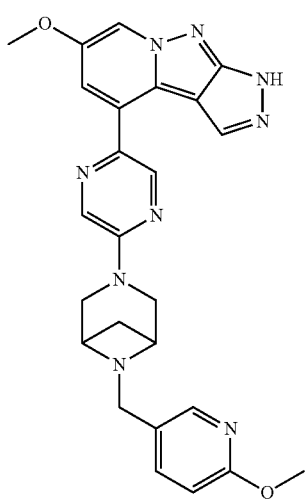
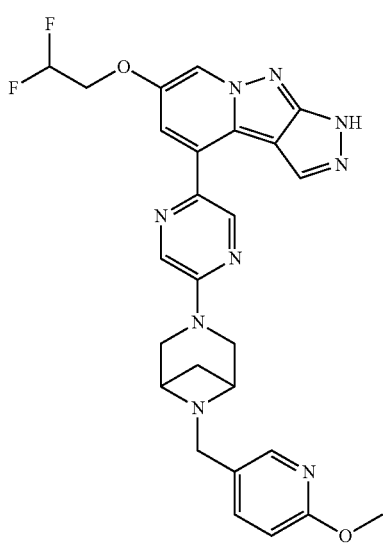
176
-continued
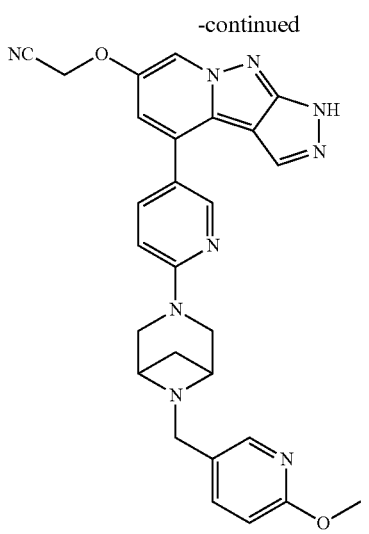
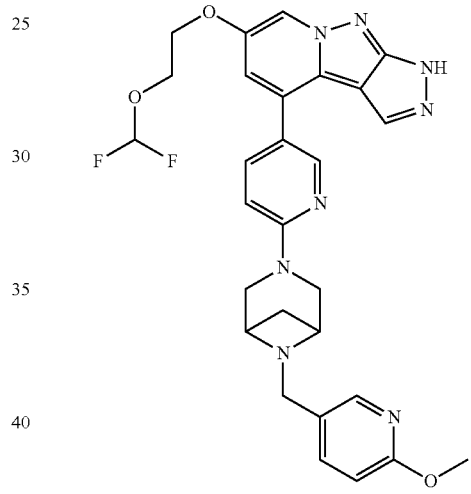
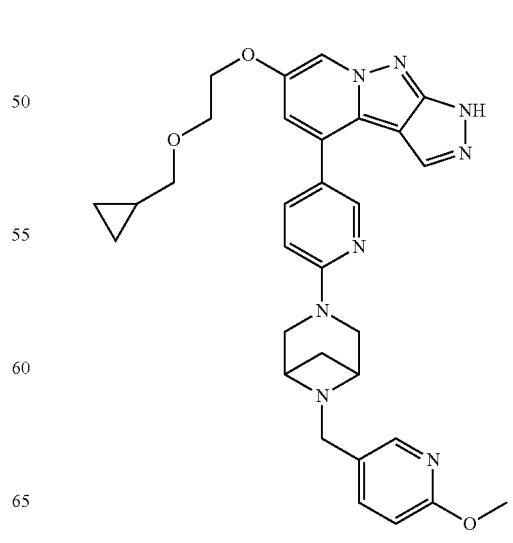

177
-continued
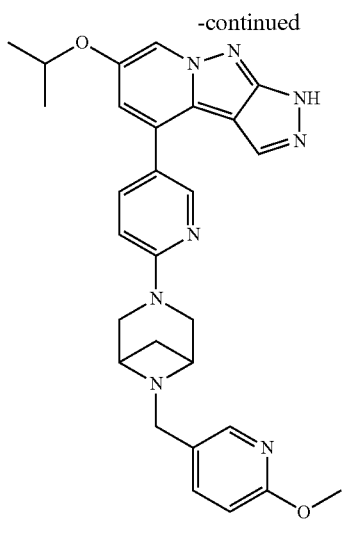
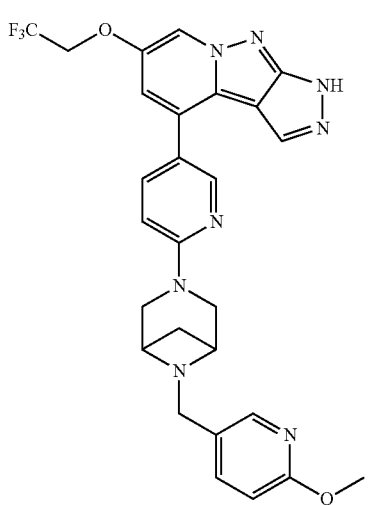
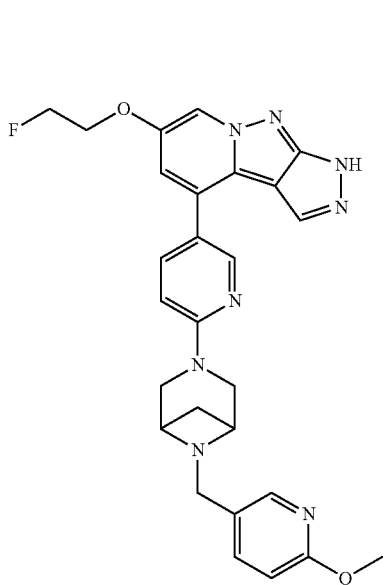
178
-continued
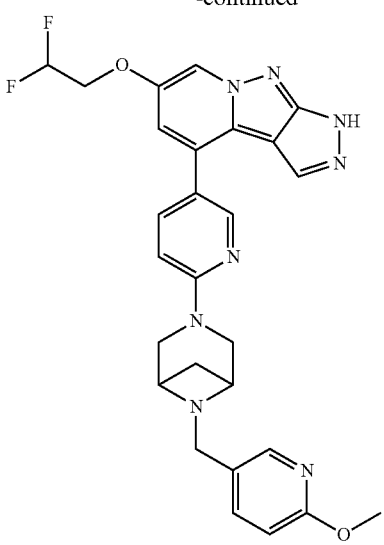
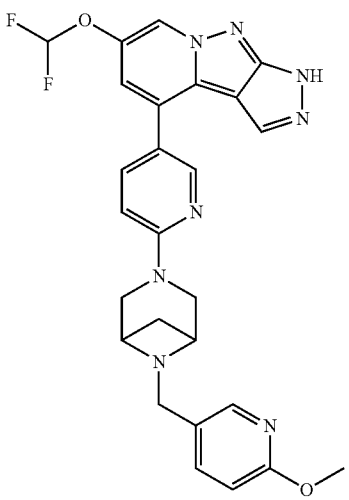
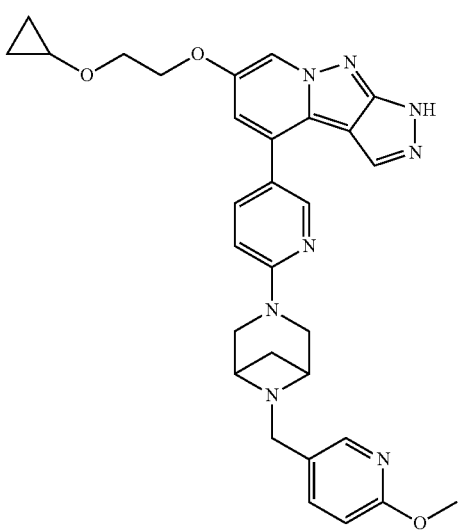

179
-continued
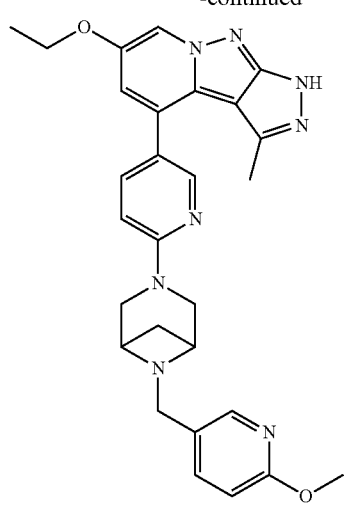
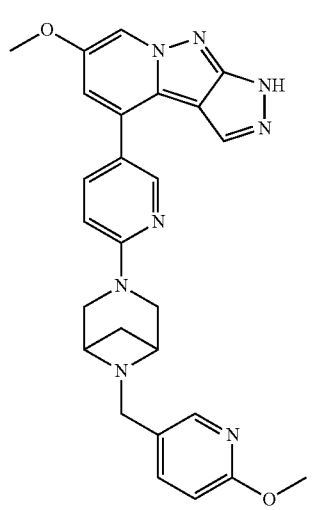
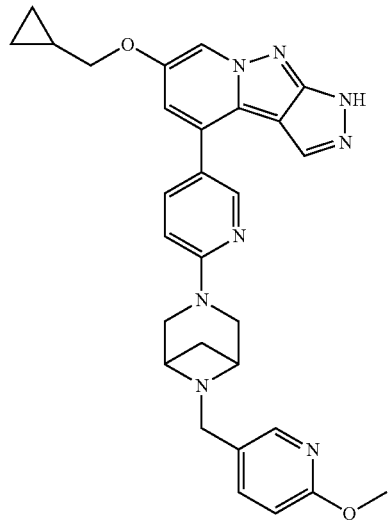
180
-continued
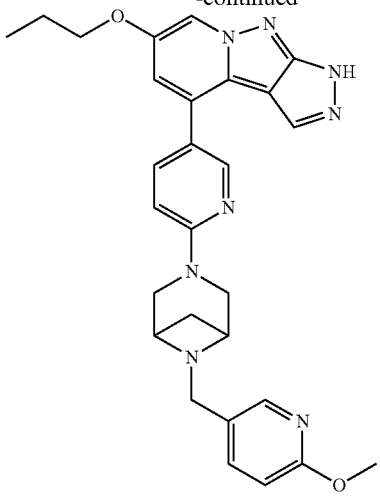
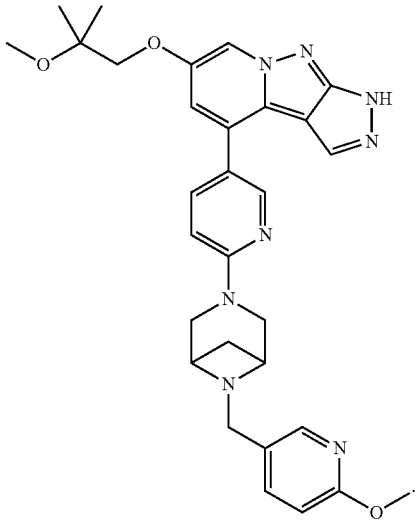

89. A process for preparing the compound according to claim 85, comprising the following steps:

reacting a compound of formula I-1 with a compound $R^{21}$-L to obtain the compound of formula I,

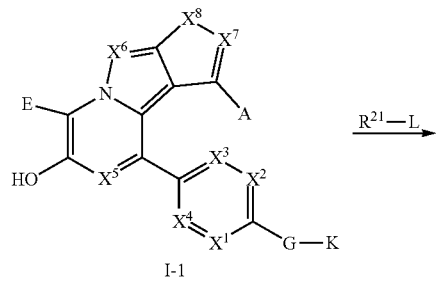

$\xrightarrow{R^{21}-L}$

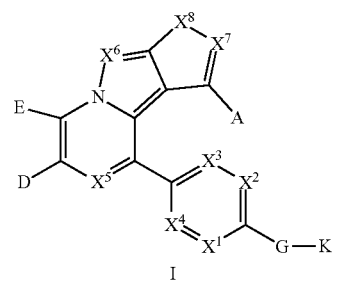

wherein A, D, E, G, K, $X^1$, $X^2$, $X^3$, $X^4$, $X^5$, $X^6$, $X^7$, $X^8$ and $R^{21}$ are defined as in claim 85; and L is selected from leaving groups.

90. A process for preparing the compound of formula I-1, comprising reacting a compound of formula I-2 to obtain the compound of formula I-1:

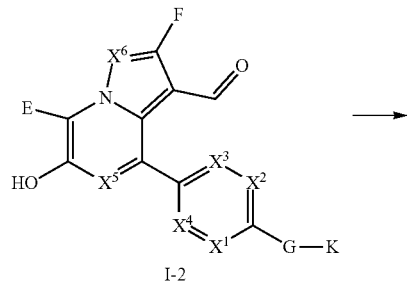

$\longrightarrow$

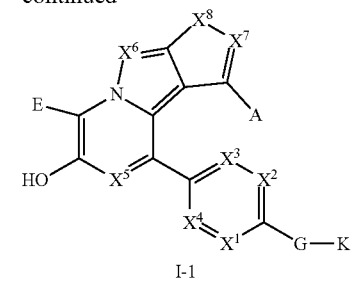

wherein A, D, E, G, K, $X^1$, $X^2$, $X^3$, $X^4$, $X^5$, $X^6$, $X^7$ and $X^8$ are defined as in claim 85.

91. A compound of formula I-1 or formula I-2:

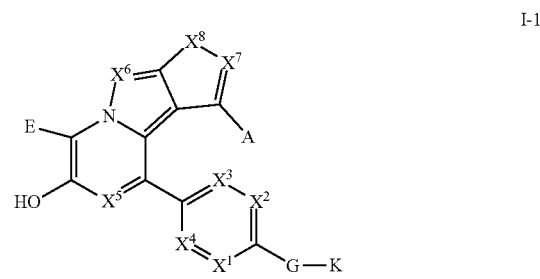

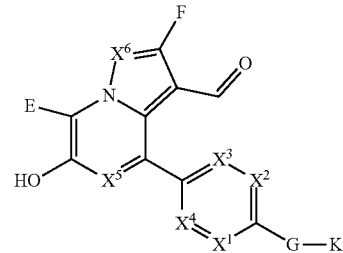

wherein A, E, G, K, $X^1$, $X^2$, $X^3$, $X^4$, $X^5$, $X^6$, $X^7$ and $X^8$ are defined as in claim 85.

92. A pharmaceutical composition, comprising a therapeutically effective amount of at least one of the compound of formula I, and the stereoisomer, the racemate, the tautomer, the isotopically labeled compound, the nitrogen oxide and the pharmaceutically acceptable salt thereof according to claim 85.

* * * * *